(12) United States Patent
Porco, Jr. et al.

(10) Patent No.: US 11,279,708 B2
(45) Date of Patent: Mar. 22, 2022

(54) AMIDINO- AND AMINO-ROCAGLATES AS NOVEL TRANSLATION INHIBITORS AND ANTICANCER AGENTS

(71) Applicant: TRUSTEES OF BOSTON UNIVERSITY, Boston, MA (US)

(72) Inventors: John A. Porco, Jr., Brookline, MA (US); Wenhan Zhang, Allston, MA (US); Gerard Pelletier, Quebec (CA); Jennifer Chu, Dorchester, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 16/898,959

(22) Filed: Jun. 11, 2020

(65) Prior Publication Data
US 2020/0392147 A1  Dec. 17, 2020

Related U.S. Application Data

(60) Provisional application No. 62/860,501, filed on Jun. 12, 2019.

(51) Int. Cl.
| | | |
|---|---|---|
| *C07D 493/22* | (2006.01) | |
| *C07D 491/048* | (2006.01) | |
| *C07D 491/147* | (2006.01) | |
| *C07D 513/14* | (2006.01) | |

(52) U.S. Cl.
CPC ..... *C07D 491/048* (2013.01); *C07D 491/147* (2013.01); *C07D 513/14* (2013.01)

(58) Field of Classification Search
CPC .......................... C07D 493/22; A61K 31/4188
USPC ....................................... 548/301.7; 514/393
See application file for complete search history.

(56) References Cited

PUBLICATIONS

Chu et al., "Amidino-Rocaglates: A Potent Class of eIF4A Inhibitors", Cell Chemical Biology, 26, 1586-1593, (2019).
Chu et al., "Rocaglates Induce Gain-of-Function Alterations to eIF4A and eIF4F", Cell Reports, 30, 2481-2488, (2020).
Zhang et al., "Intercepted Retro-Nazarov Reaction: Syntheses of Amidino-Rocaglate Derivatives and Their Biological Evaluation as eIF4A Inhibitors", Journal of the American Chemical Society, 141, 12891-12900, (2019).
Zhang et al.,Supporting Information: Intercepted Retro-Nazarov Reaction: Syntheses of Amidino-Rocaglate Derivatives and Their Biological Evaluation as eIF4A Inhibitors, Journal of the American Chemical Society, 141, S1-S135, (2019).
Yueh et al., "A Photochemical flow Reactor for Large Scale Syntheses of Aglain and rocaglate Natural Product Analogs", Bioorg. Med. Chem., 25, (23.), 6197-6202, (2017).
Zhou et al., "The Evolution of the Total Synthesis of Rocaglamide", Chemistry, 22, 15929-15936, (2016).
Langlais et al., "Rocaglates as dual-targeting agents for experimental cerebral malaris", PANS, 115, (10.), 2366-2375, (2018).
El-Neketi et al., "Cytotoxic Rocaglamide Derivatives from Agiaia duppereana", Z Naturforsch C., 68, (7-8.), 269-274, (2013).
PUB-OHEM-CID-132541904, p. 2. (2018).
International Search Report issued in PCT/US2020/37249, dated Oct. 30, 2020 (4 pp.).

*Primary Examiner* — Jeffrey H Murray
(74) *Attorney, Agent, or Firm* — Nixon Peabody LLP; Ronald I. Eisenstein; Ravinderjit Braich

(57) ABSTRACT

Herein are described the preparation of a series of synthetic rocaglates, amidino- and amino-rocaglates, which display inhibition of protein translation and tumor cell proliferation (in vitro and in vivo). The methods described herein allow the preparation of libraries of modified rocaglates. This chemical modification of the rocaglate scaffold changes the C8b-hydroxyl of the natural product series to a more optimal hydrogen bond donor/acceptor.

12 Claims, 37 Drawing Sheets
(29 of 37 Drawing Sheet(s) Filed in Color)
Specification includes a Sequence Listing.

An Alternative Approach to Aglaroxin C Led the Discovery of the Substitution of the Tertiary Alcohol.

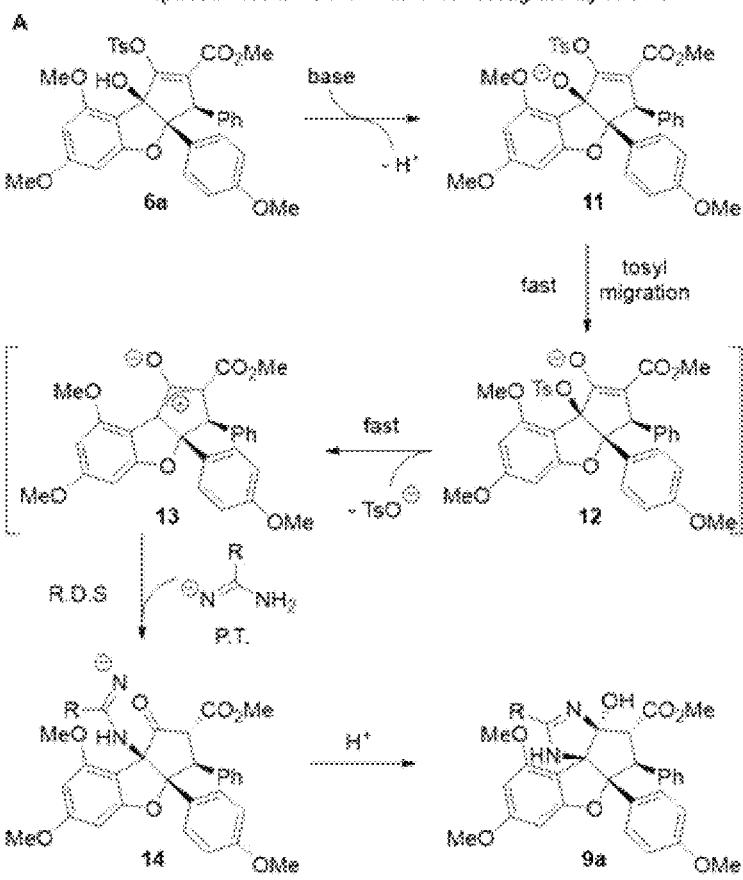
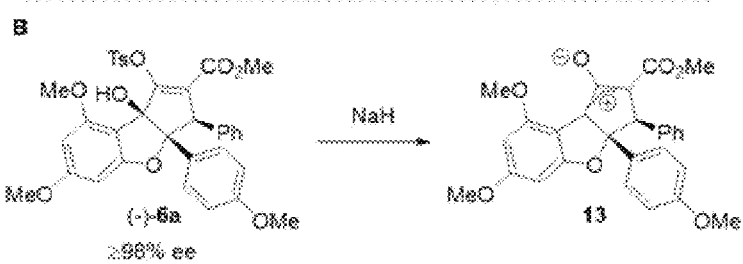
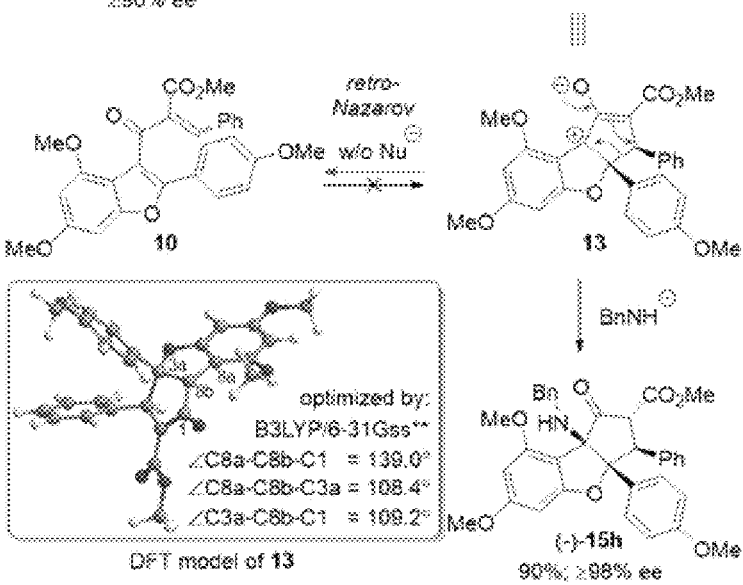
FIG. 6A
FIG. 6B

9a

X-Ray of amidino-rocaglate

Chirality-Based Biological Profiles of some compounds active enantiomers (-)-9

| | R | X | IC$_{50}$ (nM) |
|---|---|---|---|
| (-)-9b | Me | OMe | 47 |
| (-)-9n | ⊲ | OMe | 67 |
| (-)-9z | Me | NMe$_2$ | 34 |
| (-)-9aa | Me | N(OMe)Me | 39 | inactive enantiomers (+)-9

| | R | X | IC$_{50}$ (nM) |
|---|---|---|---|
| (+)-9aa | Me | N(OMe)Me | >4000 |

[a]IC$_{50}$ of indicated compound was collected using the same assay in as previously described and were calculated on the fitted sigmoid curves.

Amidino-rocaglates induced cytotoxicity against MDA-MB-231 breast cancer cells in the SRB cell viability assay. $IC_{50}$ was determined from fitted sigmoid curves; for its determination, the cells were cultured in the presence of indicated compound for 4 days prior to quantited the bound SRB dye using Spectramax M5 at OD = 510 nM.

FIG. 20
20A
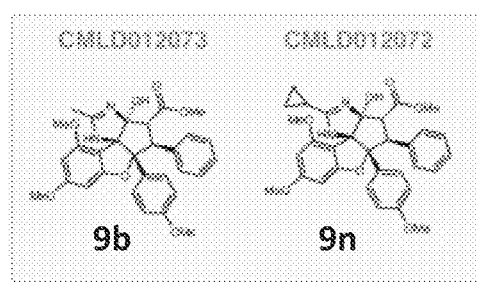
20B
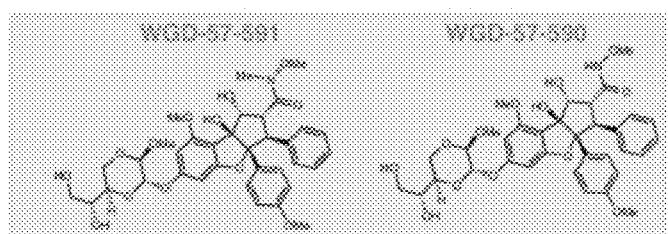
20C
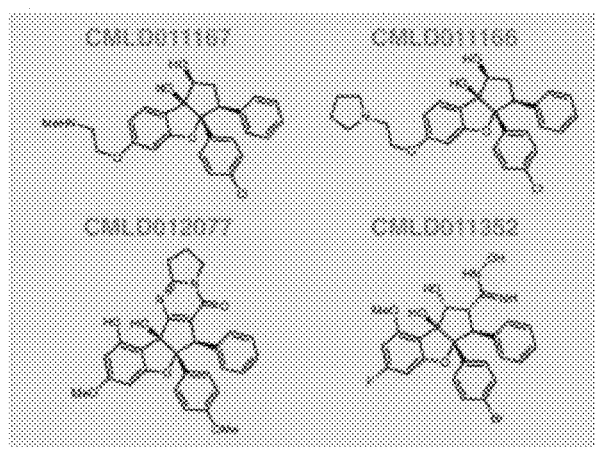

FIG. 22
22A
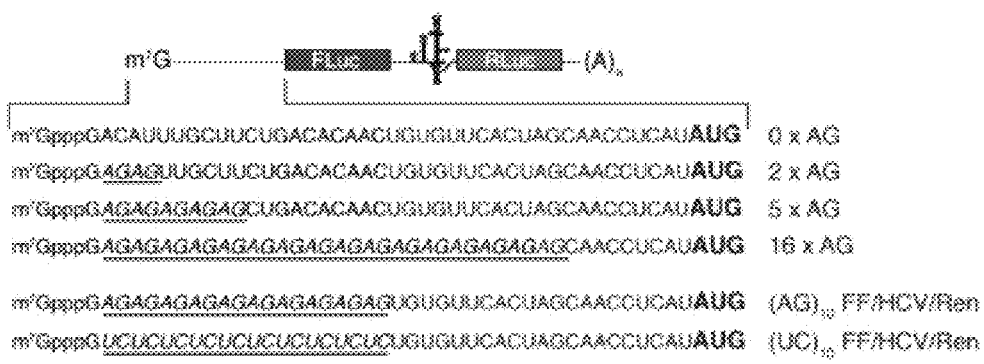
22B
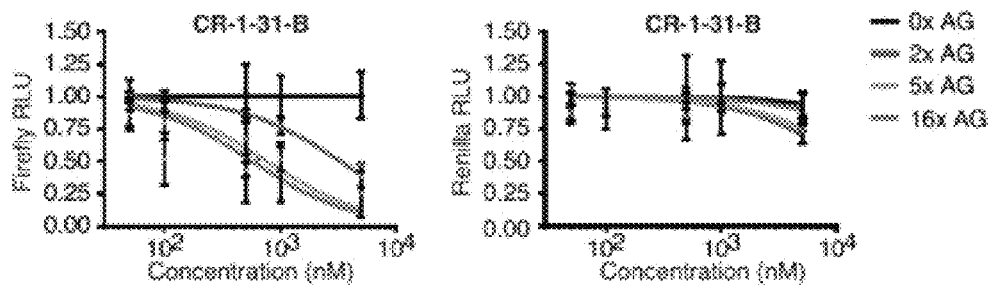
22C
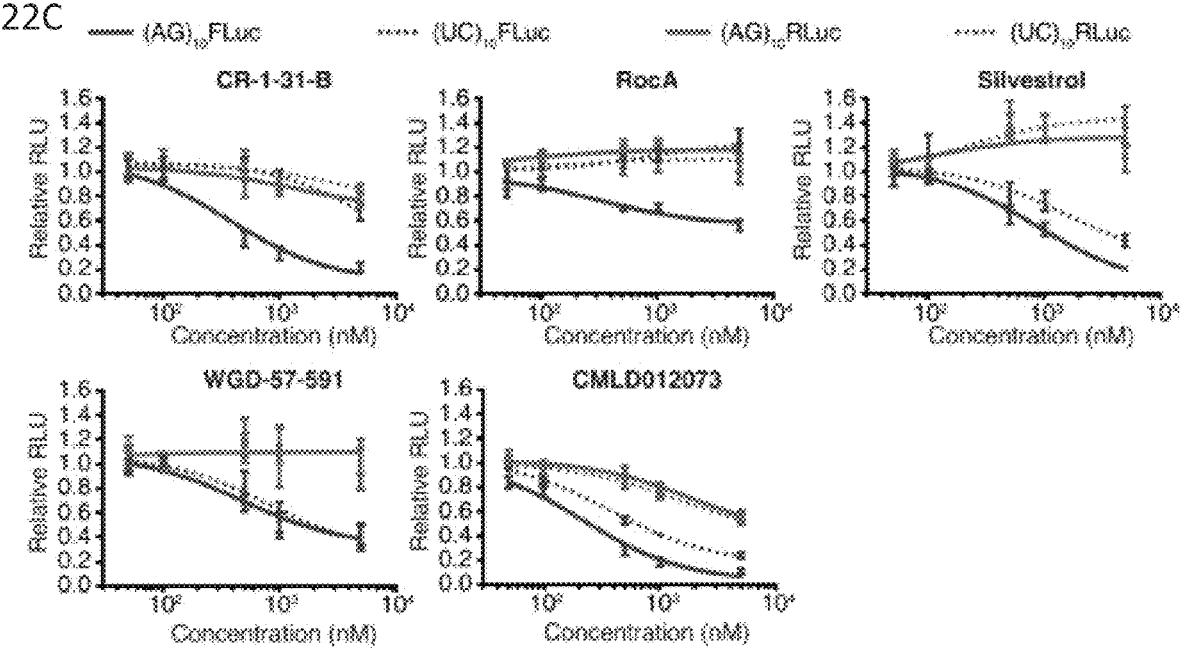

FIG. 24
24A
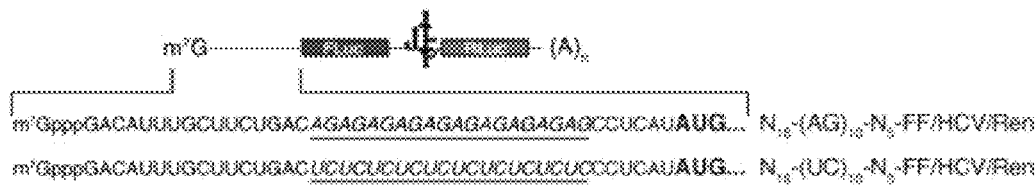
24B
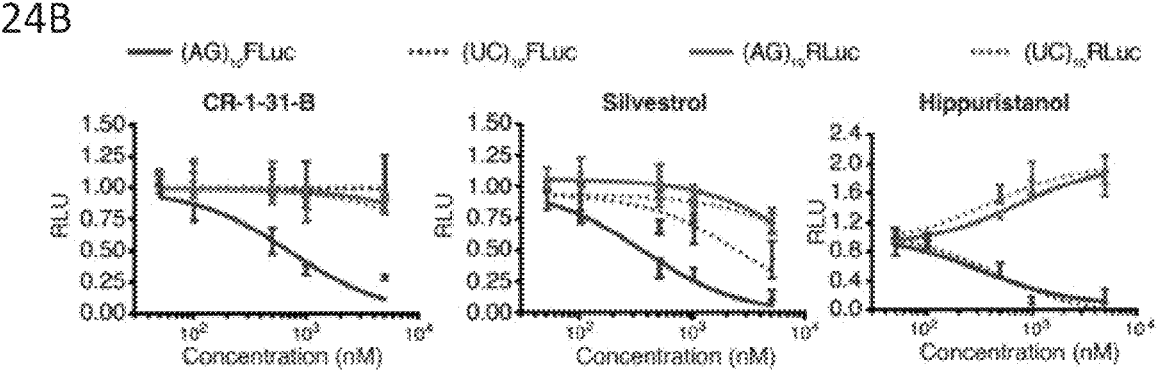
24C
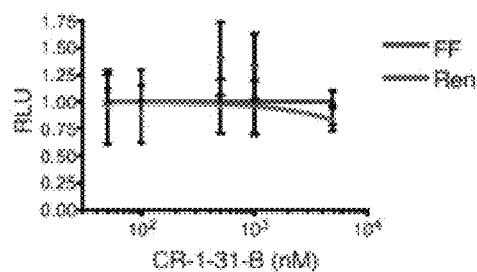

FIG. 27

| Rank Order | Compound | Structure |
|---|---|---|
| 1 | CMLD011167 | See FIG.20C |
| 2 | CMLD010853 | 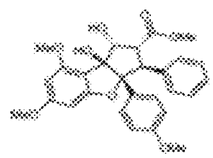 |
| 3 | SDS-1-021 | See FIG.17A |
| 4 | CMLD010513 (CR-1-31-B) (Enantioenriched) | See FIG.17A |
| 5 | CMLD010503 | 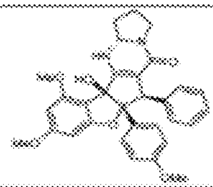 |
| 6 | CMLD010512 | 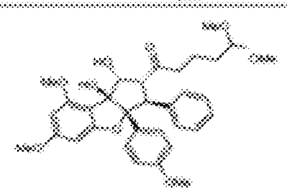 |
| 7 | 4 (RHT) Racemic | See FIG.17A |
| 8 | 4 ((-)-RHT) | See FIG.17A |
| 9 | 23 | See FIG.17A |
| 10 | 9b (CMLD012073) | 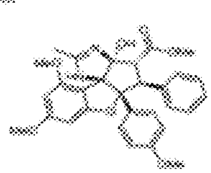 |
| 11 | CMLD011881 (SDS-1-021) (Enantioenriched) | See FIG.17A |

| Rank Order | Compound | Structure |
|---|---|---|
| 12 | 23 (Racemic) | See FIG.17A |
| 13 | CMLD010426 | 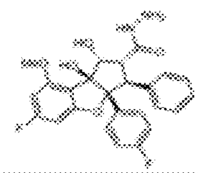 |
| 14 | 2 RocA | See FIG.17A |
| 15 | 9n CMLD012072 | 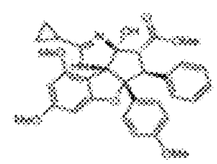 |
| 16 | CMLD010536 | 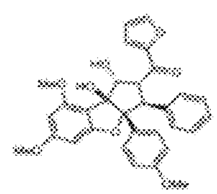 |
| 17 | CMLD011166 | See FIG.20C |

FIG. 30
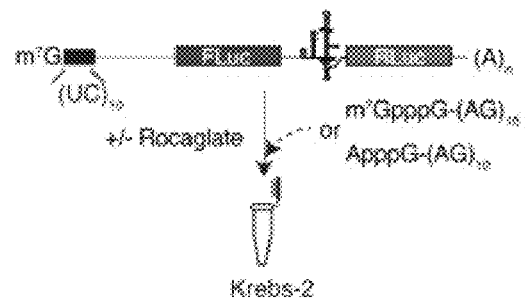
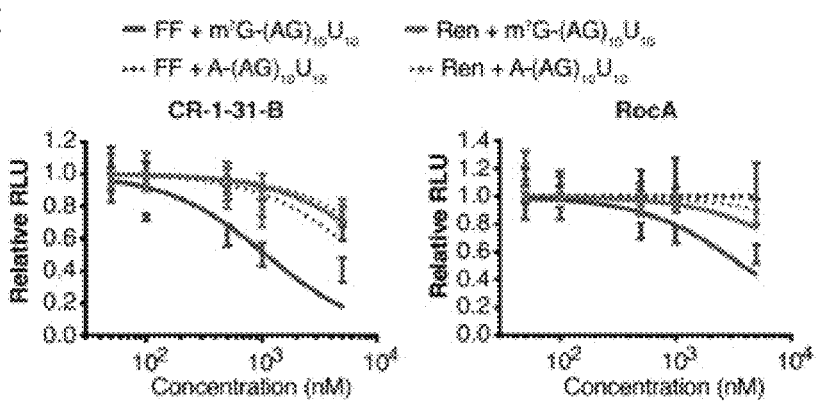
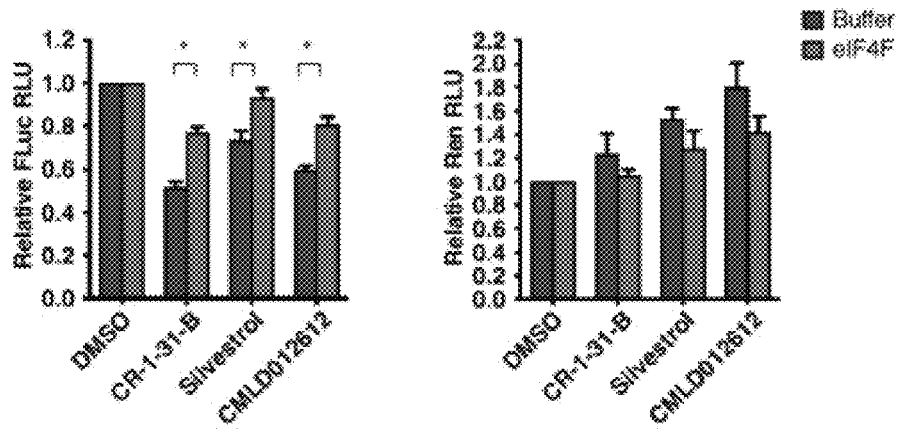

FIG. 31
31A
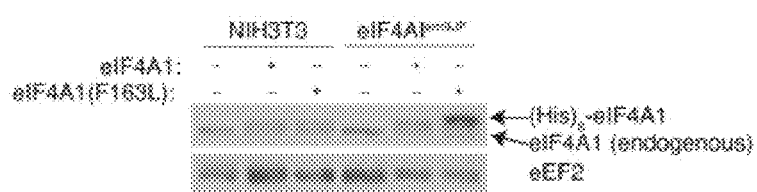
31B
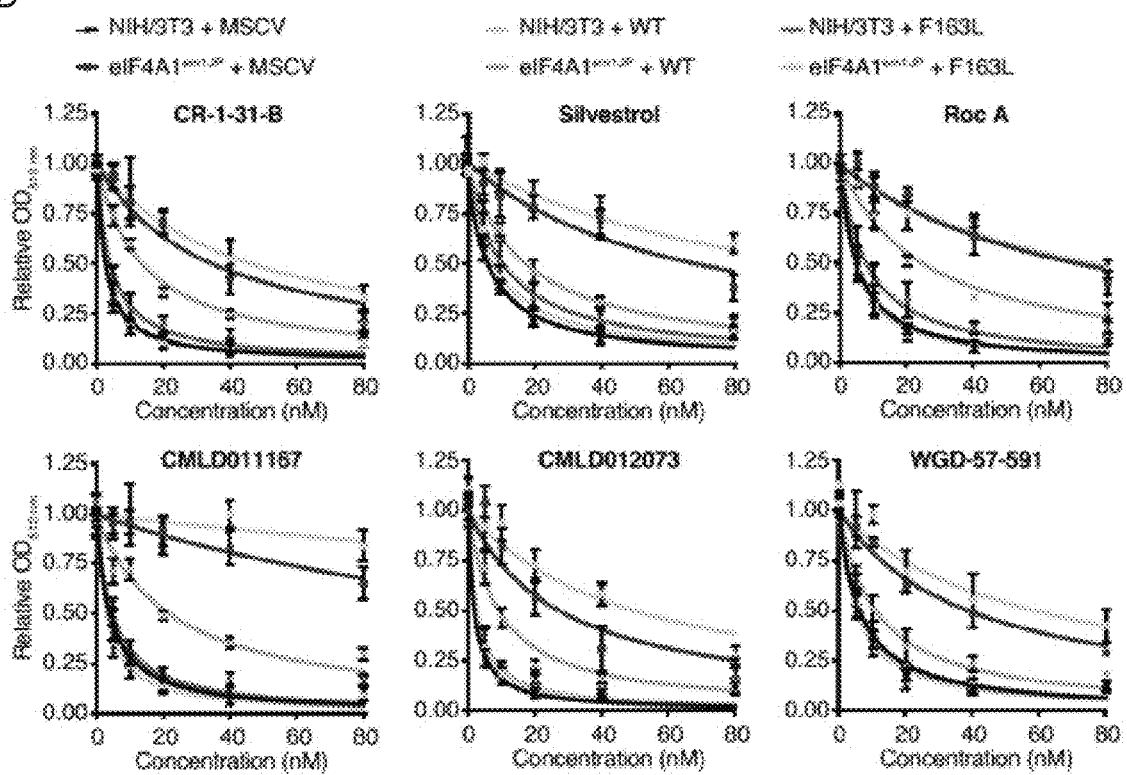

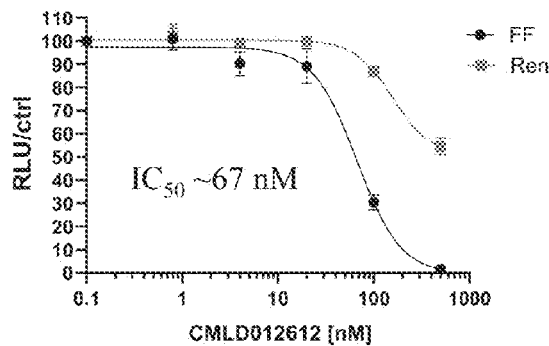
FIG. 35A CMLD012612
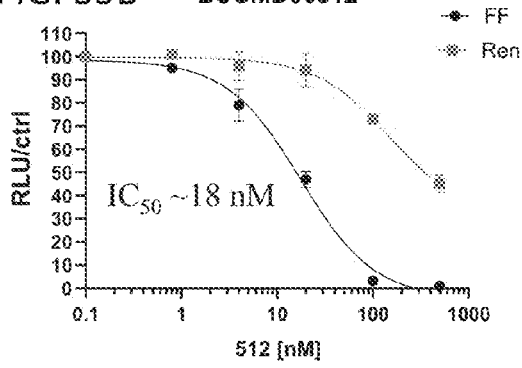
FIG. 35B BUCMD00512
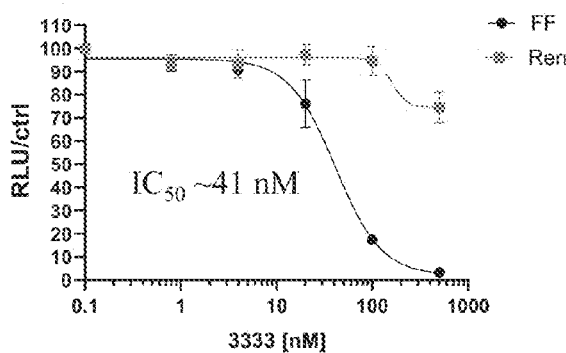
FIG. 35C CMLD013333
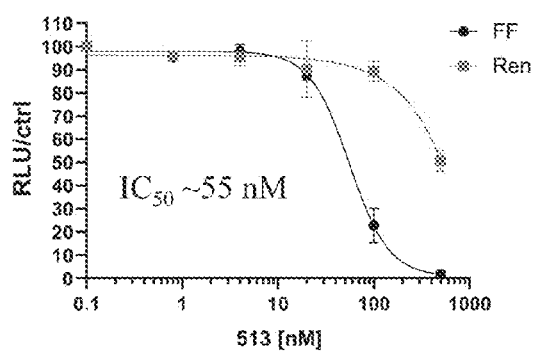
FIG. 35D BUCMD00513
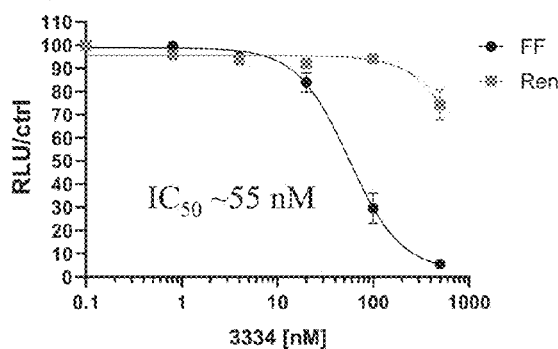
FIG. 35E CMLD013334

FIG. 36
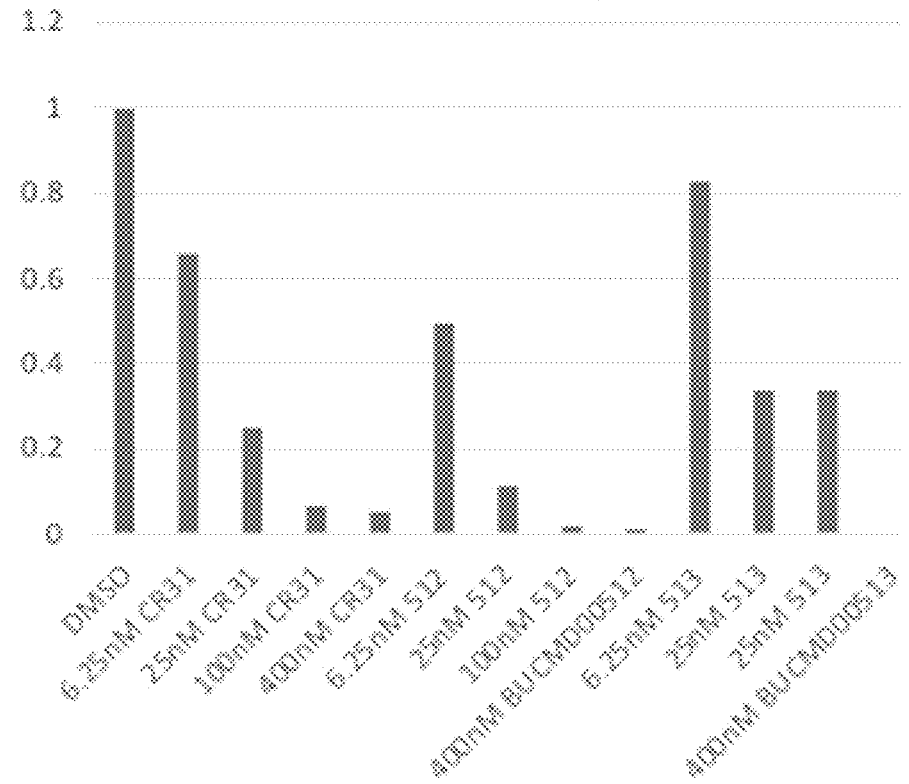
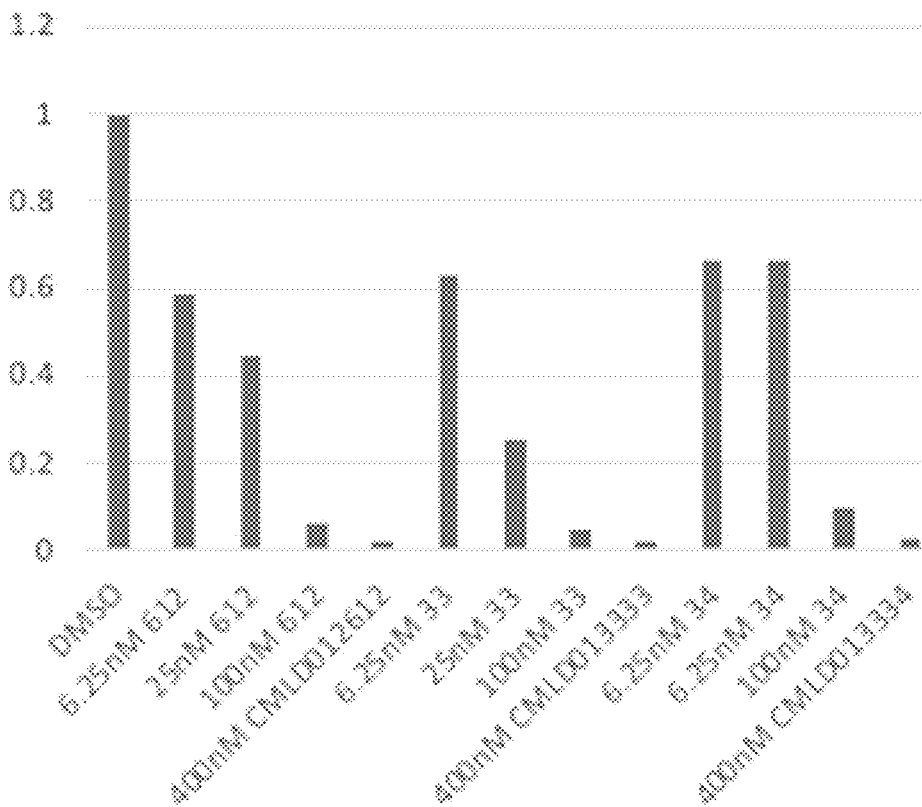

AMIDINO- AND AMINO-ROCAGLATES AS NOVEL TRANSLATION INHIBITORS AND ANTICANCER AGENTS

RELATED APPLICATIONS

This application claims benefit under 35 U.S.C. § 119(e) of the U.S. Provisional Application No. 62/860,501 filed Jun. 12, 2019, the content of which is incorporated herein by reference in its entirety.

GOVERNMENT SUPPORT

This invention was made with Government Support under grant Nos. DK088787 and GM118173 awarded by the National Institutes of Health. The Government has certain rights to the invention.

FIELD OF THE INVENTION

This invention relates to rocaglate (flavagline) derivatives. More particularly, the invention is directed to rocaglate compositions, their syntheses, and uses.

The instant application contains a Sequence Listing which has been submitted electronically in ASCII format and is hereby incorporated by reference in its entirety. Said ASCII copy, created on Aug. 14, 2020, is named 701586-095300USPT_SL.txt and is 9,733 bytes in size.

BACKGROUND

Translation is an essential step in the gene expression pathway that enables cells to make rapid and spatiotemporal alterations to the proteome. Regulation of translation is critical to a wide variety of biological processes, including cellular growth, survival, differentiation, and development. Accordingly, aberrant translational control is associated with several pathological disorders. Small molecules targeting the translation machinery show considerable promise in the treatment of a variety of human maladies including cancer, viral infection, and neurodegeneration. In particular, there is significant interest towards the development of a family of compounds collectively known as rocaglates (flavaglines), a family of natural products found in plants of the genus *Aglaia*.

*Aglaia* Lour. is a large genus of angiosperm plants containing more than 120 species. In 1982, the first rocaglate was isolated from dried roots and stems of *Aglaia elliptifolia* Merr. Since this time, over thirty natural products of the rocaglate family have been discovered sharing a highly substituted cyclopenta[b]benzofuran with five contiguous stereocenters. In the last several decades, numerous chemical syntheses of rocaglates have been reported due to their intriguing structures. These natural products exhibit many interesting biological activities including the inhibition of the eukaryotic translation apparatus. For example, the rocaglate congener silvestrol was found to inhibit the eIF4F complex by interfering with the function of the DEAD box RNA helicase eIF4A (SEQ ID NO: 1). Additionally, silvestrol has antitumor activity in a variety of pre-clinical murine cancer models including hematological and solid tumor types.

Chemical syntheses of cyclopenta[b]benzofuran natural products and analogues have revealed structure-activity relationships (SAR) for antineoplastic activity in cancer cell lines leading to improved activity. In particular, the C8a tertiary hydroxyl has been shown to be critical which appears to be related to its role as a hydrogen bond (H-bond) donor; alkylation of this tertiary hydroxyl completely eliminates cytotoxicity. Recently, Iwasaki and coworkers determined the co-crystal structure of rocaglamide bound to a human eIF4A-polypurine RNA complex which, among the interactions identified, was hydrogen bonding between the C8a tertiary hydroxyl of rocaglamide and N7 of a purine RNA base. Replacement of the tertiary hydroxyl with other substituents is an approach expressed in the literature for furthering SAR studies but has been frustrated by the difficulty in achieving chemical modification of this scaffold position.

In order to allow for broader evaluation of rocaglates as therapeutic agents, new methods for their preparation are urgently needed. In addition, expansion of SAR studies requires procurement of novel compounds. Accordingly, there is a continuing need for development of new rocaglates as therapeutic agents and synthetic methods needed to prepare these new compounds.

SUMMARY

In general, the inventions described herein relate to rocaglate compositions, methods for making rocaglates, as well as their usage as therapeutic agents. For example, the preparation and structures of rocaglates that can be used for treatments of eIF4A-dependent conditions such as cancer and other conditions are described.

A first aspect according to the description is a compound having the structure of Formula (A):

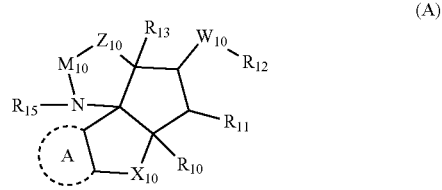

or stereoisomers, tautomers, or pharmaceutically acceptable salts thereof.

In compounds of Formula (A), $X_{10}$ is $CR^A R^B$, O, S, $NR^A$, C(O), C=$CR^A R^B$, SO, or $SO_2$; $W_{10}$ is $CHR_{16}$ or C(=$Y_{10}$) where $Y_{10}$ is O, S, or $NR^A$; $Z_{10}$ is O, S or $NR_{15}$; Ring A is a heteroaryl or aryl; $M_{10}$ is S(=O)$R_{14}R_{17}$, C($R_{14}R_{17}$), S(O), S($O_2$) C(O), C=$CHR_{14}$, or C=$NR_{14}$; $R_{10}$ is H, halogen, CN, ($C_1$-$C_8$)alkyl, ($C_1$-$C_8$)haloalkyl, ($C_2$-$C_8$)alkenyl), ($C_2$-$C_8$)alkynyl, $OR^A$, $NR^A R^B$ [($C_1$-$C_8$)alkylene]$OR^A$, [($C_1$-$C_8$)alkylene]$NR^A$, [($C_1$-$C_8$)alkylene]$NR^A R^B$, C(O)$R^A$, C(O)$NHR^A$, C(O)$NR^A R^B$, C(O)[($C_1$-$C_8$)alkylene]$NHR^A$, C(O)[($C_1$-$C_8$)alkylene]$NR^A R^B$, $CO_2 R^A$, C(S)$NHR^A$, C(S)$NR^A R^B$, $SR^A$, S(O)$R^A$, $SO_2 R^A$, $SO_2 NHR^A$, $SO_2 NR^A R^B$, NHC(O)$R^A$, $NR^A C(O)R^B$ NHC(O)$NHR^A$, NHC(O)$NR^A R^B$, $NR^A C(O)NR^B$, $NR^A C(O)NR^B R^C$, P(O)(OH)($OR^A$), P(O)($OR^A$)($OR^B$), aryl, heteroaryl, cycloalkyl or heterocyclyl; $R_{11}$ is H, halogen, $NO_2$, CN, ($C_1$-$C_8$)alkyl, ($C_1$-$C_8$)haloalkyl, ($C_2$-$C_8$)alkenyl), ($C_2$-$C_8$)alkynyl, $OR^A$, $NR^A R^B$, [($C_1$-$C_8$)alkylene]$OR^A$, [($C_1$-$C_8$)alkylene]$NHR^A$, [($C_1$-$C_8$)alkylene]$NR^A R^B$, C(O)$R^A$, C(O)$NHR^A$, C(O)$NR^A R^B$, C(O)[($C_1$-$C_8$)alkylene]$NHR^A$, C(O)[($C_1$-$C_8$)alkylene]$NR^A R^B$, $CO_2 R^A$, C(S)$NHR^A$, C(S)$NR^A R^B$, $SR^A$, S(O)$R^A$, $SO_2 R^A$, $SO_2 NHR^A$, $SO_2 NR^A R^B$, NHC(O)$R^A$, $NR^A C(O)R^B$, NHC(O)$NHR^A$, NHC(O)$NR^A R^B$ $NR^A C(O)NHR^B$, $NR^A C(O)NR^B R^C$, P(O)(OH)($OR^A$), P(O)($OR^A$)($OR^B$) aryl, heteroaryl, acyl, ester, alkyl, alkenyl, alkynyl, cycloalkyl, heterocyclyl, amido, or —$CO_2 R^A$; $R_{12}$, and $R_{13}$, independently are H, halogen, CN, ($C_1$-$C_8$)alkyl, ($C_1$-$C_8$)haloalkyl, ($C_2$-$C_8$)alkenyl), ($C_2$-$C_8$) alkynyl, $OR^A$, $NR^AR^B$, [($C_1$-$C_8$)alkylene]$OR^A$, [($C_1$-$C_8$)alkylene]$NHR^A$, [($C_1$-$C_8$)alkylene]$NR^AR^B$, $C(O)R^A$, $C(O)NHR^A$, $C(O)NR^AR^B$, $C(O)[(C_1$-$C_8)$alkylene]$NHR^A$, $C(O)[(C_1$-$C_8)$alkylene]$NR^AR^B$, $CO_2R^A$, $C(S)NHR^A$, $C(S)NR^AR^B$, $SR^A$, $S(O)R^A$, $SO_2R^A$ $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, $P(O)(OR^A)(OR^B)$, aryl, heteroaryl, cycloalkyl or heterocyclyl; or $R_{12}$ and $R_{13}$ together with the carbon atoms they are attached to form a 3-8 membered cycloalkyl, heterocyclyl; $R_{14}$ is H, halogen, ($R_{18}R_{19}$)$R_{20}$, CN, $C_1$-$C_8$(alkyl), ($C_1$—$C_8$)haloalkyl, ($C_2$-$C_8$)alkenyl, ($C_2$-$C_8$)alkynyl, $OR^A$ $NR^AR^B$, [($C_1$-$C_8$) alkylene]$OR^A$, [($C_1$-$C_8$)alkylene]$NHR^A$, [($C_1$-$C_8$)alkylene]$NR^AR^B$, $C(O)R^A$, $C(O)NHR^A$, $C(O)NR^AR^B C(O)[(C_1$-$C_8)$ alkylene]$NHR^A$, $C(O)[(C_1$-$C_8)$alkylene]$NR^AR^B$, $CO_2R^A$, $C(S)NHR^A$, $C(S)NR^AR^B$, $SR^A$, $S(O)R^A$, $SO_2R^A$, $SO_3R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$ $NR^AC(O)NR^BR^C$, $P(O)(OH)(OR^A)$, $P(O)(OR^A)(OR^B)$ aryl, heteroaryl, cycloalkyl or heterocycly; $R_{15}$ and $R_{15}'$ independently are H, halogen, CN, $C_1$-$C_8$(alkyl), ($C_1$-$C_8$)haloalkyl, ($C_2$-$C_8$)alkenyl, ($C_2$-$C_8$)alkynyl, $OR^A$, $NR^AR^B$, [($C_1$-$C_8$)alkylene]$OR^A$, [($C_1$-$C_8$)alkylene]$NHR^A$, [($C_1$-$C_8$)alkylene]$NR^AR^B$, $C(O)R^A$, $C(O)NHR^A$, $C(O)NR^AR^B C(O)[(C_1$-$C_8)$alkylene]$NHR^A$, $C(O)[(C_1$-$C_8)$alkylene]$NR^AR^B$, $CO_2R^A$, $C(S)NHR^A$, $C(S)NR^AR^B$, $SR^A$, $S(O)R^A$, $SO_2R^A$, $SO_3R^A$, $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$ $NR^AC(O)NR^BR^C$, $P(O)(OH)(OR^A)$, $P(O)(OR^A)(OR^B)$ aryl, heteroaryl, cycloalkyl or heterocyclyl; or $R_{14}$, and $R_{15}$ together with the carbon or nitrogen they are bound to form a heterocyclyl or heteroaryl, or $R_{14}$, and $R_{15}'$ together with the carbon or nitrogen they are bound to form a heterocyclyl or heteroaryl, or one of $R_{15}$ or $R_{15}'$ together with $R_{17}$ forms a second bond between the nitrogen and carbon atoms they are attached to; $R_{16}$ is H, halogen, CN, $C_1$-$C_8$(alkyl), ($C_1$-$C_8$)haloalkyl, ($C_2$-$C_8$)alkenyl, ($C_2$-$C_8$)alkynyl, $OR^A$, $NR^AR^B$ [($C_1$-$C_8$)alkylene]$OR^A$, [($C_1$-$C_8$)alkylene]$NHR^A$, [($C_1$-$C_8$)alkylene]$NR^AR^B$, $C(O)R^A$, $C(O)NHR^A C(O)NR^AR^B$, $C(O)[(C_1$-$C_8)$alkylene]$NHR^A$, $C(O)[(C_1$-$C_8)$alkylene]$NR^AR^B$, $CO_2R^A$, $C(S)NHR^A$, $C(S)NR^AR^B$, $SR^A$, $S(O)R^A$, $SO_2R^A$, $SO_3R^A$, $SO_2NHR^A$, $SO_2NR^AR^B$, $NHC(O)R^A$, $NR^AC(O)R^B$ $NHC(O)NHR^A$, $NHC(O)NR^AR^B$, $NR^AC(O)NHR^B$ $NR^AC(O)NR^BR^C$, $P(O)(OH)(OR^A)$, $P(O)(OR^A)(OR^B)$, aryl, heteroaryl, cycloalkyl or heterocyclyl; $R_{15}$, $R_{19}$ and $R_{20}$ independently are H, halogen, CN, $C_1$-$C_8$(alkyl), ($C_1$-$C_8$)haloalkyl, ($C_2$-$C_8$)alkenyl, ($C_2$-$C_8$)alkynyl, $OR^A$, $NR^AR^B$ [($C_1$-$C_8$)alkylene]$OR^A$, [($C_1$-$C_8$)alkylene]$NHR^A$, [($C_1$-$C_8$)alkylene]$NR^AR^B$, $C(O)R^A$, $C(O)NHR^A$, $C(O)NR^AR^B$, $C(O)[(C_1$-$C_8)$alkylene]$NHR^A$, $C(O)[(C_1$-$C_8)$alkylene]$NR^AR^B$, $CO_2R^A$, $C(S)NHR^A$, $C(S)NR^AR^B$, $SR^A$, $S(O)R^A$, $SO_2R^A$, $SO_3R^A$, $SO_2NHR^A$, $SO_2NR^AR^B$, $NHC(O)R^A$, $NR^AC(O)R^B$ $NHC(O)NHR^A$, $NHC(O)NR^AR^B$, $NR^AC(O)NR^AR^B$, $NR^AC(O)NR^BR^C$, $P(O)(OH)(OR^A)$, $P(O)(OR^A)(OR^B)$, aryl, heteroaryl, cycloalkyl or heterocyclyl, optionally at least one of $R_{15}$, $R_{19}$ and $R_{20}$ is not H; $R^A$, $R^B$ and $R^C$ independently are H, —OH, aryl, ($C_1$-$C_8$)alkyl, [($C_1$-$C_8$)alkyl]aryl ($C_1$-$C_8$)alkoxy, $C(O)O(C_1$-$C_8$)alkyl, ($C_1$-$C_8$)haloalkyl, cycloalkyl, heterocyclyl, [($C_1$-$C_8$)alkylene]heterocyclyl, [($C_1$-$C_8$)alkylene]aryl or heteroaryl; or $R^A$ and $R^B$ together with the nitrogen atom to which they are attached form a heterocyclyl ring. Any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$ alkyl, halogen, $NH_2$, $NH(C_1$-$C_4)$alkyl, $N[(C_1$-$C_4)$alkyl]$_2$, $C(O)NH_2$, COOH, COOMe, acetyl, ($C_1$-$C_8$)alkyl, $O(C_1$-$C_8)$ alkyl, $O(C_1$-$C_8)$haloalkyl, ($C_2$-$C_8$)alkenyl, ($C_2$-$C_8$)alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH (OH)]$_m$—$(CH_2)_p$—OH, $CH_2$—[CH(OH)]$_m$—$(CH_2)_p$—$NH_2$ or $CH_2$-aryl-alkoxy; or wherein any alkyl, cycloalkyl or heterocyclyl is optionally substituted with oxo. "m" and "p" are 1, 2, 3, 4, 5 or 6.

Optionally, the compound of Formula (A) is of Formula (I) or Formula (II):

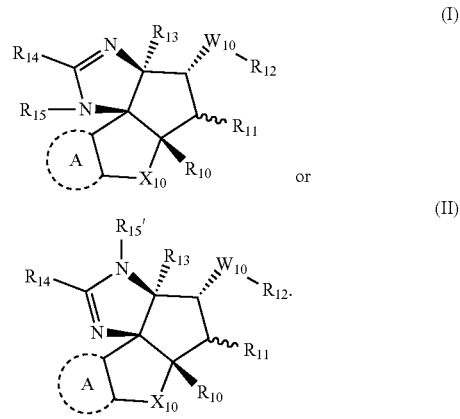

(I)

or (II)

Optionally, the compound of Formula (A) is of Formula (IV) or (IV'):

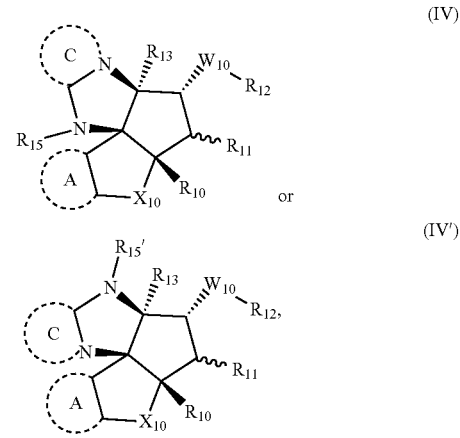

(IV)

or (IV')

wherein Ring C is heterocyclyl or heteroaryl.

A second aspect according to the description is a compound having the structure of formula (B):

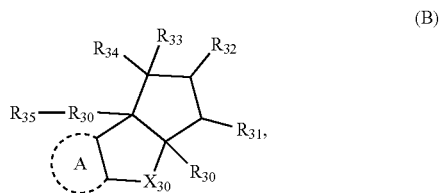

(B)

or stereoisomers, tautomers, or pharmaceutically acceptable salts thereof.

In compounds of Formula (B), $X_{30}$ is $CR^GR^H$, O, S, $NR^G$, C(O), C=$CR^GR^H$, SO, or $SO_2$; $Z_{30}$ is O, S, or $NR^G$; Ring A is a heteroaryl or aryl; $R_{30}$ is aryl, heteroaryl, cycloalkyl or heterocyclyl; $R_{31}$ is H, aryl, heteroaryl, acyl, ester, alkyl, alkenyl, alkynyl, cycloalkyl, heterocyclyl, amido, or —$CO_2R^G$; $R_{32}$, is H, halogen, CN, $(C_1-C_8)$alkyl, $(C_1-C_8)$haloalkyl, $(C_2-C_8)$alkenyl), $(C_2-C_8)$alkynyl, $OR^G$, $NR^GR^H$, $[(C_1-C_8)$alkylene$]OR^G$, $[(C_1-C_8)$alkylene$]NHR^G$, $[(C_1-C_8)$alkylene$]NR^GR^H$, $C(O)R^G$, $C(O)NHR^G$, $C(O)NR^GR^H$, $C(O)[(C_1-C_8)$alkylene$]NHR^G$, $C(O)[(C_1-C_8)$alkylene$]NR^GR^H$, $CO_2R^G$, $C(S)NHR^G$, $C(S)NR^GR^H$, $SR^G$, $S(O)R^G$, $SO_2R^G$, $SO_2NHR^G$, $SO_2NR^GR^H$, $NHC(O)R^G$, $NR^GC(O)R^H$, $NHC(O)NHR^G$, $NHC(O)NR^GR^H$, $NR^GC(O)NHR^H$, $NR^GC(O)NR^HR^J$, $P(O)(OH)(OR^G)$, $P(O)(OR^G)(OR^H)$, aryl, heteroaryl, cycloalkyl or heterocyclyl; $R_{33}$, and $R_{34}$ independently are H, halogen, CN, $(C_1-C_8)$alkyl, $(C_1-C_8)$haloalkyl, $(C_2-C_8)$alkenyl, $(C_2-C_8)$alkynyl, $OR^G$, $NR^GR^H$, $[(C_1-C_8)$alkylene$]OR^G$, $[(C_1-C_8)$alkylene$]NHR^G$, $[(C_1-C_8)$alkylene$]NR^GR^H$, $C(O)R^G$, $C(O)NHR^G$, $C(O)NR^GR^H$, $C(O)[(C_1-C_8)$alkylene$]NHR^G$, $C(O)[(C_1-C_8)$alkylene$]NR^GR^H$, $CO_2R^G$, $C(S)NHR^G$, $C(S)NR^GR^H$, $SR^G$, $S(O)R^G$, $SO_2R^G$, $SO_2NHR^G$, $SO_2NR^GR^H$, $NHC(O)R^G$, $NR^GC(O)R^H$, $NHC(O)NHR^G$, $NHC(O)NR^GR^H$, $NR^GC(O)NHR^H$, $NR^GC(O)NR^HR^J$, $P(O)(OH)(OR^G)$, $P(O)(OR^G)(OR^H)$, aryl, heteroaryl, cycloalkyl or heterocyclyl; or $R_{33}$, and $R_{34}$ together are O, S, or $NR^G$; $R^G$, $R^H$, $R^I$ and $R^J$ independently are H, —OH, aryl, $(C_1-C_8)$alkyl, $[(C_1-C_8)$alkyl]aryl $(C_1-C_8)$ alkoxy, $C(O)O(C_1-C_8)$alkyl, $(C_1-C_8)$haloalkyl, cycloalkyl, heterocyclyl, $[(C_1-C_8)$alkylene]heterocyclyl, $[(C_1-C_8)$alkylene]aryl or heteroaryl; or wherein the $R^G$ and $R^H$ together with the nitrogen atom to which they are attached form a heterocyclyl ring; or $R_{33}$, and $R_{34}$ together are $NR^G$ and $R^G$ and $R_{32}$ are connected and form part of a heterocycle; and $R_{35}$ is H, halogen, CN, $(C_1-C_8)$alkyl, $(C_1-C_8)$haloalkyl, $(C_2-C_8)$alkenyl, $(C_2-C_8)$alkynyl, $OR^G$, $NR^GR^H$ $[(C_1-C_8)$alkylene$]OR^G$, $[(C_1-C_8)$alkylene$]NHR^G$, $[(C_1-C_8)$alkylene$]NR^GR^H$, $C(O)R^G$, $C(O)NHR^G$, $C(O)NR^GR^H$, $C(O)[(C_1-C_8)$alkylene$]NHR^G$, $C(O)[(C_1-C_8)$alkylene$]NR^GR^H$, $CO_2R^G$, $C(S)NHR^G$, $C(S)NR^GR^H$, $SR^G$, $S(O)R^G$, $SO_2R^G$, $SO_2NHR^G$, $SO_2NR^GR^H$, $NHC(O)R^G$, $NR^GC(O)R^H$, $NHC(O)NHR^G$, $NHC(O)NR^GR^H$, $NR^GC(O)NHR^H$, $NR^GC(O)NR^HR^J$, $P(O)(OH)(OR^G)$, $P(O)(OR^G)(OR^H)$, aryl, heteroaryl, cycloalkyl or heterocyclyl. Any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—(CH$_2$)$_p$—OH, $CH_2$—[CH(OH)]$_m$—(CH$_2$)$_p$ NH$_2$ or $CH_2$-aryl-alkoxy; or wherein any alkyl, cycloalkyl or heterocyclyl is optionally substituted with oxo. "m" and "p" are 1, 2, 3, 4, 5 or 6.

Optionally, the compound of Formula (B) is of Formula (III):

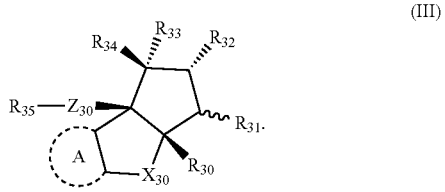

(III)

Optionally, in compound of Formula (B) $R_{33}$, and $R_{34}$ together are $NR^G$ and $R^G$ and $R_{32}$ are connected and the compound has the structure (B'):

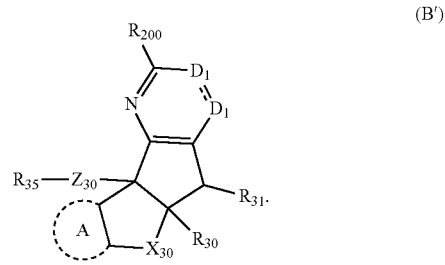

(B')

In compounds of Formula (B') $R_{200}$ is H, halogen, CN, $(C_1-C_8)$alkyl, $(C_1-C_8)$haloalkyl, $(C_2-C_8)$alkenyl), $(C_2-C_8)$alkynyl, $OR^G$ $NR^GR^H$, $[(C_1-C_8)$alkylene$]OR^G$, $[(C_1-C_8)$alkylene$]NHR^G$, $[(C_1-C_8)$alkylene$]NR^GR^H$, $C(O)R^G$, $C(O)NHR^G$, $C(O)NR^GR^H$, $C(O)[(C_1-C_8)$alkylene$]NHR^G$, $C(O)[(C_1-C_8)$alkylene$]NR^GR^H$, $CO_2R^G$, $C(S)NHR^G$, $C(S)NR^GR^H$, $SR^G$, $S(O)R^G$, $SO_2R^G$, $SO_2NHR^G$, $SO_2NR^GR^H$, $NHC(O)R^G$, $NR^GC(O)R^H$, $NHC(O)NHR^G$, $NHC(O)NR^GR^H$, $NR^GC(O)NHR^H$, $NR^GC(O)NR^HR^J$, $P(O)(OH)(OR^G)$, $P(O)(OR^G)(OR^H)$, aryl, heteroaryl, cycloalkyl or heterocyclyl. $R^G$, $R^H$, and $R^I$ independently are H, —OH, aryl, $(C_1-C_8)$alkyl, $[(C_1-C_8)$alkyl]aryl $(C_1-C_8)$alkoxy, $C(O)O(C_1-C_8)$alkyl, $(C_1-C_8)$haloalkyl, cycloalkyl, heterocyclyl, $[(C_1-C_8)$alkylene]heterocyclyl, $[(C_1-C_8)$alkylene]aryl or heteroaryl; or wherein the $R^G$ and $R^H$ together with the nitrogen atom to which they are attached form a heterocyclyl ring; and $D_1$ is N, C(O), NH or $CR_{210}$; $D_2$ is N, C(O), NH or $CR_{220}$; $R_{210}$ and $R_{220}$ are independently are H, halogen, CN, $C_1-C_8$(alkyl), $(C_1-C_8)$haloalkyl, $(C_2-C_8)$alkenyl, $(C_2-C_8)$alkynyl, $OR^O$, $NR^OR^P$, $[(C_1-C_8)$alkylene$]OR^O$, $[(C_1-C_8)$alkylene$]NHRA$, $[(C_1-C_8)$alkylene$]NR^OR^P$, $C(O)R^O$, $C(O)NHR^O$, $C(O)NR^OR^P$, $C(O)[(C_1-C_8)$alkylene$]NHR^O$, $C(O)[(C_1-C_8)$alkylene$]NR^OR^P$, $CO_2R^O$, $C(S)NHR^O$, $C(S)NR^OR^P$, $SR^O$, $S(O)R^O$, $SO_2R^O$, $SO_2NHR^O$, $SO_2NR^OR^P$, $NHC(O)R^O$, $NR^OC(O)R^P$, $NHC(O)NHR^O$, $NHC(O)NR^OR^P$, $NR^OC(O)NHR^P$, $NR^OC(O)NR^PR^Q$, $P(O)(OH)(OR^O)$, $P(O)(OR^O)(OR^P)$, tosylate, aryl, heteroaryl, cycloalkyl or heterocyclyl. $R^O$, $R^P$ and $R^Q$ independently are H, —OH, aryl, $(C_1-C_8)$alkyl, $[(C_1-C_8)$alkyl]aryl $(C_1-C_8)$alkoxy, $(C_1-C_8)$haloalkyl, cycloalkyl, heterocyclyl, $[(C_1-C_8)$alkylene]heterocyclyl, $[(C_1-C_8)$alkylene]aryl or heteroaryl; or $R^O$ and $R^P$ together with the nitrogen atom to which they are attached form a heterocyclyl ring.

Optionally, the compound of Formula (B') is of Formula (III'),

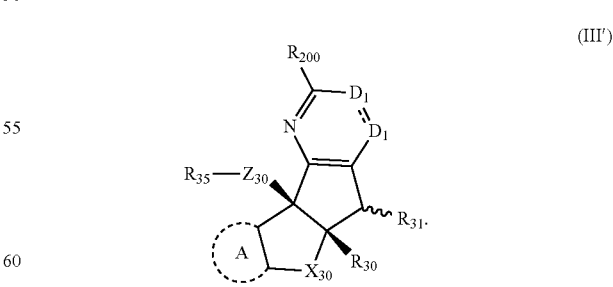

(III')

A third aspect according to the description is a method for preparing a compound having the Formula (A). The method comprises providing a solution of a compound having Formula (V), and reacting the compound (VI), or salts thereof, with a base to provide an intermediate in the solution, and reacting the intermediate with the compound having Formula (VI) or salts thereof. The structures of (V) and (VI) are;

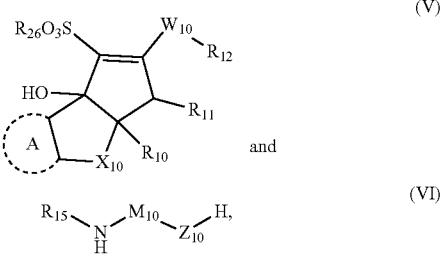

where $R_{26}$ is a $(C_1-C_3)$alkyl, $CH_3$, aryl, $CF_3$, alkyl substituted aryl, or methyl aryl.

Optionally, the compound of Formula (V) is of Formula (V'):

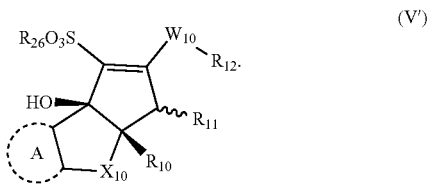

A fourth aspect according to the description is a method for preparing a compound having the Formula (B). the method comprises providing a solution of a compound having Formula (IX), and reacting the compound (X) or salts thereof, with a base to provide an intermediate in the solution, and reacting the intermediate with the compound having Formula (IX). The structures of (IX) and (X) are as follows:

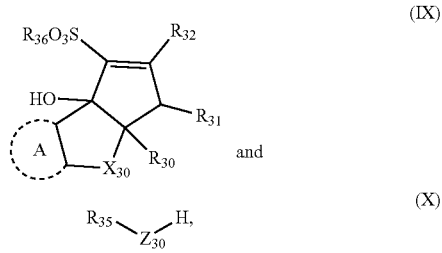

where $R_{36}$ is a $(C_1-C_3)$alkyl, $CH_3$, aryl, $CF_3$, alkyl substituted aryl, or methyl aryl.

Optionally, the compound of Formula (IX) is of Formula (IX'):

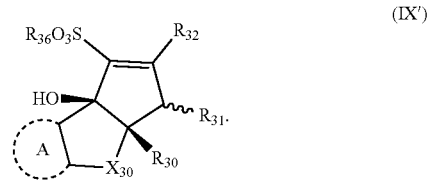

A fifth aspect according to the description is a pharmaceutical composition comprising a compound according to any one of the first, second, third, and fourth aspects and a pharmaceutically acceptable carrier, diluent, or excipient is described.

A sixth aspect according to the description is a method for treating an eIF4A-dependent condition in a subject in need thereof is described. The method comprises administering to the subject a therapeutically effective amount of a compound according to any one of the first, second, third, or fourth aspects.

A seventh aspect according to the description is an antibody-drug conjugate (ADC) is described. The antibody-drug conjugate comprising an antibody covalently attached through a linker to a compound having a structure according the first, second, third, or fourth aspects.

An eighth aspect according to the description is a pharmaceutical composition of the antibody-drug conjugate according to the seventh aspect including a pharmaceutically acceptable carrier, diluent, or excipient is described.

A ninth aspect according to the description is a method for treating an eIF4A-dependent condition in a subject in need thereof is described. The method comprising administering to the subject a therapeutically effective amount of an antibody-drug conjugate according to the seventh or eighth aspect.

Rocaglates described herein show high cytotoxicity against cancer cells. The methods for producing modified rocaglates described herein greatly expands the available rocaglates as bioactive agents.

BRIEF DESCRIPTION OF THE FIGURES

This patent or application file contains at least one drawing executed in color. Copies of this patent or patent application publication with color drawings will be provided by the Office upon request and payment of the necessary fee.

FIG. 6A shows a mechanism for amidino-rocaglate synthesis.

FIG. 6B shows the retro-Nazarov reaction mechanism.

FIG. 17A shows the chemical structure of select rocaglates used in biological studies. FIG. 17B shows a picture of Coomassie blue staining of an SDS-PAGE showing eIF4A1 and eIF4A2. FIG. 17C shows a bar plot relating to the change in fluorescence polarization (FP) obtained relative to vehicle controls, and discloses SEQ ID NOS 2 and 4-7, respectively, in order of appearance. FIG. 17D shows a binding plot of eIF4A1 and eIF4A2 to RNA measured in FP assay, and discloses "$(AG)_8$," as SEQ ID NO: 2. FIG. 17E shows a bar plot of the change in FP in the presence of the rocaglate, CR-1-31-B, relative to vehicle controls, and discloses SEQ ID NOS 2 and 4-7, respectively, in order of appearance. Stimulation of eIF4A1:RNA binding by CR-1-31-B shows preference for polypurine-enriched sequences. FAM-labelled RNA was incubated in the presence of 500 nM eIF4A1 and the indicated concentration of CR-1-31-B for 30 min, after which time FP measurements were obtained. The change in FP relative to vehicle controls is presented. n=3 SD.

FIG. 17F A bar plot of the change in FP obtained relative to vehicle controls is presented. n=3±SD. The extent of eIF4A1:RNA binding stimulated by CR-1-31-B scales with polypurine content. FAM-labelled RNA was incubated with 500 nM eIF4A1 and the indicated concentration of CR-1-31-B for 30 min, after which time FP measurements were obtained. The change in FP obtained relative to vehicle controls is presented. n=3±SD. h. The location of a single AG dinucleotide within a poly r(U) track promotes rocaglate-stimulated eIF4A1:RNA binding. The RNA sequences used in this experiment are indicated to the left and the FP results obtained with these are plotted to the right. eIF4A1:RNA binding assays were performed in the presence of vehicle or 50 μM of CR-1-31-B. n=4±SD. The figure also discloses SEQ ID NOS 13-16 and 2, respectively, in order of appearance.

FIG. 19A Assessing eIF4A1:poly r(AG)$_8$ (SEQ ID NO: 2) RNA binding by FP in the presence of 10 M rocaglate. Values are expressed relative to vehicle controls and data is rank ordered. n=3±SD. FIG. 19B Change in polarization obtained with eIF4A1:poly r(AG)$_8$ (SEQ ID NO: 2) and eIF4A2:poly r(AG)$_8$ (SEQ ID NO: 2) RNA. Pearson r=0.814; p<0.0001. FIG. 19C shows a plot of inhibition of cap-dependent translation by rocaglates, and discloses SEQ ID NO: 26.

FIGS. 20A-20C show comparisons of rocaglate biological activity. FIG. 20A shows structures of the two potent rocaglates that show activity towards stimulating eIF4A1:RNA binding and inhibiting cap-dependent translation. 20B shows structures of two rocaglates that potently inhibit cap-dependent translation, but modestly stimulate eIF4A1:RNA binding. FIG. 20C shows structures of four rocaglates that potently stimulate eIF4A1:RNA binding, but are inactive or show weak activity as protein synthesis inhibitors in vitro.

FIG. 22A shows a schematic diagram of FF/HCV/Ren mRNA reporters containing cap-proximal (AG) or (UC) dinucleotide repeats, and discloses SEQ ID NOS 27-32, respectively, in order of appearance. FIG. 22B shows firefly and renilla luciferase activity in response to the indicated CR-1-31-B (23) concentrations (relative to DMSO controls) in Krebs-2 extracts programmed with 4 ng/uL of the indicated mRNAs. n=3±SEM. FIG. 22C shows dose response of some indicated compounds in Krebs-2 extracts programmed. n=3±SEM.

FIG. 24A shows a schematic diagram of FF/HCV/Ren mRNA reporters containing $(AG)_{10}$ or $(UC)_{10}$ tracks embedded within the 5' leader region, and discloses SEQ ID NOS 33 and 34, respectively, in order of appearance. FIG. 24B shows firefly and renilla luciferase activity in response to the indicated compound concentrations (relative to DMSO controls) in Krebs-2 extracts programmed with 4 ng/μL of the indicated mRNAs. FIG. 24C shows a plot and sequence showing assessment of CR-1-31-B (23) responsiveness on translation of a reporter mRNA harboring a polypurine track within the 3' untranslated region, and discloses SEQ ID NOS 37, 32, and 35, respectively, in order of appearance.

FIG. 27 shows structures of the most potent cytotoxic rocaglates exhibiting activity towards NIH/3T3 cells.

FIG. 30A shows RPDs performed with m$^7$GpppG-capped RNA incubated in the presence of retic lysate and either vehicle or 500 nM rocaglate. FIG. 30B shows a schematic diagram showing assay assessing trans-inhibition of rocaglates, and discloses SEQ ID NOS 36 and 10-11, respectively, in order of appearance. FIG. 30C The presence of m$^7$GpppG-capped, but not ApppG-capped, purine-rich RNAs sensitizes the RocA/CR-1-31-B-unresponsive m$^7$GpppG(UC)$_{10}$-FF/HCV/Ren mRNA reporter. Translation reactions were performed in Krebs-2 extracts with 10 nM mRNA reporter and 250 nM of competitor RNA. n=3±SEM. FIG. 30D Addition of purified eIF4F rescues rocaglate-mediated translation inhibition. The m$^7$GpppG(AG)$_{10}$-FF/HCV/Ren reporter was added to Krebs-2 translation extracts in the presence eIF4F (10 nM) and 100 nM of the indicated compound. n≥3±SEM.

FIG. 31A shows Western blot documenting endogenous and ectopic eIF4A1 levels. FIG. 31B are plots showing viability of cells in rocaglate-resistant cells sensitizes these to cell death. Ectopic expression of wt eIF4A1 sensitizes rocaglate-resistant cells to cell death. NIH/3T3 or eIF4A1$^{em1JP}$ cells were infected with an empty MSCV cassette or expressing either wt eIF4A1 or eIF4A1(F163L). Viability was assessed following a 4-day exposure to 40 nM of compound using SRB assays. n=3±SEM.

FIG. 35A-35E are plots showing dose-response curves of FF-HCV-Ren mRNA translation in Krebs extracts with IC$_{50}$s shown for inhibition of cap-dependent protein synthesis. FIG. 35A CMLD012612; FIG. 35B BUCMD00512; FIG. 35C CMLD013333; FIG. 35D BUCMD00513; FIG. 35E CMLD013334.

FIG. 36 is a bar plot showing Titrations on HEK 293 cells for compounds according to some implementations of the disclosure.

DETAILED DESCRIPTION

The present disclosure relates to a rocaglates and methods for preparation of rocaglates. In addition, the use of rocaglates for treatment of treatments of eIF4A-dependent and other conditions such as cancer are described.

Figure 1:
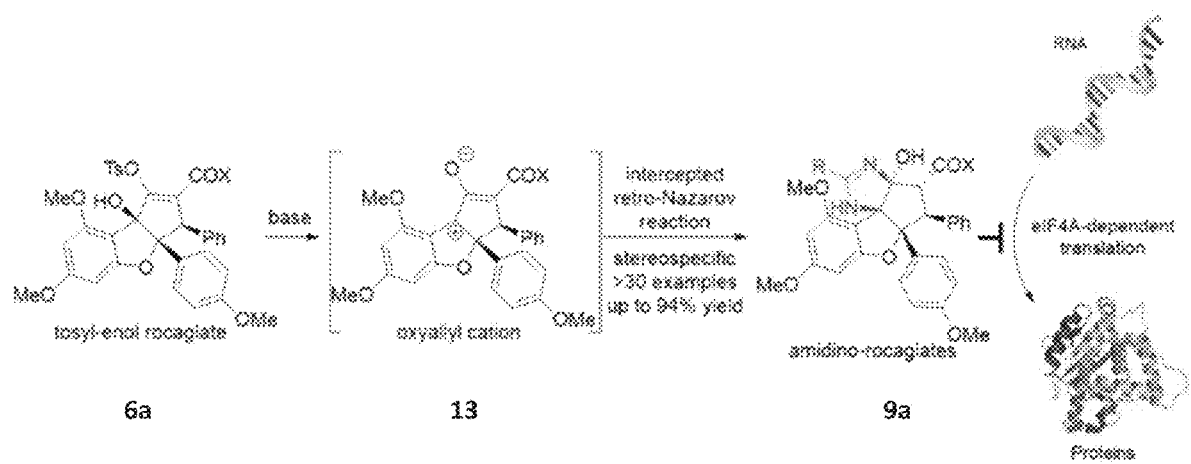
FIG. 1 Shows an embodiment for preparing rocaglates and their use for blocking eIF4A-dependent translation.

An embodiment of some rocaglates that can be made by the methods described herein is shown by FIG. 1. Where the aspects herein are not limited by any particular proposed mechanism, it has been discovered herein that a tosyl-enol rocaglate (6a) can be treated with a base and the intermediate (13), shown as an oxyallyl cation, can be trapped to afford amidino-rocaglates (9a). In some embodiments, the rocaglates have been shown to inhibit eIF4A-dependent translation of RNA.

An embodiment according to some implementation is a compound having structure (A) or stereoisomers, tautomers, or pharmaceutically acceptable salts thereof. In some embodiments, the compound having structure (A) can be made by reacting precursor (V) with base and amidine (VI) or a salt thereof as shown in Scheme 1.

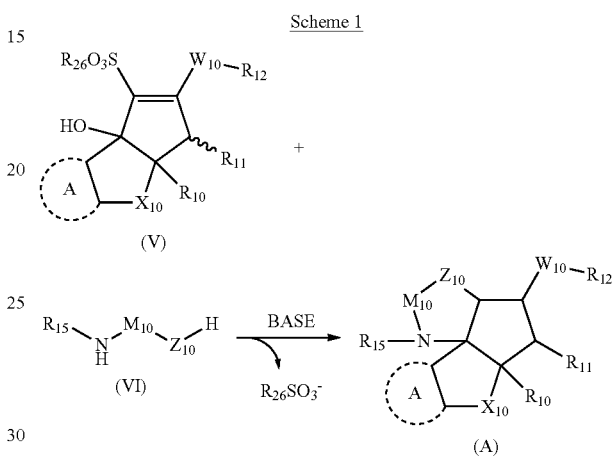

Scheme 1

Wherein: X$_{10}$ is CR$^A$R$^B$, O, S, NR$^A$, C(O), C=CR$^A$R$^B$, SO, or SO$_2$; W$_{10}$ is CHR$_{16}$ or C(=Y$_{10}$) where Y$_{10}$ is O, S, or NR$^A$; Z$_{10}$ is O, S or NR$_{15}$'; Ring A is a heteroaryl or aryl; M$_{10}$ is S(=)R$_4$R$_7$, C(R$_{14}$R$_{17}$), S(O), S(O$_2$) C(O), C=CHR$_{14}$, or C=NR$_{14}$; R$_{10}$ is H, halogen, CN, (C$_1$-C$_8$)alkyl, (C$_1$-C$_8$)haloalkyl, (C$_2$-C$_8$)alkenyl), (C$_2$-C$_8$)alkynyl, OR$^A$, NR$^A$R$^B$, [(C$_1$-C$_8$)alkylene]OR$^A$, [(C$_1$-C$_8$)alkylene]NR$^A$, [(C$_1$-C$_8$)alkylene]NR$^A$R$^B$, C(O)R$^A$, C(O)NHR$^A$, C(O)NR$^A$R$^B$C(O)[(C$_1$-C$_8$)alkylene]NHR$^A$, C(O)[(C$_1$-C$_8$)alkylene]NR$^A$R$^B$, CO$_2$R$^A$, C(S)NHR$^A$, C(S)NR$^A$R$^B$, SR$^A$, S(O)R$^A$, SO$_2$R$^A$, SO$_2$NHR$^A$, SO$_2$NR$^A$R$^B$, NHC(O)R$^A$, NR$^A$C(O)R$^B$, NHC(O)NHR$^A$, NHC(O)NR$^A$R$^B$, NR$^A$C(O)NHR$^B$, NR$^A$C(O)NR$^B$R$^C$, P(O)(OH)(OR$^A$), P(O)(OR$^A$)(OR$^B$) aryl, heteroaryl, cycloalkyl or heterocyclyl; R$_{11}$ is H, halogen, NO$_2$, CN, (C$_1$-C$_8$)alkyl, (C$_1$-C$_8$)haloalkyl, (C$_2$-C$_8$)alkenyl), (C$_2$-C$_8$)alkynyl, OR$^A$, NR$^A$R$^B$, [(C$_1$-C$_8$)alkylene]OR$^A$, [(C$_1$-C$_8$)alkylene]NHR$^A$, [(C$_1$-C$_8$)alkylene]NR$^A$R$^B$, C(O)R$^A$, C(O)NHR$^A$, C(O)NHR$^A$R$^B$, C(O)[(C$_1$-C$_8$)alkylene]NHR$^A$, C(O)[(C$_1$-C$_8$)alkylene]NR$^A$R$^B$, CO$_2$R$^A$, C(S)NHR$^A$, C(S)NR$^A$R$^B$, SR$^A$, S(O)R$^A$, SO$_2$R$^A$, SO$_2$NHR$^A$, SO$_2$NR$^A$R$^B$, NHC(O)R$^A$, NR$^A$C(O)R$^B$, NHC(O)NHR$^A$, NHC(O)NR$^A$R$^B$, NR$^A$C(O)NHR$^B$, NR$^A$C(O)NR$^B$R$^C$, P(O)(OH)(OR$^A$), P(O)(OR$^A$)(OR$^B$), aryl, heteroaryl, acyl, ester, alkyl, alkenyl, alkynyl, cycloalkyl, heterocyclyl, amido, or —CO$_2$R$^A$; R$_{12}$, and R$_{13}$, independently are H, halogen, CN, (C$_1$-C$_8$)alkyl, (C$_1$-C$_8$)haloalkyl, (C$_2$-C$_8$)alkenyl), (C$_2$-C$_8$)alkynyl, OR$^A$, NR$^A$R$^B$, [(C$_1$-C$_8$)alkylene]OR$^A$, [(C$_1$-C$_8$)alkylene]NHR$^A$, [(C$_1$-C$_8$)alkylene]NR$^A$R$^B$, C(O)R$^A$, C(O)NHR$^A$, C(O)NR$^A$R$^B$, C(O)[(C$_1$-C$_8$)alkylene]NHR$^A$, C(O)[(C$_1$-C$_8$)alkylene]NR$^A$R$^B$, CO$_2$R$^A$, C(S)NHR$^A$, C(S)NR$^A$R$^B$, SR$^A$, S(O)R$^A$, SO$_2$R$^A$ SO$_2$NHR$^A$, SO$_2$NR$^A$R$^B$, NHC(O)R$^A$, NR$^A$C(O)R$^B$, NHC(O)NHR$^A$, NHC(O)NR$^A$R$^B$, NR$^A$C(O)NHR$^B$, NR$^A$C(O)NR$^B$R$^C$, P(O)(OH)(OR$^A$), P(O)(OR$^A$)(OR$^B$), aryl, heteroaryl, cycloalkyl or heterocyclyl; or R$_{12}$ and R$_{13}$ together with the carbon atoms they are attached to form a 3-8 membered cycloalkyl, heterocyclyl; $R_{14}$, $R_{15}$ and $R_{15}'$ independently are H, halogen, CN, $C_1$-$C_8$(alkyl), ($C_1$-$C_8$) haloalkyl, ($C_2$-$C_8$)alkenyl, ($C_2$-$C_8$)alkynyl, $OR^A$, $NR^AR^B$, [($C_1$-$C_8$)alkylene]$OR^A$, [($C_1$-$C_8$)alkylene]$NHR^A$, [($C_1$-$C_8$)alkylene]$NR^AR^B$, $C(O)R^A$, $C(O)NHR^AC(O)NR^AR^B$, $C(O)$[($C_1$-$C_8$)alkylene]$NHR^A$, $C(O)$[($C_1$-$C_8$)alkylene]$NR^AR^B$, $CO_2R^A$, $C(S)NHR^A$, $C(S)NR^AR^B$, $SR^A$, $S(O)R^A$, $SO_2R^A$, $SO_3R^A$, $SO_2NHR^A$, $SO_2NR^AR^B$, $NHC(O)R^A$, $NR^AC(O)R^B$ $NHC(O)NHR^A$, $NHC(O)NR^AR^B$, $NR^AC(O)NHR^B$, $NR^AC(O)NR^BR^C$, $P(O)(OH)(OR^A)$, $P(O)(OR^A)(OR^B)$, aryl, heteroaryl, cycloalkyl or heterocyclyl; or $R_{14}$, and $R_{15}$ together with the carbon or nitrogen they are bound to form a heterocyclyl or heteroaryl, or $R_{14}$, and $R_{15}'$ together with the carbon or nitrogen they are bound to form a heterocyclyl or heteroaryl, or one of $R_{15}$ or $R_{15}'$ together with $R_{17}$ forms a second bond between the nitrogen and carbon atoms they are attached to; $R_{16}$ is H, halogen, CN, $C_1$-$C_8$(alkyl), ($C_1$-$C_8$) haloalkyl, ($C_2$-$C_8$)alkenyl, ($C_2$-$C_8$)alkynyl, $OR^A$, $NR^AR^B$, [($C_1$-$C_8$)alkylene]$OR^A$, [($C_1$-$C_8$)alkylene]$NHR^A$, [($C_1$-$C_8$)alkylene]$NR^AR^B$, $C(O)R^A$, $C(O)NHR^A$, $C(O)NR^AR^B$, $C(O)$[($C_1$-$C_8$)alkylene]$NHR^A$, $C(O)$[($C_1$-$C_8$)alkylene]$NR^AR^B$, $CO_2R^A$, $C(S)NHR^A$, $C(S)NR^AR^B$, $SR^A$, $S(O)R^A$, $SO_2R^A$, $SO_3R^A$ $SO_2NHR^A$, $SO_2NR^AR^B$, $NHC(O)R^A$, $NR^AC(O)R^B$, $NHC(O)NHR^A$, $NHC(O)NR^AR^B$, $NR^AC(O)NHR^B$, $NR^AC(O)NR^BR^C$, $P(O)(OH)(OR^A)$, $P(O)(OR^A)(OR^B)$, aryl, heteroaryl, cycloalkyl or heterocyclyl; $R_{26}$ is a ($C_1$-$C_3$)alkyl, $CH_3$, aryl, $CF_3$, alkyl substituted aryl, or methyl aryl; $R^A$, $R^B$ and $R^C$ independently are H, —OH, aryl, ($C_1$-$C_8$)alkyl, [($C_1$-$C_8$)alkyl]aryl ($C_1$-$C_8$)alkoxy, $C(O)O(C_1$-$C_8$)alkyl, ($C_1$-$C_8$)haloalkyl, cycloalkyl, heterocyclyl, [($C_1$-$C_8$)alkylene]heterocyclyl, [($C_1$-$C_8$)alkylene]aryl or heteroaryl; or $R^A$ and $R^B$ together with the nitrogen atom to which they are attached form a heterocyclyl ring. Any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl]$_2$, $C(O)NH_2$, COOH, COOMe, acetyl, ($C_1$-$C_8$)alkyl, $O(C_1$-$C_8)$alkyl, $O(C_1$-$C_8)$haloalkyl, ($C_2$-$C_8$)alkenyl, ($C_2$-$C_8$)alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy; or wherein any alkyl, cycloalkyl or heterocyclyl is optionally substituted with oxo. "m" and "p" are 1, 2, 3, 4, 5 or 6.

An embodiment according to some implementation of the description is a compound having structure (B) or stereoisomers, tautomers, or pharmaceutically acceptable salts thereof. In some embodiments, structure (B) can be accessed by reacting precursor (IX) with base and trapping compound (X) or a salt thereof, as shown in Scheme 2.

Scheme 2

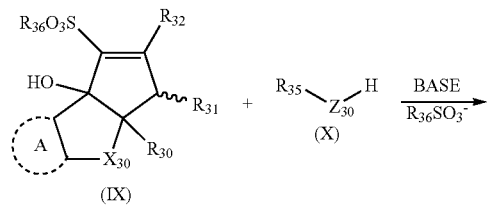

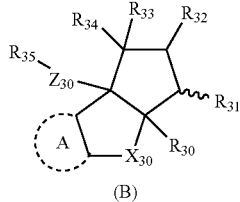

(B)

Wherein: $X_{30}$ is $CR^GR^H$, O, S, $NR^G$, C(O), $C=CR^GR^H$, SO, or $SO_2$; $Z_{30}$ is O, S, or $NR^G$; Ring A is a heteroaryl or aryl; $R_{30}$ is aryl, heteroaryl, cycloalkyl or heterocyclyl; $R_{31}$ is H, aryl, heteroaryl, acyl, ester, alkyl, alkenyl, alkynyl, cycloalkyl, heterocyclyl, amido, or —$CO_2R^G$; $R_{32}$, is H, halogen, CN, ($C_1$-$C_8$)alkyl, ($C_1$-$C_8$)haloalkyl, ($C_2$-$C_8$)alkenyl), ($C_2$-$C_8$)alkynyl, $OR^G$, $NR^GR^H$ [($C_1$-$C_8$)alkylene]$OR^G$, [($C_1$-$C_8$)alkylene]$NHR^G$, [($C_1$-$C_8$)alkylene]$NR^GR^H$, $C(O)R^G$, $C(O)NHR^G$, $C(O)NR^GR^H$, $C(O)$[($C_1$-$C_8$)alkylene]$NHR^G$, $C(O)$[($C_1$-$C_8$)alkylene]$NR^GR^H$, $CO_2R^G$, $C(S)NHR^G$, $C(S)NR^GR^H$, $SR^G$, $S(O)R^G$, $SO_2R^G$, $SO_2NHR^G$, $SO_2NR^GR^H$, $NHC(O)R^G$, $NR^GC(O)R^H$ $NHC(O)NHR^G$, $NHC(O)NR^GR^H$, $NR^GC(O)NHR^H$, $NR^GC(O)NHR^J$, $P(O)(OH)(OR^G)$, $P(O)(OR^G)(OR^H)$, aryl, heteroaryl, cycloalkyl or heterocyclyl; $R_{33}$, and $R_{34}$ independently are H, halogen, CN, ($C_1$-$C_8$)alkyl, ($C_1$-$C_8$)haloalkyl, ($C_2$-$C_8$)alkenyl, ($C_2$-$C_8$)alkynyl, $OR^G$, $NR^GR^H$[($C_1$-$C_8$)alkylene]$OR^G$, [($C_1$-$C_8$)alkylene]$NHR^G$, [($C_1$-$C_8$)alkylene]$NR^GR^H$, $C(O)R^G$, $C(O)NHR^G$, $C(O)NR^GR^H$, $C(O)$[($C_1$-$C_8$)alkylene]$NHR^G$, $C(O)$[($C_1$-$C_8$)alkylene]$NR^GR^H$, $CO_2R^G$, $C(S)NHR^G$, $C(S)NR^GR^H$, $SR^G$, $S(O)R^G$, $SO_2R^G$, $SO_2NHR^G$, $SO_2NR^GR^H$, $NHC(O)R^G$, $NR^GC(O)R^H$ $NHC(O)NHR^G$, $NHC(O)NR^GR^H$, $NR^GC(O)NHR^H$, $NR^GC(O)NHR^J$, $P(O)(OH)(OR^G)$, $P(O)(OR^G)(OR^H)$, aryl, heteroaryl, cycloalkyl or heterocyclyl; or $R_{33}$, and $R_{34}$ together are O, S, or $NR^G$, $R^G$, $R^H$, $R^I$ and $R^J$ independently are H, —OH, aryl, ($C_1$-$C_8$)alkyl, [($C_1$-$C_8$)alkyl]aryl ($C_1$-$C_8$)alkoxy, $C(O)O(C_1$-$C_8$)alkyl, ($C_1$-$C_8$)haloalkyl, cycloalkyl, heterocyclyl, [($C_1$-$C_8$)alkylene]heterocyclyl, [($C_1$-$C_8$)alkylene]aryl or heteroaryl; or wherein the $R^G$ and $R^H$ together with the nitrogen atom to which they are attached form a heterocyclyl ring; or $R_{33}$, and $R_{34}$ together are $NR^G$, and $R^G$ and $R_{32}$ are connected and form part of a heterocycle; $R_{35}$ is H, halogen, CN, ($C_1$-$C_8$)alkyl, ($C_1$-$C_8$)haloalkyl, ($C_2$-$C_8$)alkenyl, ($C_2$-$C_8$)alkynyl, $OR^G$, $NR^GR^H$, [($C_1$-$C_8$)alkylene]$OR^G$, [($C_1$-$C_8$)alkylene]$NHR^G$, [($C_1$-$C_8$)alkylene]$NR^GR^H$, $C(O)R^G$, $C(O)NHR^G$, $C(O)NR^GR^H$, $C(O)$[($C_1$-$C_8$)alkylene]$NHR^G$, $C(O)$[($C_1$-$C_8$)alkylene]$NR^GR^H$, $CO_2R^G$, $C(S)NHR^G$, $C(S)NR^GR^H$, $SR^GS(O)R^G$, $SO_2R^G$, $SO_2NHR^G$, $SO_2NR^GR^H$, $NHC(O)R^G$, $NR^GC(O)R^H$, $NHC(O)NHR^G$, $NHC(O)NR^GR^H$, $NR^GC(O)NHR^H$, $NR^GC(O)NR^HR^J$, $P(O)(OH)(OR^G)$, $P(O)(OR^G)(OR^H)$, aryl, heteroaryl, cycloalkyl or heterocyclyl; and $R_{36}$ is a ($C_1$-$C_3$) alkyl, $CH_3$, aryl, $CF_3$, alkyl substituted aryl, or methyl aryl. Any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl]$_2$, $C(O)NH_2$, COOH, COOMe, acetyl, ($C_1$-$C_8$)alkyl, $O(C_1$-$C_8)$ alkyl, $O(C_1$-$C_8)$haloalkyl, ($C_2$-$C_8$)alkenyl, ($C_2$-$C_8$)alkynyl, haloalkyl, thioalkyl, cyanomethylene, alkylaminyl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$— $(CH_2)_p$—OH, $CH_2$—[CH(OH)]$_m$—$(CH_2)_p$— $NH_2$ or $CH_2$-aryl-alkoxy; or wherein any alkyl, cycloalkyl or heterocyclyl is optionally substituted with oxo. "m" and "p" are 1, 2, 3, 4, 5 or 6.

In some embodiments, any of compounds (A) or (B) may be reacted by known methods to further elaborate the available rocaglates and provide new structures. In addition, the available rocaglates that can be made by the schemes outlined in Schemes 1-2 can be further expanded by modification of the starting materials. Starting material can be made by known methods for example, the method described as General Methods 1 through 12 in U.S. Pat. No. 9,957,277, which is hereby incorporated by reference in its entirety.

As use herein a "stereoisomer" refers to each of two or more compounds differing only in the spatial arrangement of their atom.

As used herein "tautomers" refers to two molecules with the same molecular formula but different connectivity, for example, a keto-enol pair.

The compound in some embodiments, can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, some embodiments, encompass compounds and their uses as described herein in the form of their optical isomers, diastereoisomers and mixtures thereof, including a racemic mixture. Optical isomers of the compounds according to some embodiments, can be obtained by known techniques such as asymmetric synthesis, chiral chromatography, or via chemical separation of stereoisomers through the employment of optically active resolving agents.

Unless otherwise indicated "stereoisomer" means one stereoisomer of a compound that is substantially free of other possible stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure dominates. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As use herein a "pharmaceutically acceptable salt" refers to an excipient that is useful in preparing a pharmaceutical composition that is generally safe, non-toxic, and desirable. Without limitation, pharmaceutically acceptable salts include, e.g. alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

As used herein the term "aryl", whether alone or as part of a substituent group, refers to an unsubstituted carboxylic aromatic ring comprising between 6 and 14 carbon atoms. Suitable examples include, but are not limited to, phenyl, and naphthyl.

As used herein "cycloalkyl" refers to a stable non-aromatic monocyclic or polycyclic hydrocarbon group consisting solely of carbon and hydrogen atoms. The cycloalkyl can be a monocyclic, bicyclic, tricyclic or tetracyclic ring system, which may include fused, spiro or bridged ring systems, having from three to fifteen carbon atoms, in some embodiments, having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic variants include, for example, cyclopropyl, cyclobutyl, cyclopentyl, cyclohexyl, cycloheptyl, and cyclooctyl. Polycyclic variants include, for example, adamantyl, norbornyl, decalinyl, 7,7-dimethyl-bicyclo[2.2.1]heptanyl, and the like.

As used herein "heterocyclyl", "heterocycle", or "heterocyclic ring" refers to a stable 3- to 18-membered saturated or unsaturated group which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated variantss, stable 3-12 membered saturated or unsaturated variants, stable 3-9 membered saturated or unsaturated variants, stable 8-membered saturated or unsaturated variants, stable 7-membered saturated or unsaturated variants, stable 6-membered saturated or unsaturated variants, or stable 5-membered saturated or unsaturated variants.

Unless stated otherwise specifically in the specification, the heterocyclyl group may be a monocyclic, bicyclic, tricyclic or tetracyclic ring system, which may include fused, spiro or bridged ring systems; and the nitrogen, carbon or sulfur atoms in the heterocyclyl variant may be optionally oxidized; the nitrogen atom may be optionally quaternized; and the heterocyclyl variant may be partially or fully saturated. Examples of non-aromatic heterocyclyl variants include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxothiomorpholinyl. Heterocyclyls include heteroaryls as defined herein, and examples of aromatic heterocyclyls are listed in the definition of heteroaryls below.

As used herein the term "heteroaryl" or "heteroarylene" refers to a 5- to 14-membered ring system group comprising hydrogen atoms, one to thirteen carbon atoms, one to six heteroatoms selected from the group consisting of nitrogen, oxygen and sulfur, and at least one aromatic ring. In some embodiments, the heteroaryl variant may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl variant may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (e.g. thienyl).

As used herein the term "acyl" refers to a group of the Formula —CO—$C_n$ wherein $C_n$ represent a straight or branched alkyl chain wherein n can be 1, 2, 3, 4, 5, 6, 7, 8, 9 or 10.

As used herein a "ester" refers to a group of the formula —C(O)—O$C_n$ $C_n$ represent a straight or branched alkyl chain wherein n can be 1, 2, 3, 4, 5, 6, 7, 8, 9 or 10. For example a chemical compound derived from an acid in which at least one —OH (hydroxyl) group is replaced by an —O-alkyl (alkoxy) group.

As used herein the term "alkyl", whether alone or as part of a substituent group, refers to a saturated $C_1$-$C_n$ carbon chain, wherein the carbon chain may be straight or branched; wherein n can be 2, 3, 4, 5, 6, 7, 8, 9 or 10. Suitable examples include, but are not limited to methyl, ethyl, propyl, isopropyl, butyl, isobutyl, sec-butyl, t-butyl, n-pentyl and n-hexyl.

As used herein the term "alkenyl", whether alone or as part of a substituent group, refers to a $C_2$-$C_n$ carbon chain, wherein the carbon chain may be straight or branched, wherein the carbon chain contains at least one carbon-carbon double bond, and wherein n can be 3, 4, 5, 6, 7, 8, 9, or 10.

As used herein the term "alkynyl", whether alone or as part of a substituent group, refers to a $C_2$-$C_n$ wherein the carbon chain may be straight or branched, wherein the carbon chain contains at least one carbon-carbon triple bond, and wherein n can be 3, 4, 5, 6, 7, 8, 9, or 10.

The groups of the present disclosure can be unsubstituted or substituted, as herein defined. In addition, the substituted groups can be substituted with one or more groups such as a $C_1$-$C_6$ alkyl, $C_{1-4}$ alkyl, —O—$C_{1-4}$ alkyl, hydroxyl, amino, ($C_{1-4}$ alkyl)amino, di($C_{1-4}$ alkyl)amino, —S—($C_{1-4}$ alkyl), —SO—($C_{1-4}$ alkyl), —SO$_2$—($C_{1-4}$ alkyl), halogen, aryl, heteroaryl, and the like.

With reference to substituents, the term "independently" means that when more than one of such substituents is possible, such substituents may be the same or different from each other.

"Amino" refers to a —NH$_2$ substituent.

"Aminocarbonyl" or "Amido" or "amido" refers to a group containing a carbonyl group linked to a nitrogen atom. The amide group is represented by RC(O)NR'R". In some embodiments, the amide has a formula —NHC(O)—$C_n$, or —C(O)NH—$C_n$, wherein $C_n$ represent a straight, branched and optionally substituted alkyl chain wherein n can be 1, 2, 3, 4, 5, 6, 7, 8, 9, or 10. In some options the hydrogen (H) atom is replaced by a second alkyl chain Cm which is a straight, branched and optionally substituted alkyl chain wherein n can be 1, 2, 3, 4, 5, 6, 7, 8, 9, or 10. In some embodiments, the amide has a formula —C(O)NH—$C_n$. In some embodiments, the alkyl chains represented by $C_n$ and Cm are linked, for example making a cyclic structure.

"Carboxyl" refers to the —CO$_2$H substituent.

"Carbonyl" refers to a —C(O)—, —(CO)— or —C(=O)— group. All notations are used interchangeably within the specification.

"Cyano" refers to the —C≡N substituent.

"Hydroxy" or "hydroxyl" refers to the —OH substituent.

"Oxo" refers to a =O substituent

"Thio" or "thiol" refer to a-SH substituent.

Compound words have the meaning of the individual functional groups or fragments as would be understood in the art. For example, "hydroxyalkyl" refers to the -(alkyl)-OH substituent, "thioalkyl" refers to the -(alkyl)-SH substituent, "cyanoalkylene" refers to the -(alkylene)C≡N substituent; "hydroxyalkylene" refers to the -(alkylene)OH substituent; "arylmethoxy" refers to a methoxy substituted aryl group.

In some embodiments of compounds of Formula (A), the compound is of Formula (A'):

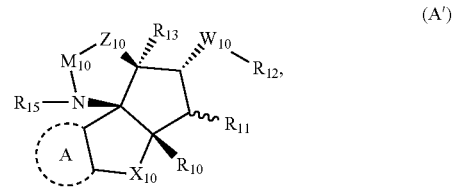

(A')

wherein the stereochemistry of $R_{11}$ is either α or β.

In some compounds of Formula (A), $M_{10}$ is $C(R_{14}R_{17})$ and $Z_{10}$ is $NR_{15}'$.

In some compounds of Formula (A), $M_{10}$ is $C(R_{14}R_{17})$ and $Z_{10}$ is $NR_{15}'$, and $R_{15}'$ together with $R_{17}$ forms a second bond between the nitrogen and carbon atoms they are attached to, such that the compound is of Formula (I):

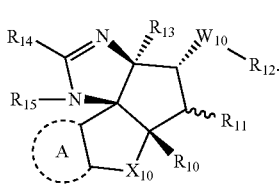

(I)

In some compounds of Formula (A), $X_{10}$ is O, S, NH, $N(C_1-C_8)$alkyl; N(aryl), N(heteroaryl), N(cycloalkyl), or $N[(C(O)O(C_1-C_8)$alkyl]; $R_{10}$ is an aryl or heteroaryl; $R_{11}$ is CN, $NO_2$, $SO_2R^A$, aryl, heteroaryl, $C(O)O(C_1-C_8)$alkyl, $(C_2-C_8)$alkenyl), $C(O)N^AR^B$ or $-CO_2H$; $W_{10}$ is $C(=Y_{10})$ where $Y_{10}$ is O, NH, S, NHOH, or NHOMe; $R_{12}$ is H, OH, aryl, heteroaryl, cycloalkyl, $C_1-C_8$(alkyl), $O(C_1-C_8)$alkyl, $N[O(C_1-C_8)$alkyl][$(C_1-C_8)$alkyl], $NH[(C_1-C_8)$alkyl], $N(OMe)(C_1-C_8)$alkyl, $NH[(C_1-C_8)$alkyl] or $N[(C_1-C_8)$alkyl]$_2$; $R_{13}$ is OH, SH, $NH_2$, $NH[(C_1-C_8)$alkyl] or $N[(C_1-C_8)$alkyl]$_2$, $R_{14}$ is H, $(C_1-C_8)$alkyl, aryl, heteroaryl, heteroalkyl, cycloalkyl, acyl, allyl, CN, $NH_2$, $NH[(C_1-C_8)$alkyl], $N[(C_1-C_8)$alkyl]$_2$, OMe, SMe, or OH; $R_{15}$ is H, $(C_1-C_8)$alkyl, aryl, heteroaryl, heteroalkyl, cycloalkyl, acyl, allyl, CN, $NH_2$, $NH[(C_1-C_8)$alkyl], $N[(C_1-C_8)$alkyl]$_2$, OMe, SMe, $SO_3R^A$, OH, or SH. In some embodiments, $Y_{10}$ is O; $R_{12}$ is aryl, heteroaryl, $C_1-C_8$(alkyl), $O(C_1-C_8)$alkyl, $N[O(C_1-C_8)$alkyl][$(C_1-C_8)$alkyl], $N(OMe)(C_1-C_8)$alkyl, $NH[O(C_1-C_8)$alkyl]$_2$, $N[(C_1-C_8)$alkyl]$_2$, or $NH[(C_1-C_8)$alkyl].

In some embodiments, $X_{10}$ is O; $R_{10}$ is aryl; $R_{11}$ is CN, $NO_2$, $SO_2R^A$ or aryl; $R_{13}$ is OH; $R_{14}$ is $(C_1-C_8)$alkyl, cycloalkyl, or $NH_2$; $R_{15}$ is $(C_1-C_8)$alkyl, cycloalkyl, or $NH_2$. According to some implementations, $R_{10}$ and $R_{11}$ have syn relative stereochemistry.

In some compounds of Formula (A), $M_{10}$ is $C(R_{14}R_{17})$ and $Z_{10}$ is $NR_{15}'$, and $R_{15}$ together with $R_{17}$ forms a second bond between the nitrogen and carbon atoms they are attached to, such that the structure is of Formula (II):

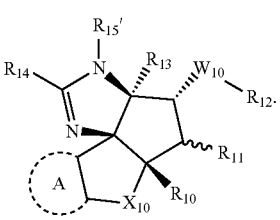

(II)

In some compounds of Formula (A), $X_{10}$ is O, S, C(O), NH, $N(C_1-C_8)$alkyl; N(aryl), N(heteroaryl), N(cycloalkyl), $N[(C(O)O(C_1-C_8)$alkyl]; $R_{10}$ is an aryl or heteroaryl; $R_{11}$ is CN, $NO_2$, $SO_2R^A$, aryl, heteroaryl, $C(O)O(C_1-C_8)$alkyl, $(C_2-C_8)$alkenyl), $C(O)NR^DR^E$ or $-CO_2H$; $W_{10}$ is $CH_2$ $R_{12}$ is H, OH, aryl, heteroaryl, cycloalkyl, $C_1-C_8$(alkyl), $O(C_1-C_8)$alkyl, $N(OMe)(C_1-C_8)$alkyl, $NH[((C_1-C_8)$alkyl) or $N[(C_1-C_8)$alkyl]$_2$; $R_{13}$ is OH, SH, $NH_2$, $NH[(C_1-C_8)$alkyl] or $N[(C_1-C_8)$alkyl]$_2$, $R_{14}$ is H, $(C_1-C_8)$alkyl, aryl, heteroaryl, heteroalkyl, cycloalkyl, acyl, allyl, CN, $NH_2$, $NH[(C_1-C_8)$alkyl], $N[(C_1-C_8)$alkyl]$_2$, OMe, SMe, OH; $R_{15}'$ is H, $(C_1-C_8)$alkyl, aryl, heteroaryl, heteroalkyl, cycloalkyl, acyl, allyl, CN, $NH_2$, $NH[(C_1-C_8)$alkyl], $N[(C_1-C_8)$alkyl]$_2$, OMe, SMe, $SO_3R^D$, OH, or SH.

In some embodiments of Formula (A), $X_{10}$ is O, S, NH, $N(C_1-C_8)$alkyl; N(aryl), N(heteroaryl), N(cycloalkyl), or $N[(C(O)O(C_1-C_8)$alkyl]; $R_{10}$ is an aryl or heteroaryl; $R_{11}$ is CN, $NO_2$, $SO_2R^A$, aryl, heteroaryl, $C(O)O(C_1-C_8)$alkyl, $(C_2-C_8)$alkenyl), $C(O)NR^DR^E$ or $-CO_2H$; $W_{10}$ is $Y_{20}$ where $Y_{20}$ is O, NH, S, NHOH, or NHOMe; $R_{12}$ is H, OH, aryl, heteroaryl, cycloalkyl, $C_1-C_8$(alkyl), $O(C_1-C_8)$alkyl, $N[(C_1-C_8)$alkyl]$_2$, $N[O(C_1-C_8)$alkyl][$(C_1-C_8)$alkyl], $N(OMe)(C_1-C_8)$alkyl, $NH[(C_1-C_8)$alkyl] or $N[(C_1-C_8)$alkyl]$_2$; $R_{13}$ is OH, SH, $NH_2$, $NH[(C_1-C_8)$alkyl] or $N[(C_1-C_8)$alkyl]$_2$, $R_{14}$ is H, $(C_1-C_8)$alkyl, aryl, heteroaryl, heteroalkyl, cycloalkyl, acyl, allyl, CN, $NH_2$, $NH[(C_1-C_8)$alkyl], $N[(C_1-C_8)$alkyl]$_2$, OMe, SMe, OH; $R_{15}'$ is H, $(C_1-C_8)$alkyl, aryl, heteroaryl, heteroalkyl, cycloalkyl, acyl, allyl, CN, $NH_2$, $NH[(C_1-C_8)$alkyl], $N[(C_1-C_8)$alkyl]$_2$, OMe, SMe, $SO_3R^D$, OH, or SH. In some embodiments, $X_{10}$ is O; $R_{10}$ is aryl; $R_{11}$ is CN, $NO_2$, $SO_2R^A$ or aryl; $Y_{10}$ is O; $R_{12}$ is $(C_1-C_8)$alkyl, $O(C_1-C_8)$alkyl, $N(OMe)(C_1-C_8)$alkyl, or $N[(C_1-C_8)$alkyl]$_2$; $R_{13}$ is OH; $R_{14}$ is $(C_1-C_8)$alkyl, cycloalkyl, or $NH_2$; $R_{15}'$ is $(C_1-C_8)$alkyl, cycloalkyl, or $NH_2$. Optionally, $R_{10}$ and $R_{11}$ have syn relative stereochemistry.

In some compounds of Formula (A), $X_{10}$ is O, S, C(O), NH, $N(C_1-C_8)$alkyl, N(aryl), N(heteroaryl), N(cycloalkyl), $N[(C(O)O(C_1-C_8)$alkyl], CH2, $C[((C_1-C_8)$alkyl]$_2$, $C(aryl)_2$. In some compounds of Formula (A), $X_{10}$ is O, S, or NH. In some compounds of Formula (A), $X_{10}$ is O.

In some compounds of Formula (A), $R_{10}$ is an aryl or heteroaryl. In some compounds of Formula (A), $R_{10}$ an aryl. In some compounds of Formula (A), $R_{10}$ is a heteroaryl. In some compounds of Formula (A), $R_{10}$ is an arylmethoxy.

In some compounds of Formula (A), $R_{11}$ is aryl, heteroaryl, $C(O)O(C_1-C_8)$alkyl, $(C_2-C_8)$alkenyl), $C(O)NR^AR^B$ or $-CO_2H$. For example, $R_{11}$ is aryl or heteroaryl. In some compounds of Formula (A), $R_{11}$ is an arylmethoxy.

In some compounds of Formula (A), $R_{16}$ is H or $C_1-C_8$ (alkyl). For example, $R_{16}$ is H, methyl, ethyl, propyl, isopropyl, 1-methylpropyl, 2-methylpropyl, butyl, isobutyl, or pentyl. In some compound of Formula (A), $R_{16}$ is H or methyl In some compounds of Formula (A), $W_{10}$ is $CH_2$. In some other compounds of Formula (A), $W_{10}$ is $C(=Y_{10})$.

In some embodiments, $R_{12}$ is H, OH, aryl, heteroaryl, cycloalkyl, $C_1-C_8$(alkyl), $O(C_1-C_8)$alkyl, $N(OMe)(C_1-C_8)$alkyl, $NH[(C_1-C_8)$alkyl] or $N[(C_1-C_8)$alkyl]$_2$. In some embodiments, $R_{12}$ is OH, $C_1-C_8$(alkyl), $O(C_1-C_8)$alkyl, $N(OMe)(C_1-C_8)$alkyl, $NH[(C_1-C_8)$alkyl] or $N[(C_1-C_8)$alkyl]$_2$. In some embodiments, $R_{12}$ is $N(OMe)(C_1-C_8)$alkyl, $NH[(C_1-C_8)$alkyl] or $N[(C_1-C_8)$alkyl]$_2$. In some embodiments, $R_{12}$ is OH. In some additional embodiments $R_{12}$ is OMe.

In some embodiments, $R_{13}$ is OH, SH, $NH_2$, $NH[(C_1-C_8)$alkyl] or $N[(C_1-C_8)$alkyl]$_2$. In some embodiments, $R_{13}$ is OH, SH or $NH_2$. In some embodiments, $R_{13}$ is OH.

In some embodiments, $R_{14}$ is H, $(C_1-C_8)$alkyl, aryl, heteroaryl, heteroalkyl, cycloalkyl, acyl, allyl, CN, $NH_2$, $NH[(C_1-C_8)$alkyl], $N[(C_1-C_8)$alkyl]$_2$, OMe, SMe, or OH. In some embodiments, $R_{14}$ is H, $(C_1-C_8)$alkyl, aryl, heteroaryl, heteroalkyl, cycloalkyl, acyl, allyl, $NH[(C_1-C_8)$alkyl], $N[(C_1-C_8)$alkyl]$_2$. In some embodiments, $R_{14}$ is $(C_1-C_8)$ alkyl or cycloalkyl. In some embodiments, $R_{14}$ is H, $(C_1-C_8)$alkyl, aryl, heteroaryl, heteroalkyl, cycloalkyl, acyl, allyl, $NH[(C_1-C_8)$alkyl], $N[(C_1-C_8)$alkyl]$_2$.

In some embodiments, $R_{15}$ or $R_{15}'$ is H, $(C_1-C_8)$alkyl, aryl, heteroaryl, heteroalkyl, cycloalkyl, acyl, allyl, CN, $NH_2$, $NH[(C_1-C_8)$alkyl], $N[(C_1-C_8)$alkyl]$_2$, OMe, SMe, $SO_3R^A$, OH, or SH. In some embodiments, $R_{15}$ or $R_{15}'$ is ($C_1$-$C_8$)alkyl, cycloalkyl, or $NH_2$. In some embodiments, $R_{15}$ or $R_{15}'$ is H or ($C_1$-$C_8$)alkyl. In some embodiments, $R_{15}$ or $R_{15}'$ is H.

In some embodiments, $X_{10}$ is O, S, C(O), NH, N($C_1$-$C_8$)alkyl, N(aryl), N(heteroaryl), N(cycloalkyl), N[(C(O)O($C_1$-$C_8$)alkyl], $CH_2$, C[($C_1$-$C_8$)alkyl]$_2$, C(aryl)$_2$; $R_{10}$ is an aryl or heteroaryl; $R_{11}$ is aryl, heteroaryl, C(O)O($C_1$-$C_8$)alkyl, ($C_2$-$C_8$)alkenyl), C(O)NR$^A$R$^B$ or —CO$_2$H. $W_{10}$ is $CH_2$; $R_{12}$ is H, OH, aryl, heteroaryl, cycloalkyl, $C_1$-$C_8$(alkyl), O($C_1$-$C_8$)alkyl, N(OMe)($C_1$-$C_8$)alkyl, NH[($C_1$-$C_8$)alkyl] or N[($C_1$-$C_8$)alkyl]$_2$; $R_{13}$ is OH, SH, $NH_2$, NH[($C_1$-$C_8$)alkyl] or N[($C_1$-$C_8$)alkyl]$_2$; $R_{14}$ is H, ($C_1$-$C_8$)alkyl, aryl, heteroaryl, heteroalkyl, cycloalkyl, acyl, allyl, CN, $NH_2$, NH[($C_1$-$C_8$)alkyl], N[($C_1$-$C_8$)alkyl]$_2$, OMe, SMe, or OH; and $R_{15}$ or $R_{15}'$ is H, ($C_1$-$C_8$)alkyl, aryl, heteroaryl, heteroalkyl, cycloalkyl, acyl, allyl, CN, $NH_2$, NH[($C_1$-$C_8$)alkyl], N[($C_1$-$C_8$)alkyl]$_2$, OMe, SMe, SO$_3$R$^A$, OH, or SH.

In some embodiments, $X_{10}$ is O, S, NH, N($C_1$-$C_8$)alkyl; N(aryl), N(heteroaryl), N(cycloalkyl), or N[(C(O)O($C_1$-$C_8$)alkyl]; $R_{10}$ is an aryl or heteroaryl; $R_{11}$ is aryl, heteroaryl, C(O)O($C_1$-$C_8$)alkyl, ($C_2$-$C_8$)alkenyl), C(O)NR$^A$R$^B$ or —CO$_2$H; $W_{10}$ is C(=$Y_{10}$) where $Y_{10}$ is O, NH, S, NHOH, or NHOMe; $R_{12}$ is H, OH, aryl, heteroaryl, cycloalkyl, $C_1$-$C_8$(alkyl), O($C_1$-$C_8$)alkyl, N[O($C_1$-$C_8$)alkyl][($C_1$-$C_8$)alkyl], NH[($C_1$-$C_8$)alkyl], N(OMe)($C_1$-$C_8$)alkyl, NH[($C_1$-$C_8$)alkyl] or N[($C_1$-$C_8$)alkyl]$_2$; $R_{13}$ is OH, SH, $NH_2$, NH[($C_1$-$C_8$)alkyl] or N[($C_1$-$C_8$)alkyl]$_2$; $R_{14}$ is H, ($C_1$-$C_8$)alkyl, aryl, heteroaryl, heteroalkyl, cycloalkyl, acyl, allyl, CN, $NH_2$, NH[($C_1$-$C_8$)alkyl], N[($C_1$-$C_8$)alkyl]$_2$, OMe, SMe, or OH; $R_{15}$ or $R_{15}'$ is H, ($C_1$-$C_8$)alkyl, aryl, heteroaryl, heteroalkyl, cycloalkyl, acyl, allyl, CN, $NH_2$, NH[($C_1$-$C_8$)alkyl], N[($C_1$-$C_8$)alkyl]$_2$, OMe, SMe, SO$_3$R$^A$, OH, or SH.

In some embodiments, $Y_{10}$ is O; and $R_{12}$ is aryl, heteroaryl, $C_1$-$C_8$(alkyl), O($C_1$-$C_8$)alkyl, N[O($C_1$-$C_8$)alkyl][($C_1$-$C_8$)alkyl], N(OMe)($C_1$-$C_8$)alkyl, NH[O($C_1$-$C_8$)alkyl]$_2$, N[($C_1$-$C_8$)alkyl]$_2$, or NH[($C_1$-$C_8$)alkyl]. In some embodiments, $X_{10}$ is O; $R_{10}$ is aryl; $R_{11}$ is aryl; $R_{13}$ is OH; $R_{14}$ is ($C_1$-$C_8$)alkyl, cycloalkyl, or $NH_2$; and $R_{15}$ or $R_{15}'$ is ($C_1$-$C_8$)alkyl, cycloalkyl, or $NH_2$.

In some embodiments, of compound (A) $M_{10}$ is C($R_{14}R_{17}$) and $Z_{10}$ is NR$_{15}'$ and $R_{14}$ is C($R_{18}R_{19}$)$R_{20}$, where $R_{15}$, $R_{19}$ and $R_{20}$ independently are H, halogen, CN, $C_1$-$C_8$ (alkyl), ($C_1$-$C_8$)haloalkyl, ($C_2$-$C_8$)alkenyl, ($C_2$-$C_8$)alkynyl, OR$^A$, NR$^A$R$^B$, [($C_1$-$C_8$)alkylene]OR$^A$, [($C_1$-$C_8$)alkylene]NHR$^A$, [($C_1$-$C_8$)alkylene]NR$^A$R$^B$, C(O)R$^A$, C(O)NHR$^A$, C(O)NR$^A$R$^B$C(O)[($C_1$-$C_8$)alkylene]NHR$^A$, C(O)[($C_1$-$C_8$)alkylene]NR$^A$R$^B$, CO$_2$R$^A$, C(S)NHR$^A$, C(S)NR$^A$R$^B$, SR$^A$, S(O)R$^A$, SO$_2$R$^A$, SO$_3$R$^A$, SO$_2$NHR$^A$, SO$_2$NR$^A$R$^B$, NHC(O)R$^A$, NR$^A$C(O)R$^B$, NHC(O)NHR$^A$, NHC(O)NR$^A$R$^B$, NR$^A$C(O)NHR$^B$, NR$^A$C(O)NR$^B$R$^C$, P(O)(OH)(OR$^A$), P(O)(OR$^A$)(OR$^B$), aryl, heteroaryl, cycloalkyl or heterocyclyl, provided that at least one of $R_{18}$, $R_{19}$ and $R_{20}$ is not H. In some implementations at least one of $R_{18}$, $R_{19}$ and $R_{20}$ is F, Cl, Br, I or an electrophile.

In some implementations, $R_{18}$ and $R_{19}$ independently are F, Cl, Br, I or other electrophile. For example, in some implementations, the compound has the structure (VIIa):

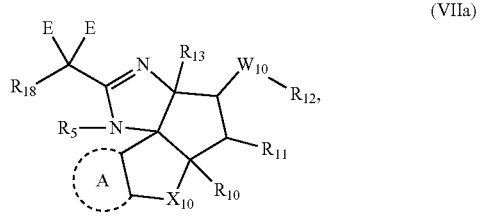

(VIIa)

wherein E can be an electrophile such as a halide (e.g., fluorine, chlorine, bromine, iodine). In some implementations, $R_{13}$ is OH. In some compounds the $R_{18}$ group can be MeO, OH, Cl and H. In some implementations $R_{13}$ is OH.

In some embodiments, $M_{10}$ is C(O), C(S) or C=NR$_{14}$; and $Z_{10}$ is NR$_{15}'$. In some embodiments, $R_{15}$ and $R_{15}'$ are H and the structure is (VIIb):

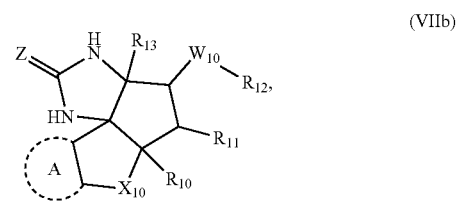

(VIIb)

wherein Z is C(O), C(S) or C=NR$_{14}$.

In some compounds of (VIIb), $R_{13}$ is OH. In some compounds of (VIIb), $W_{10}$ is C(O).

In some embodiments of compound (A), $M_{10}$ is S(=O)$R_{14}R_{17}$; and $Z_{10}$ is NR$_{15}'$. In some implementations, $R_{17}$ and $R_{15}'$ together form a double bond. For example, in some implementations, the compound has the structure (VIIc);

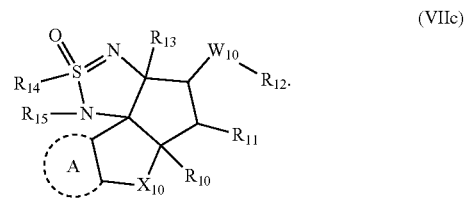

(VIIc)

In some compounds of (VIIc), $R_{13}$ is OH. In some compounds of (VIIc), $W_{10}$ is C(O).

In some embodiments, of compound (A), $M_{10}$ is S(O) having structure (VIId), or in some embodiments, $M_{10}$ is S(O$_2$) having structure (VIIe). For example, the compound is of Formula (VIId) or (VIIe):

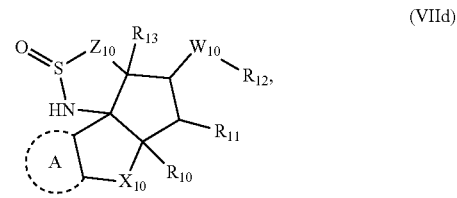

(VIId)

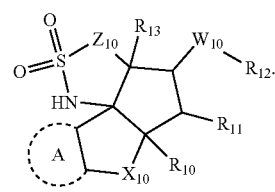

(VIIe)

Optionally, $R_{13}$ is OH in compounds of Formula (VIId) or (VIIe). In some compounds of Formula (VIId) or (VIIe), $W_{10}$ is C(O).

In some embodiments of compound (A), $R_{12}$ and $R_{13}$ together with the carbon atoms they are attached to form a 3-8 membered heterocyclyl. For example, $R_{12}$ forms a bond connecting $W_{10}$ and the $R_{13}$ group. In some embodiments, the compound has the structure (II'):

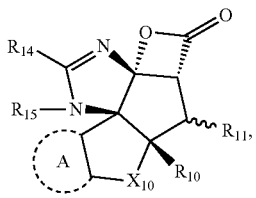
(II')

wherein the regioselectivity of $R_{11}$ is either α or β.

In embodiments of compound (A) the compound is of Formula (IV) or (IV'):

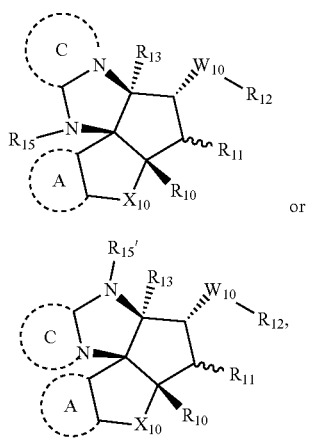
(IV)

(IV')

wherein Ring C is cycloalkyl or heteroaryl.

In some embodiments, Ring C is an heteroaryl.

In some embodiments, Ring C has the structure of Formula (XIII):

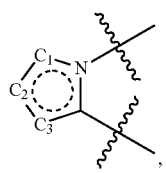
(XIII)

wherein; $C_1$ is N, O, S or $CR_{110}$; $C_2$ is N, O, S or $CR_{111}$; and $C_3$ is N, O, S or $CR_{112}$. $R_{111}$ and $R_{112}$ independently are H, CN, halogen, $OR^M$, $SR^M$, $(C_1-C_8)$alkyl, $C(O)O(C_1-C_8)$alkyl, $C(O)(C_1-C_8)$alkyl, $SO_2(C_1-C_8)$alkyl, $SO_2NR^MR^N$, $C(O)NR^MR^N$, $NR^MR^N$ or $NR^MC(O)R^N$, and $R_{111}$ is H or $(C_1-C_8)$alkyl; $R^M$ and $R^N$, independently are H, —OH, aryl, $(C_1-C_8)$alkyl, $[(C_1-C_8)$alkyl]aryl $(C_1-C_8)$alkoxy, $(C_1-C_8)$haloalkyl, cycloalkyl, heterocyclyl, $[(C_1-C_8)$alkylene]heterocyclyl, $[(C_1-C_8)$alkylene]aryl or heteroaryl. Optionally, $R^M$ and $R^N$ together with the nitrogen atom to which they are attached to, $NR^MR^N$ or $NR^MC(O)R^N$, optionally form a heterocyclyl ring.

In some implementations, Ring C is a heterocycle selected from the group consisting of a diazole, a triazole, a tetrazole, an imidazole, a thiadiazole, an oxazole, a thiazole and an oxadiazole. In some embodiments of Formula (XIII), $C_1$ is N and $R_{111}$ and $R_{112}$ are H. In some embodiments of Formula (XIII), $C_1$ and $C_2$ are N and $R_{112}$ is H.

According to some implementations of the description, a compound of Formula (B) is of Formula (III):

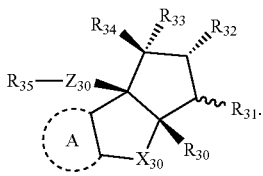
(III)

In some embodiments of compounds of Formula (B), $X_{30}$ is O, S, $CH_2$, NH, $N(C_1-C_8)$alkyl; N(aryl), N(heteroaryl), N(cycloalkyl), $N[(C(O)O(C_1-C_8)$alkyl]; $R_{30}$ is aryl or heteroaryl; $R_{31}$ is aryl, heteroaryl, $C(O)O(C_1-C_8)$alkyl, $(C_2-C_8)$alkenyl), $C(O)N^GR^H$ or —$CO_2H$; $R_{32}$ is OH, $CON[(C_1-C_8)$alkyl]$_2$, CON(OMe)$[(C_1-C_8)$alkyl], $CO[O(C_1-C_8)$alkyl], $CH_2[O(C_1-C_8)$alkyl], $CH_2OH$, or $(C_1-C_8)$alkyl; $R_{33}$ is H; $R_{34}$ is OH, SH, $NH_2$, $NH(C_1-C_8)$alkyl or $N[C_1-C_8)$alkyl]$_2$; Z is O, S, NH or $NR^G$; $R_{35}$ is H, $(C_1-C_8)$alkyl, aryl, heteroaryl, cyclalkyl, $C(O)O(C_1-C_8)$alkyl, $NMe_2$ or OMe.

In some embodiments, $X_{30}$ is O; $R_{30}$ is aryl; $R_{31}$ is aryl; $R_{32}$ is $CON[(C_1-C_8)$alkyl]$_2$, CON(OMe)$[(C_1-C_8)$alkyl], $CO[O(C_1-C_8)$alkyl] or $(C_1-C_8)$alkyl; and $R_{33}$ is H; $R_{34}$ is OH; $R_{35}$ is H, $(C_1-C_8)$alkyl, or cycloalkyl. In some embodiments, $R_{30}$ and $R_{31}$ have syn relative stereochemistry.

In some embodiments of compounds of Formula (B), $X_{30}$ is O, S, NH, $N(C_1-C_8)$alkyl; N(aryl), N(heteroaryl), N(cycloalkyl), $N[(C(O)O(C_1-C_8)$alkyl]; $R_{30}$ is aryl or heteroaryl; $R_{31}$ is aryl, heteroaryl, $C(O)O(C_1-C_8)$alkyl, $(C_2-C_8)$alkenyl), $C(O)NR^GR^H$ or —$CO_2H$; $R_{32}$ is OH, $CON[(C_1-C_8)$alkyl]$_2$, CON(OMe)$[(C_1-C_8)$alkyl], $CO[O(C_1-C_8)$alkyl], $CH_2[O(C_1-C_8)$alkyl], $CH_2OH$, or $(C_1-C_8)$alkyl; $R_{33}$ is OH, SH, $NH_2$, $NH(C_1-C_8)$alkyl or $N[C_1-C_8)$alkyl]$_2$; $R_{34}$ is H; Z is O, S or NH; and $R_{35}$ is H, $(C_1-C_8)$alkyl, aryl, heteroaryl, cyclalkyl, $C(O)O(C_1-C_8)$alkyl, $NMe_2$ or OMe. In some embodiments, $X_{30}$ is O; $R_{30}$ is aryl; $R_{31}$ is aryl; $R_{33}$ is OH; $R_{34}$ is H; $R_{35}$ is H, $(C_1-C_8)$alkyl, or cycloalkyl.

In some embodiments, the compound has the structure of Formula (B), wherein; $X_{30}$ is O, S, NH, $N(C_1-C_8)$alkyl; N(aryl), N(heteroaryl), N(cycloalkyl), $N[(C(O)O(C_1-C_8)$alkyl]; $R_{30}$ is aryl or heteroaryl; $R_{31}$ is aryl or heteroaryl, $R_{33}$ and $R_{34}$ combined are O, S, NH, $N(C_1-C_8)$alkyl or NOH; $Z_{30}$ is O, S or NH; $R_{35}$ is H, $(C_1-C_8)$alkyl, aryl, heteroaryl, cyclalkyl, $C(O)O(C_1-C_8)$alkyl, $NMe_2$ or OMe. In some embodiments, $X_{30}$ is O; $R_{30}$ is aryl; $R_{31}$ is aryl; $R_{33}$ and $R_{34}$ combined are O; $R_{35}$ is H, $(C_1-C_8)$alkyl, or cycloalkyl.

In some embodiments, the compound has the structure of Formula (B), and $R_{33}$, and $R_{34}$ together are $NR^G$ and $R^G$ and $R_{32}$ are connected and the compound is of Formula (B'):

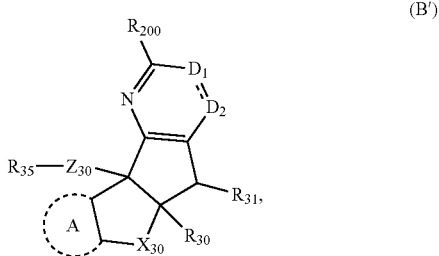
(B')

where $R_{200}$ is H, halogen, CN, $(C_1-C_8)$alkyl, $(C_1-C_8)$haloalkyl, $(C_2-C_8)$alkenyl), $(C_2-C_8)$alkynyl, $OR^G$, $NR^GR^H$, $[(C_1-$ $C_8$)alkylene]OR$^G$, [($C_1$-$C_8$)alkylene]NHR$^G$, [($C_1$-$C_8$)alkylene]NR$^G$R$^H$, C(O)R$^G$, C(O)NHR$^G$, C(O)NR$^G$R$^H$, C(O)[($C_1$-$C_8$)alkylene]NHR$^G$, C(O)[($C_1$-$C_8$)alkylene]NR$^G$R$^H$, CO$_2$R$^G$, C(S)NHR$^G$, C(S)NR$^G$R$^H$, SR$^G$, S(O)R$^G$, SO$_2$R$^G$, SO$_2$NHR$^G$, SO$_2$NR$^G$R$^H$, NHC(O)R$^G$, NR$^G$C(O)R$^H$, NHC(O)NHR$^G$, NHC(O)NR$^G$R$^H$, NR$^G$C(O)NHR$^H$ NR$^G$C(O)NHR$^J$, P(O)(OH)(OR$^G$), P(O)(OR$^G$)(OR$^H$), aryl, heteroaryl, cycloalkyl or heterocyclyl. R$^G$, R$^H$, and R$^I$ independently are H, —OH, aryl, ($C_1$-$C_8$)alkyl, [($C_1$-$C_8$)alkyl]aryl ($C_1$-$C_8$) alkoxy, C(O)O($C_1$-$C_8$)alkyl, ($C_1$-$C_8$)haloalkyl, cycloalkyl, heterocyclyl, [($C_1$-$C_8$)alkylene]heterocyclyl, [($C_1$-$C_8$)alkylene]aryl or heteroaryl; or wherein the R$^G$ and R$^H$ together with the nitrogen atom to which they are attached form a heterocyclyl ring. $D_1$ is N, C(O), NH or CR$_{210}$; $D_2$ is N, C(O), NH or CR$_{220}$; $R_{210}$ and $R_{220}$ are independently are H, halogen, CN, $C_1$-$C_8$(alkyl), ($C_1$-$C_8$)haloalkyl, ($C_2$-$C_8$)alkenyl, ($C_2$-$C_8$)alkynyl, OR$^O$, NR$^O$R$^P$, [($C_1$-$C_8$)alkylene]OR$^O$, [($C_1$-$C_8$)alkylene]NHRA, [($C_1$-$C_8$)alkylene]NR$^O$R$^P$, C(O)R$^O$, C(O)NHR$^O$, C(O)NR$^O$R$^P$, C(O)[($C_1$-$C_8$)alkylene]NHR$^O$, C(O)[($C_1$-$C_8$)alkylene]NR$^O$R$^P$, CO$_2$R$^O$, C(S)NHR$^O$, C(S)NR$^O$R$^P$, SR$^O$, S(O)R$^O$, SO$_2$R$^O$, SO$_2$NHR$^O$, SO$_2$NR$^O$R$^P$, NHC(O)R$^O$, NR$^O$C(O)R$^P$, NHC(O)NHR$^O$, NHC(O)NR$^O$R$^P$, NR$^O$C(O)NHR$^P$, NR$^O$C(O)NR$^P$R$^Q$, P(O)(OH)(OR$^O$), P(O)(OR$^O$)(OR$^P$), tosylate, aryl, heteroaryl, cycloalkyl or heterocyclyl. R$^O$, R$^P$ and R$^Q$ independently are H, —OH, aryl, ($C_1$-$C_8$)alkyl, [($C_1$-$C_8$)alkyl]aryl ($C_1$-$C_8$) alkoxy, ($C_1$-$C_8$)haloalkyl, cycloalkyl, heterocyclyl, [($C_1$-$C_8$) alkylene]heterocyclyl, [($C_1$-$C_8$)alkylene]aryl or heteroaryl; or R$^O$ and R$^P$ together with the nitrogen atom to which they are attached form a heterocyclyl ring.

In some embodiments, a compound of Formula (B') has Formula (III'):

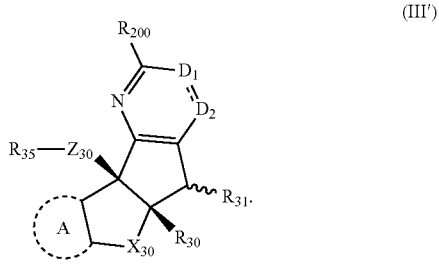

(III')

In some embodiments, $X_{30}$ is O, S, $CH_2$, NH, N($C_1$-$C_8$) alkyl N(aryl), N(heteroaryl), N(cycloalkyl), or N[(C(O)O ($C_1$-$C_8$)alkyl]. In some embodiments, $X_{30}$ is O, S, or NH. In some further embodiments $X_{30}$ is O.

In some embodiments, $R_{30}$ is aryl or heteroaryl. In some embodiments, $R_{30}$ an aryl. In some further embodiments $R_{30}$ is a heteroaryl. In some embodiment $R_{30}$ is an arylmethoxy.

In some embodiments, $R_{31}$ is aryl, heteroaryl, C(O)O($C_1$-$C_8$)alkyl, ($C_2$-$C_8$)alkenyl), C(O)NR$^G$R$^H$ or —CO$_2$H. In some embodiments, $R_{31}$ is aryl or heteroaryl. In some further embodiments $R_{31}$ is an arylmethoxy.

In some embodiments, $R_{32}$ is H, OH, aryl, heteroaryl, cycloalkyl, $C_1$-$C_8$(alkyl), O($C_1$-$C_8$)alkyl, N(OMe)($C_1$-$C_8$) alkyl, NH[(($C_1$-$C_8$)alkyl) or N[($C_1$-$C_8$)alkyl]$_2$. In some embodiments, $R_{32}$ is OH, $C_1$-$C_8$(alkyl), O($C_1$-$C_8$)alkyl, N(OMe)($C_1$-$C_8$)alkyl, NH[($C_1$-$C_8$)alkyl] or N[($C_1$-$C_8$) alkyl]$_2$. In some embodiments, $R_{32}$ is N(OMe)($C_1$-$C_8$)alkyl, NH[($C_1$-$C_8$)alkyl] or N[($C_1$-$C^8$)alkyl]$_2$. In some further embodiments $R_{32}$ is OH. In some additional embodiments $R_{32}$ is OMe.

In some embodiments, $R_{33}$ is H, OH, SH, $NH_2$, NH($C_1$-$C_8$)alkyl or N[$C_1$-$C_8$)alkyl]$_2$. In some embodiments, $R_{33}$ is H. In some embodiments. $R_{33}$ is OH. In some embodiments, $R_{33}$ is OH, SH, $NH_2$, NH[($C_1$-$C_8$)alkyl] or N[($C_1$-$C_8$)alkyl]$_2$. In other embodiments $R_{33}$ is OH, SH or $NH_2$. In some further embodiments $R_{33}$ is OH. In some further embodiments $R_{33}$ is H.

In some embodiments, $R_{34}$ is H, OH, SH, $NH_2$, NH($C_1$-$C_8$)alkyl or N[$C_1$-$C_8$)alkyl]$_2$. In some embodiments, $R_{34}$ is OH, SH, $NH_2$. In some embodiments, $R_{34}$ is OH. In some embodiments, $R_{34}$ is H.

In some embodiments, $R_{35}$ is H, ($C_1$-$C_8$)alkyl, aryl, heteroaryl, cyclalkyl, C(O)O($C_1$-$C_8$)alkyl, $NMe_2$ or OMe. In some embodiments, $R_{35}$ is H, ($C_1$-$C_8$)alkyl, or cyclalkyl. In some embodiments, $R_{35}$ is aryl or heteroaryl. In some embodiments, $R_{35}$ is C(O)O($C_1$-$C_8$)alkyl, $NMe_2$. In some embodiments, $R_{35}$ is OMe.

In some embodiments, $R_{30}$ and $R_{31}$ have syn relative stereochemistry.

In some embodiments of the third aspect, $X_{30}$ is O, S, $CH_2$, NH, N($C_1$-$C_8$)alkyl; N(aryl), N(heteroaryl), N(cycloalkyl), N[(C(O)O($C_1$-$C_8$)alkyl]; $R_{30}$ is aryl or heteroaryl; $R_{31}$ is aryl, heteroaryl, C(O)O($C_1$-$C_8$)alkyl, ($C_2$-$C_8$)alkenyl), C(O)NR$^G$R$^H$ or —CO$_2$H; $R_{32}$ is OH, CON[($C_1$-$C_8$)alkyl]$_2$, CON(OMe)[($C_1$-$C_8$)alkyl], CO[O($C_1$-$C_8$)alkyl], $CH_2$[O($C_1$-$C_8$)alkyl], $CH_2$OH, or ($C_1$-$C_8$)alkyl; $R_{33}$ is H; $R_{34}$ is OH, SH, $NH_2$, NH($C_1$-$C_8$)alkyl or N[$C_1$-$C_8$)alkyl]$_2$; Z is O, S or NH; $R_{35}$ is H, ($C_1$-$C_8$)alkyl, aryl, heteroaryl, cyclalkyl, C(O)O($C_1$-$C_8$)alkyl, $NMe_2$ or OMe.

In some embodiments, $X_{30}$ is O; $R_{30}$ is aryl; $R_{31}$ is aryl; $R_{32}$ is CON[($C_1$-$C_8$)alkyl]$_2$, CON(OMe)[($C_1$-$C_8$)alkyl], CO[O($C_1$-$C_8$)alkyl] or ($C_1$-$C_8$)alkyl; $R_{33}$ is H; $R_{34}$ is OH; and $R_{35}$ is H, ($C_1$-$C_8$)alkyl, or cyclalkyl.

In some embodiments according to the third aspect, $X_{30}$ is O, S, NH, N($C_1$-$C_8$)alkyl; N(aryl), N(heteroaryl), N(cycloalkyl), N[(C(O)O($C_1$-$C_8$)alkyl]; $R_{30}$ is aryl or heteroaryl; $R_{31}$ is aryl, heteroaryl, C(O)O($C_1$-$C_8$)alkyl, ($C_2$-$C_8$)alkenyl), C(O)NR$^G$R$^H$ or —CO$_2$H; $R_{32}$ is OH, CON[($C_1$-$C_8$)alkyl]$_2$, CON(OMe)[($C_1$-$C_8$)alkyl], CO[O($C_1$-$C_8$)alkyl], $CH_2$[O($C_1$-$C_8$)alkyl], $CH_2$OH, or ($C_1$-$C_8$)alkyl; $R_{33}$ is OH, SH, $NH_2$, NH($C_1$-$C_8$)alkyl or N[$C_1$-$C_8$)alkyl]$_2$; $R_{34}$ is H; Z is O, S or NH; $R_{35}$ is H, ($C_1$-$C_8$)alkyl, aryl, heteroaryl, cycloalkyl, C(O)O($C_1$-$C_8$)alkyl, $NMe_2$ or OMe.

In some embodiments of the third aspect $X_{30}$ is O; $R_{30}$ is aryl; $R_{31}$ is aryl; $R_{33}$ is OH; $R_{34}$ is H; and $R_{35}$ is H, ($C_1$-$C_8$)alkyl, or cyclalkyl.

In some embodiments, $X_{30}$ is O, S, NH, N($C_1$-$C_8$)alkyl; N(aryl), N(heteroaryl), N(cycloalkyl), N[(C(O)O($C_1$-$C_8$)alkyl]. $R_{30}$ is aryl or heteroaryl. $R_{31}$ is aryl or heteroaryl. $R_{33}$ and $R_{34}$ combined are O, S, NH, N($C_1$-$C_8$)alkyl or NOH. $Z_{30}$ is O, S or NH. $R_{35}$ is H, ($C_1$-$C_8$)alkyl, aryl, heteroaryl, cyclalkyl, C(O)O($C_1$-$C_8$)alkyl, $NMe_2$ or OMe. In some embodiments, $X_{30}$ is O; $R_{30}$ is aryl; $R_{31}$ is aryl; $R_{33}$ and $R_{34}$ combined are O; $R_{35}$ is H, ($C_1$-$C_8$)alkyl, or cycloalkyl.

In some compounds of Formula (A) or Formula (B), Ring A has the structure of formula (XIV):

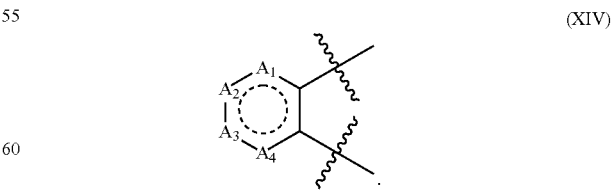

(XIV)

In Formula (XIV), $A_1$ is N, C(O), NH or CR$_{120}$; $A_2$ is N, C(O), NH or CR$_{121}$; $A_3$ is N, C(O), NH or CR$_{122}$; $A_4$ is N, C(O), NH or CR$_{123}$. $R_{120}$, $R_{121}$, $R_{122}$ and $R_{123}$ are independently are H, halogen, CN, $C_1$-$C_8$(alkyl), ($C_1$-$C_8$)haloalkyl, ($C_2$-$C_8$)alkenyl, ($C_2$-$C_8$)alkynyl, OR$^O$, NR$^O$R$^P$, [($C_1$-$C_8$)

alkylene]OR$^O$, [(C$_1$-C$_8$)alkylene]NHRA, [(C$_1$-C$_8$)alkylene]NR$^O$R$^P$, C(O)R$^O$, C(O)NHR$^O$, C(O)NR$^O$R$^P$, C(O)[(C$_1$-C$_8$)alkylene]NHR$^O$, C(O)[(C$_1$-C$_8$)alkylene]NR$^O$R$^P$, CO$_2$R$^O$, C(S)NHR$^O$, C(S)NR$^O$R$^P$, SR$^O$, S(O)R$^O$, SO$_2$R$^O$, SO$_2$NHR$^O$, SO$_2$NR$^O$R$^P$, NHC(O)R$^O$, NR$^O$C(O)R$^P$, NHC(O)NHR$^O$, NHC(O)NR$^O$R$^P$, NR$^O$C(O)NHR$^P$, NR$^O$C(O)NR$^P$R$^Q$, P(O)(OH)(OR$^O$), P(O)(OR$^O$)(OR$^P$), tosylate, aryl, heteroaryl, cycloalkyl or heterocyclyl. R$^O$, R$^P$ and R$^Q$ independently are H, —OH, aryl, (C$_1$-C$_8$)alkyl, [(C$_1$-C$_8$)alkyl]aryl (C$_1$-C$_8$)alkoxy, (C$_1$-C$_8$)haloalkyl, cycloalkyl, heterocyclyl, [(C$_1$-C$_8$)alkylene]heterocyclyl, [(C$_1$-C$_8$)alkylene]aryl or heteroaryl; or R$^O$ and R$^P$ together with the nitrogen atom to which they are attached form a heterocyclyl ring.

In some embodiments, A$_1$ is CR$_{120}$; A$_2$ is CR$_{121}$; A$_3$ is CR$_{122}$; A$_4$ is CR$_{123}$; and R$_{120}$, R$_{121}$, R$_{122}$ and R$_{123}$ independently are H or OR$^O$ and at least one of R$_{120}$, R$_{121}$, R$_{122}$ and R$_{123}$ are OR$^O$. In some embodiments, A$_1$ CR$_{120}$ where R$_{120}$ is methoxy, A$_3$ is methoxy is CR$_{122}$ where R$_{122}$ is methoxy, A$_2$ is CR$_{121}$ where R$_{121}$ is H, and A$_4$ is CR$_{123}$ where R$_{123}$ is H.

In some embodiments, A$_1$ is CR$_{120}$ where R$_{120}$ is a halide, A$_3$ is methoxy where is CR$_{122}$ where R$_{122}$ is methoxy, A$_2$ is N, and A$_4$ is CR$_{123}$ where R$_{123}$ is H.

In some embodiments, A$_1$ CR$_{120}$ where R$_{120}$ is methoxy, A$_3$ is CR$_{122}$ where R$_{122}$ is methoxy, A$_2$ is N, and A$_4$ is CR$_{123}$ where R$_{123}$ is H.

In some embodiments, A$_1$ is N, A$_3$ is methoxy is CR$_{122}$ where R$_{122}$ is methoxy, A$_2$ is CR$_{121}$ where R$_{121}$ is H, and A$_4$ is CR$_{123}$ where R$_{123}$ is H. In some embodiments, A$_1$ is C(C=O) or NH, A$_4$ is C(C=O) or NH, A$_2$ is CR$_{121}$, and A$_3$ is CR$_{123}$. In some embodiments, A$_1$ is C(C=O), A$_4$ is NH, A$_2$ is CR$_{121}$, and A$_3$ is CR$_{123}$. In some embodiments, A$_1$ is C(C=O), A$_4$ is NH, A$_2$ is CR$_{121}$, and A$_3$ is CR$_{123}$ wherein R$_{123}$ is methoxy. In some embodiments, A$_1$ is C(C=O), A$_4$ is N, and A$_3$ is CR$_{123}$ wherein R$_{123}$ is methoxy.

In some embodiments, A$_1$ is CR$_{120}$ where R$_{120}$ is H, A$_3$ is CR$_{122}$ where R$_{120}$ is H, A$_2$ is CR$_{121}$ and A$_4$ is CR$_{123}$; where at least one of R$_{121}$ or R$_{123}$ are NR$^O$R$^P$ and R$_{121}$ and R$_{123}$ together with the carbon to which they are attached for a heterocycle. In some further embodiments and R$_{120}$, R$_{121}$, R$_{122}$ and R$_{123}$ independently are H or OR$^O$ and at least one of R$_{120}$, R$_{121}$, R$_{122}$ and R$_{123}$ are OR$^O$ In some compounds of Formula (A) or Formula (B), Ring A has the structure of formula (XV):

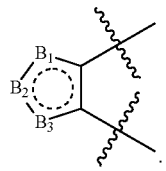

(XV)

In Formula (XV), any two of B$_1$, B$_2$ and B$_3$ are CR$_{130}$ and N and the remaining ring atom is N(R$_{131}$) or S, wherein R$_{130}$ is H, CN, halogen, OR$^R$, SR$^R$, (C$_1$-C$_8$)alkyl, C(O)O(C$_1$-C$_8$)alkyl, C(O)(C$_1$-C$_8$)alkyl, SO$_2$(C$_1$-C$_8$)alkyl, SO$_2$NR$^R$R$^S$, C(O)NR$^R$R$^S$, NR$^R$R$^S$ or NR$^R$C(O)R$^S$, and R$_{131}$ is H or (C$_1$-C$_8$)alkyl. R$^R$ and R$^S$, independently are H, —OH, aryl, (C$_1$-C$_8$)alkyl, [(C$_1$-C$_8$)alkyl]aryl (C$_1$-C$_8$)alkoxy, (C$_1$-C$_8$)haloalkyl, cycloalkyl, heterocyclyl, [(C$_1$-C$_8$)alkylene]heterocyclyl, [(C$_1$-C$_8$)alkylene]aryl or heteroaryl; or the R$^R$ and R$^S$ together with the nitrogen atom to which they are attached of NR$^R$R$^S$ or NR$^R$C(O)R$^S$, optionally form a heterocyclyl ring. In some embodiments, B$_1$ is N or S, B$_3$ is N or S, and B$_2$ is CR$_{130}$) wherein R$_{130}$ is a methoxy. In some embodiments, B$_1$ is N, B$_3$ is S, and B$_2$ is CR$_{130}$ wherein R$_{130}$ is a methoxy. In some embodiments, B$_1$ is CR$_{130}$ where R$_{130}$ is H, B$_2$ is S or N, and B$_3$ is S or N. In some embodiments, B$_1$ is CR$_{130}$ where R$_{130}$ is H, B$_2$ is S, and B$_3$ is N In some embodiments, the compound of Formula (A) is selected from the following structures:

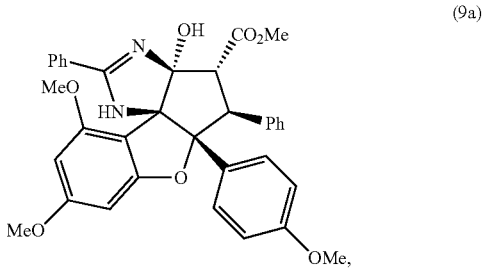

(9a)

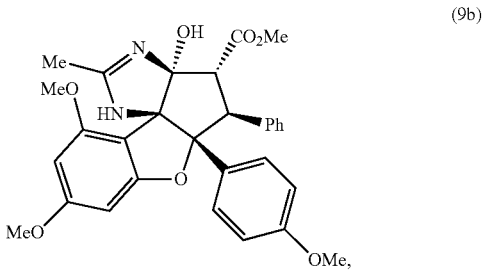

(9b)

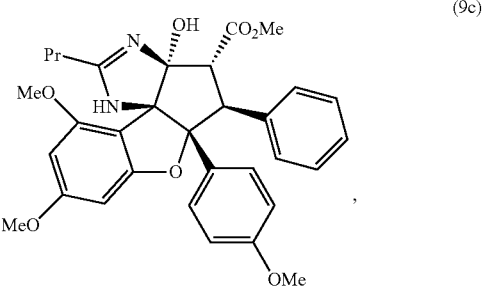

(9c)

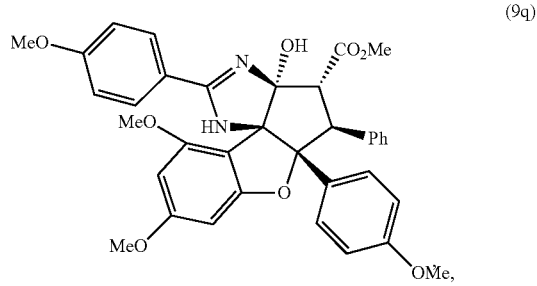

(9q)

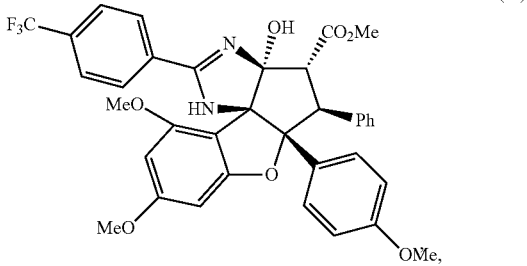

(9r)

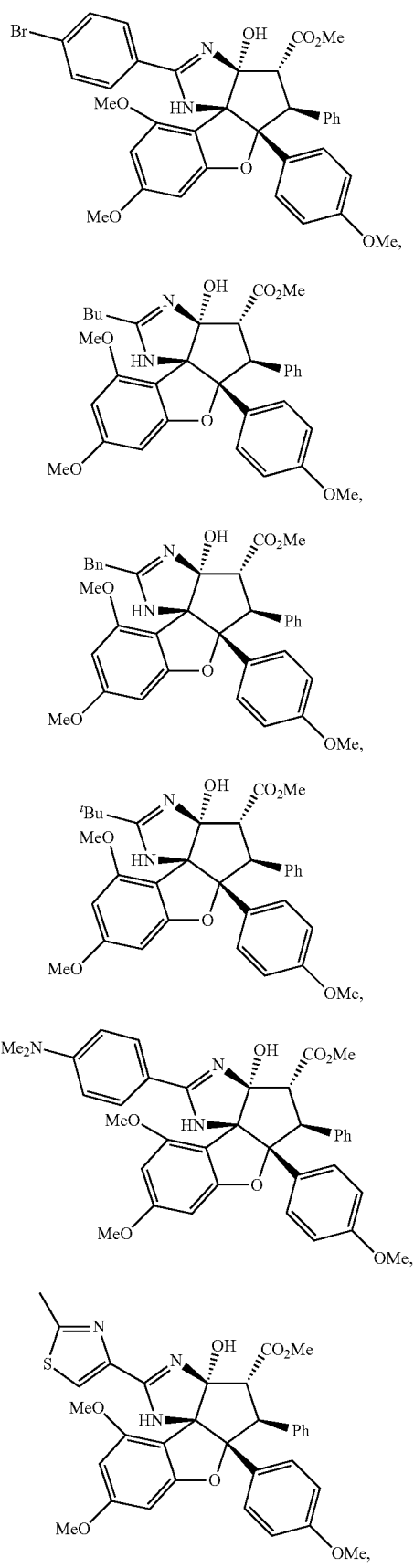
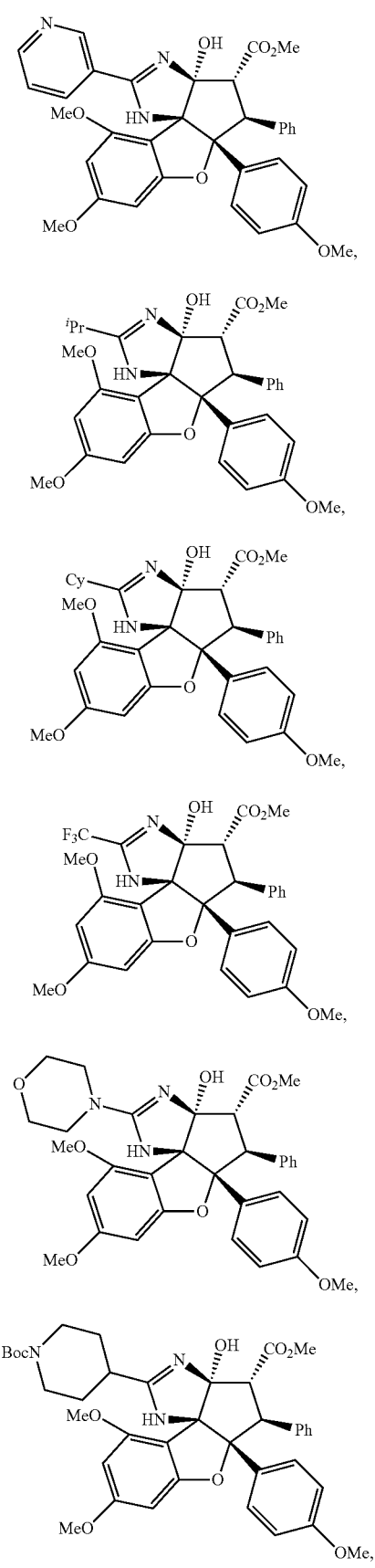

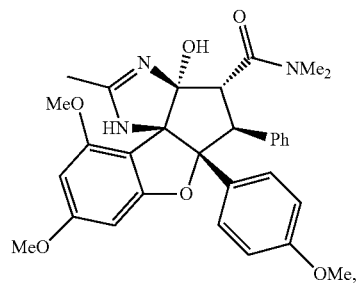
(9z)
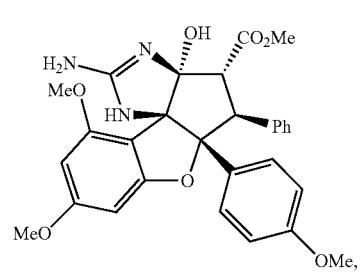
(9j)
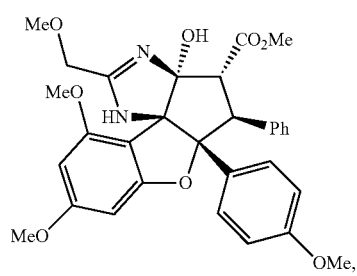
(9k)
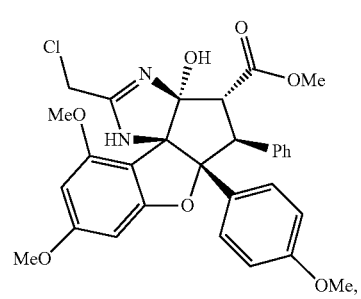
(9l)
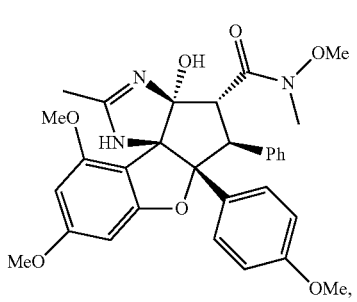
(9aa)
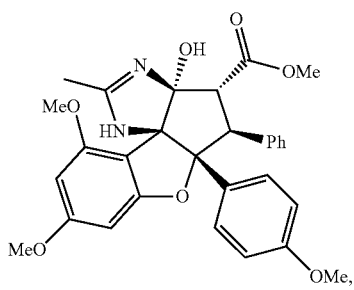
(9ab)
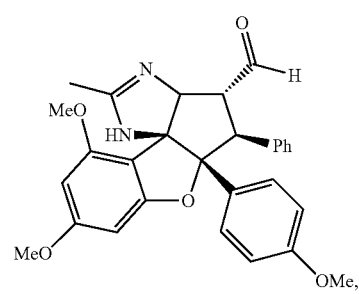
(Iy)
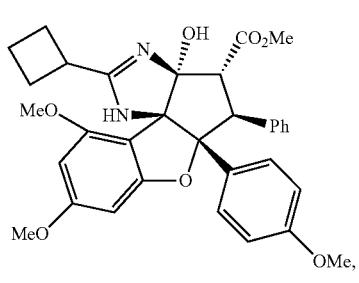
(9m)
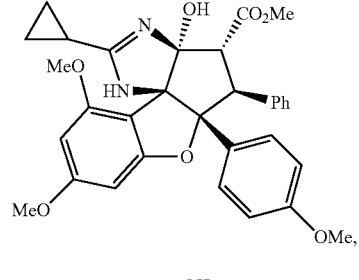
(9n)
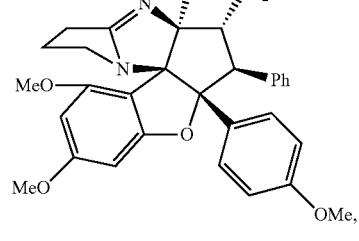
(9o)
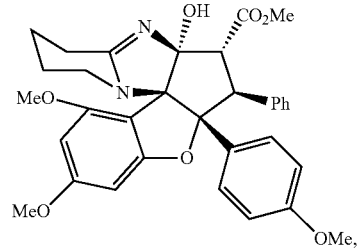
(9p)

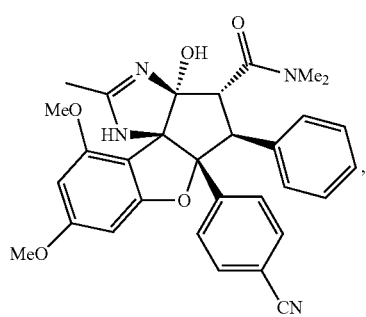
(Iad)
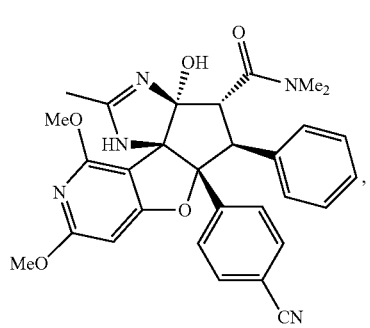
(Iae)
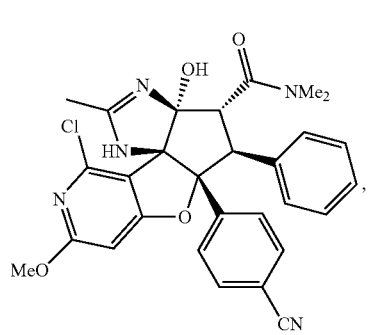
(Iaf)
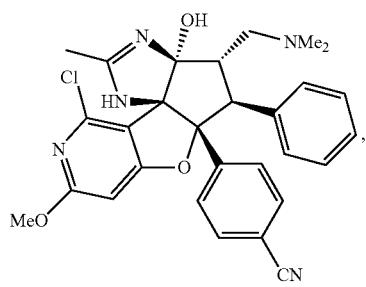
(Iag)
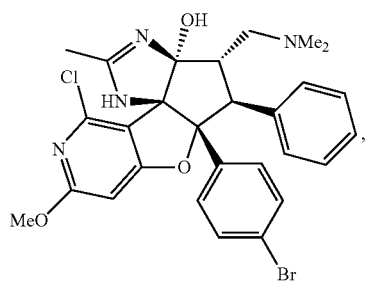
(Iah)
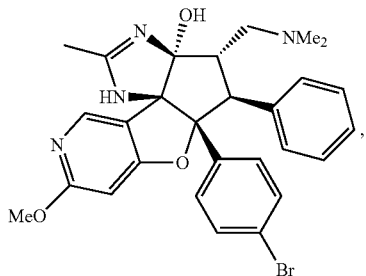
(Iai)
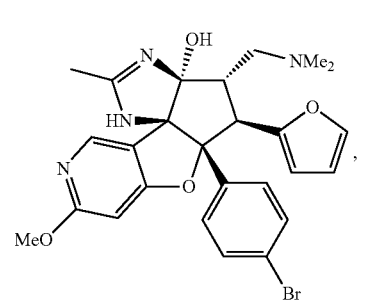
(Iaj)
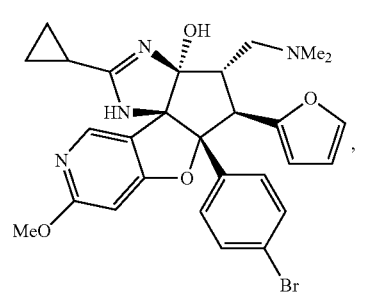
(Iak)
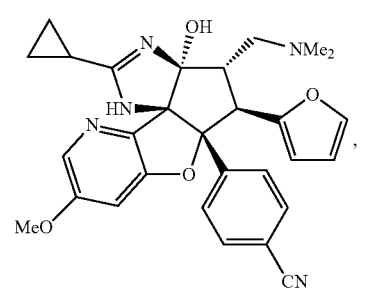
(Ial)
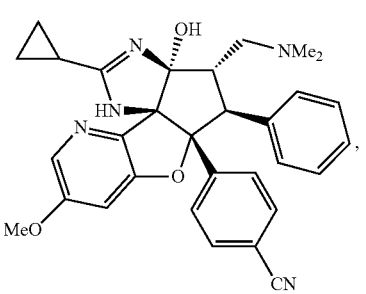
(Iam)

-continued
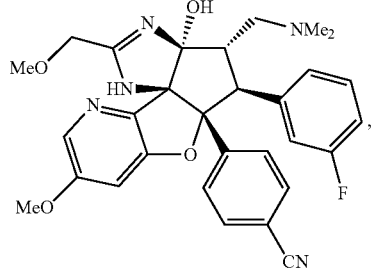
(Ian)
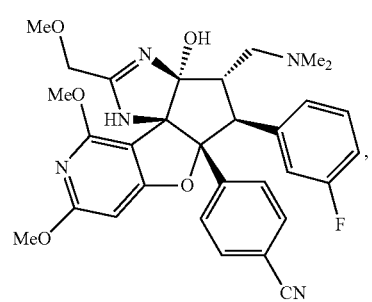
(Iao)
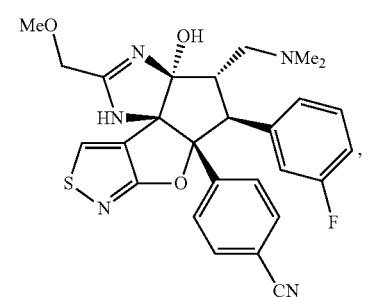
(Iap)
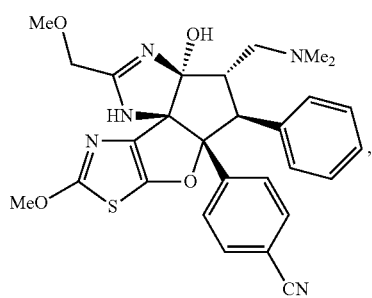
(Iaq)
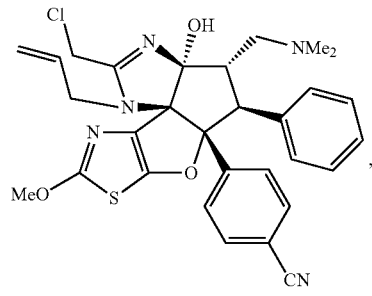
(Iar)
-continued
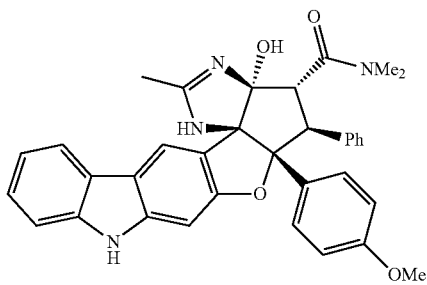
(Ias)
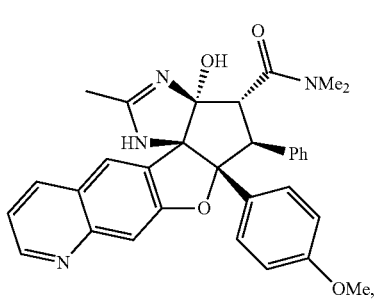
(Iat)
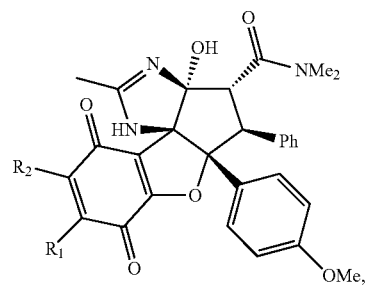
(Iau)
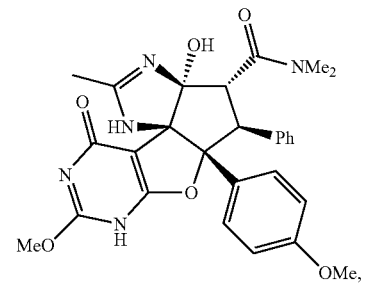
(Iav)
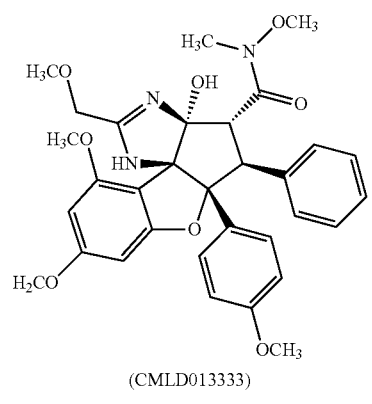
(CMLD013333)

-continued
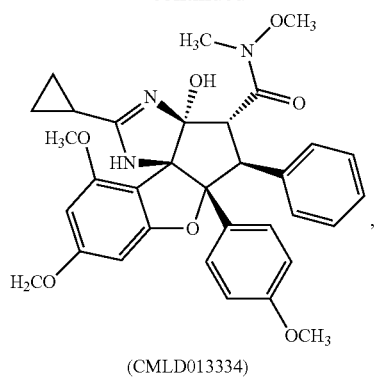
(CMLD013334)
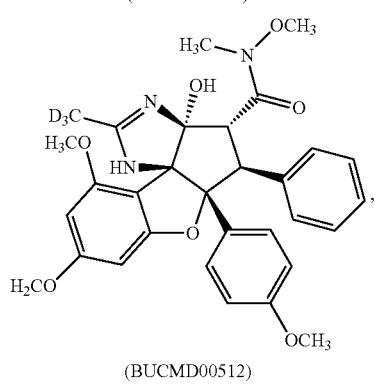
(BUCMD00512)
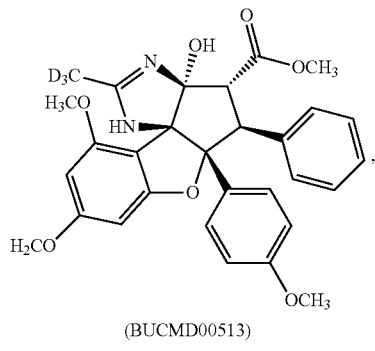
(BUCMD00513)
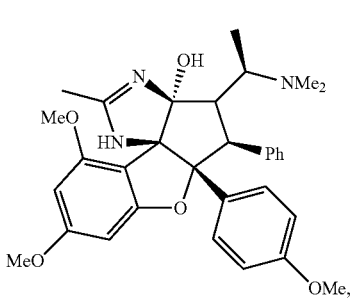
(Iaw)
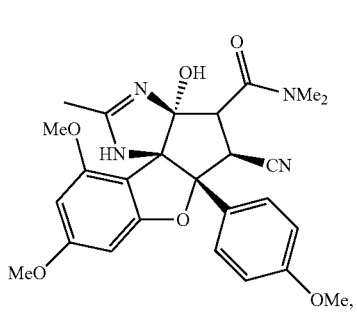
(Iax)
-continued
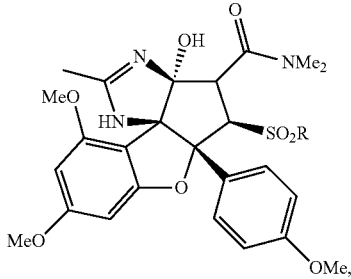
(Iaz)
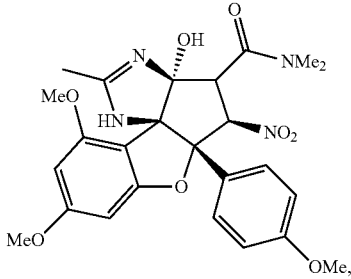
(Iba)
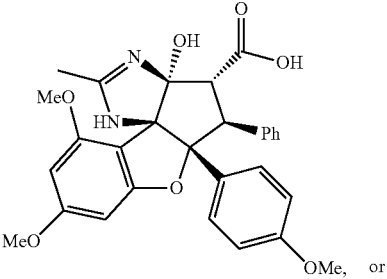
(Ibb)
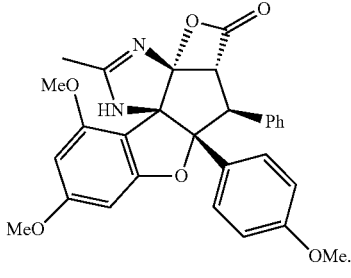
(Ibc)
In some embodiments, the compound of Formula (A) is selected from the following structures:
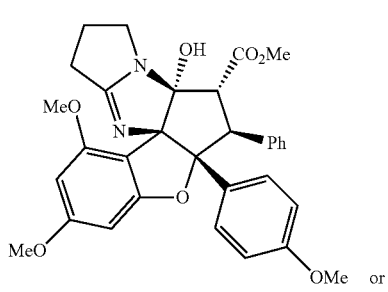
(IIa)
or -continued
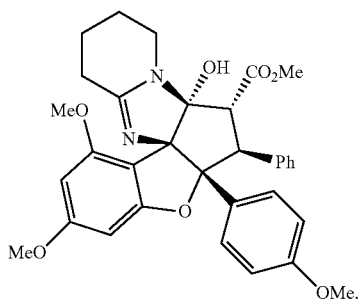
(IIb)
In some embodiments, the compound of Formula (B) is selected from the following structures:
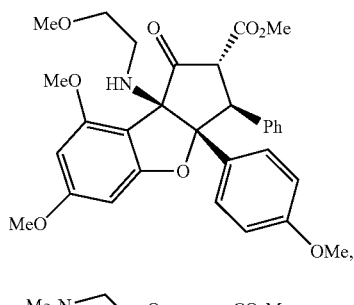
(15a)
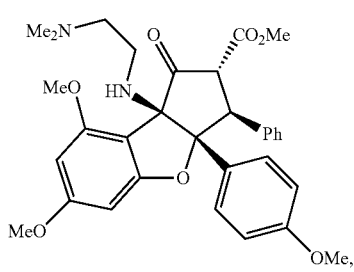
(15b)
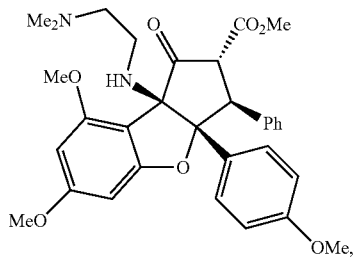
(15c)
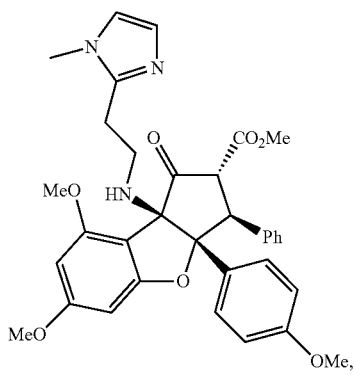
(15p)
-continued
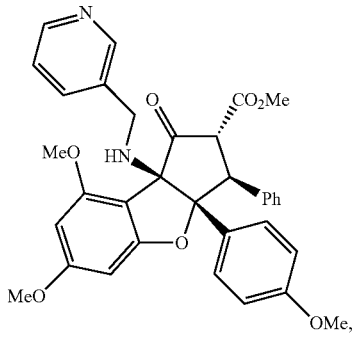
(15q)
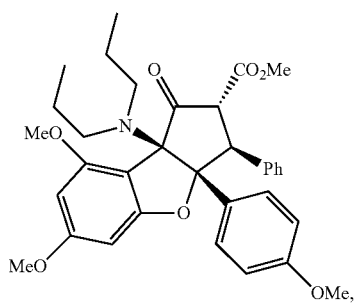
(15r)
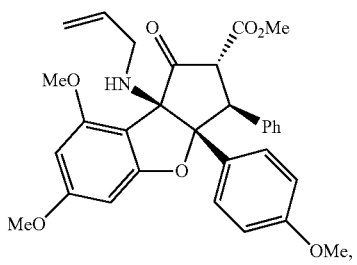
(15d)
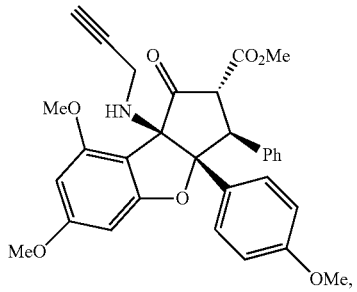
(15e)
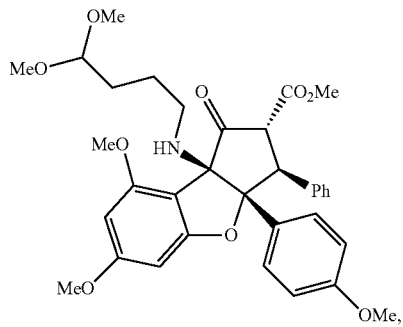
(15f)

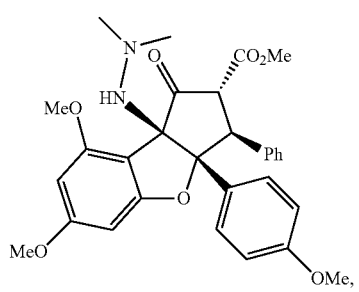
(15s)
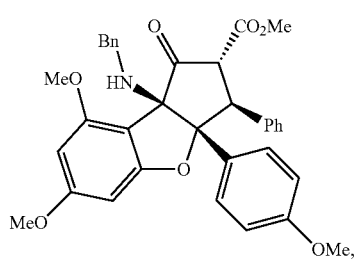
(15h)
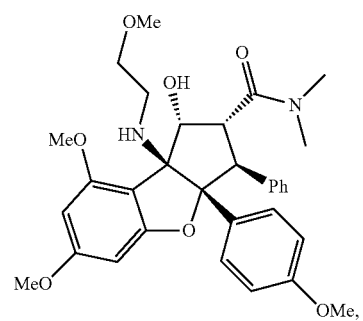
(18)
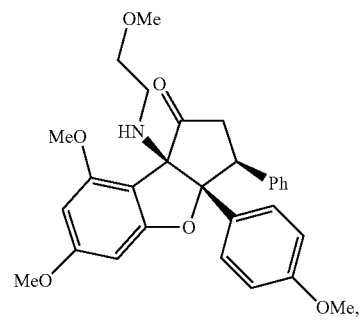
(19)
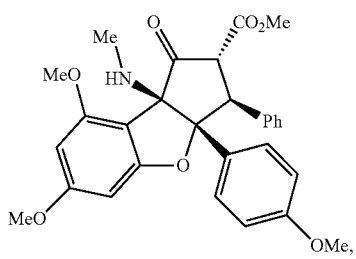
(22)
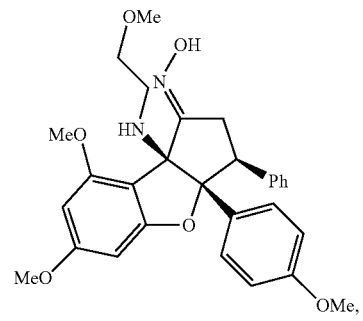
(21)
(15g)
(15l)
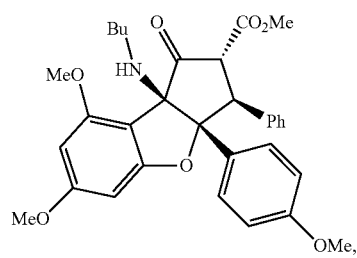
(15i)

-continued
(15j)
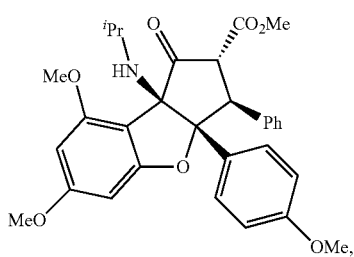
(15k)
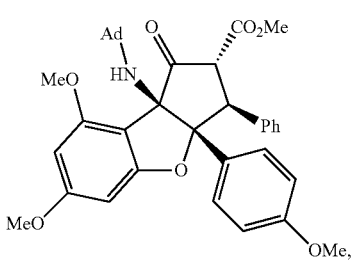
(20)
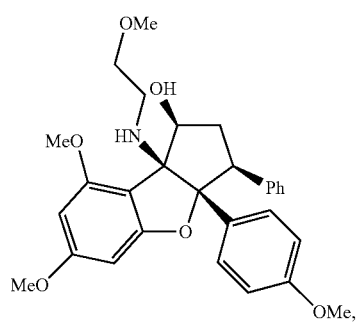
(15o)
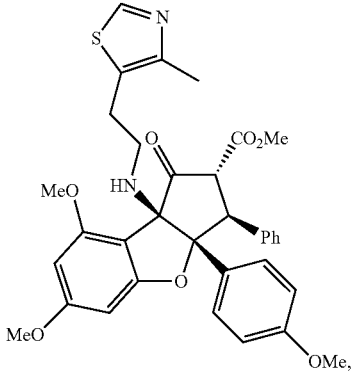
(15m)
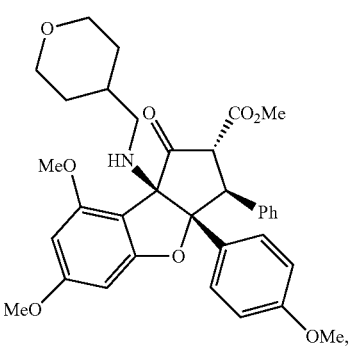
-continued
(15n)
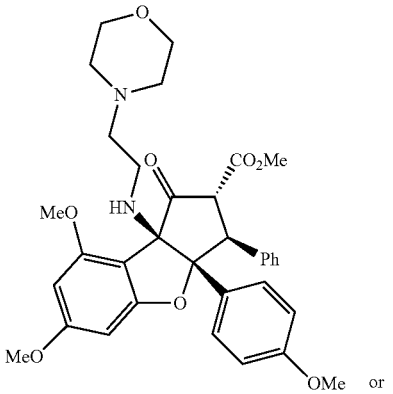
or
(16)
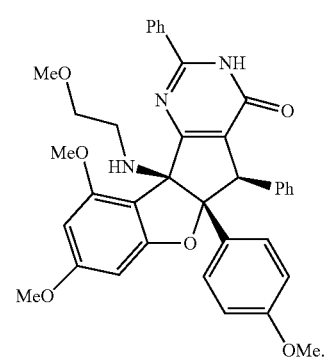
In some embodiments, the compound of Formula (A) is selected from the following structures;
(IVa)
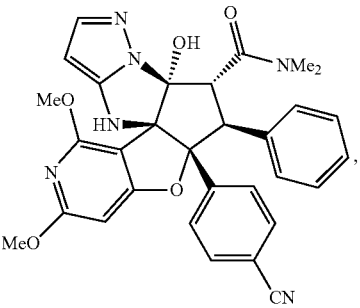
(IVb)
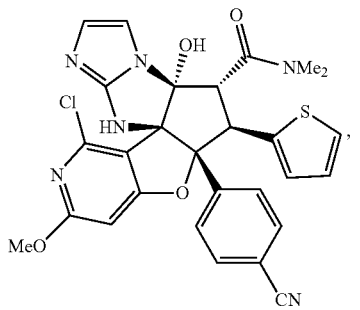

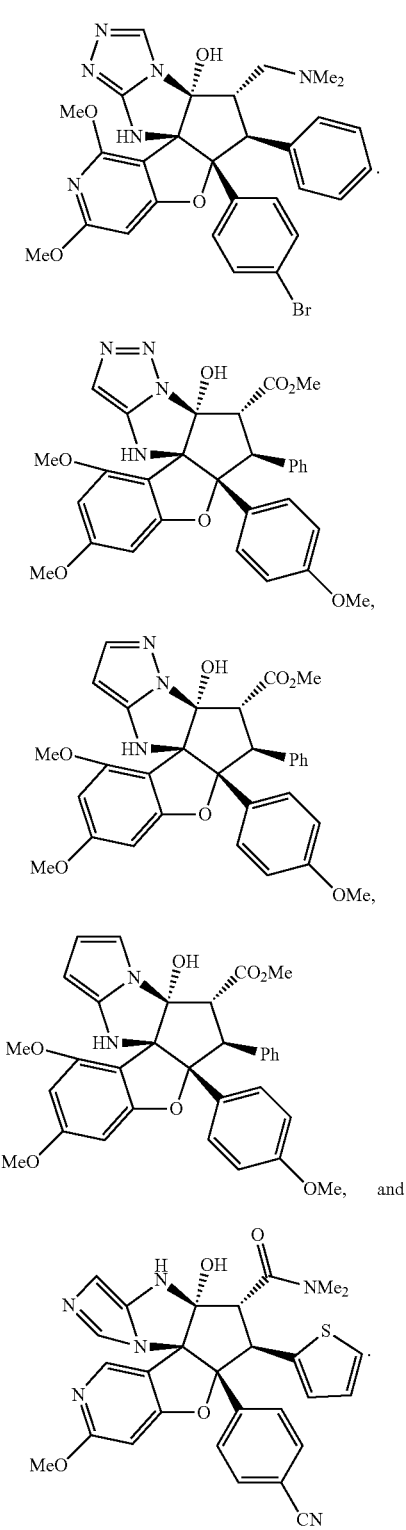

In some embodiments, for preparation of compounds of Formula (A) or Formula (B), a precursor such as compound (V) or (IX) is reacted with abase, as shown in Schemes 1 and 2. In some embodiments, the reaction is performed in a solution. For example, the precursor is partially or fully dissolved into the solution. In some embodiments, the solution comprises an inert solvent. For example, the solvent can include one or more organic solvent selected from ethers (e.g. diethyl ether, t-butyl ethers), tetrahydrofuran (THF), dimethylformamide (DMF), 4-Dimethylaminopyridine (DMAP), acetonitrile, alkanes (e.g. pentane, hexane), and aromatic solvents (e.g. toluene, m-xylene). In some embodiments, the solvent is THF. In some embodiments, the precursor concentration is between about 1 mM and 1 M in the solution (e.g. between about 0.05M and about 0.5 M, such as about 0.1 M).

In some embodiments, the base is selected from sodium hydride (NaH), lithium aluminum hydride, alkyl lithium salts (e.g. t-butyl lithium), sodium borohydride. In some embodiments, the base is NaH. In some embodiments, the base is used in excess of the precursor. For example, more than 1 equivalent is used (e.g. more than about 2 equivalents, more than about 3 equivalents, more than about 4 equivalents, more than about 5 equivalents, more than about 6 equivalents, more than about 7 equivalents, more than about 8 equivalents). In some embodiment the base has a pKa greater than about 16 (e.g. greater than about 16, 17, 18, 19, or 20).

In some embodiments, the precursor is cooled to a low temperature that is less than about 0° C. (e.g. less than about −20° C., less than about −40° C., less than about −60° C., less than about −80° C.) prior to reaction with the base. For example, in some embodiments, the solution can be cooled to −78° C. In some embodiment, the solution is maintained at the low temperature for at least 1 minute (e.g. at least 5 minutes, at least 30 min, at least one hour). In some embodiments, the reaction of the base with the precursor is allowed to proceed while warming the solution up from the low temperature, for example to room temperature (rt). For example, the solution is warmed to room temperature over more than about 5 minutes (e.g. over more than about 10 min, over more than about 30 min, over more than an hour). As used herein, room temperature is ambient temperature. For example, room temperature can be between about 20° C. and 35° C. In some embodiments, reaction of the base with the precursor is completed at any temperature between the low temperature and room temperature. By completed it is meant, without being bound to any specific mechanism, that a desired intermediate or intermediates are formed and can be reacted with a trapping agent to from the product (or another intermediate product). As used herein an "intermediate" can refer to one or more compounds that in some embodiments, can be structurally identified or are known, while in other embodiments they are not structurally identified or identifiable. In some embodiment the intermediates can be isolated while in other embodiments the intermediates cannot be isolated. In some embodiments, several intermediates are formed, for example, sequentially, at different temperatures. In some embodiments, a desired intermediate can be reacted with a compound such as (VI) or (X) which is the trapping agent. In some embodiments, the intermediate can be partially formed and trapped, for example, the precursor, base, intermediates and trapping agent can be present at one time in the solution while the product is being formed.

Products (e.g. intermediate or final products) can be isolated using any useful method. For example, a method selected from crystallization, concentration, distillation, drying, spray drying, precipitation, chromatographic separation, extraction, filtering or combinations thereof. In some embodiments, the products are isolated in greater than 50% yield, greater than 60%, greater than 70% yield, greater than 80% yield, greater than 90% or greater than 95% yield. In some embodiments, the products are isolated or can be further purified to provide an enantiomerically pure compound such as having greater than 80% ee or greater than 90% ee (e.g. >95% ee, >99% ee).

Some embodiments are for a composition comprising a compound of Formula (A) or Formula (B) and a pharmaceutically acceptable carrier, diluent or excipient. As used herein a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Also provide herein are pharmaceutical compositions containing a therapeutically effective amount of a compound described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g. oral, parenteral). Thus, for liquid oral preparations such as suspensions, elixirs, and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions according to some embodiments, one or more compounds described herein as the active ingredient is intimately admixed with a pharmaceutical carrier according to conventional pharmaceutical compounding techniques, which carrier may take a wide variety of forms depending of the form of preparation desired for administration, e.g. oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenteral administration, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g. tablet, capsule, powder, injection, teaspoonful, and the like, an amount of the active ingredient necessary to deliver an effective dose as described above. The pharmaceutical compositions herein will contain, per dosage unit, e.g. tablet, capsule, powder, injection, suppository, teaspoonful, and the like, of from about 0.01 mg to about 1000 mg or any amount or range therein, and may be given at a dosage of from about 0.01 mg/kg/day to about 300 mg/kg/day, or any amount or range therein, for example from about 0.1 mg/kg/day to about 50 mg/kg/day, or any amount or range therein, or for example from about 0.05 mg/kg/day to about 15 mg/kg/day, or any amount or range therein. In some embodiments, a recommended starting dosage is from 5 mg/kg/day to about 20 mg/kg/day, or any amount or range therein. In some embodiments, the dosage is administered over several smaller dosages, for example a 5 mg/kg/day can be administered in two dosages of 2.5 mg/kg approximately every 12 hours (e.g. 8 am and 8 pm). The dosages may be varied depending upon the requirement of the patients, the severity of the condition being treated and the compound being employed. The use of either daily administration or post-periodic dosing may be employed.

In some embodiments, these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the invention. In one embodiment, the solid preformulation composition is subdivided into unit dosage forms containing from about 0.01 mg to about 0.1 mg. In another embodiment, the solid preformulation composition is subdivided into unit dosage forms containing from about 0.05 mg to about 0.5 mg. In another embodiment, the solid preformulation composition is subdivided into unit dosage forms containing from about 0.1 mg to about 1 mg. In another embodiment, the solid preformulation composition is subdivided into unit dosage forms containing from about 0.5 mg to about 5 mg. In another embodiment, the solid preformulation composition is subdivided into unit dosage forms containing from about 1 mg to about 10 mg. In another embodiment, the solid preformulation composition is subdivided into unit dosage forms containing from about 5 mg to about 50 mg. In another embodiment, the solid preformulation composition is subdivided into unit dosage forms containing from about 10 mg to about 100 mg. In another embodiment, the solid preformulation composition is subdivided into unit dosage forms containing from about 50 mg to about 500 mg. In another embodiment, the solid preformulation composition is subdivided into unit dosage forms containing from about 250 mg to about 750 mg. In another embodiment, the solid preformulation composition is subdivided into unit dosage forms containing from about 500 mg to about 1000 mg.

The tablets or pills of the composition according to some embodiments, can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol, and cellulose acetate.

The liquid forms in which the compositions may be incorporated for administration orally or by injection include, aqueous solutions, suitably flavored syrups, aqueous or oil suspensions, and flavored emulsions with edible oils such as cottonseed oil, hemp seed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, or gelatin.

In some embodiments, a compound of Formula (A) or Formula (B) or a pharmecutical composition including one of more of these compounds is used for treatment of a subject or patient in need thereof. The subject is administered a therapeutically effective amount of one or more of these compounds.

The terms "administered" and "subjected" are used interchangeably in the context of treatment of a disease or disorder. Both terms refer to a subject being treated with an effective dose of a compound or pharmaceutical composition as described herein by methods of administration such as parenteral or systemic administration.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of a pharmaceutical composition comprising at least one rocaglate derivative as disclosed herein such that it enters the animal's system and, thus, is subject to metabolism and other like processes, for example, subcutaneous administration. In some embodiments, the administration is oral administration. Without limitations, oral administration can be in the form of solutions, suspensions, tablets, pills, capsules, sustained-release formulations, oral rinses, powders and the like.

The terms "treat", "treatment" and "treating" used interchangeably, with respect to treatment of a disease or disorder, mean preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis in a subject who is at risk of the disease, as well as slowing or reducing progression of existing disease. The term treating encompasses reducing or alleviating at least one adverse effect or symptom of a condition, disease or disorder associated with inappropriate proliferation, for example cancer.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g. monkey and human). In one embodiment, a patient is a human, such as a human infant (e.g. less than 1 years old), child (e.g. between 1 and 12 years old), adolescent (e.g. between 12 and 18 years old), adult (e.g. 18 to 65 years), or elderly (e.g. older than 65).

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a compound of the invention which, when administered to a subject, for example a human, is sufficient to effect treatment, as defined below, of a eIF4A related condition or disease in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

In certain embodiments, the disclosed compounds are useful for inhibiting the activity of eIF4A and/or can be useful in analyzing eIF4A signaling activity in model systems and/or for preventing, treating, or ameliorating a symptom associated with a disease, disorder, or pathological condition involving eIF4A, including a disease caused by a parasite, a virus, a fungus or a neurodegenerative disease requiring neuroprotection, for example one afflicting humans. A compound which inhibits the activity of eIF4A will be useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by eIF4A, such as, for example, haematological tumors, solid tumors, and/or metastases thereof, including leukaemias and myelodysplastic syndrome, Waldenstrom macroglobulinemia, and malignant lymphomas, for example, B-cell lymphoma, T-cell lymphoma, hairy cell lymphoma, Hodgkin's lymphoma, non-Hodgin's lymphoma, and Burkitt's lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof. In some embodiments, the eIF4A-dependent condition is diffuse large B-cell lymphoma, hepatocellular cancers, acute myeloid leukemia, breast cancer, colorectal cancer, small cell lung cancer, metastasis of tumors and non-small cell lung cancer. In some embodiments, the eIF4A-dependent condition is a drug resistant cancer.

In some embodiments, the compounds or pharmaceutically acceptable salt thereof may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e. sequentially; combination therapy is understood to include all these regimens.

In some embodiments, of the various aspects disclosed herein, the composition or method can further comprise administering an additional anti-cancer therapy to the subject. For example, administering a standard of care chemotherapeutic to the subject. Non-limiting examples of a standard of care chemotherapeutics or other anti-cancer therapy can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g. calicheamicin, especially calicheamicin gamma1I and calicheamicin omegaI(see, e.g. Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g. erlotinib (Tarceva®)) and VEGF-A that reduce cell proliferation and pharmaceutically acceptable salts, acids or derivatives of any of the above. Additional anti-cancer treatment can further include the use of radiation or radiation therapy. Further, the additional anti-cancer treatment can also include the use of surgical treatments.

In some embodiments, of the various aspects disclosed herein, the treatment is administered to a subject currently receiving standard of care chemotherapeutics or other alternative anti-cancer treatments. Generally, cancer treatment may involve one or more of the treatment options, but not limited to surgery, radiation, chemotherapy, immunotherapy, targeted therapy and hormonal therapy. The single agent therapy or current combination therapies for the treatment of cancer cause side effects such as nausea, rashes, swelling, flu-like symptoms, fatigue, digestive tract problems, allergic reactions and immunosuppression. In some embodiments, the invention described herein provides a more effective treatment of cancer by administering one or more compounds represented by Formula (A)-(III) in combination with other cancer treatments. In some embodiments, the combination therapy induces additive or synergistic therapeutic effect. In some embodiments, the method described herein can reduce or prevent one or more adverse effects or toxicities associated with the administration of a chemotherapeutic agent or radiation therapy. In some embodiments, the method described herein can increase the anti-tumor activity of a chemotherapeutic agent or radiation therapy or increase the selective cytotoxicity of a chemotherapeutic agent.

In some embodiments, the combination therapy includes administering therapeutic, diagnostic or preventive monoclonal antibodies. Without limitation these can be selected from comprising burosumab, brolucizumab, suvizumab, secukinumab, enfortumab vedotin, minretumomab, sacituzumab govitecan, pateclizumab, teprotumumab, caplacizumab, biciromab, duligotuzumab, metelimumab, olendalizumab, zolimomab aritox, belimumab, anifrolumab, rontalizumab, tefibazumab, ibi, nimotuzumab, zalutumumab, bivatuzumab mertansine, elezanumab, varlilumab, intetumumab, cixutumumab, ramucirumab, rilotumumab, volociximab, vesencumab, lirilumab, mitumomab, rovalpituzumab tesirine, sifalimumab, crizanlizumab, aselizumab, ligelizumab, bertilimumab, edobacomab, pagibaximab, afelimomab, nebacumab, golimumab, zanolimumab, fezakinumab, toralizumab, ocrelizumab, monalizumab, adalimumab, infliximab, sarilumab, clazakizumab, clenoliximab, fletikumab, gimsilumab, mavrilimumab, olokizumab, sirukumab, tocilizumab, ruplizumab, roledumab, idarucizumab, felvizumab, motavizumab, palivizumab, nirsevimab, tisotumab vedotin, pexelizumab, lerdelimumab, derlotuximab biotin, refanezumab, foravirumab, rafivirumab, briakinumab, siplizumab, efalizumab, guselkumab, itolizumab, mirikizumab, panobacumab, capromab pendetide, adecatumumab, gosuranemab, cedelizumab, daclizumab, odulimomab, basiliximab, muromonab-cd, blinatumomab, rmab, abciximab, brodalumab, netakimab, tadocizumab, eculizumab, ravulizumab, prasinezumab, clivatuzumab tetraxetan, oleclumab, placulumab, fulranumab, tanezumab, catumaxomab, citatuzumab bogatox, igovomab, abagovomab, farletuzumab, mirvetuximab soravtansine, oregovomab, pankomab, sofituzumab vedotin, denosumab, blosozumab, romosozumab, sulesomab, otilimab, ranevetmab, bleselumab, carlumab, suvratoxumab, tremelimumab, naptumomab estafenatox, anatumomab mafenatox, necitumumab, racotumomab, tislelizumab, bectumomab, ibritumomab tiuxetan, veltuzumab, satralizumab, dinutuximab, rinucumab, bimagrumab, stamulumab, landogrozumab, trevogrumab, ustekinumab, natalizumab, ublituximab, afasevikumab, alemtuzumab, opicinumab, lucatumumab, milatuzumab, daratumumab, elotuzumab, isatuximab, fremanezumab, eptinezumab, erenumab, galcanezumab, cabiralizumab, cetuximab, bevacizumab, etaracizumab, glembatumumab vedotin, pembrolizumab, flanvotumab, ipilimumab, pdr, relatlimab, spartalizumab, trbs, suptavumab, ecromeximab, ranibizumab, rituximab, detumomab, efungumab, diridavumab, besilesomab, letolizumab, abrilumab, etrolizumab, vobarilizumab, reslizumab, ozoralizumab, vepalimomab, tildrakizumab, fresolimumab, pamrevlumab, alirocumab, evolocumab, frovocimab, lodelcizumab, iratumumab, tnx-, brentuximab vedotin, ibalizumab, naxitamab, camrelizumab, exbivirumab, lenvervimab, libivirumab, emapalumab, atorolimumab, flotetuzumab, apolizumab, ulocuplumab, dacetuzumab, erlizumab, moxetumomab pasudotox, rovelizumab, emicizumab, gavilimomab, inolimomab, Depatuxizumab mafodotin, Lampalizumab, Solitomab, Arcitumomab, IMAB, DS-zolbetuximab, claudiximab, andecaliximab, bemarituzumab, tositumomab, simtuzumab, nemolizumab, porgaviximab, cosfroviximab, larcaviximab, bococizumab, evinacumab, ralpancizumab, domagrozumab, polatuzumab vedotin, utomilumab, urtoxazumab, lemalesomab, plozalizumab, otelixizumab, teplizumab, gevokizumab, crotedumab, regavirumab, sevirumab, cemiplimab, canakinumab, eldelumab, vedolizumab, visilizumab, certolizumab pegol, risankizumab, priliximab, fontolizumab, brazikumab, ravagalimab, SHP, matuzumab, votumumab, edrecolomab, cantuzumab mertansine, altumomab pentetate, bermekimab, labetuzumab, nacolomab tafenatox, panitumumab, sutimlimab, actoxumab, bezlotoxumab, lokivetmab, girentuximab, lenzilumab, TGN, ofatumumab, cirmtuzumab, lumiliximab, FBTA, obinutuzumab, tuvirumab, keliximab, sonepcizumab, inclacumab, imeiromab, cantuzumab ravtansine, taplitumomab paptox, bavituximab, inebilizumab, epratuzumab, dalotuzumab, drozitumab, enavatuzumab, ficlatuzumab, icrucumab, urelumab, pidilizumab, nofetumomab merpentan, satumomab pendetide, abituzumab, alacizumab pegol, amatuximab, anetumab ravtansine, ascrinvacumab, atezolizumab, avelumab, azintuxizumab vedotin, belantamab mafodotin, brontictuzumab, cbr-doxorubicin immunoconjugate, cergutuzumab amunaleukin, cetrelimab, cibisatamab, codrituzumab, cofetuzumab pelidotin, coltuximab ravtansine, conatumumab, cusatuzumab, demcizumab, denintuzumab mafodotin, dostarlimab, durvalumab, duvortuxizumab, elgemtumab, emactuzumab, emibetuzumab, enapotamab vedotin, enoblituzumab, ensituximab, futuximab, gancotamab, ganitumab, gatipotuzumab, iladatuzumab vedotin, imalumab, imgatuzumab, indatuximab ravtansine, indusatumab vedotin, lacnotuzumab, ladiratuzumab vedotin, lexatumumab, lifastuzumab vedotin, lilotomab satetraxetan, lintuzumab, loncastuximab tesirine, lorvotuzumab mertansine, losatuxizumab vedotin, lumretuzumab, mapatumumab, modotuximab, mosunetuzumab, narnatumab, navicixizumab, nesvacumab, nivolumab, ocaratuzumab, olaratumab, omburtamab, onartuzumab, ontuxizumab, otlertuzumab, parsatuzumab, pasotuxizumab, patritumab, pemtumomab, pertuzumab, pinatuzumab vedotin, radretumab, robatumumab, rosmantuzumab, samalizumab, samrotamab vedotin, seribantumab, sibrotuzumab, siltuximab, sirtratumab vedotin, tacatuzumab tetraxetan, tarextumab, tavolimab, telisotuzumab vedotin, tenatumomab, tepoditamab, tetulomab, tigatuzumab, timigutuzumab, tiragotumab, tomuzotuximab, tovetumab, tucotuzumab celmoleukin, vandortuzumab vedotin, vanticizumab, vanucizumab, vonlerolizumab, vorsetuzumab mafodotin, zatuximab, zenocutuzumab, ertumaxomab, margetuximab, trastuzumab, trastuzumab emtansine, pritumumab, marstacimab, concizumab, oportuzumab monatox, obiltoxaximab, dusigitumab, galiximab, camidanlumab tesirine, tabalumab, ianalumab, tibulizumab, teneliximab, ixekizumab, lulizumab pegol, OMS, dupilumab, tezepelumab, tralokinumab, mepolizumab, anrukinzumab, benralizumab, enokizumab, lebrikizumab, oxelumab, pascolizumab, quilizumab, perakizumab, fanolesomab, raxibacumab, bimekizumab, carotuximab, faricimab, varisacumab, lanadelumab, birtamimab, aducanumab, bapineuzumab, crenezumab, gantenerumab, ponezumab, solanezumab, ozanezumab, talizumab, gomiliximab, omalizumab, inotuzumab ozogamicin, istiratumab, mogamulizumab, figitumumab, pintumomab, fasinumab, vadastuximab talirine, gemtuzumab ozogamicin, SGN-CD A, Iomab-B, abrezekimab, aprutumab ixadotin, atidortoxumab, atinumab, begelomab, berlimatoxumab, bersanlimab, dapirolizumab pegol, dectrekumab, dezamizumab, dorlimomab aritox, elsilimomab, enlimomab pegol, enoticumab, epitumomab cituxetan, etigilimab, faralimomab, fibatuzumab, firivumab, foralumab, frunevetmab, gedivumab, gilvetmab, ifabotuzumab, imaprelimab, iscalimab, laprituximab emtansine, lendalizumab, leronlimab, lesofavumab, lupartumab amadotin, lutikizumab, nerelimomab, onvatilimab, pogalizumab, prezalizumab, pritoxaximab, remtolumab, rivabazumab pegol, romilkimab, rozanolixizumab, selicrelumab, setoxaximab, setrusumab talacotuzumab, vanalimab, vopratelimab, vunakizumab, xentuzumab, ziralimumab, blontuvetmab, maslimomab, morolimumab, namilumab, naratuximab emtansine, navivumab, orticumab, sontuzumab, tamtuvetmab, telimomab aritox, tesidolumab, timolumab, tosatoxumab, tregalizumab, vapaliximab, and vatelizumab.

In some embodiments, the compound such as (A) or (III) are administered to a patient with one or more additional antiviral agent. In some embodiments, the antiviral compound is one or more of ribavirin, daclatasvir, sofosbuvir, velpatasvir, ledipasvir/sofosbuvir, telaprevir, interferon aphacon-1, interferon alpha-2b, glecaprevir and pibrentasvir, simeprevir, pegylated interferon, pegylated interferon alpha-2b, interferon alpha-2a, elbasvir, and grazoprevir.

Furthermore, in some embodiments, the compounds and their pharmaceutical compositions are candidate therapeutics for the prophylaxis and/or therapy of cytokine related diseases, such as inflammatory diseases, allergies, or other conditions associated with proinflammatory cytokines. Exemplary inflammatory diseases include without limitation, chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, goodpasture's disease, crescentic, glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies. Yet further, the inventive compounds and their pharmaceutical compositions are candidate therapeutics for the prophylaxis and/or therapy of fibrotic diseases, such as various forms of fibrosis, fibromas or any disease giving rise to fibrosis whether as a main or a secondary symptom. Exemplary fibrotic diseases include without limitation, viral hepatitis, hepatic fibrosis, liver fibrosis, renal fibrosis, schistosomiasis, steatohepatitis (alcoholic or non-alcoholic (NASH)), cirrhosis, idiopathic pulmonary fibrosis (IPF), systemic sclerosis (scleroderma), nephrogenic systemic fibrosis (NSF), diabetes, untreated hypertension, heart attack, hypertension, atherosclerosis, restenosis, macular degeneration, retinal and vitreal retinopathy, keloids, hypertrophic scars, Crohn's disease and Alzheimer's disease.

Although inflammation is the unifying pathogenic process of these diseases, current therapies only treat the symptoms of the disease and not the underlying cause of inflammation. The compositions of the present invention are useful for the treatment and/or prophylaxis of inflammatory diseases and related complications and disorders.

To prepare a pharmaceutical composition according to some embodiments, a compound prepared according to any of the processes described herein as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain, the entirety of which is incorporated herein by reference.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc., the entirety of which are incorporated herein by reference.

For oral administration, the compositions in some embodiments, are provided in the form of tablets containing, about 0.01 mg, about 0.05 mg, about 0.1 mg, about 0.5 mg, about 1.0 mg, about 2.5 mg, about 5.0 mg, about 10.0 mg, about 15.0 mg, about 25.0 mg, about 50.0 mg, about 100 mg, about 150 mg, about 200 mg, about 250 mg, and/or about 500 mg of the active ingredient for the symptomatic adjustment of the dosage to the patient to be treated. An effective amount of the drug is ordinarily supplied at a dosage level of from about 0.01 mg % kg to about 500 mg/kg of body weight per day, or any amount or range therein. In some embodiments, the range is from about 0.1 to about 50.0 mg/kg of body weight per day, or any amount or range therein. In some embodiments, the dosage is from about 0.5 to about 15.0 mg/kg of body weight per day, or any amount or range therein. In some embodiments, the dosage is from about 1.0 to about 7.5 mg/kg of body weight per day, or any amount or range therein. In some embodiments, the dosage is from about 5 mg/kg/day to about 20 mg/kg/day or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known, and generally accepted cell and/or animal models are predictive of the ability of a test compound to treat or prevent a given disorder.

One skilled in the art will further recognize that human clinical trials, including first-in-human, dose ranging, and efficacy trials, in healthy patients and/or those suffering from a given disorder, may be completed according to methods well known in the clinical and medical arts.

"Antibody-drug conjugates" are targeted chemotherapeutic molecules comprising which combine properties of both antibodies and cytotoxic drugs by targeting potent cytotoxic drugs to antigen-expressing tumor cells (Teicher, B. A. (2009) Current Cancer Drug Targets 9: 982-1004), thereby enhancing the therapeutic index by maximizing efficacy and minimizing off-target toxicity (Carter, P. J. and Senter P. D. (2008) The Cancer Jour. 14(3): 154-169; Chari, R. V. (2008) *Acc. Chem. Res.* 4: 98-107. For example, as described in W2017214024A1 which is incorporated herein by referenc.

In some embodiments, the antibody-drug conjugate comprises an antibody covalently attached to a compound of Formula (A) or Formula (B). In some embodiments, these can be combined with antiviral drugs and cancer thereapies as described herein.

The term "antibody" herein is used in the broadest sense and specifically covers monoclonal antibodies, polyclonal antibodies, dimers, multimers, multispecific antibodies (e.g. bispecific antibodies), and antibody fragments, as long as they exhibit the desired biological activity (Miller et al. (2003) Jour, of Immunology 170:4854-4861). Antibodies may be murine, human, humanized, chimeric, or derived from other species. An antibody is a protein generated by the immune system that is capable of recognizing and binding to a specific antigen. (Janeway, C, Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full-length antibody, generally the antigen binding or variable region thereof. Examples of antibody fragments include Fab, Fab', F(ab')2, and Fv fragments; diabodies; linear antibodies; minibodies (Olafsen et al. (2004) Protein Eng. Design & Sel. 17(4):315-323), fragments produced by a Fab expression library, anti-idiotypic (anti-Id) antibodies, CDR (complementary determining region), and epitope-binding fragments of any described herein which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see for example: U.S. Pat. Nos. 4,816,567; 5,807,715). The monoclonal antibodies may also be isolated from phage antibody libraries using the techniques described in Clackson et al. (1991) *Nature,* 352:624-628; Marks et al. (1991) *J. Mol. Biol,* 222:581-597.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA,* 81: 6851-6855). Chimeric antibodies of interest herein include "primatized" antibodies comprising variable domain antigen-binding sequences derived from a non-human primate (e.g. Old World Monkey, Ape, etc.) and human constant region sequences.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. IgGi, IgG$_2$, IgG$_3$, IgGi, IgAi, and IgA$_2$. The heavy chain constant domains that correspond to the different classes of immunoglobulins are called α, δ, ε, γ, and μ, respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g. CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g. a non-human antibody, refers to an antibody that has undergone humanization.

An "intact antibody" herein is one comprising a VL and VH domains, as well as a light chain constant domain (CL) and heavy chain constant domains, CHI, CH2 and CH3. The constant domains may be native sequence constant domains (e.g. human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include CI q binding; complement dependent cytotoxicity; Fc receptor binding; antibody-dependent cell-mediated cytotoxicity (ADCC); phagocytosis; and down regulation of cell surface receptors such as B cell receptor and BCR. Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g. IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al. (1998) J. Immunol. 161:4083-4090; Lund et al. (2000) Eur. J. Biochem. 267:7246-7256; US 2005/0048572; US 2004/0229310).

A "cysteine-engineered antibody" or "cysteine-engineered antibody variant" is an antibody in which one or more residues of an antibody are substituted with cysteine residues. In accordance with the present disclosure, the thiol group(s) of the cysteine engineered antibodies can be conjugated to silvestrol to form a THIOMAB™ antibody (i.e., a THIOMAB™ drug conjugate (TDC), wherein in accordance with the present disclosure the drug is a silvestrol derivative). In particular embodiments, the substituted residues occur at accessible sites of the antibody. By substituting those residues with cysteine, reactive thiol groups are thereby positioned at accessible sites of the antibody and may be used to conjugate the antibody to the drug moiety to create an immunoconjugate, as described further herein. For example, a THIOMAB™ antibody may be an antibody with a single mutation of a non-cysteine native residue to a cysteine in the light chain (e.g. G64C, K149C or R142C according to Kabat numbering) or in the heavy chain (e.g. D 101 C or V184C or T205C according to Kabat numbering). In specific examples, a THIOMAB™ antibody has a single cysteine mutation in either the heavy or light chain such that each full-length antibody (i.e., an antibody with two heavy chains and two light chains) has two engineered cysteine residues. Cysteine engineered antibodies and preparatory methods are disclosed by US 2012/0121615 A1 (incorporated by reference herein in its entirety).

In some embodiments, antibodies that provide for site-specific conjugation of a drug to the antibody through cysteine substitutions at sites where the engineered cysteines are available for conjugation but do not perturb immunoglobulin folding and assembly or alter antigen binding and effector functions are used as describe in Junutula, et al, 2008b Nature Biotech., 26(8): 925-932; Doman et al. (2009) Blood 1 14(13):2721-2729; U.S. Pat. Nos. 7,521,541; 7,723, 485; and WO2009/052249; all of which are herein incorporated by reference. These THIOMAB™ antibodies can then be conjugated to any of the rocaglate derivatives described herein through the engineered cysteine thiol groups to obtain THIOMAB™ drug conjugates (TDC) with uniform stoichiometry (e.g. up to 2 drugs per antibody in an antibody that has a single engineered cysteine site).

A "Linker" (L) is a bifunctional or multifunctional moiety that can be used, according to some embodiments, to link one or more of the Rocaglate compounds (I), (II), (III) (IV) or (IV') to an antibody (Ab) to form an antibody-drug conjugate (ADC) of Formulas Ila and lib. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In some embodiments, a linker has a functionality that is capable of reacting with a free cysteine present on an antibody to form a covalent bond. Nonlimiting exemplary such reactive functionalities include maleimide, haloacetamides, haloacetyl, pyridyl disulfide, activated esters such as succinimide esters, N-hydroxysuccinimide, 4-nitrophenyl esters, pentafluorophenyl esters, tetrafluorophenyl esters, anhydrides, acid chlorides, sulfonyl chlorides, isocyanates, and isothiocyanates. For example, see the conjugation method on page 766 of Klussman et. al. (2004), *Bioconjugate Chemistry* 15(4): 765-773 and the examples cited therein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary reactive functionalities include, but are not limited to, hydrazide, oxime, amino, hydrazine, thiosemicarbazone, hydrazine carboxylate, and arylhydrazide groups.

A linker may comprise one or more linker components, including but not limited to, a stretcher unit, a peptidomimetic unit, a peptide unit, and a spacer unit. Exemplary linker components include 6-maleimidocaproyl ("MC"), maleimidopropanoyl ("MP"), valine-citrulline ("val-cit" or "vc"), alanine-phenylalanine ("ala-phe"), phenylalanine-lysine (phe-lys), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g. comprising hydrazone), protease-sensitive (e.g. peptidase-sensitive) linkers, photolabile linkers, or disulfide-containing linkers (Chari et. al. Cancer Research 52: 127-131 (1992); U.S. Pat. No. 5,208,020).

Exemplary embodiments of linkers are described in U.S. Pat. No. 7,498,298, which is expressly incorporated herein by reference.

Embodiments of various aspects described herein can be defined as in any of the following numbered paragraphs:

1. A compound of Formula (A) or stereoisomers, tautomers, or pharmaceutically acceptable salts thereof.
2. The compound of paragraph 1, wherein the compound is of Formula (A').
3. The compound of paragraph 1 or 2, wherein the regioselectivity of $R_{11}$ is either α or β
4. The compound of any one of paragraphs 1-3, wherein $W_{10}$ is $CHR_{16}$.
5. The compound of any one of paragraphs 1-7, wherein $W_{10}$ is $C(O)R_{12}$.
6. The compound of any one of paragraphs 1-4, wherein $R_{16}$ is H or $C_1$-$C_8$(alkyl).
7. The compound of any one of paragraphs 1-5, wherein $R_{16}$ is H, methyl, ethyl, propyl, isopropyl, 1-methylpropyl, 2-methylpropyl, butyl, isobutyl, or pentyl.
8. The compound of any one of paragraphs 1-6, wherein $R_{16}$ is H or methyl.
9. The compound of any one of paragraphs 1-8, wherein $X_{10}$ is O, S or $NR^A$.
10. The compound of any one of paragraphs 1-9, wherein $X_{10}$ is O, S, NH, $N(C_1$-$C_8)$alkyl.
11. The compound of any one of paragraphs 1-10, wherein $X_{10}$ is O.
12. The compound of any one of paragraphs 1-11, wherein $Z_{10}$ is $NR_{15}'$.
13. The compound of any one of paragraphs 1-12, wherein one of $R_{15}$ and $R_{15}'$ is H, $(C_1$-$C_8)$alkyl, aryl, heteroaryl, heteroalkyl, cycloalkyl, acyl, allyl, CN, $NH_2$, $NH[(C_1$-$C_8)$alkyl], $N[(C_1$-$C_8)$alkyl]$_2$, OMe, SMe, $SO_3R^A$, OH, or SH, or together with $R_{17}$ forms a second bond between the nitrogen and carbon atoms they are attached to.
14. The compound of any one of paragraphs 1-13, wherein one of $R_{15}$ and $R_{15}'$ is H or $(C_1$-$C_8)$alkyl, or together with $R_{17}$ forms a second bond between the nitrogen and carbon atoms they are attached to.
15. The compound of any one of paragraphs 1-14, wherein one of $R_{15}$ and $R_{15}'$ is H, or together with $R_{17}$ forms a second bond between the nitrogen and carbon atoms they are attached to.
16. The compound of any one of paragraphs 1-15, wherein $R_{15}$ is is H, $(C_1$-$C_8)$alkyl, aryl, heteroaryl, heteroalkyl, cycloalkyl, acyl, allyl, CN, $NH_2$, $NH[(C_1$-$C_8)$alkyl], $N[(C_1$-$C_8)$alkyl]$_2$, OMe, SMe, $SO_3R^A$, OH, or SH, or $R_{15}$ together with $R_{17}$ forms a second bond between the nitrogen and carbon atoms they are attached to.
17. The compound of any one of paragraphs 1-16, wherein $R_{15}$ is H or $(C_1$-$C_8)$alkyl, or SH, or $R_{15}$ together with $R_{17}$ forms a second bond between the nitrogen and carbon atoms they are attached to.
18. The compound of any one of paragraphs 1-17, wherein $R_{15}$ is H, or SH, or $R_{15}$ together with $R_{17}$ forms a second bond between the nitrogen and carbon atoms they are attached to.
19. The compound of any one of paragraphs 1-18, wherein $R_{15}'$ is H, $(C_1$-$C_8)$alkyl, aryl, heteroaryl, heteroalkyl, cycloalkyl, acyl, allyl, CN, $NH_2$, $NH[(C_1$-$C_8)$alkyl], $N[(C_1$-$C_8)$alkyl]$_2$, OMe, SMe, $SO_3R^A$, OH, or SH, or SH, or $R_{15}'$ together with $R_{17}$ forms a second bond between the nitrogen and carbon atoms they are attached to.
20. The compound of any one of paragraphs 1-19, wherein $R_{15}'$ is H or $(C_1$-$C_8)$alkyl, or $R_{15}'$ together with $R_{17}$ forms a second bond between the nitrogen and carbon atoms they are attached to.
21. The compound of any one of paragraphs 1-20, wherein $R_{15}'$ is H, or $R_{15}'$ together with $R_{17}$ forms a second bond between the nitrogen and carbon atoms they are attached to.
22. The compound of any one of paragraphs 1-21, wherein one of $R_{15}$ or $R_{15}'$ together with $R_{17}$ forms a second bond between the nitrogen and carbon atoms they are attached to.
23. The compound of any one of paragraphs 1-22, wherein $R_{15}$ together with $R_{17}$ forms a second bond between the nitrogen and carbon atoms they are attached to.
24. The compound of any one of paragraphs 1-23, wherein $R_{15}'$ together with $R_{17}$ forms a second bond between the nitrogen and carbon atoms they are attached to.
25. The compound of any one of paragraphs 1-24, wherein $M_{10}$ is $C(R_{14}R_{17})$.
26. The compound of any one of paragraphs 1-25, wherein $M_{10}$ is $C(R_{14}R_{17})$ and $Z_{10}$ is $NR_{15}'$, optionally one of $R_{15}$ or $R_{15}'$ together with $R_{17}$ forms a second bond between the nitrogen and carbon atoms they are attached to.
27. The compound of any one of paragraphs 1-24, wherein $M_{10}$ is C(O), C(S) or C=$NR_{14}$.
28. The compound of any one of paragraphs 1-24, wherein $M_{10}$ is C(O), C(S) or C=$NR_{14}$ and $Z_{10}$ is $NR_{15}'$, optionally, $R_{15}$ and $R_{15}'$ are H.
29. The compound of any one of paragraphs 1-24, wherein $M_{10}$ is S(=O)$R_{14}R_{17}$.
30. The compound of any one of paragraphs 1-25, wherein $M_{10}$ is S(=O)$R_{14}R_{17}$ and $Z_{10}$ is $NR_{15}'$.
31. The compound of any one of paragraphs 1-26, wherein $M_{10}$ is S(=O)$R_{14}R_{17}$ and $Z_{10}$ is $NR_{15}'$, and wherein $R_{17}$ and $R_{15}'$ together form a double bond.
32. The compound of any one of paragraphs 1-24, wherein $M_{10}$ is S(O).
33. The compound of any one of paragraphs 1-24, wherein $M_{10}$ is $S(O_2)$.
34. The compound of any one of paragraphs 1-33, wherein $R_{14}$ is H, $(C_1$-$C_8)$alkyl, $OR^A$, aryl, heteroaryl, cycloalkyl, heterocyclyl, acyl, allyl, CN, $NH_2$, $NH[(C_1$-$C_8)$alkyl], $N[(C_1$-$C_8)$alkyl]$_2$, OMe, SMe, OH, or $C(R_{18}R_{19})R_{20}$.
35. The compound of any one of paragraphs 1-34, wherein $R_{14}$ is $(C_1$-$C_8)$alkyl, $OR^A$, aryl, heteroaryl, cycloalkyl, heterocylyl, allyl, OH, $NH_2$, $NH[(C_1$-$C_8)$alkyl], $N[(C_1$-$C_8)$alkyl]$_2$, SMe, or $C(R_{18}R_{19})R_{20}$.
36. The compound of any one of paragraphs 1-35, wherein $R^A$ is H or $(C_1$-$C_8)$alkyl.
37. The compound of any one of paragraphs 1-35, wherein $R^A$ is methyl, ethyl, butyl, propyl, isopropyl, 1-methyl propyl, 2-methyl, butyl, t-butyl, or pentyl,
38. The compound of any one of paragraphs 1-36, wherein $R_{14}$ is methyl, ethyl, butyl, propyl, isopropyl, 1-methyl propyl, 2-methyl, butyl, t-butyl, pentyl, methoxy, ethoxy, propoxy, butoxy, pentoxy, $CD_3$, $CF_3$, allyl, OH, $NH_2$, $NMe_2$, NHMe, phenyl, substituted phenyl, pyridinyl, substituted pyridinyl, thiazolyl, substituted thiazolyl, cyclopropyl, cyclobutyl, morpholinyl, substituted morpholinyl, piperidinyl, substituted piperdinyl, or $C(R_{18}R_{19})R_{20}$.

39. The compound of anyone of paragraphs 1-38, wherein two of $R_{18}$, $R_{19}$ and $R_{20}$ are same.

40. The compound of any one of paragraphs 1-39, wherein at least one of $R_{18}$, $R_{19}$ and $R_{20}$ is H, F, Cl, Br, I or an electrophile.

41. The compound of any one of paragraphs 1-40, wherein $R_{18}$ and $R_{19}$ are independently H, F, Cl, Br, I or an electrophile.

42. The compound of any one of paragraphs 1-41, wherein $R_{18}$ and $R_{19}$ are F.

43. The compound of any one of paragraphs 1-42, wherein $R_{20}$ is $(C_1-C_8)$alkyl.

44. The compound of any one of paragraphs 1-43, wherein $R_{20}$ is methyl, ethyl, butyl, propyl, isopropyl, 1-methyl propyl, 2-methyl, butyl, t-butyl or pentyl.

45. The compound of any of any one of paragraphs 1-44, wherein $R_{10}$ is H, $(C_1-C_8)$alkyl, $(C_1-C_8)$haloalkyl, $(C_2-C_8)$alkenyl), $(C_2-C_8)$alkynyl, aryl, heteroaryl, cycloalkyl or heterocyclyl.

46. The compound of any one of paragraphs 1-45, wherein $R_{10}$ is aryl or heteroaryl.

47. The compound of any one of paragraphs 1-46, wherein $R_{10}$ is aryl.

48. The compound of any one of paragraphs 1-47, wherein $R_{10}$ is phenyl, optionally substituted with 1, 2 or 3 independently selected substituents.

49. The compound of any one of paragraphs 1-48, wherein $R_{10}$ is phenyl, optionally substituted with one substituent at the para position.

50. The compound of any one of paragraphs 1-49, wherein $R_{10}$ is phenyl, 4-methoxyphenyl, 4-cyanophenyl, 4-bromophenyl, or 4-fluorophenyl.

51. The compound of any one of paragraphs 1-50, wherein $R_{11}$ is aryl, heteroaryl, CN, $SO_2R^A$, $NO_2$, $C(O)O(C_1-C_8)$alkyl, $(C_2-C_8)$alkenyl), $C(O)NR^AR^B$ or $-CO_2H$.

52. The compound of any one of paragraphs 1-51, wherein $R_{11}$ is aryl, heteroaryl, CN, $SO_2R^A$, or $NO_2$.

53. The compound of any one of paragraphs 1-52, wherein $R_{11}$ is aryl or heteroaryl.

54. The compound of any one of paragraphs 1-53, wherein $R_{11}$ is thiophenyl or phenyl optionally substituted with 1, 2 or 3 independently selected substituents.

55. The compound of any one of paragraphs 1-54, wherein $R_{11}$ is thiophenyl or phenyl, optionally substituted with one substituent.

56. The compound of any one of paragraphs 1-55, wherein $R_{11}$ is thiophenyl, phenyl, 3-fluorophenyl, or 3-bromophenyl.

57. The compound of any one of paragraphs 1-56, wherein $R_{10}$ and $R_{11}$ have syn relative stereochemistry.

58. The compound of any one of paragraphs 1-57, wherein $R_{12}$ is H, OH, aryl, heteroaryl, cycloalkyl, $C_1-C_8$(alkyl), $O(C_1-C_8)$alkyl, $N[O(C_1-C_8)$alkyl][$(C_1-C_8)$alkyl], $NH[(C_1-C_8)$alkyl], $N(OMe)(C_1-C_8)$alkyl, $NH[(C_1-C_8)$alkyl] or $N[(C_1-C_8)$alkyl]$_2$, or $R_{12}$ and $R_{13}$ together with the carbon atoms they are attached to form a 3-8 membered heterocyclyl, e.g., $R_{12}$ forms a bond between $W_{10}$ and $R_{13}$.

59. The compound of any one of paragraphs 1-58, wherein $R_{12}$ is H, $(C_1-C_8)$alkyl, $O(C_1-C_8)$alkyl, $N[O-(C_1-C_8)$alkyl)]$(C_1-C_8)$alkyl, or $N[(C_1-C_8)$alkyl]$_2$, or $R_{12}$ and $R_{13}$ together with the carbon atoms they are attached to form a 3-8 membered heterocyclyl, e.g., $R_{12}$ forms a bond between $W_{10}$ and $R_{13}$.

60. The compound of any one of paragraphs 1-59, wherein $R_{12}$ is H, methyl, ethyl, propyl, isopropyl, butyl, methoxy, ethoxy, propoxy, isopropoxy, butoxy, $N(OMe)(C_1-C_8)$alkyl, or $N[(C_1-C_8)$alkyl]$_2$, or $R_{12}$ and $R_{13}$ together with the carbon atoms they are attached to form a 3-8 membered heterocyclyl, e.g., $R_{12}$ forms a bond between $W_{10}$ and $R_{13}$.

61. The compound of any one of paragraphs 1-60, $R_{12}$ is H, methyl, methoxy, $N(OMe)CH_3$ or $N(CH_3)_2$, or $R_{12}$ and $R_{13}$ together with the carbon atoms they are attached to form a 3-8 membered heterocyclyl, e.g., $R_{12}$ forms a bond between $W_{10}$ and $R_{13}$.

62. The compound of any one of paragraphs 1-61, wherein $R_{13}$ is OH, SH, $NH_2$, $NH[(C_1-C_8)$alkyl] or $N[(C_1-C_8)$alkyl]$_2$, or $R_{12}$ and $R_{13}$ together with the carbon atoms they are attached to form a 3-8 membered heterocyclyl, e.g., $R_{12}$ forms a bond between $W_{10}$ and $R_{13}$.

63. The compound of any one of paragraphs 1-62, wherein $R_{13}$ is OH, or $R_{12}$ and $R_{13}$ together with the carbon atoms they are attached to form a 3-8 membered heterocyclyl, e.g., $R_{12}$ forms a bond between $W_{10}$ and $R_{13}$.

64. The compound of any one of paragraphs 1-63, wherein $R_{12}$ and $R_{13}$ together with the carbon atoms they are attached to form a 3-8 membered heterocyclyl, e.g., $R_{12}$ forms a bond between $W_{10}$ and $R_{13}$.

65. The compound of any one of paragraphs 1-64, wherein $X_{10}$ is O, S, NH, $N(C_1-C_8)$alkyl; N(aryl), N(heteroaryl), N(cycloalkyl), or $N[(C(O)O(C_1-C_8)$alkyl]; $R_{10}$ is an aryl or heteroaryl; $R_{11}$ is aryl, heteroaryl, $C(O)O(C_1-C_8)$alkyl, $(C_2-C_8)$alkenyl), $C(O)NR^AR^B$ or $-CO_2H$; $W_{10}$ is $C(=Y_{10})$ where $Y_{10}$ is O, NH, S, NHOH, or NHOMe; $R_{12}$ is H, OH, aryl, heteroaryl, cycloalkyl, $C_1-C_8$(alkyl), $O(C_1-C_8)$alkyl, $N[O(C_1-C_8)$alkyl]][$(C_1-C_8)$alkyl], $NH[(C_1-C_8)$alkyl], $N(OMe)(C_1-C_8)$alkyl, $NH[(C_1-C_8)$alkyl] or $N[(C_1-C_8)$alkyl]$_2$; $R_{13}$ is OH, SH, $NH_2$, $NH[(C_1-C_8)$alkyl] or $N[(C_1-C_8)$alkyl]$_2$; $R_{14}$ is H, $(C_1-C_8)$alkyl, aryl, heteroaryl, heteroalkyl, cycloalkyl, acyl, allyl, CN, $NH_2$, $NH[(C_1-C_8)$alkyl], $N[(C_1-C_8)$alkyl]$_2$, OMe, SMe, or OH; and $R_{15}$ is is H, $(C_1-C_8)$alkyl, aryl, heteroaryl, heteroalkyl, cycloalkyl, acyl, allyl, CN, $NH_2$, $NH[(C_1-C_8)$alkyl], $N[(C_1-C_8)$alkyl]$_2$, OMe, SMe, $SO_3R^A$, OH, or SH, optionally, $R_{12}$ and $R_{13}$ together with the carbon atoms they are attached to form a 3-8 membered cyclyl or heterocyclyl.

66. The compound of any one of paragraphs 1-65, wherein $X_{10}$ is O and $R_{12}$ is aryl, heteroaryl, $C_1-C_8$(alkyl), $O(C_1-C_8)$alkyl, $N[O(C_1-C_8)$alkyl]][$(C_1-C_8)$alkyl], $N(OMe)(C_1-C_8)$alkyl, $NH[O(C_1-C_8)$alkyl]$_2$, $N[(C_1-C_8)$alkyl]$_2$, or $NH[(C_1-C_8)$alkyl], optionally, $R_{12}$ and $R_{13}$ together with the carbon atoms they are attached to form a 3-8 membered cyclyl or heterocyclyl.

67. The compound of paragraph 1-66, wherein $X_{10}$ is O; $R_{10}$ is aryl; $R_{11}$ is aryl; $R_{13}$ is OH; $R_{14}$ is $(C_1-C_8)$alkyl, cycloalkyl, or $NH_2$; and $R_{15}$ is $(C_1-C_8)$alkyl, cycloalkyl, or $NH_2$.

68. The compound of any one of paragraphs 1-65, wherein $X_{10}$ is O, S, C(O), NH, $N(C_1-C_8)$alkyl; N(aryl), N(heteroaryl), N(cycloalkyl), $N[(C(O)O(C_1-C_8)$alkyl]; $R_{10}$ is an aryl or heteroaryl; $R_{11}$ is aryl, heteroaryl, C(O)O($C_1$-$C_8$)alkyl, ($C_2$-$C_8$)alkenyl), C(O)NR$^D$R$^E$ or —$CO_2$H; $W_{10}$ is $CH_2$; $R_{12}$ is H, OH, aryl, heteroaryl, cycloalkyl, $C_1$-$C_8$(alkyl), O($C_1$-$C_8$)alkyl, N(OMe)($C_1$-$C_8$)alkyl, NH[(($C_1$-$C_8$)alkyl) or N[($C_1$-$C_8$)alkyl]$_2$; $R_{13}$ is OH, SH, $NH_2$, NH[($C_1$-$C_8$)alkyl] or N[($C_1$-$C_8$)alkyl]$_2$; $R_{14}$ is H, ($C_1$-$C_8$)alkyl, aryl, heteroaryl, heteroalkyl, cycloalkyl, acyl, allyl, CN, $NH_2$, NH[($C_1$-$C_8$)alkyl], N[($C_1$-$C_8$)alkyl]$_2$, OMe, SMe, OH; and $R_{15}$' is H, ($C_1$-$C_8$)alkyl, aryl, heteroaryl, heteroalkyl, cycloalkyl, acyl, allyl, CN, $NH_2$, NH[($C_1$-$C_8$)alkyl], N[($C_1$-$C_8$)alkyl]$_2$, OMe, SMe, $SO_3R^D$, OH, or SH, optionally, $R_{12}$ and $R_{13}$ together with the carbon atoms they are attached to form a 3-8 membered cyclyl or heterocyclyl.

69. The compound of any one of paragraphs 1-67, wherein $X_{10}$ is O, S, NH, N($C_1$-$C_8$)alkyl; N(aryl), N(heteroaryl), N(cycloalkyl), or N[(C(O)O($C_1$-$C_8$)alkyl]; $R_{10}$ is an aryl or heteroaryl; $R_{11}$ is aryl, heteroaryl, C(O)O($C_1$-$C_8$)alkyl, ($C_2$-$C_8$)alkenyl), C(O)NR$^D$R$^E$ or —$CO_2$H; $W_{10}$ is $Y_{20}$ where $Y_{20}$ is O, NH, S, NHOH, or NHOMe; $R_{12}$ is H, OH, aryl, heteroaryl, cycloalkyl, $C_1$-$C_8$(alkyl), O($C_1$-$C_8$)alkyl, N[($C_1$-$C_8$)alkyl]$_2$, N[O($C_1$-$C_8$)alkyl][($C_1$-$C_8$)alkyl], N(OMe)($C_1$-$C_8$)alkyl, NH[($C_1$-$C_8$)alkyl] or N[($C_1$-$C_8$)alkyl]$_2$; $R_{13}$ is OH, SH, $NH_2$, NH[($C_1$-$C_8$)alkyl] or N[($C_1$-$C_8$)alkyl]$_2$; $R_{14}$ is H, ($C_1$-$C_8$)alkyl, aryl, heteroaryl, heteroalkyl, cycloalkyl, acyl, allyl, CN, $NH_2$, NH[($C_1$-$C_8$)alkyl], N[($C_1$-$C_8$)alkyl]$_2$, OMe, SMe, OH; and $R_{15}$' is H, ($C_1$-$C_8$)alkyl, aryl, heteroaryl, heteroalkyl, cycloalkyl, acyl, allyl, CN, $NH_2$, NH[($C_1$-$C_8$)alkyl], N[($C_1$-$C_8$)alkyl]$_2$, OMe, SMe, $SO_3R^D$, OH, or SH, optionally, $R_{12}$ and $R_{13}$ together with the carbon atoms they are attached to form a 3-8 membered cyclyl or heterocyclyl.

70. The compound of any one of paragraphs 1-68, wherein $X_{10}$ is O; $R_{10}$ is aryl; $R_{11}$ is aryl; $Y_{10}$ is O; $R_{12}$ is ($C_1$-$C_8$)alkyl, O($C_1$-$C_8$)alkyl, N(OMe)($C_1$-$C_8$)alkyl, or N[($C_1$-$C_8$)alkyl]$_2$; $R_{13}$ is OH; $R_{14}$ is ($C_1$-$C_8$)alkyl, cycloalkyl, or $NH_2$; and $R_{15}$' is ($C_1$-$C_8$)alkyl, cycloalkyl, or $NH_2$, optionally, $R_{12}$ and $R_{13}$ together with the carbon atoms they are attached to form a 3-8 membered cyclyl or heterocyclyl.

71. The compound of any one of paragraphs 1-68, wherein the compound is of Formula (I).

72. The compound of any one of paragraphs 1-68, wherein the compound is of Formula (II).

73. The compound of any one of paragraphs 1-68, wherein the compound is of Formula (II').

74. The compound of any one of paragraphs 1-68, wherein the compound is of Formula (IV) or (IV').

75. The compound of paragraph 74, wherein Ring C in Formula (IV) or (IV') is of Formula (XIII).

76. The compound of paragraph 74 or 75, wherein Ring C in Formula (IV) or (IV') is heteroaryl or heterocycle.

77. The compound of any one of paragraphs 74-76, wherein $C_1$ is N and $R_{111}$ H.

78. The compound of any one of paragraphs 74-77, wherein $C_2$ is N and $R_{112}$ is H.

79. The compound of any one of paragraphs 74-78, wherein $C_1$ and $C_2$ are N; and $R_{111}$ and $R_{112}$ are H.

80. The compound of any one of paragraphs 74-79, wherein Ring C in Formula (IV) or (IV') is a heterocycle selected from the group consisting of a diazole, a triazole, a tetrazole, an imidazole, a thiadiazole, an oxazole, a thiazole and an oxadiazole, each of which can be optionally substituted.

81. A compound having the structure of Formula (B), or stereoisomers, tautomers, or pharmaceutically acceptable salts thereof.

82. The compound of paragraph 81, wherein $X_{30}$ is O, S, $CH_2$, NH, N($C_1$-$C_8$)alkyl; N(aryl), N(heteroaryl), N(cycloalkyl), or N[(C(O)O($C_1$-$C_8$)alkyl].

83. The compound of paragraph 81 or 82, wherein $X_{30}$ is O, S, NH or N($C_1$-$C_8$)alkyl.

84. The compound of any one of paragraphs 81-83, wherein $X_{30}$ is O or S.

85. The compound of any one of paragraphs 81-84, wherein $X_{30}$ is O.

86. The compound of any one of paragraphs 81-85, wherein $R_{30}$ is H, ($C_1$-$C_8$)alkyl, ($C_1$-$C_8$)haloalkyl, ($C_2$-$C_8$)alkenyl), ($C_2$-$C_8$)alkynyl, aryl, heteroaryl, cycloalkyl or heterocyclyl.

87. The compound of any one of paragraphs 81-86, wherein $R_{30}$ is aryl or heteroaryl.

88. The compound of any one of paragraphs 81-87, wherein $R_{30}$ is aryl.

89. The compound of any one of paragraphs 81-88, wherein $R_{30}$ is phenyl, optionally substituted with 1, 2 or 3 independently selected substituents.

90. The compound of any one of paragraphs 81-89, wherein $R_{30}$ is phenyl, optionally substituted with one substituent at the para position.

91. The compound of any one of paragraph 81-90, wherein $R_{30}$ is phenyl or 4-methoxyphenyl.

92. The compound of any one of paragraphs 81-91, wherein $R_{31}$ is aryl, heteroaryl, CN, $SO_2R^A$ $NO_2$, C(O)O($C_1$-$C_8$)alkyl, ($C_2$-$C_8$)alkenyl), C(O)NR$^A$R$^B$ or —$CO_2$H.

93. The compound of any one of paragraphs 81-92, wherein $R_{31}$ is aryl, heteroaryl. CN, $SO_2R^A$ or $NO_2$, 94. The compound of any one of paragraphs 81-93, wherein $R_{31}$ is aryl, heteroaryl. CN or $NO_2$ 95. The compound of any one of paragraphs 81-94, wherein $R_{31}$ is aryl or heteroaryl.

96. The compound of any one of paragraphs 81-95, wherein $R_{31}$ is phenyl optionally substituted with 1, 2 or 3 independently selected substituents.

97. The compound of any one of paragraphs 81-96, wherein $R_{31}$ is a phenyl, optionally substituted with one substituent.

98. The compound of any one of paragraphs 81-97, wherein $R_{31}$ is a phenyl.

99. The compound of any one of paragraphs 81-88, wherein $R_{30}$ and $R_{31}$ have syn relative stereochemistry.

100. The compound of any one of paragraphs 81-99, wherein $R_{32}$ is H, OH, CON[($C_1$-$C_8$)alkyl]$_2$, CON(O$C_1$-$C_8$)alkyl)[($C_1$-$C_8$)alkyl], $CO_2$H, CO[O($C_1$-$C_8$)alkyl], $CH_2$[O($C_1$-$C_8$)alkyl], $CH_2$OH, or ($C_1$-$C_8$)alkyl, or $R_{33}$, and $R_{34}$ together are NR$^G$, and R$^G$ and $R_{32}$ are connected and form part of a heterocycle or heteroaryl.

101. The compound of any one of paragraphs 81-100, wherein $R_{32}$ is H, CON[($C_1$-$C_8$)alkyl]$_2$, $CO_2$H, or CO[O($C_1$-$C_8$)alkyl], or $R_{33}$, and $R_{34}$ together are NR$^G$, and R$^G$ and $R_{32}$ are connected and form part of a heterocycle or heteroaryl.

102. The compound of any one of paragraphs 81-101, wherein $R_{32}$ is H, CONMe$_2$, or $CO_2CH_3$, or $R_{33}$, and $R_{34}$ together are NR$^G$, and R$^G$ and $R_{32}$ are connected and form part of a heterocycle or heteroaryl.

103. The compound of any one of paragraphs 81-102, wherein $R_{33}$ is H, halogen, CN, ($C_1$-$C_8$)alkyl, ($C_1$-$C_8$)haloalkyl, OR$^G$, or NR$^G$R$^H$, or $R_{33}$, and $R_{34}$ together are O, S, or NR$^G$ 104. The compound of any one of paragraphs 81-103, wherein $R_{33}$ is H, $OR^G$, or $R_{33}$, and $R_{34}$ together are O or $NR^G$.

105. The compound of any one of paragraphs 81-104, wherein $R_{33}$ is H, OH, or $R_{33}$, and $R_{34}$ together are O, NH, N($C_1$-$C_8$)alkyl or NOH.

106. The compound of any one of paragraphs 81-105, wherein $R_{33}$ is H, OH, or $R_{33}$, and $R_{34}$ together are O or NOH.

107. The compound of any one of paragraphs 81-106, wherein $R_{34}$ is H, halogen, CN, ($C_1$-$C_8$)alkyl, ($C_1$-$C_8$) haloalkyl, $OR^G$, or $NR^GR^H$, or $R_{33}$, and $R_{34}$ together are O, S, or $NR^G$ 108. The compound of any one of paragraphs 81-106, wherein $R_{34}$ is H, $OR^G$, or $R_{33}$, and $R_{34}$ together are O or $NR^G$.

109. The compound of any one of paragraphs 81-108, wherein $R_{34}$ is H, OH, or $R_{33}$, and $R_{34}$ together are O, NH, N($C_1$-$C_8$)alkyl or NOH.

110. The compound of any one of paragraphs 81-109, wherein $R_{34}$ is H, OH, or $R_{33}$, and $R_{34}$ together are O or NOH 111. The compound of any one of paragraphs 81-110, wherein one of $R_{33}$ and $R_{34}$ is H and the other is not H.

112. The compound of any one of paragraphs 81-110, wherein $R_{33}$ and $R_{34}$ together are O, S, or $NR^G$.

113. The compound of any one of paragraphs 81-112, wherein $R_{33}$ and $R_{34}$ together are O, or $NR^G$.

114. The compound of any one of paragraphs 81-113, wherein $R_{33}$ and $R_{34}$ together are O, NH, N($C_1$-$C_8$) alkyl or NOH.

115. The compound of any one of paragraphs 81-114, wherein $R_{33}$ and $R_{34}$ together are O or NOH.

116. The compound of any one of paragraphs 81-115, wherein $Z_{30}$ is O or $NR^G$.

117. The compound of any one of paragraphs 81-116, wherein $Z_{30}$ is $NR^G$.

118. The compound of any one of paragraphs 81-117, wherein $Z_{30}$ is NH, N($C_1$-$C_8$)alkyl, N(aryl), N(heteroaryl), N(cyclolkyl) or N(heterocyclyl).

119. The compound of any one of paragraphs 81-118, wherein $Z_{30}$ is N(methyl), N(ethyl), N(propyl), N(isopropyl), N(1-methylpropyl), N(2-methylpropyl), N(butyl), N(t-butyl), N(pentyl), N(allyl), N(propynyl), N(4),4-dimethoxybutyl), N(2-methoxyethyl), N(N,N-dimethyl-2-aminoethyl), N(N-dimethyl-2-aminoethyl), N(2-imidazolidinylmethyl), N(pyridinylmethyl), N(adamantlyl), N(2-thiazolylethyl), N(tetrahydopyranylmethyl), N(morpholinylethyl), N(benzyl), and N(phenyl)

120. The compound of any one of paragraphs 81-119, wherein $Z_{30}$ is NH or N(ethyl).

121. The compound of any one of paragraphs 81-120, wherein $R_{35}$ is H, ($C_1$-$C_8$)alkyl, ($C_1$-$C_8$)alkenyl, ($C_1$-$C_8$)alkynyl, aryl, heteroaryl, cyclalkyl, C(O)O($C_1$-$C_8$) alkyl, NH($C_1$-$C_8$)alkyl, N([($C_1$-$C_8$)alkyl]$_2$, OH or O—($C_1$-$C_8$)alkyl.

122. The compound of any one of paragraphs 81-121, wherein $R_{35}$ is H, ($C_1$-$C_8$)alkyl, ($C_1$-$C_8$)alkenyl, ($C_1$-$C_8$)alkynyl, or N([($C_1$-$C_8$)alkyl]$_2$.

123. The compound of any one of paragraphs 81-122, wherein $R_{35}$ is H, methyl, ethyl, propyl, isopropyl, 1-methylpropyl, 2-methylpropyl, butyl, t-butyl, pentyl, allyl, propynyl, 4,4-dimethoxybutyl, 2-methoxyethyl, N,N-dimethyl-2-aminoethyl, N-dimethyl-2-aminoethyl, 2-imidazolidinylethyl, pyridinylmethyl, adamantlyl, 2-thiazolylethyl, tetrahydopyranylmethyl, morpholinylethyl, benzyl, and phenyl.

124. The compound of any one of claims 81-123, wherein $X_{30}$ is O, S, $CH_2$, NH, N($C_1$-$C_8$)alkyl; N(aryl), N(heteroaryl), N(cycloalkyl), N[(C(O)O($C_1$-$C_8$)alkyl]; $R_{30}$ is aryl or heteroaryl; $R_{31}$ is aryl, heteroaryl, C(O)O($C_1$-$C_8$)alkyl, ($C_2$-$C_8$)alkenyl), C(O)$NR^GR^H$ or $CO_2H$; $R_{32}$ is H, OH, CON[($C_1$-$C_8$)alkyl]$_2$, CON(OMe)[($C_1$-$C_8$)alkyl], CO[O($C_1$-$C_8$)alkyl], $CH_2$[O($C_1$-$C_8$)alkyl], $CH_2$OH, or ($C_1$-$C_8$)alkyl; $R_{33}$ and $R_{34}$ independently are H, $OR^G$, SH, $NH_2$, NH($C_1$-$C_8$)alkyl or N[$C_1$-$C_8$) alkyl]$_2$, or $R_{33}$, and $R_{34}$ together are O or $NR^G$; Z is O, S or NH or N[$C_1$-$C_8$)alkyl)], or $R_{33}$, and $R_{34}$ together are $NR^G$, and $R^G$ and $R^{32}$ together form a heterocylyl or heteroaryl; $R_{35}$ is H, ($C_1$-$C_8$)alkyl, aryl, heteroaryl, cyclalkyl, heterocyclyl, C(O)O($C_1$-$C_8$)alkyl, $NMe_2$ or OMe.

125. The compound of any one of paragraphs 81-124, wherein $X_{30}$ is O; $R_{30}$ is aryl; $R_{31}$ is aryl; $R_{32}$ is CON[($C_1$-$C_8$)alkyl]$_2$, CON(OMe)[($C_1$-$C_8$)alkyl], CO[O($C_1$-$C_8$)alkyl] or ($C_1$-$C_8$)alkyl; $R_{33}$ is H; $R_{34}$ is OH; $R_{35}$ is H, ($C_1$-$C_8$)alkyl, or cycloalkyl.

126. The compound of any one of paragraphs 81-126, wherein $X_{30}$ is O, S, NH, N($C_1$-$C_8$)alkyl; N(aryl), N(heteroaryl), N(cycloalkyl), N[(C(O)O($C_1$-$C_8$)alkyl]; $R_{30}$ is aryl or heteroaryl; $R_{31}$ is aryl, heteroaryl, C(O)O($C_1$-$C_8$)alkyl, ($C_2$-$C_8$)alkenyl), C(O)$NR^GR^H$ or —$CO_2H$; $R_{32}$ is H, OH, CON[($C_1$-$C_8$)alkyl]$_2$, CON(OMe)[($C_1$-$C_8$)alkyl], CO[O($C_1$-$C_8$)alkyl], $CH_2$[O($C_1$-$C_8$)alkyl], $CH_2$OH, or ($C_1$-$C_8$)alkyl; $R_{33}$ is OH, SH, $NH_2$, NH($C_1$-$C_8$)alkyl or N[$C_1$-$C_8$)alkyl]$_2$; $R_{34}$ is H; Z is O, S or NH; and $R_{35}$ is H, ($C_1$-$C_8$)alkyl, aryl, heteroaryl, cyclalkyl, C(O)O($C_1$-$C_8$)alkyl, $NMe_2$ or OMe.

127. The compound of any one of paragraphs 81-126, wherein $X_{30}$ is O; $R_{30}$ is aryl; $R_{31}$ is aryl; $R_{33}$ is OH; $R_{34}$ is H; and $R_{35}$ is H, ($C_1$-$C_8$)alkyl, or cycloalkyl.

128. The compound of any one of paragraphs 81-127, wherein $X_{30}$ is O, S, NH, N($C_1$-$C_8$)alkyl; N(aryl), N(heteroaryl), N(cycloalkyl), N[(C(O)O($C_1$-$C_8$)alkyl]; $R_{30}$ is aryl or heteroaryl; $R_{31}$ is aryl or heteroaryl, $R_{33}$ and $R_{34}$ combined are O, S, NH, N($C_1$-$C_8$)alkyl or NOH; $Z_{30}$ is O, S or NH; and $R_{35}$ is H, ($C_1$-$C_8$)alkyl, aryl, heteroaryl, cyclalkyl, C(O)O($C_1$-$C_8$)alkyl, $NMe_2$ or OMe.

129. The compound of any one of paragraphs 81-128, wherein $X_{30}$ is O; $R_{30}$ is aryl; $R_{31}$ is aryl; $R_{33}$ and $R_{34}$ combined are O; and $R_{35}$ is H, ($C_1$-$C_8$)alkyl, or cyclalkyl.

130. The compound of any one of paragraphs 81-128, wherein $R_{33}$, and $R_{34}$ together are $NR^G$ and $R^G$ and $R_{32}$ are connected and form a hetercyclyl or heteroaryl.

131. The compound of any one of paragraphs 81-130, wherein the compound is of Formula (B').

132. The compound of any one of paragraphs 81-131, wherein the compound is of Formula (III').

133. The compound of any one of paragraphs 1-132, wherein Ring A has the structure of formula (XIV).

134. The compound of any one of paragraphs 1-133, wherein Ring A has the structure of formula (XIII).

135. The compound of any one of paragraphs 1-134, wherein Ring A has the structure of formula (XV).

136. A method for preparing a compound having the Formula (A), the method comprising: providing a solution of a compound having Formula (V), and reacting the compound (VI) or salts thereof, with a base to provide an intermediate in the solution, and reacting the intermediate with the compound having Formula (VI) or salts thereof.

137. The method of paragraph 136, wherein the solution of a compound having Formula (V) and a base is maintained at less than 0° C. for at least 1 minute and warmed to room temperature over at least five minutes.

138. The method of paragraph 136 or 137, wherein the solution comprises an organic solvent and the base has a pKa is greater than about 16.

139. A method for preparing a compound having the Formula (III), the method comprising: providing a solution of a compound having Formula (IX), and reacting the compound (X) or salts thereof, with a base to provide an intermediate in the solution, and reacting the intermediate with the compound having Formula (IX).

140. The method of paragraph 139, wherein the solution of a compound having Formula (IX) and a base is maintained at less than 0° C. for at least 1 minute and warmed to room temperature over at least five minutes.

141. The method of paragraph 139 or 140, wherein the solution comprises an organic solvent and the base has a pKa is greater than about 16.

142. A pharmaceutical composition comprising a compound of any one of paragraphs, 1-135 and a pharmaceutically acceptable carrier, diluent or excipient.

143. An antibody-drug conjugate (ADC) comprising an antibody linked to a compound of any one of paragraphs 1-135.

144. A pharmaceutical composition comprising an antibody-drug conjugate of paragraph 143 and a pharmaceutically acceptable carrier, diluent or excipient.

145. A method for treating a eIF4A-dependent condition in a subject in need thereof, the method comprising administering to the subject a therapeutically effective amount of a compound according to any one of paragraphs 1-135 or an antibody-drug conjugate of paragraph 143.

146. The method of paragraph 145, wherein the eIF4A dependent condition is a disease of uncontrolled cell growth, proliferation and/or survival, a disease of inappropriate cellular inflammatory responses, a disease caused by a parasite or a neurodegenerative disease requiring neuroprotection.

147. The method of any one of paragraphs 145 or 146, further comprising administering one or more additional therapy.

148. The method of paragraph 147, wherein the one or more additional therapy is an anti-cancer therapy.

149. The method of paragraph 147 or 148, wherein the one or more additional therapy is an antiviral agent.

150. The method of any one of paragraphs 147-149, wherein the one or more additional therapy is a monoclonal antibody therapy.

The embodiments will be more readily understood by reference to the following examples, which are included merely for purposes of illustration of certain aspects and embodiments of the present invention, and should not be construed as limiting. As such, it will be readily apparent that any of the disclosed specific constructs and experimental plan can be substituted within the scope of the present disclosure.

EXAMPLES

Example 1: Intercepted Retro-Nazarov Reaction: Syntheses of Amidino-Rocaglate Derivatives and their Biological Evaluation as eIF4A Inhibitors Rocaglates are a family of natural products isolated from the *Aglaia* genus which possess a highly substituted cyclopenta[b]benzofuran skeleton and inhibit eukaryotic protein synthesis. Rocaglates are attractive compounds due to their potential for inhibiting tumor cell maintenance in vivo by specifically targeting eukaryotic initiation factor 4A (eIF4A) and interfering with recruitment of ribosomes to mRNA. Referencing FIG. 1, herein is described an intercepted retro-Nazarov reaction utilizing intramolecular tosyl migration to generate a reactive oxyallyl cation on the rocaglate skeleton. Trapping of the oxyallyl cation with a range of nucleophiles has been used to generate over fifty novel amidino-rocaglate (ADR) and amino-keto-rocaglate derivatives. Subsequently, the derivatives were evaluated for their ability to inhibit cap-dependent protein synthesis where they were found to outperform previous lead compounds including the rocaglate hydroxamate CR-1-31-B (23).

Figure 2:
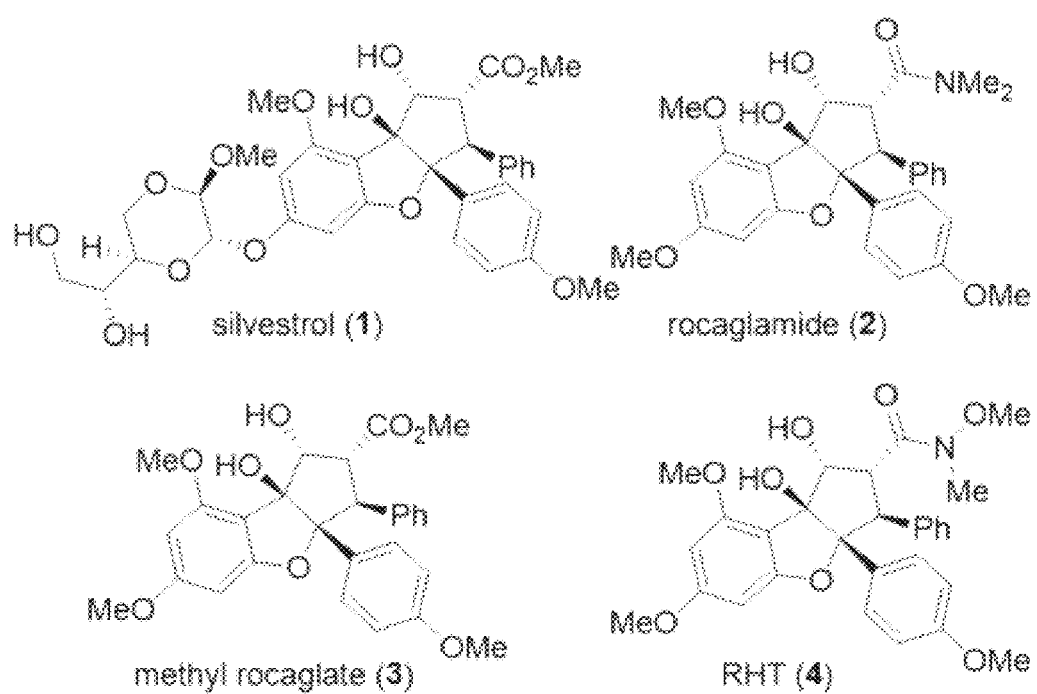
FIG. 2 shows structures of representative rocaglates.

*Aglaia Lour.* is a large genus of angiosperm plants containing more than 120 species. In 1982, the first rocaglate was isolated from dried roots and stems of *Aglaia elliptifolia* Merr.; since this time, over thirty natural products of the rocaglate family have been discovered sharing a highly substituted cyclopenta[b]benzofuran with five contiguous stereocenters. In the past several decades, numerous syntheses of rocaglates have been reported due to their intriguing structures. Some rocaglates are shown in FIG. 2. These natural products exhibit many interesting biological activities through targeting the eukaryotic translation apparatus. For example, the congener silvestrol (1) was found to inhibit the eIF4F complex by interfering with the function of the Dead box RNA helicase eIF4A (SEQ ID NO: 1). Additionally, silvestrol has antitumor activity in a variety of preclinical murine cancer models including hematological and solid tumor types. Rocaglamide (2), methyl rocaglate (3), and the synthetic derivative RHT (4) have also displayed significant anticancer properties.

Figure 3:
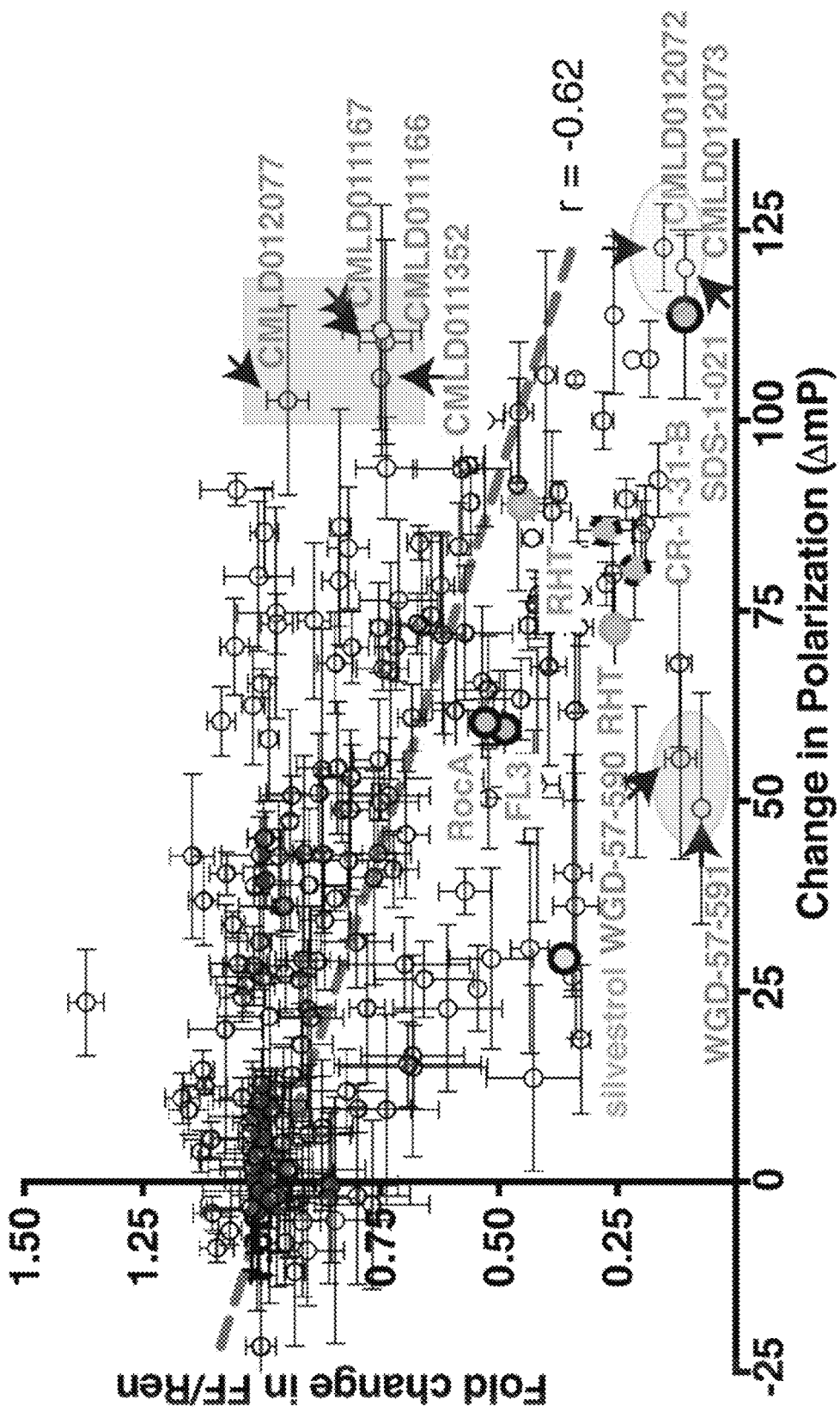
FIG. 3 shows a plot for comparison biological activity of rocaglates. Polypurine clamping is a correlative, but not universal, predictor of cap dependent inhibition. The ΔmP obtained with eIF4A1:poly r(AG)$_8$ (SEQ ID NO: 2) RNA was measured for each compound (10 μM) and is plotted against the fold inhibition for cap-dependent translation (2 μM) of FF/HCV/Ren mRNA in Krebs-2. Note the duplicate values for RHT (open circles) are due to two preparations of different enantiomeric purity, and for CR-1-31-B (dotted circles) are due to two different compound batches (see Table S1). Pearson r=−0.62; p<0.0001.

Chemical syntheses of cyclopenta[b]benzofuran natural products and analogues have revealed structure-activity relationships (SAR) for antineoplastic activity in cancer cell lines. FIG. 3 show a plot for comparison of rocaglate biological activity, by plotting translation inhibition (Fold change in FF/Ren) vs RNA Binding (change in polarization-ΔmP). Polypurine clamping is strongly correlative potency as an inhibitor of cap-dependent translation. The change in polarization obtained with eIF4A-poly r(AG)$_8$ (SEQ ID NO: 2) RNA was measured for each compound compound (at 10 µM concentration) and is plotted against the fold inhibition for cap-dependent protein synthesis (at 2 µM concentration) obtained in Krebs-2 extracts programmed with FF/HCV/Ren mRNA (relative to vehicle control). (Note the duplicate values for RHT (4) (open circles) and CR-1-31-B (23) (dotted circles) are due to the presence of two different preparations of these compounds in our library collection). Experiments were performed in biological triplicates. Pearson r=−0.62; p<0.0001. In particular, SAR studies have defined chemically allowable modifications for rocaglates leading to improved activity. In particular, the C$_8$b tertiary hydroxyl moiety (red) has been shown to be critical which appears to be related to its role as a hydrogen bond (H-bond) donor (FIG. 4); alkylation of this tertiary hydroxyl completely eliminates cytotoxic activity. Recently, Iwasaki and coworkers determined the co-crystal structure of rocaglamide (2) bound to a human eIF4A-polypurine RNA complex which, among the interactions identified, was hydrogen bonding between the $C_8$b hydroxyl of 2 and N7 of a guanine base. Accordingly, we have considered replacing the tertiary hydroxyl with nitrogen substituents which would allow for additional attachment of functional groups and manipulation of the binding affinity to the eIF4A-RNA complex through hydrogen bonding. In this regard, Déesaubry and coworkers have reported acylamino- and sulfonamino-substitution at the $C_8$b position of the epi-rocaglaol scaffold as potential bioisosteric replacements; unfortunately, these derivatives were not cytotoxic. A comprehensive SAR study of $C_8$b-amino-substitution was not performed, which may be due to difficulty in achieving chemical modification of this position.

Results and Discussion

Figure 5:
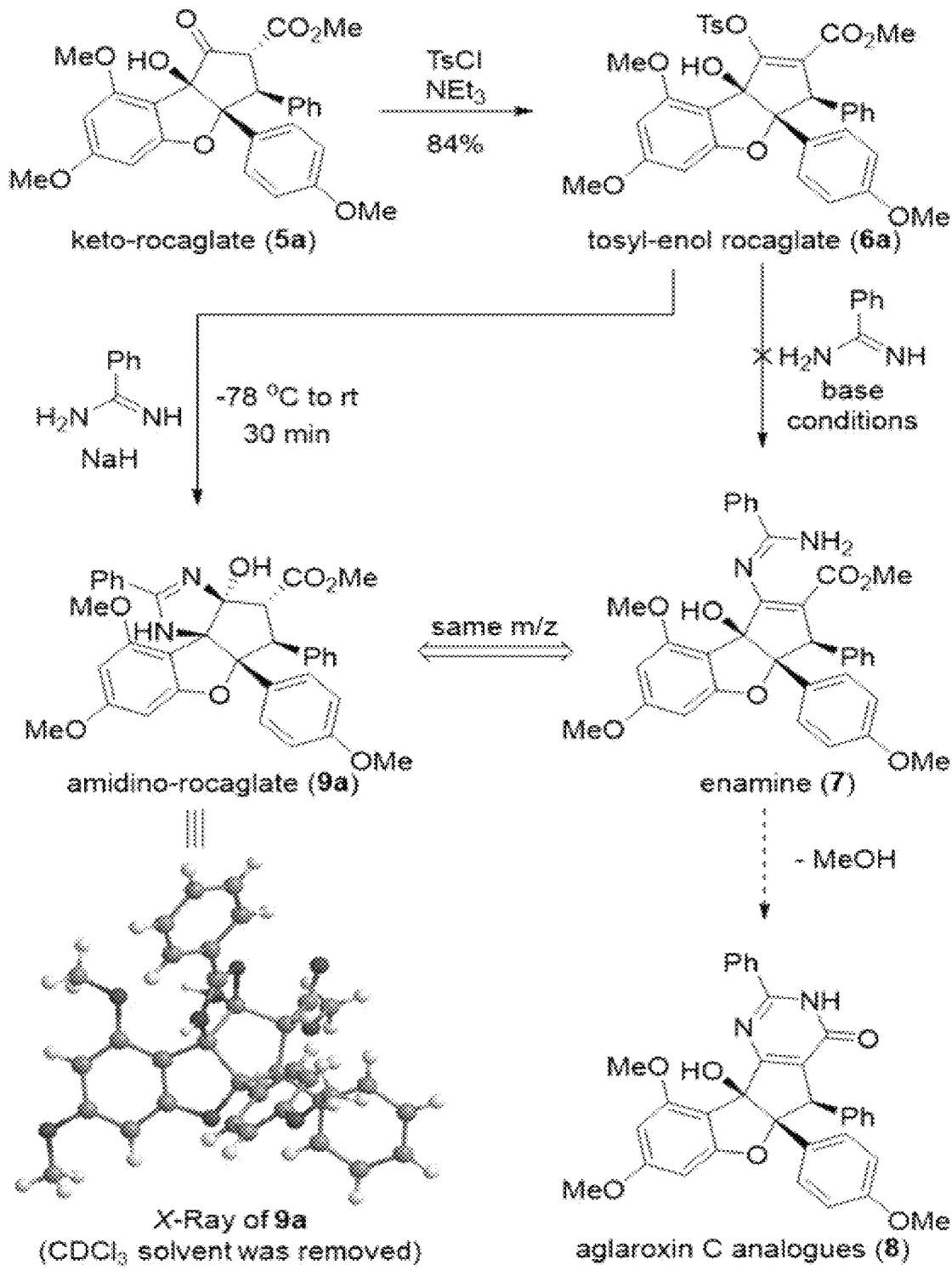
FIG. 5 shows a scheme for the discovery of reactions to access modified rocaglates.

Discovery of the Intercepted Retro-Nazarov Reaction. Tosyl-enol rocaglate 6a was synthesized from keto-rocaglate 5a in an effort to access second-generation aglaroxin C derivatives (8, FIG. 5). In this transformation, amidine addition followed by tosylate extrusion is expected to afford imine 7 under basic conditions followed by cyclization to pyrimidinone 8. During the attempted addition of amidines to 6a, an unknown product was isolated which had the same molecular weight of 7 but did not undergo subsequent pyrimidinone cyclization. $^1$H NMR studies failed to characterize the structure due to the lack of proton signals on the cyclopenta[b]benzofuran core. Accordingly, X-ray crystal structure analysis was used to confirm the new structure as the amidino-rocaglate (ADR). 9a. Notably, in the solid-state structure the N—H of the emerged imidazoline moiety resides on the nitrogen replacing the hydroxyl moiety, thereby retaining the relative stereochemistry of the rocaglate $C_8$b tertiary hydroxyl. Generally speaking, an imidazoline N—H has a lower pKa (26.7-30.7 in DMSO) than the hydroxyl ($^t$BuO-H: 32.2-32.5 in DMSO) and thus may serve as a suitable hydrogen-bond donor for biological target engagement. In addition, the emerged hemiaminal hydroxyl group on the imidazoline ring is situated on the α-face corresponding to the same stereochemistry of the secondary alcohol in rocaglates. The overall retention of functional group stereochemistry on the rocaglate core was later determined to be important to maintain inhibition of eIF4A-dependent protein synthesis.

Proposed Mechanistic Pathway. FIG. 6A shows a mechanistic proposal for amidino rocaglate synthesis. It is proposed that the amidine substitution proceeds through an intercepted retro-Nazarov reaction process. According to the reaction protocol, sodium hydride (NaH) deprotonates the tertiary alcohol of 6a which may be followed by the intramolecular tosyl migration which converts the tertiary alkoxide of 11 to the tosylate enolate 12. Subsequent ionization of the tertiary tosylate facilitates formation of the stabilized oxyallyl cation 13. Based on the reactivity observed, generation of the oxyallyl cation occurs during warming and is a fast process. We have found that the rates of subsequent trapping of oxyallyl cation 13 vary for different amidines (vide infra), which suggests that this is the rate determining step for the process. After formation of the C—N bond in 14, rapid cyclization completed the transformation and led to construction of hemiaminal 9a. As shown in FIG. 6B, to further probe the reaction mechanism, enantioenriched (−)-6a (>98% ee) was used as starting material and was synthesized using either using asymmetric ESIPT-mediated [3+2] photocycloaddition or biomimetic kinetic resolution of an aglain ketone precursor. Compound (−)-6a was then subjected to amination using NaH and benzylamine. In the event, oxyallyl cation 13 was trapped with benzylamine to afford amino-rocaglate (−)-15 h in 90% yield. As expected, complete retention of chirality for amino-rocaglate 15 h (>98% ee) demonstrated that the retro-Nazarov reaction was irreversible from dienone 10. Otherwise, loss of enantiopurity of the amino-rocaglate product would be observed. Additionally, when bulky nucleophiles or no nucleophile were used in the reaction, retro-Nazarov products 10 were obtained (cf arrows, FIG. 6B).

To further understand the stereoselectivity of the intercepted retro-Nazarov reaction, a DFT analysis of proposed intermediate 13 was performed at the B3LYP/6-31G** level which has been extensively used for computation of oxyallyl cation intermediates. The DFT model of 13 (FIG. 6B) showed a trigonal pyramidal carbocation at the $C_7$ position which correlates well with the trapping of oxyallyl cation 13 with nucleophiles such as amidines and amines from the convex face. Oxygen-based nucleophiles, including water and methanol, were also used to trap the oxyallyl cation to afford keto-rocaglate 5a and O-methyl-rocaglate 5b.

Figure 7:
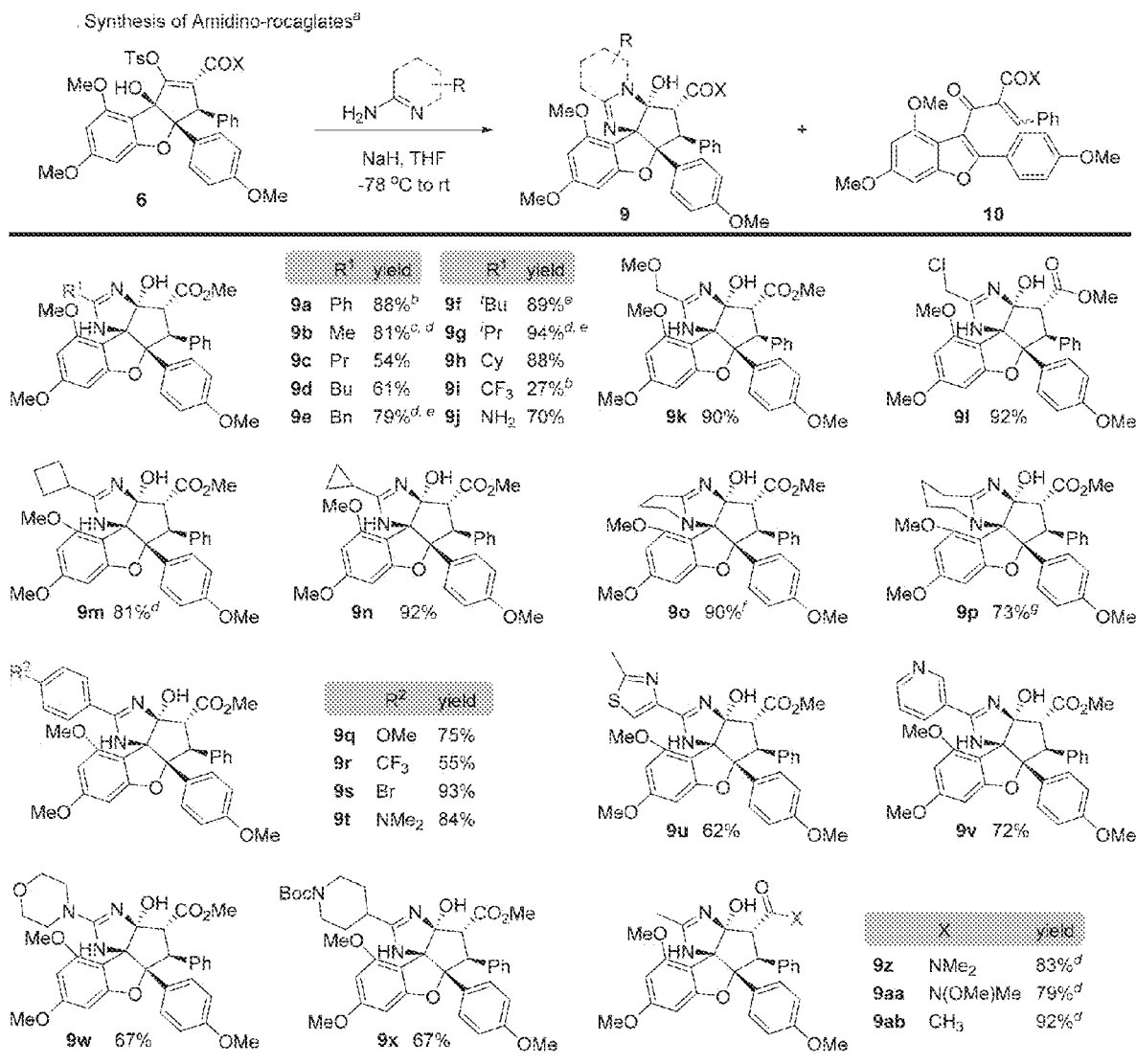
FIG. 7 shows a reaction scheme for amidino-rocaglates.

Synthesis of Amidino-Rocaglates. The intercepted retro-Nazarov reaction was found to tolerate a wide range of amidine and guanidine reaction partners as shown by the reaction scheme of FIG. 7. The reagents and conditions for FIG. 7 are as follows: (a) Reagents and conditions 6 (25 mg, 1.0 equiv), amidine hydrochloride (3. Equiv), NaH (8.0 equiv), THR (0.1M), −78° C. to rt; (b) amidine (3.0 equiv), NaH (5.0 equiv); (c) 500 mg Scale; 74% yield on 25 mg scale; (d) amidine salt was azeotroped with benzene under vacuum; (e) 25 mol % NaHMDS was added at rt; (f) inseparable regioisomers (>10:1); major isomer is shown as 9o; (g) inseparable regioisomers (2:1); major isomer is shown as 9p.

Rocaglates with various carbonyl substitutions were found to be workable. Generally, the intercepted retro-Nazarov reaction was robust and straightforward to set up; 29 amidino-rocaglates were synthesized in good yields. To a combined mixture of amidine hydrochloride salts and sodium hydride solution, solution of tosyl-enol rocaglate 6 was added followed by warming from −78° C. to room temperature. The reaction was generally complete in 30-90 minutes at room temperature. A general issue for this reaction was found when using hygroscopic amidine salts which introduced trace amounts of water competing with amidine nucleophiles to afford keto-rocaglate 5. The water content of amidines varies from batches and vendors, so we did not optimize reaction conditions for each substrate. However, simple azeotropic drying of the amidine salt using benzene improved yields of products (e.g. 9e from 47% to 79%; 9g from 29% to 94%). Additionally, several amidine salts were found to have poor solubility in reactions leading to recovery of 6; in such cases, 25 mol % of NaHMDS (1M in THF) was used as a proton shuttle (9e-g, 9m).

After having initial success using benzamidine to generate 9a (88% yield), we next evaluated use of aliphatic amidines. With increasing steric size of amidine substitutions (from methyl to tert-butyl), we observed decreasing reaction rates and production of the retro-Nazarov product 10 and keto-rocaglate 5a as major side products. Use of acetamidine afforded the corresponding adduct 9b in 81% yield, whereas the highly hygroscopic butylamidine and pentylamidine afforded products 9c and 9d in lower yields (54% and 61%). Likewise, when a benzyl amidine reagent was used, a 47% yield of adduct 9e was obtained. However, bulkier amidines such as neo-pentylamidine and iso-propionamidine resulted in good yields of the desired products 9f and 9g (88% and 94%, respectively). Similarly, the cyclohexyl-substituted product 9i was formed in 88% yield. Interestingly, the parent amidine guanidine successfully generated 9j in a 70% yield. We employed 2-methoxyl- and 2-chloroacetamidine to access the ADR structures with modification handles in excellent 90% (9k) and 92% (9l) yields. Additionally, strained cyclopropyl and cyclobutyl amidines were also tolerated in the reaction, affording 9m and 9n in 81% and 92% yields, respectively. Unsymmetrical amidines generated 9o and 9p in excellent yields (90% and 73%). Of note, 9o and 9p were formed as the major regioisomers, whereas the unfavored regioisomers were formed through trapping by the exocyclic nitrogen atom of the amidine reagents.

In addition, we found that heteroaryl and aryl amidines with various electronic properties provided the desired adducts in reasonable yields (75% for 9q; 55% for 9r; 93% for 9s; 84% for 9t; 62% for 9u; 72% for 9v). Moreover, both Boc-protected piperidinyl and N-morpholinyl amidines were used to generate 9v and 9w in 67% yields. We also tested a variety of rocaglate derivatives in reactions with acetamidine. To this end, tosyl-enol rocaglamide 6z yielded 9z in 83% yield, and tosyl-enol 6aa led to compound 9aa in 79% yield. To our delight, we found that the amidine addition could also tolerate ketone (9ab, 92%) and aldehyde functional groups on the rocaglate skeleton. Interestingly, the aldehyde product subsequently underwent dehydration yielding the α,β-unsaturated aldehyde 9ac. Overall, this powerful late-stage functionalization method enabled a rapid and diverse library synthesis of more than thirty amidino-rocaglate (ADR) derivatives.

Figure 8:
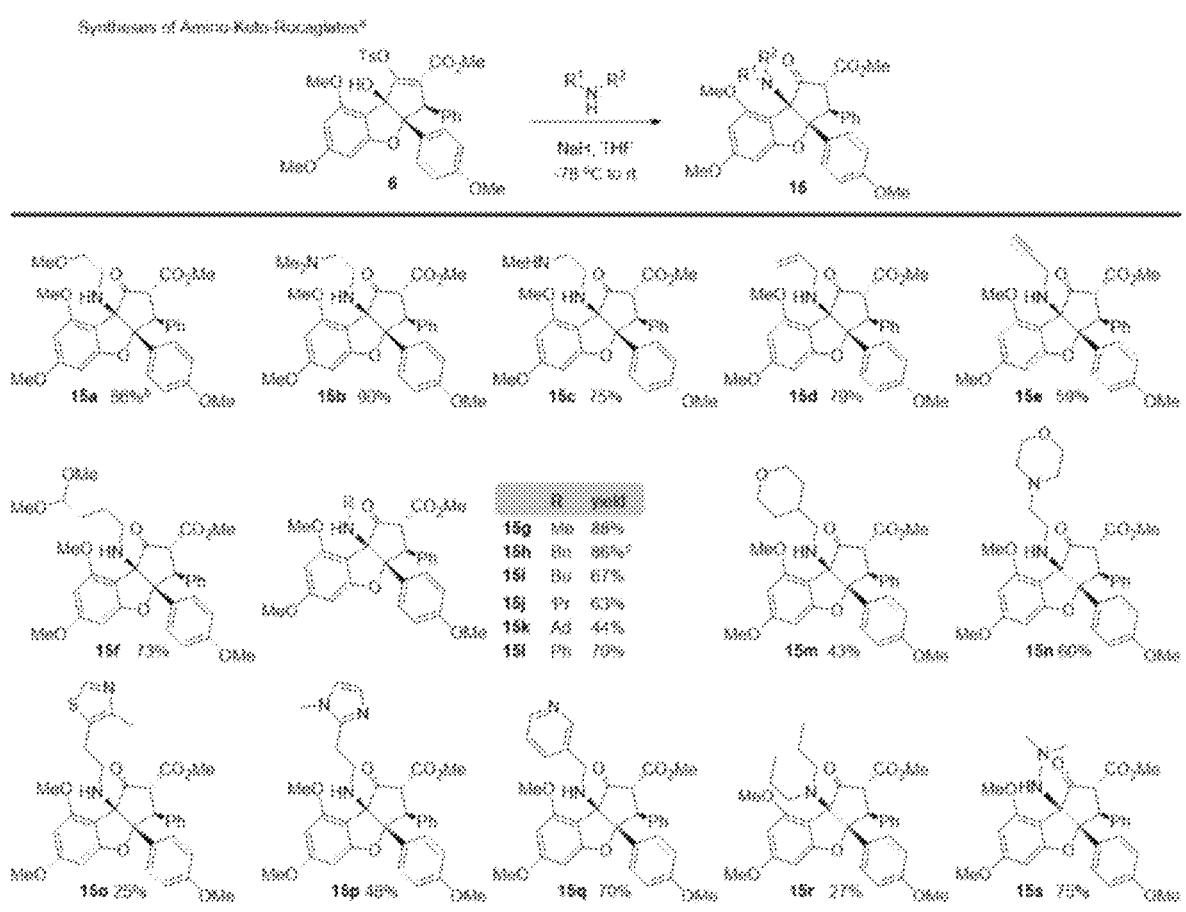
FIG. 8 shows a synthesis of amino-keto-rocaglates.

Synthesis of Amino-Rocaglates. Inspired by the mechanism elucidation, we proceeded to study the synthesis of amino-rocaglates utilizing amines as nucleophiles to trap oxyallyl cation intermediate 13. Accordingly, we explored the substrate scope of amino-rocaglate synthesis under the same conditions as depicted by FIG. 8. Reagents and conditions are as follows: (a) 6 (1.0 equiv), NaH (5.0 equiv), amine (3.0 equiv), THF (0.1-0.2 M), 15 min at −78°, rt 30-120 min; (b)$_{500}$ mg scale, 83% on 25 mg scale; (c)$_{250}$ mg scale, 90% on 25 mg scale. Our initial attempts employed several primary amine derivatives to generate amino-rocaglates in good yields (86% for 15a; 90% for 15b; 75% for 15c). Of note, the use of N-methyl ethylenediamine (for 15c) underscored that the oxyallyl cation intermediate prefers to be trapped by the less hindered primary amine moiety. The secondary amine residue in 15c may also be utilized to introduce biological tag reagents. Moreover, use of an allyl amine afford 15d in 79% yield; propargylamide was also used to form alkynylated derivative 15e in 59% yield which may serve as a click-chemistry handle. Likewise, we introduced an additional functionalized side chain using butylamine dimethyl acetal to access compound 15f in 73% yield. The acetal group may eventually be converted into a pendant aldehyde as a handle for further functionalization. In addition to amines with useful modification handles, we also investigated the steric effect of amines. From methyl to adamantyl amine (15g to 15k), we observed a slight decrease in yields of the desired amino-rocaglates from (88% to 44%) and an increased trend of retro-Nazarov products generation. Intriguingly, the weak nucleophile, aniline, could also trap the oxyallyl cation affording 15l (70%). We found that tethered heterocycles were workable for amino-keto-rocaglate synthesis, which was expected to provide extra protein binding groups. For example, a tetrahydropyranyl amine was a successful trapping reagent affording amino-rocaglate 15m (43%), while N-morpholinyl ethyleneamine provided 15n with a remote morpholine functional group in a moderate yield (60%). Nevertheless, the introduction of thiazole and imidazole heterocycles was more challenging using the same method. In particular, we obtained a 25% yield of 15o bearing the thiazole functional group, whereas use of an imidazole-tethered amine afforded product 15p in 49% yield. To our delight, 3-picolylamine underwent the desired reaction to afford a 70% yield of amino-rocaglate 15q. In addition, use of secondary amine such as diethylamine led to a 27% yield of 15r along with significant yield of retro-Nazarov products as the major product of this reaction, highlighting limitations with use of hindered amines. Finally, dimethyl hydrazine broadened the scope of the intercepted retro-Nazarov reaction to afford rocaglate hydrazine derivative 15s in 75% yield.

Figure 9A:
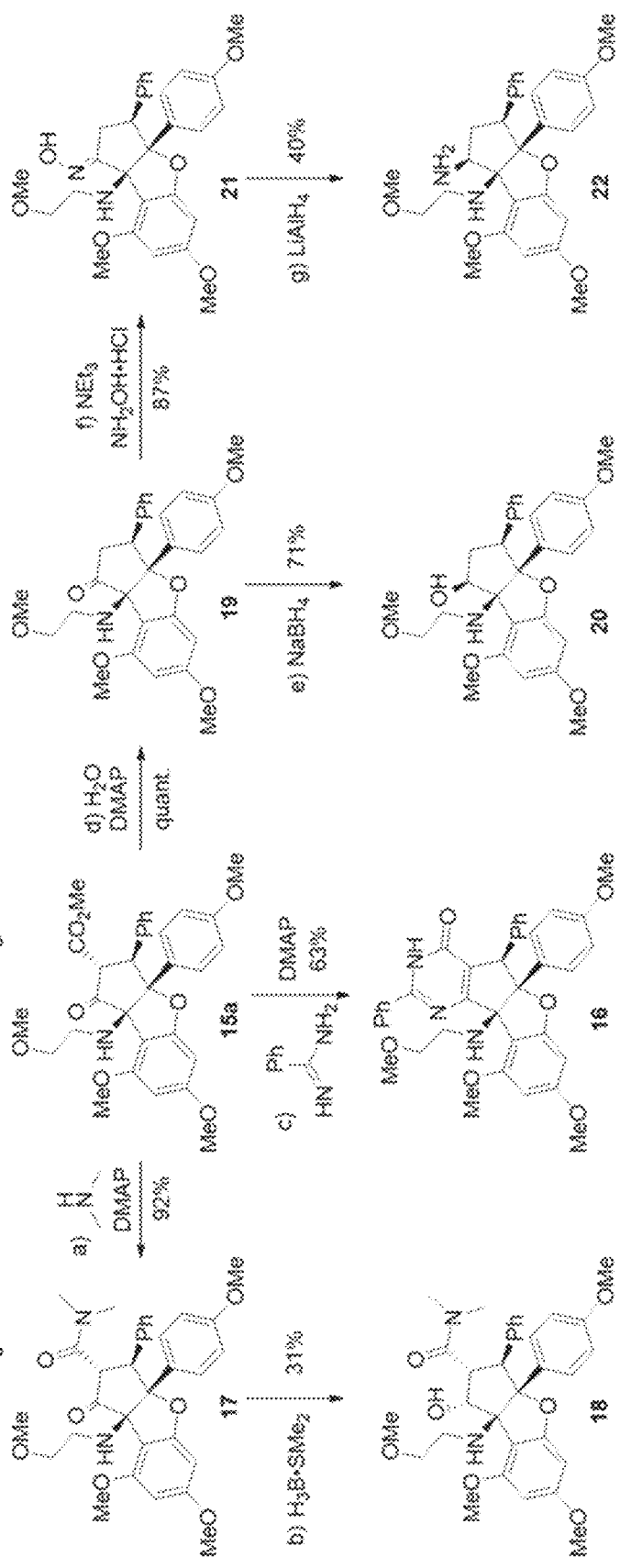
FIG. 9A shows the late-stage functionalization of amino-keto-rocaglates.

Late-Stage Functionalization of Amino-Rocaglates. Amino-rocaglates 15 possess a higher oxidation state than the natural rocaglates such as silvestrol 1, rocaglamide 2, and rocaglaol (not shown). FIG. 9A show late-stage functionalization of amino-keto-rocaglates. The reagents and conditions are: (a) HNMe$_2$ (2.0 equiv, 2.0 M in THF), 20 mol % DMAP, toluene (0.1 M), 90° C., 3 h, 92%; (b) H$_3$B.SMe$_2$ (3.0 equiv, 1.0 M in TF), THE (0.05 M), rt, 12 h, 31%; (c) benzamidine (3.0 equiv), 30 mol % DMAP, m-xylene (0.025 M), 130° C., 45 min, 3%; (d) H$_2$O (10 equiv), 20 mol % DMAP, toluene (0.1 M), 90° C., 3 h, quant. yield; (e) NaBH$_4$ (20 equiv), MeOH (0.02 M), rt, overnight, 71%; (f) NEt$_3$ (2.0 equiv), NH$_2$OH HCl(3.0 equiv), MeOH (0.1 M), 37° C., overnight, 87%; g) LiAlH$_4$ (5.0 equiv), THF (0.05 M), rt, overnight, 40%. To compare the biological activity of amino-rocaglates with natural rocaglates, we studied reductions of amino-rocaglate substrate 15a which contains an O-methyl ethylene as a structural surrogate for a possible PEGylated sidechain. We also synthesized amino-aglaroxin 16 in 63% yield. Additionally, we were interested in the synthesis of amino-rocaglamide derivatives given that rocaglamide 2 and RHT (4) display greater cytotoxicity than methyl rocaglate 3 against several cancer cell lines. We found that amide exchange of 15a generated amino-keto-rocaglamide 17 as a useful synthetic precursor. Subsequent reduction generated amino-rocaglamide 18 (31%) using borane dimethyl sulfide complex. On the other hand, DMAP facilitated decarboxylation of 15a to afford amino ketone 19 which was further reduced to amino-rocaglaol 20 in 71% yield. Using sodium borohydride as reductant, syn-stereochemistry between the amino-group and alcohol was observed. Additionally, oxime 21 was synthesized using hydroxyl amine and triethylamine, and a subsequent LiAlH$_4$ reduction afforded diamino-rocaglate 22.

Figure 9B:
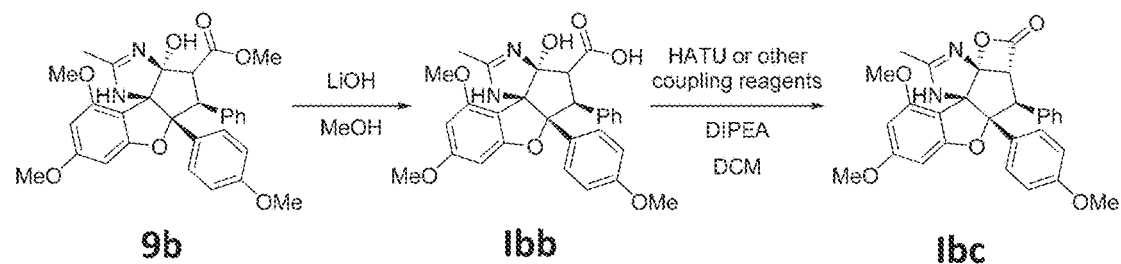
FIG. 9B shows a further transformation for amidino-rocaglates.

FIG. 9B shows a further transformation scheme for amidino-rocoglate in two steps.

Step 1. To an amidino rocaglate solution in methanol (0.1 M) was added aqueous lithium hydroxide solution (1.5 equiv., 1.0 M). The reaction mixture was stirred at room temperature for 12 hours. After concentration, ammonium chloride saturated aqueous solution was added followed by addition of ethyl acetate. The aqueous phase was extracted three times using ethyl acetate, and the organic phase was combined, dried, and concentrated to afford the amidino-rocaglate acid without any further purification.

Step 2. The amidino-rocaglate acid was dissolved in methylene chloride (0.1 M), which was added diisopropylethylamine (1.1 equiv.) followed by HATU (1.0 equiv). The reaction was stirred for an additional 4 hours, and was quenched by addition of ammonium chloride saturated aqueous solution. The aqueous phase was extracted three times using ethyl acetate, and the organic phase was combined, dried, and concentrated to afford the crude β-lactone product.

Figure 9C:
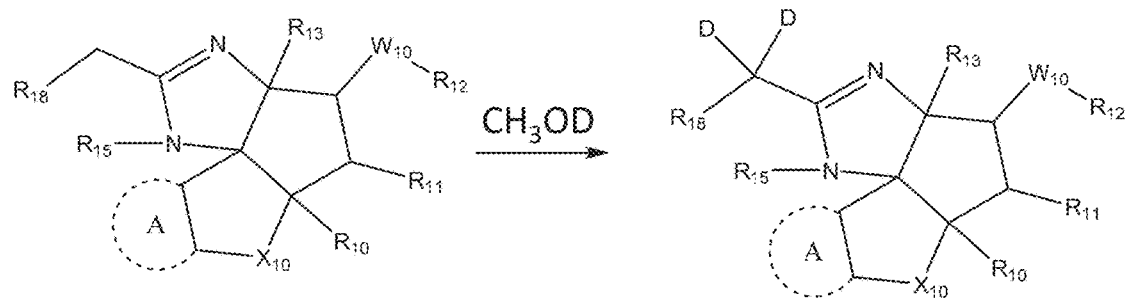
FIG. 9C shows deuteration of amidino-rocaglates.

FIG. 9C shows a scheme for deuteration of amidino-rocaglates. Amidino-rocaglates can be dissolved and stirred in methanol-d1 for 72 hours. After concentration, the deuterated amidino-rocaglate was generated in quantitative yield.

Figure 9D:
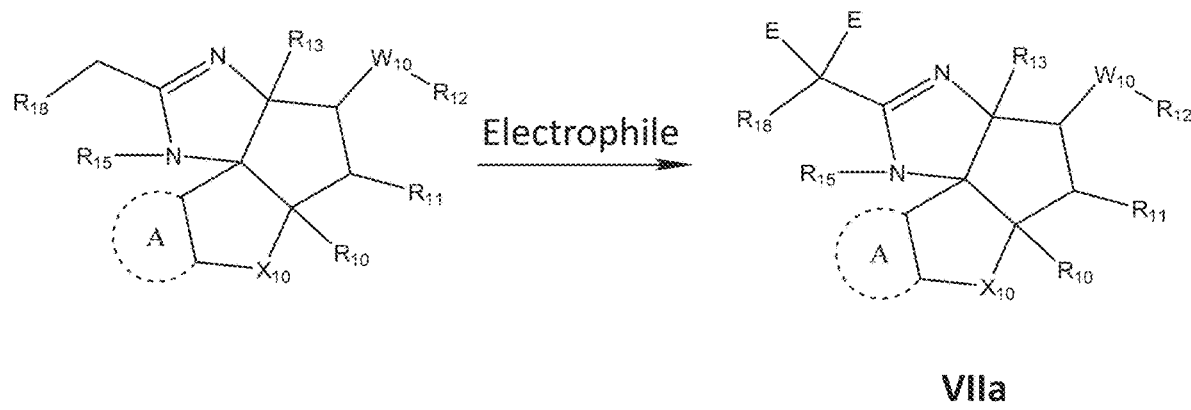
FIG. 9D shows a scheme for reaction of an amido-rocaglate with an electrophile.

FIG. 9D shows a scheme for reacting an amidino-rocaglate with an electrophile. The electrophile provides the group E which can be a halogen or another electrophile.

Figure 9E:
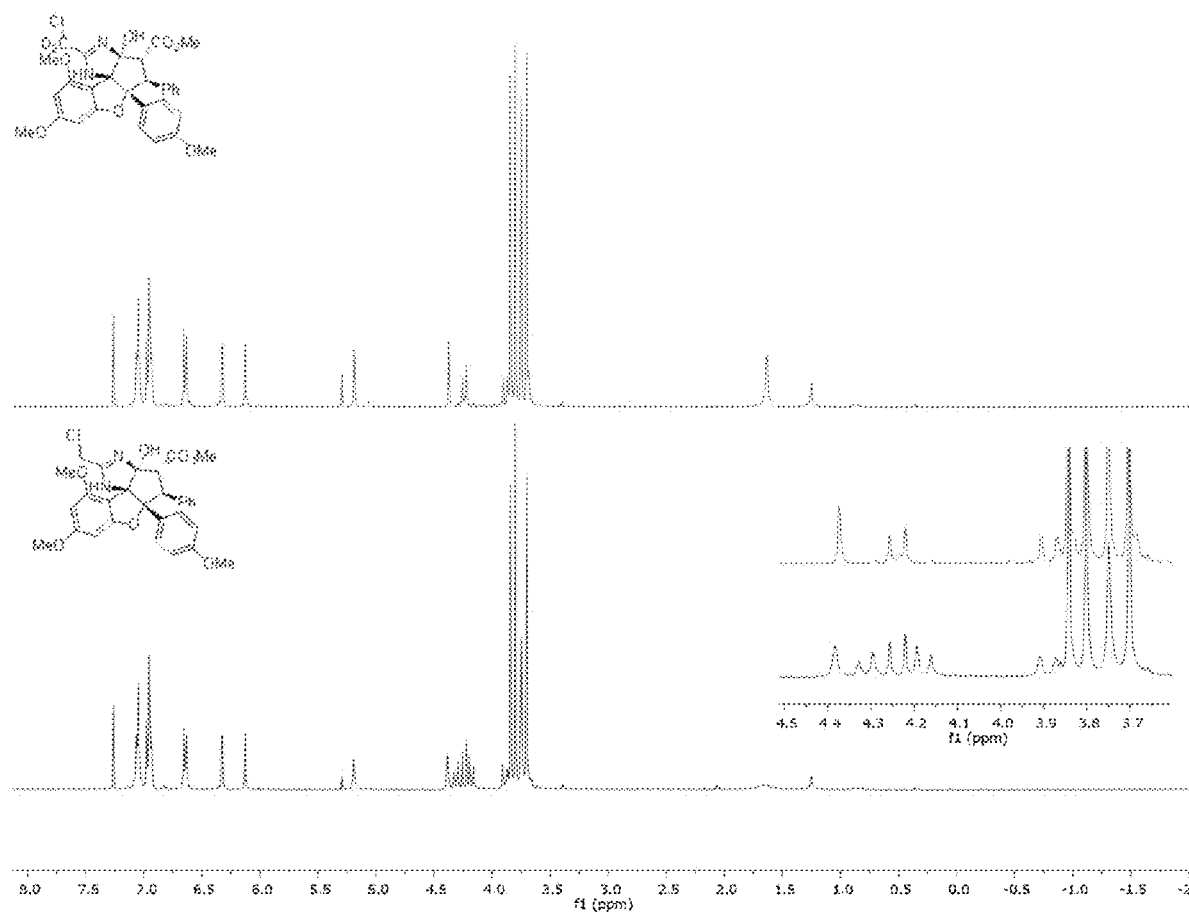
FIG. 9E shows NMR spectra of a deuterated and non-deuterated amidino-rocaglates.

As a further example, FIG. 9E shows the NMR spectra before (bottom) and after (top) deuteration of a chloro-amidino-rocaglate derivative with methanol-dl.

Figure 10:
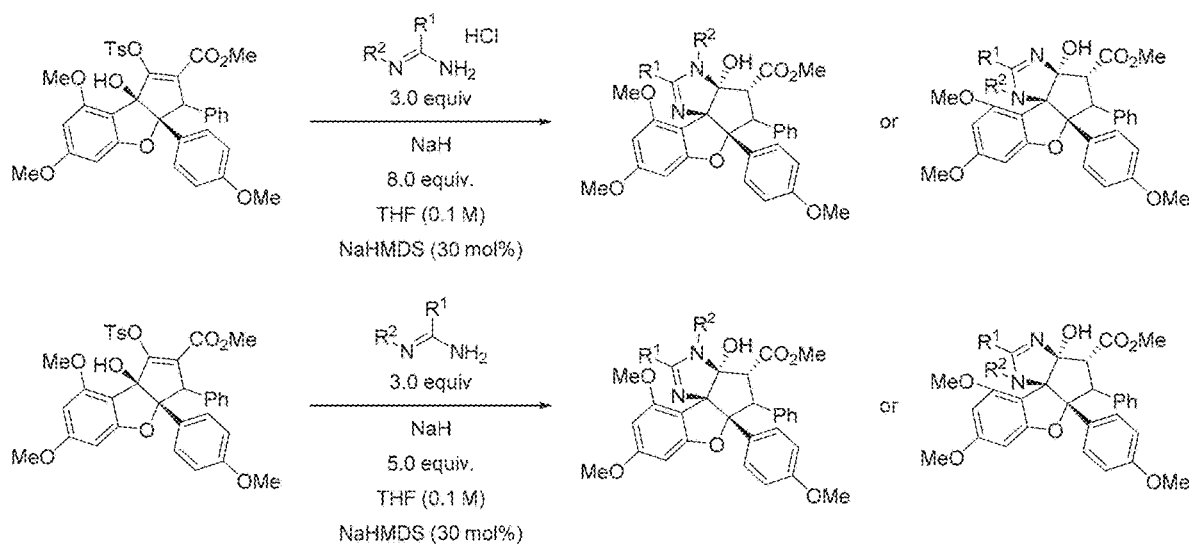
FIG. 10 shows reaction schemes for amidino-rocaglate synthesis.
Figure 11:
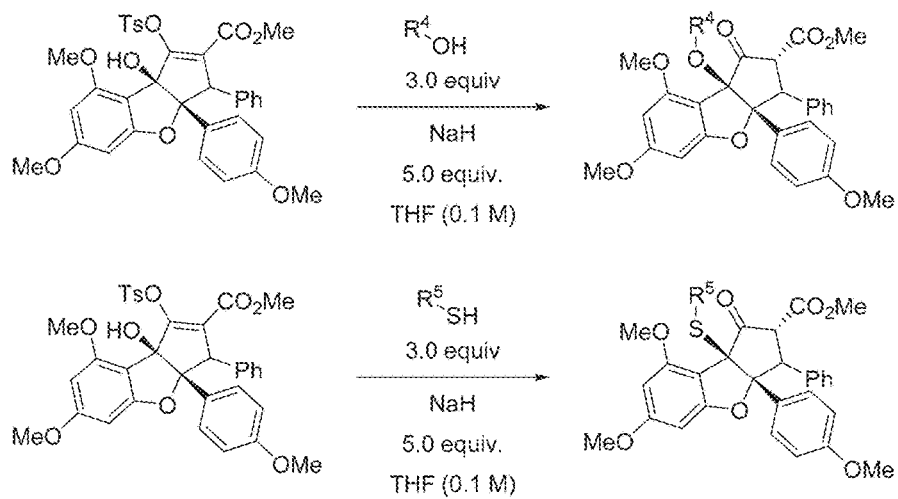
FIG. 11 shows the reaction scheme for thioyl and alkoxy-rocaglate synthesis.
Figure 12:
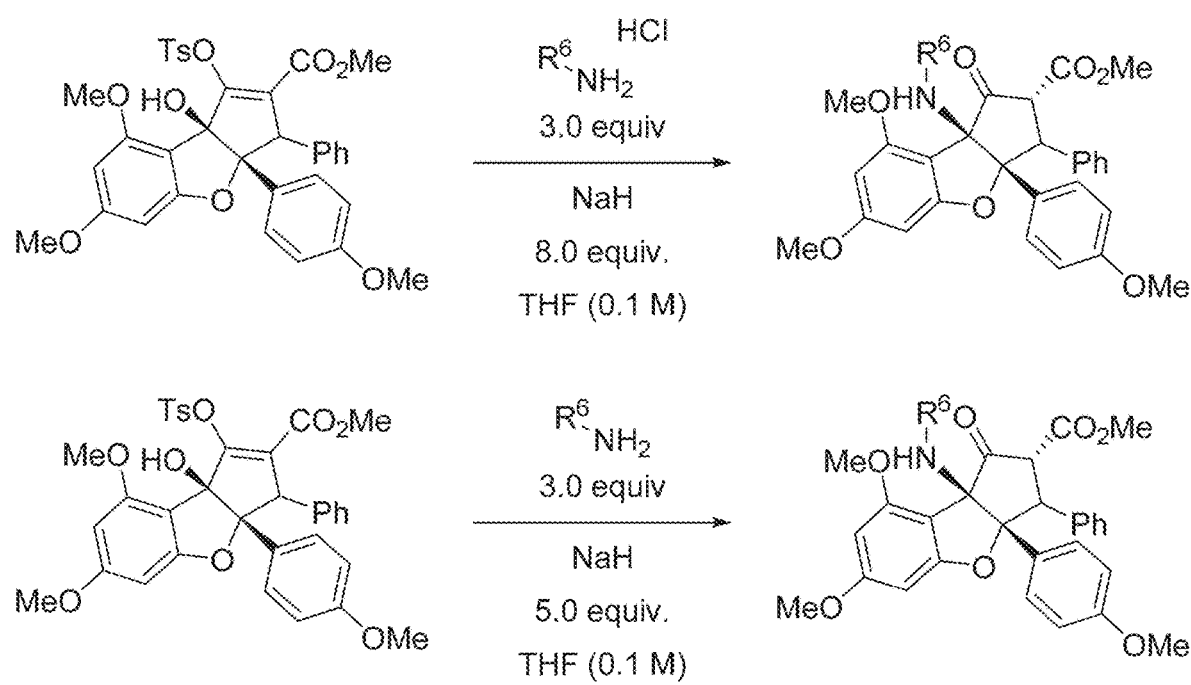
FIG. 12 shows the reaction scheme for amino-rocaglate synthesis.
Figure 13:
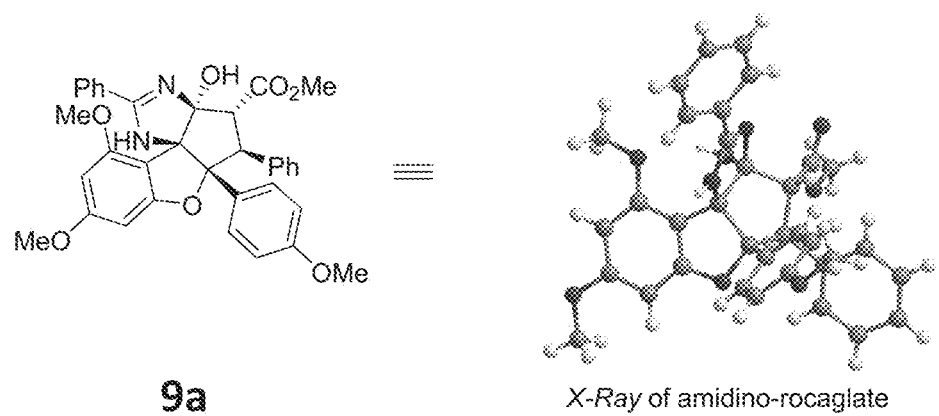
FIG. 13 shows the X-ray crystal structure of an amidino-rocaglate.

FIG. 10 shows the reaction scheme for amidino-rocaglate synthesis. FIG. 11 shows a reaction scheme for thioyl and alkoxy-rocaglate synthesis. FIG. 12 shows a reaction scheme for amino-rocaglate synthesis. FIG. 13 shows the X-ray crystal structure of an amidino-rocaglate.

Biological Studies

Figure 14:
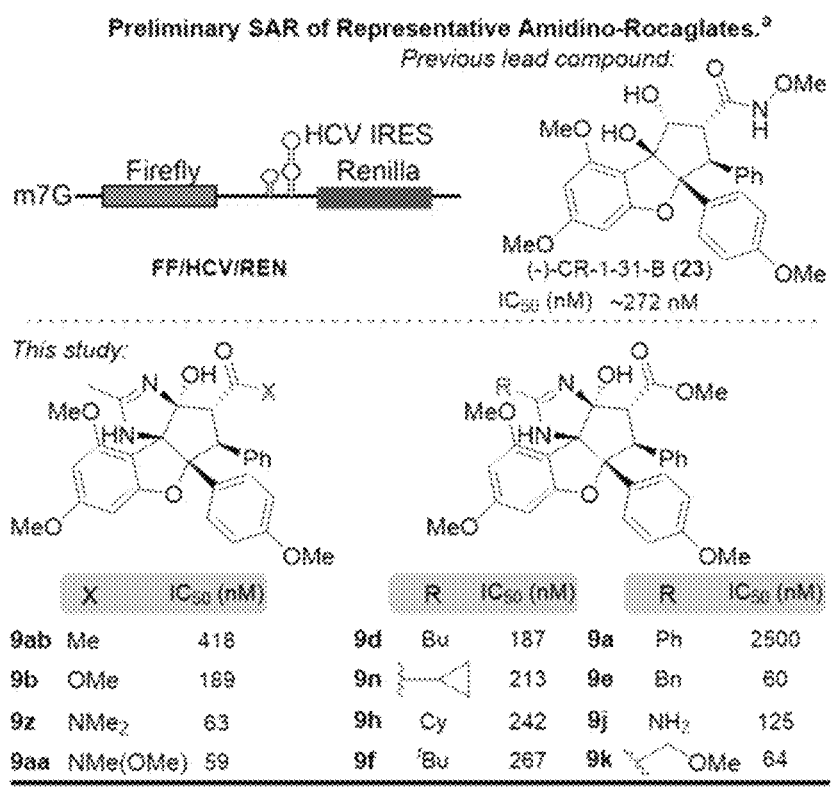
FIG. 14 shows structure activity relationships of amidino-rocaglates in in vitro translation assay using a bicistronic FF/HCV/Ren reporter.

Structure-Activity Relationships. With a number of amidino-rocaglates and amino-rocaglates in hand, we evaluated their inhibition of eIF4A-dependent translation using an in vitro assay as depicted in FIG. 14, where a bicistronic reporter mRNA was designed for translation in Krebs-2 extracts. In FIG. 14 the following description applies (a) $IC_{50}$ was determined from fitted sigmoid curves; $IC_{80}$ indicates the concentration of compound that inhibits cap-dependent translation by 50%, which was normalized by cap-independent translation. For its determination, the bicistronic reporter FF/HCV/Ren mRNA was used to produce Firefly luciferase (cap-dependent) and Renilla luciferase (cap-independent) in Krebs-2 extracts in the presence of indicated compounds at various concentrations. In particular, translation of Firefly luciferase (FF) is cap-dependent and depends on eIF4A activity; in contrast, translation of Renilla luciferase (REN) utilizes the HCV internal ribosome entry site (IRES) which functions independently of eIF4A. $IC_{50}$'s were determined by the inhibition of FF relative to REN obtained in the presence of compound relative to vehicle controls and normalized to REN as an internal control. Our previous lead compound, (−)-CR-1-31-B (23), exhibited an $IC_{50}$ of 272 nM in the bicistronic reporter assay. As expected, amidino-rocaglates generally showed overall improvements in $IC_{50}$ and representative compounds are displayed for a preliminary discussion of SAR (Table 3). In accordance with the eIF4A-RNA-rocaglamide (2) co-crystallographic analysis (FIG. 4), the amide carbonyl of 2 interacts with Gln195 of eIF4A as a H-bond acceptor, while the tertiary hydroxyl of 2 serves as a H-bond donor to an RNA base. A correlated trend of $IC_{50}$'s was observed for carbonyl substitutions (X═N(OMe)Me≥NMe₂>OMe>Me), where 9aa and 9z indicated excellent $IC_{50}$'s of 59 and 63 nM, respectively. In contrast, the ester (9b, $IC_{50}$=189 nM) and ketone (9ab, $IC_{50}$=418 nM) were found to be less potent supporting that the amide carbonyl of 9aa and 9z are more optimal H-bond donors to Gln195 of eIF4A. According to our previous findings, alkylation of the tertiary hydroxyl of RHT (4) and rocaglamide (2) eliminated the inhibition of RNA translation which was likely caused by disabling their ability as H-bond donors. To further verify the hypothesis, amidino-rocaglates (pKa of N—H~26.7-30.7 in DMSO, strong H-bond donors) and amino-rocaglates (pKa of N—H~36 to 44 in DMSO, weak H-bond donors) were next evaluated. As expected, no translation inhibition by amino-rocaglates 15 and their derivatives 18, 20, and 22 were observed. Preliminary SAR for ADR's showed that the less sterically demanding alkyl amidines slightly increased potency for translation inhibition ranging from $IC_{50}$=187 nM for the butyl derivative (9d) to $IC_{50}$=267 nM for the tert-butyl derivative (9f). Intriguingly, aryl amidines (e.g. 9a) were found to have dramatically decreased activity ($IC_{80}$=2500 nM) which may be caused by conformational restrictions. Conversely, benzyl amidine 9e had $IC_{50}$=60 nM, whereas the methylene tether may allow conformational adjustment to avoid rigid repulsion in the binding pocket. Moreover, the guanidine-type structure (9j) as well as methoxyl amidine (9k) also retained potent translation inhibition ($IC_{50}$=125 and 64 nM, respectively).

Figure 15:
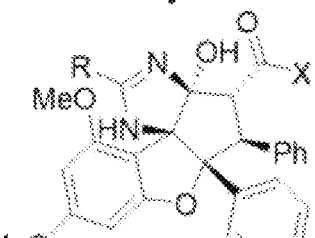
FIG. 15 shows chirality-based biological profiles of some compounds.

To further characterize the chirality of amidino-rocaglates and their properties as translation inhibitors, we synthesized enantioenriched analogues (−)-9b, (−)-9n, (−)-9z, (−)-9aa, and (+)-9aa shown in FIG. 15. As expected, only the natural enantiomers inhibited in vitro eIF4A-dependent translation with an $IC_{50}$ as low as 34 nM, which is an approximately 9-fold increase in potency relative to the previous lead compound, (−)-23. On the other hand, the unnatural enantiomer (+)-9aa showed minimal activity. The $IC_{50}$ was collected as previously described for FIG. 14.

Figure 16:
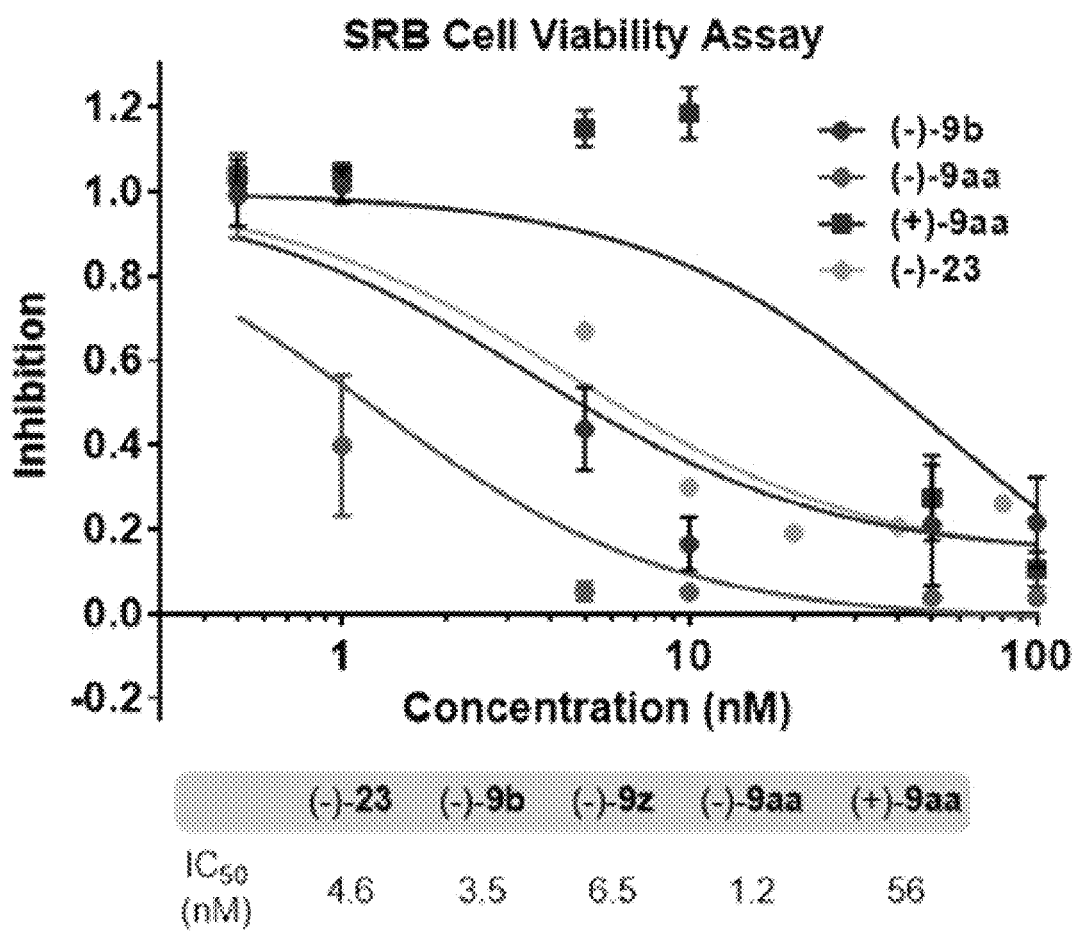
FIG. 16 is an inhibition plot for representative rocaglates against cancer cells.

Translation Inhibition by Amidino-Rocaglates Induces Cytotoxicity. We next evaluated amidino-rocaglates in an SRB cell viability assay using MDA-MB-231 breast cancer cells for cellular readout of translation inhibition (FIG. 16). In particular, (−)-9b, (−)-9aa, and (+)-9aa were compared with rocaglate hydroxamate (−)-23. We found excellent cytotoxicity of the ADR (−)-9aa with an $IC_{50}$=1.2 nM with a nearly 4-fold increase in potency over the previous lead-compound (−)-23, whereas the $IC_{50}$ of (−)-9b with methyl ester was determined to be 3.5 nM showing a similar overall trend as we have observed in the FF/HCV/REN assay. The inspiring high-potency of amidino-rocaglates underscores their utility as promising agents for anticancer treatment combined with the appropriate formulation and drug-delivery strategies. Interestingly, we also noticed minimal cytotoxicity induced by the unnatural enantiomer (+)-9aa ($IC_{50}$=56 nM); this result warrants further investigation for an as-yet undefined mechanism of action. The subsequent biological evaluation of the modified rocaglate derivatives revealed preliminary SAR for the inhibition of eIF4A-dependent translation, which identified amidino-rocaglate (−)-9aa with a 7-fold increase in potency in comparison to (−)-CR-1-31-B (23). In agreement with the recently reported X-ray crystallographic analysis of eIF4A-RocA-polypurine RNA, we demonstrated that the lower pKa of amidine N—H vs. the original tertiary hydroxyl likely contributes to improved translation inhibition. Meanwhile, amide carbonyls of 9z and 9aa served as H-bond acceptors likely improving interactions with Gln195 of eIF4A, although this awaits structural confirmation. The SRB cell viability assay in MDA-MB-231 cells demonstrated that amidino-rocaglates can serve as valuable agents in chemotherapies for cancers. Our studies further illustrate the power of chemical synthesis enabling structural and biological improvement of complex natural products using targeted modifications. Additional biological studies of amidino-, amino-rocaglates, and related compounds including RNA binding studies are currently in progress and will be reported in due course.

In summary, we have discovered an intercepted retro-Nazarov reaction providing an oxyallyl cation precursor for the late-stage modification of rocaglate natural products. Through this unified substitution strategy of rocaglates' tertiary hydroxide, we synthesized a library of over 30 amidino-rocaglates and 20 amino-rocaglates as natural product derivatives with novel scaffolds. The subsequent biological evaluation of the modified rocaglate derivatives revealed preliminary SAR for the inhibition of eIF4A-dependent translation, which identified amidino-rocaglate (−)-9aa with a 7-fold increase in potency in comparison to (−)-CR-1-31-B (23). In agreement with recently reported X-ray crystallographic analysis of eIF4A-RocA-polypurine RNA, we demonstrated that the lower pKa of amidine N—H vs the original O—H likely contributed to improved translation inhibition. Meanwhile, amide carbonyls of 9z and 9aa served as H-bond acceptors likely improving interactions with Gln195 of eIF4A, although this awaits structural confirmation. The SRB cell viability assay in MDA-MB-231 cells demonstrated that amidino-rocaglates could potentially serve as valuable agents in chemotherapies for cancers. Our studies further illustrate the power of chemical synthesis enabling structural and biological improvement of complex natural products using targeted modifications. Additional biological studies of amidino-, amino-rocaglates, and related compounds including RNA binding studies are currently in progress and will be reported in due course.

References (1) For general review of rocaglate natural products, see: (a) Ebada, S. S.; Lajkiewicz, N.; Porco, J. A., Jr.; Li-Weber, M.; Proksch, P. Chemistry and Biology of Rocaglamides (=Flavaglines) and Related Derivatives from *Aglaia* Species (Meliaceae). In *Progress in the Chemistry of Organic Natural Products* Vol. 94; Kinghorn, A. D., Falk, H., Kobayashi, J., Eds.; Springer Vienna: Vienna, 2011, p 1. (b) Ribeiro, N.; Thuaud, F.; Nebigil, C.; Désaubry, L. Recent Advances in the Biology and Chemistry of the Flavaglines. *Bioorg. Med. Chem.* 2012, 20, 1857. (c) Pan, L.; Woodard, J. L.; Lucas, D. M.; Fuchs, J. R.; Douglas Kinghorn, A. Rocaglamide, silvestrol and structurally related bioactive compounds from *Aglaia* species. *Nat. Prod. Rep.* 2014, 31, 924.

(2) Lu King, M.; Chiang, C.-C.; Ling, H.-C.; Fujita, E.; Ochiai, M.; McPhail, A. T. X-Ray Crystal Structure of Rocaglamide, a Novel Antileulemic 1H-Cyclopenta[b]benzofuran from *Aglaia elliptifolia*. J. Chem. Soc., Chem. Commun. 1982, 1150.

(3) For reviews of the synthesis of rocaglates, see: (a) Peter, P.; RuAngelie, E.; Rainer, E.; Frank, I. B.; Bambang, W. N. Chemistry and Biological Activity of Rocaglamide Derivatives and Related Compounds in *Aglaia* Species (Meliaceae) *Curr. Org. Chem.* 2001, 5, 923. (b) Cai, X.-h.; Xie, B.; Guo, H. Progress in the Total Synthesis of Rocaglamide. *ISRN Org. Chem.* 2011, 2011, 7. (c) Qian, Z.; Hussein, A.-H.; Laurent, D. Recent Advances in the Synthesis of Flavaglines, a Family of Potent Bioactive Natural Compounds Originating from Traditional Chinese Medicine. *Eur. J. Org. Chem.* 2016, 2016, 5908.

(4) For representative syntheses of rocaglate natural products, see: (a) Kraus, G. A.; Sy, J. O. A Synthetic Approach to Rocaglamide via Reductive Cyclization of δ-Keto Nitriles. *J. Org. Chem.* 1989, 54, 77. (b) Trost, B. M.; Greenspan, P. D.; Yang, B. V.; Saulnier, M. G. An Unusual Oxidative Cyclization. A Synthesis and Absolute Stereochemical Assignment of (−)-Rocaglamide. *J. Am. Chem. Soc.* 1990, 112, 9022. (c) Davey, A. E.; Schaeffer, M. J.; Taylor, R. J. K. Enantioselective Synthesis of Cyclopenta[b]benzofurans via An Organocatalytic Intramolecular Double Cyclization. *J. Chem. Soc., Chem. Commun.* 1991, 1137. (d) Davey, A. E.; Schaeffer, M. J.; Taylor, R. J. K. Synthesis of the Novel Anti-leukaemic Tetrahydrocyclopenta[b]benzofuran, Rocaglamide and Related Synthetic Studies. *J. Chem. Soc., Perkin Trans.* 1 1992, 2657. (e) Dobler, M. R.; Bruce, I.; Cederbaum, F.; Cooke, N. G.; Diorazio, L. J.; Hall, R. G.; Irving, E. Total Synthesis of (±)-Rocaglamide and Some Aryl Analogues. *Tetrahedron Lett.* 2001, 42, 8281. (f) Thede, K.; Diedrichs, N.; Ragot, J. P. Stereoselective Synthesis of (±)-Rocaglaol Analogues. *Org. Lett.* 2004, 6, 4595. (g) Gerard, B.; Jones, G.; Porco, J. A., Jr. A Biomimetic Approach to the Rocaglamides Employing Photogeneration of Oxidopyryliums Derived from 3-Hydroxyflavones. *J. Am. Chem. Soc.* 2004, 126, 13620. (h) Diedrichs, N.; Ragot, J. P.; Thede, K. A Highly Efficient Synthesis of Rocaglaols by a Novel α-Arylation of Ketones. *Eur. J. Org. Chem.* 2005, 2005, 1731. (i) Gerard, B.; Sangji, S.; O'Leary, D. J.; Porco, J. A., Jr. Enantioselective Photocycloaddition Mediated by Chiral Brønsted Acids: Asymmetric Synthesis of the Rocaglamides. *J. Am. Chem. Soc.* 2006, 128, 7754. (j) El Sous, M. E.; Khoo, M. L.; Holloway, G.; Owen, D.; Scammells, P. J.; Rizzacasa, M. A. Total Synthesis of (−)-Episilvestrol and (−)-Silvestrol. *Angew. Chem., Int. Ed.* 2007, 46, 7835. (k) Baudouin, G.; Cencic, R.; Pelletier, J.; Porco, J. A., Jr. *Angew. Chem., Int. Ed.* 2007, 46, 783. (l) Malona, J. A.; Cariou, K.; Frontier, A. J. Nazarov Cyclization Initiated by Peracid Oxidation: The Total Synthesis of (±)-Rocaglamide. *J. Am. Chem. Soc.* 2009, 131, 7560. (m) Magnus, P.; Freund, W. A.; Moorhead, E. J.; Rainey, T. Nazarov Cyclization Initiated by Peracid Oxidation: The Total Synthesis of (±)-Rocaglamide. *J. Am. Chem. Soc.* 2012, 134, 6140. (n) Lajkiewicz, N. J.; Roche, S. P.; Gerard, B.; Porco, J. A., Jr. Enantioselective Photocycloaddition of 3-Hydroxyflavones: Total Syntheses and Absolute Configuration Assignments of (+)-Ponapensin and (+)-Elliptifoline. *J. Am. Chem. Soc.* 2012, 134, 13108. (o) Stone, S. D.; Lajkiewicz, N. J.; Whitesell, L.; Hilmy, A.; Porco, J. A., Jr. Biomimetic Kinetic Resolution: Highly Enantio- and Diastereoselective Transfer Hydrogenation of Aglain Ketones to Access Flavagline Natural Products. *J. Am. Chem. Soc.* 2015, 137, 525. (p) Zhou, Z.; Tius, M. A. Synthesis of Each Enantiomer of Rocaglamide by Means of a Palladium(0)-Catalyzed Nazarov-Type Cyclization. *Angew. Chem., Int. Ed* 2015, 54, 6037. (q) Zhou, Z.; Dixon, D. D.; Jolit, A.; Tius, M. A. The Evolution of the Total Synthesis of Rocaglamide. *Chem. Eur. J.* 2016, 22, 15929.

(5) For representative medicinal remodeling of rocaglates from academia, see: (a) Roche, S. P.; Cencic, R.; Pelletier, J.; Porco, J. A., Jr. Biomimetic Photocycloaddition of 3-Hydroxyflavones: Synthesis and Evaluation of Rocaglate Derivatives as Inhibitors of Eukaryotic Translation. *Angew. Chem., Int. Ed* 2010, 49, 6533. (b) Thuaud, F.; Ribeiro, N.; Gaiddon, C.; Cresteil, T.; Désaubry, L. Novel Flavaglines Displaying Improved Cytotoxicity. *J. Med Chem.* 2011, 54, 411. (c) Rodrigo, C. M.; Cencic, R.; Roche, S. P.; Pelletier, J.; Porco, J. A., Jr. Synthesis of Rocaglamide Hydroxamates and Related Compounds as Eukaryotic Translation Inhibitors: Synthetic and Biological Studies. *J. Med Chem.* 2012, 55, 558. (d) Hawkins, B. C.; Lindqvist, L. M.; Nhu, D.; Sharp, P. P.; Segal, D.; Powell, A. K.; Campbell, M.; Ryan, E.; Chambers, J. M.; White, J. M.; Rizzacasa, M. A.; Lessene, G.; Huang, D. C. S.; Burns, C. J. Simplified Silvestrol Analogues with Potent Cytotoxic Activity. *ChemMedChem* 2014, 9, 1556. (e) Lajkiewicz, N. J.; Cognetta, A. B.; Niphakis, M. J.; Cravatt, B. F.; Porco, J. A., Jr. Remodeling Natural Products: Chemistry and Serine Hydrolase Activity of a Rocaglate-Derived β-Lactone. *J. Am. Chem. Soc.* 2014, 136, 2659. (f) Wang, W.; Cencic, R.; Whitesell, L.; Pelletier, J.; Porco, J. A., Jr. Synthesis of Aza-Rocaglates via ESIPT-Mediated (3+2) Photocycloaddition. *Chem.—*

Eur. J. 2016, 22, 12006. (g) Zhao, Q.; Tijeras-Raballand, A.; de Gramont, A.; Raymond, E.; Desaubry, L. Bioisosteric Modification of Flavaglines. *Tetrahedron Lett.* 2016, 57, 2943. (h) Wang, T. T.; Liu, S.; Wang, W.; Lajkiewicz, N.; Porco, J. A., Jr. Aglaroxin C and Derivatives as HCV Entry Inhibitors. U.S. Pat. No. 10,085,988 B1, 2018. (i) Zhang, W.; Liu, S.; Maiga, R. I.; Pelletier, J.; Brown, L. E.; Wang, T. T.; Porco, J. A., Jr. Chemical Synthesis Enables Structural Reengineering of Aglaroxin C Leading to Inhibition Bias for Hepatitis C Viral Infection. *J. Am. Chem. Soc.* 2019, 141, 1312.

(6) For representative medicinal remodeling of rocaglates from industry, see: (a) Bruce, I.; Cooke, N. G.; Diorazio, L. J.; Hall, R. G.; Irving, E. Synthesis of the Carbocyclic Analogue of (±)-Rocaglamide. *Tetrahedron Lett.* 1999, 40, 4279. (b) Hall Roger, G.; Szczepanski, H.; Bruce, I A. N.; Cooke Nigel, G.; Diorazio Louis, J.; Dobler, M.; Cederbaum, F. DE Patent DE 199 34 952 A1, 2000. (c) Liu, T.; Nair, S. J.; Lescarbeau, A.; Belani, J.; Peluso, S.; Conley, J.; Tillotson, B.; O'Hearn, P.; Smith, S.; Slocum, K.; West, K.; Helble, J.; Douglas, M.; Bahadoor, A.; Ali, J.; McGovern, K.; Fritz, C.; Palombella, V. J.; Wylie, A.; Castro, A. C.; Tremblay, M. R. Synthetic Silvestrol Analogues as Potent and Selective Protein Synthesis Inhibitors. *J. Med. Chem.* 2012, 55, 8859. (d) Ernst, J. T.; Reich, S. H.; Sprengeler, P. A.; Tran, C. V.; Packard, G. K.; Xiang, A. X.; Nilewski, C.; Michels, T. U.S. Pat. No. 9,957,277 B2, 2018.

(7) (a) Bordeleau, M.-E.; Robert, F.; Gerard, B.; Lindqvist, L.; Chen, S. M. H.; Wendel, H.-G.; Brem, B.; Greger, H.; Lowe, S. W.; Porco, J. A., Jr.; Pelletier, J. Therapeutic Suppression of Translation Initiation Modulates Chemosensitivity in a Mouse Lymphoma Model. *J. Cin. Invest.* 2008, 118, 2651. (b) Cencic, R.; Carrier, M.; Galicia-Vázquez, G.; Bordeleau, M.-E.; Sukarieh, R.; Bourdeau, A.; Brem, B.; Teodoro, J. G.; Greger, H.; Tremblay, M. L.; Porco, J. A., Jr.; Pelletier, J. Antitumor Activity and Mechanism of Action of the Cyclopenta[b]benzofuran, Silvestrol. *PLoS One* 2009, 4, e5223. (c) Chu, J.; Galicia-Vázquez, G.; Cencic, R.; Mills, John R.; Katigbak, A.; Porco, J. A., Jr.; Pelletier, J. CRISPR-Mediated Drug-Target Validation Reveals Selective Pharmacological Inhibition of the RNA Helicase, eIF4A. *Cell Rep.* 2016, 15, 2340. (d) Itoua Maïga, R.; Cencic, R.; Chu, J.; Waller, D. D.; Brown, L. E.; Devine, W. G.; Zhang, W.; Sebag, M.; Porco, J. A., Jr.; Pelletier, J. Oxo-aglaiastatin-Mediated Inhibition of Translation Initiation. *Sci. Rep.* 2019, 9, 1265.

(8) (a) Hwang, B. Y.; Su, B.-N.; Chai, H.; Mi, Q.; Kardono, L. B. S.; Afriastini, J. J.; Riswan, S.; Santarsiero, B. D.; Mesecar, A. D.; Wild, R.; Fairchild, C. R.; Vite, G. D.; Rose, W. C.; Farnsworth, N. R.; Cordell, G. A.; Pezzuto, J. M.; Swanson, S. M.; Kinghorn, A. D. Silvestrol and Episilvestrol, Potential Anticancer Rocaglate Derivatives from *Aglaia silvestris*. *J. Org. Chem.* 2004, 69, 3350; (b) Meurer-Grimes, B. M.; Yu, J.; Vairo, G. L. U.S. Patent 2004, U.S. Pat. No. 6,710,075 B2.

(9) (a) Chu, J.; Cencic, R.; Wang, W.; Porco, J. A., Jr.; Pelletier, J. Translation Inhibition by Rocaglates Is Independent of eIF4E Phosphorylation Status. *Mol. Cancer Ther.* 2016, 15,136; (b) Liu, S.; Wang, W.; Brown, L. E.; Qiu, C.; Lajkiewicz, N.; Zhao, T.; Zhou, J.; Porco, J. A., Jr.; Wang, T. T. A Novel Class of Small Molecule Compounds that Inhibit Hepatitis C Virus Infection by Targeting the Prohibitin-CRaf Pathway. *EBioMedicine* 2015, 2, 1600.

(10) Iwasaki, S.; Iwasaki, W.; Takahashi, M.; Sakamoto, A.; Watanabe, C.; Shichino, Y.; Floor, S. N.; Fujiwara, K.; Mito, M.; Dodo, K.; Sodeoka, M.; Imataka, H.; Honma, T.; Fukuzawa, K.; I to, T.; Ingolia, N. T. The Translation Inhibitor Rocaglamide Targets a Bimolecular Cavity between eIF4A and Polypurine RNA. *Mol. Cell* 2019, 73, 738.

(11) For pKa of tertiary hydroxide (pKa of $^t$BuOH is 32.2-32.5 in DMSO), see: (a) Olmstead, W. N.; Margolin, Z.; Bordwell, F. G. Acidities of Water and Simple Alcohols in Dimethyl Sulfoxide Solution. *J. Org. Chem.* 1980, 45, 3295. For pKa of amidine (pKa of amidines locates between 26.7-30.7 in DMSO), see: (b) Bordwell, F. G.; Ji, G. Z. Effects of Structural Changes on Acidities and Homolytic Bond Dissociation Energies of the Hydrogen-Nitrogen Bonds in Amidines, Carboxamides, and Thiocarboxamides. *J. Am. Chem. Soc.* 1991, 113, 8398.

(12) For reviews of intercepted Nazarov reaction, see: (a) Grant, T. N.; Rieder, C. J.; West, F. G. Interrupting the Nazarov Reaction: Domino and Cascade Processes Utilizing Cyclopentenyl Cations. *Chem. Commun.* 2009, 5676. (b) Li, H.; Wu, J. (3+2)-Cycloaddition Reactions of Oxyallyl Cations. *Synthesis* 2015, 47, 23.

(13) For recent examples of intercepted Nazarov reaction, see: (a) Wei, L.; Vivek, K.; Baburaj, B.; Markus, S.; Kamal, K. Branching Cascades: A Concise Synthetic Strategy Targeting Diverse and Complex Molecular Frameworks. *Angew. Chem., Int. Ed.* 2011, 50, 6900. (b) Kwon, Y.; McDonald, R.; West, F. G. Organoaluminum-Mediated Interrupted Nazarov Reaction. *Angew. Chem., Int. Ed.* 2013, 52, 8616. (c) Wu, Y.-K.; Dunbar, C. R.; McDonald, R.; Ferguson, M. J.; West, F. G. Experimental and Computational Studies on Interrupted Nazarov Reactions: Exploration of Umpolung Reactivity at the α-Carbon of Cyclopentanones. *J. Am. Chem. Soc.* 2014, 136, 14903. (d) William, R.; Leng, W. L.; Wang, S.; Liu, X.-W. The First Intermolecular Interrupted Imino-Nazarov Reaction: Expeditious Access to Carbocyclic Nucleoside Analogues. *Chem. Sci.* 2016, 7, 1100. (e) Wu, Y.-K.; Lin, R.; West, F. G. Intercepting the Nazarov Oxyallyl Intermediate with α-Formylvinyl Anion Equivalents to Access Formal Morita-Baylis-Hillman Alkylation Products. *Synlett* 2017, 28, 1486. (f) Hu, L.; Rombola, M.; Rawal, V. H. Synthesis of 1,2-Oxazinanes via Hydrogen Bond Mediated [3+3] Cycloaddition Reactions of Oxyallyl Cations with Nitrones. *Org. Lett.* 2018, 20, 5384.

(14) For an O- to O-1,4-tosyl shift, see: (a) Zagorevskii, V. A.; Kirsanova, Z. D. *Khim. Geterots. Soedin.* 1970, 6, 309. For N- to N-1,3-tosyl shift, see (b) Mertens, M. D.; Pietsch, M.; Schnakenburg, G.; Gütschow, M. Regioselective Sulfonylation and N- to O-Sulfonyl Migration of Quinazolin-4(3H)-ones and Analogous Thienopyrimidin-4(3H)-ones. *J. Org. Chem.* 2013, 78, 8966 and reference therein. For O- to N-1,4-tosyl shift, see (c) Andersen, K. K.; Gowda, G.; Jewell, L.; McGraw, P.; Phillips, B. T. Substitution at Tetracoordinate Sulfur(VI). Rearrangement of 2-Aminoaryl Arenesulfonates to N-(2-Hydroxyaryl)arenesulfonamides. *J. Org. Chem.* 1982, 47, 1884.

(15) For asymmetric [3+2]-photocycloadditions using ESIPT, see: (a) Xia, B.; Gerard, B.; Solano, D. M.; Wan, J.; Jones, G.; Porco, J. A., Jr. ESIPT-Mediated Photocycloadditions of 3-Hydroxyquinolinones: Development of a Fluorescence Quenching Assay for Reaction Screening. *Org. Lett.* 2011, 13, 1346. (b) Wenyu, W.; Anthony, C.; Retheesh, K.; J., L. N.; E., B. L.; Jayaraman, S.; Porco, J. A., Jr. Total Syntheses of the Isomeric Aglain Natural Products Foveoglin A and Perviridisin B: Selective ExcitedState Intramolecular Proton-Transfer Photocycloaddition. *Angew. Chem., Int. Ed.* 2017, 56, 14479.
(16) For concept and examples of intercepted retro-Nazarov reaction, see: (a) Fort, A. W. Evidence for a Delocalized Intermediate in the Favorskii Rearrangement. 2,6-Lutidine-promoted Methanolysis of α-Chlorodibenzyl Ketone. *J. Am. Chem. Soc.* 1962, 84, 2620. (b) Harmata, M.; Huang, C.; Rooshenas, P.; Schreiner, P. R. An Interrupted [4+3]Cycloaddition Reaction: A Hydride Shift (Ene Reaction) Intervenes. *Angew. Chem., Int. Ed.* 2008, 47, 8696. (c) Tang, Q.; Chen, X.; Tiwari, B.; Chi, Y. R. Addition of Indoles to Oxyallyl Cations for Facile Access to α-Indole Carbonyl Compounds. *Org. Lett.* 2012, 14, 1922. (d) Vander Wal, M. N.; Dilger, A. K.; MacMillan, D. W. C. Development of a Generic Activation Mode: Nucleophilic α-Substitution of Ketones via Oxy-allyl Cations. *Chem. Sci.* 2013, 4, 3075. (e) Luo, J.; Zhou, H.; Hu, J.; Wang, R.; Tang, Q. Efficient Catalytic-free Method to Produce α-Aryl Cycloalkanones through Highly Chemoselective Coupling of Aryl Compounds with Oxyallyl Cations. *RSC Adv.* 2014, 4, 17370. (f) Dange, N. S.; Stepherson, J. R.; Ayala, C. E.; Fronczek, F. R.; Kartika, R. Cooperative Benzylic-Oxyallylic Stabilized Cations: Regioselective Construction of α-Quaternary Centers in Ketone-derived Compounds. *Chem. Sci.* 2015, 6, 6312. (g) Ayala, C. E.; Dange, N. S.; Fronczek, F. R.; Kartika, R. Brønsted Acid Catalyzed α'-Functionalization of Silylenol Ethers with Indoles. *Angew. Chem., Int. Ed.* 2015, 54, 4641. (h) Liu, C.; Oblak, E. Z.; Vander Wal, M. N.; Dilger, A. K.; Almstead, D. K.; MacMillan, D. W. C. Oxy-Allyl Cation Catalysis: An Enantioselective Electrophilic Activation Mode. *J. Am. Chem. Soc.* 2016, 138, 2134.
(17) The retro-Nazarov products are thermal dynamically favored, where Frontier and co-workers proved the forbiddance of Nazarov reaction convert 10 to 6, see: Malona, J. A.; Cariou, K.; Spencer, W. T.; Frontier, A. J. Total Synthesis of (±)-Rocaglamide via Oxidation-Initiated Nazarov Cyclization. *J. Org. Chem.* 2012, 77, 1891.
(18) (a) Lee, C.; Yang, W.; Parr, R. G. Development of the Colle-Salvetti Correlation-Energy Formula into a Functional of the Electron Density. *Phys. Rev. B* 1988, 37, 785. (b) Becke, A. D. Density-Functional Thermochemistry. III. The Role of Exact Exchange. *J. Chem. Phys.* 1993, 98, 5648.
(19) (a) Sáez, J. A.; Arnó, M.; Domingo, L. R. Lewis Acid-Catalyzed [4+3] Cycloaddition of 2-(Trimethyl Silyloxy)acrolein with Furan. Insight on the Nature of the Mechanism from a DFT Analysis. *Org. Lett.* 2003, 5, 4117. (b) Lohse, A. G.; Krenske, E. H.; Antoline, J. E.; Houk, K. N.; Hsung, R. P. Regioselectivities of (4+3) Cycloadditions between Furans and Oxazolidinone-Substituted Oxyallyls. *Org. Lett.* 2010, 12, 5506. (c) Krenske, E. H.; Houk, K. N.; Lohse, A. G.; Antoline, J. E.; Hsung, R. P. Stereoselectivity in Oxyallyl-Furan (4+3) Cycloadditions: Control of Intermediate Conformations and Dispersive Stabilization in Cycloadditions Involving Oxazolidinone Auxiliaries. *Chem. Sci.* 2010, 1, 387. (d) Antoline, J. E.; Krenske, E. H.; Lohse, A. G.; Houk, K. N.; Hsung, R. P. Stereoselectivities and Regioselectivities of (4+3) Cycloadditions Between Allenamide-Derived Chiral Oxazolidinone-Stabilized Oxyallyls and Furans: Experiment and Theory. *J. Am. Chem. Soc.* 2011, 133, 14443.
(20) (a) Bordwell, F. G.; Drucker, G. E.; Fried, H. E. Acidities of Carbon and Nitrogen Acids: the Aromaticity of the Cyclopentadienyl Anion. *J. Org. Chem.* 1981, 46, 632. (b) Bordwell, F. G. Equilibrium Acidities in Dimethyl Sulfoxide Solution. *Acc. Chem. Res.* 1988, 21, 456.

Example 2: A Large-Scale Comparative Study of eIF4A-Targeting Rocaglates

Rocaglates are a family of biologically active molecules sharing a common cyclopenta[b] benzofuran core that augment the RNA binding activity of eukaryotic initiation factor (eIF) 4A leading to translation inhibition. Interest towards the application of rocaglates in anti-neoplastic strategies has led to the vast expansion of this family, and to date, hundreds of distinct rocaglates have been acquired either from natural sources or through chemical synthesis. Here, is presented a comprehensive study comparing the biological activities of >200 rocaglates. It was found that while most rocaglates preferentially repress the translation of transcripts containing purine rich 5' leaders, certain family members lack this sequence selectivity. In addition, a novel aspect of rocaglate mechanism of action was uncovered in which the eIF4F complex is inactivated through the generation of "dead-end" translation complexes achieved by clamping of eIF4F at cap-proximal polypurine sequences. Disclosed herein is also the characterization of a new class of synthetic rocaglates (amidino-rocaglates) that possess potent biological activity in vitro and in vivo.

Translation is an essential step in the gene expression pathway that enables cells to make rapid and spatiotemporal alterations to the proteome. Regulation of translation is critical to a wide variety of biological processes, including cellular growth, survival, differentiation, and development. Accordingly, aberrant translational control is associated with several pathological disorders. Much of translation regulation is imposed at the initiation phase, which is an intricate process involving the coordination of multiple essential factors. In the canonical mechanism of translation initiation, the eukaryotic initiation factor (eIF) 4F complex (comprised of eIF4A, 4E, and 4G) first binds to the mRNA 5'-terminal $m^7GpppN$ cap structure and remodels proximal RNA structural elements to facilitate recruitment of 43S pre-initiation complexes (PIC: comprised of the 40S small ribosomal subunit and associated factors). The 43S PIC then scans the mRNA 5' leader in search of an appropriate initiation codon. Features present within the 5' leader (e.g. RNA structure, GC content, protein binding sites) can affect an mRNA's dependency on eIF4F and consequently influence its ability to recruit a 43S PIC and/or alter the scanning efficacy of the 43S PIC.

Small molecules targeting the translation machinery show considerable promise in the treatment of a variety of human maladies including cancer, viral infection, and neurodegeneration. In particular, there is significant interest towards the development of a family of compounds collectively known as rocaglates. Rocaglates are a class of translation inhibitors that possess potent cytotoxic activity against tumor cells. This family of small molecules share a common cyclopenta[b]benzofuran core and were originally isolated from extracts of the *Aglaia* species of angiosperms. To date, numerous rocaglate analogs have been synthesized with the goal of improving potency and bioavailability. Studies using silvestrol, a natural product isolated from *Aglaia foveolata*, indicate that rocaglates enhance the RNA binding affinity of eIF4A. A rocaglate-resistant eIF4A1 mutant (F163L) has been characterized and introduction of this allele into cells using CRISPR/Cas9 mediated gene editing confers resistance to rocaglate cytotoxicity, further demonstrating that the mechanism of action of these compounds is dependent on their ability to interfere with eIF4A activity. A current prevailing model proposes that eIF4A is stabilized by rocaglates onto mRNA 5' leader regions, leading to the formation of steric barriers that impede 43S PIC scanning. In addition, prolonged exposure (4 h) of cells to silvestrol leads to a reduction in the amount of eIF4A in the eIF4F complex which may also be a contributing factor to their inhibitory mechanism.

The interest towards rocaglates as potential anti-neoplastic agents is rising; the significant efforts made towards the development of synthetic strategies have greatly expanded the number of members in this family. However, it has also meant that various laboratories are employing different rocaglates in biological studies, usually due to limitations in accessing specific structural entities. Examples of commonly used rocaglates include the naturally occurring compounds, silvestrol 1 and rocaglamide A (RocA) (2), as well as synthetically-accessible compounds such as CR-1-31-B (23), SDS-1-021, RHT (4), and FL3 (FIG. 17A). One outstanding question is whether structural variations present in different rocaglates influence the same spectrum of translationally inhibited mRNAs. To date, three ribosome profiling studies have been undertaken with rocaglates: two using silvestrol and the other using RocA (2). In these studies, different mRNA features were identified as rocaglate-sensitizing elements. In a comprehensive, genome-wide ribosome profiling approach using silvestrol on MDA-MB-231 cells, 5' leader regions with long, structured sequences, and low overall GC content were identified as features that imparted compound sensitivity. In a second study, longer 5' leader regions and the presence of $(CGG)_{3-4}$ motifs (SEQ ID NO: 3) were identified as silvestrol-sensitizing attributes. In contrast, exposure of HEK 293 cells to RocA (2) recognized that eIF4A clamping to polypurine stretches within 5' leaders formed steric barriers and proposed that these could block 43S PIC scanning. A clamping mechanism of action is consistent with recent structural information revealing direct interactions of RocA (2) as an interfacial inhibitor with both eIF4A1 and a polypurine RNA substrate.

In this study, is addressed the question of whether universal conclusions can be drawn across the rocaglate family of compounds through systematic testing of diverse analogues, and whether potency towards inhibiting translation correlates with clamping activity and cellular cytotoxicity. To this end, we screened a collection of >200 rocaglate derivatives to identify the most active family members and gain insight into how structural modifications of the rocaglate core impact protein/RNA interaction. A good correlation between the ability of a rocaglate to stimulate binding of eIF4A1 to a polypurine-containing RNA and their ability to inhibit translation was found. However, there were clear outliers suggesting that caution must be taken in formulating global conclusions across all rocaglate family members. It is also reported herein that rocaglates can stabilize the eIF4F complex at the cap structure contributing directly, and through a bystander effect, to the inhibitory mechanism of action of these compounds. A novel class of rocaglates, amidino-rocaglates (ADRs), that ranks among the most potent synthetic derivatives identified to date have also been uncovered.

Results and Discussion

Rocaglates similarly enhance RNA binding of eIF4A1 and eIF4A2. In order to rapidly evaluate the ability of rocaglates to stimulate binding of eIF4A to RNA, a fluorescence polarization (FP) assay using a FAM (fluorescein amidite)-labelled RNA probe (FIG. 18A) was used. The ATPase activity of eIF4A1 was stimulated by the presence of RNA; previous studies assessing the RNA sequence dependency of this event reported that the homoribopolymers poly r(A) and poly r(U) are more potent than poly r(C), poly r(I), poly r(G), globin mRNA, tRNA, poly r(I-C), or poly r(A)•poly r(U) substrates, suggesting that eIF4A has an inherent nucleotide bias for RNA binding. Using the FP assay, the RNA sequence specificity of eIF4A1 and eIF4A2 we revisited and it was found that both proteins have a preference for mixed polypurine (poly $r(AG)_8$ (SEQ ID NO: 2) or poly $rA(GAA)_5$) (SEQ ID NO: 4) sequences versus poly $r(A)_{16}$ (SEQ ID NO: 5), poly $r(C)_{16}$ (SEQ ID NO: 6), or mixed polypyrimidine (poly $r(UC)_8$) (SEQ ID NO: 7) (FIGS. 17B and 17C). CR-1-31-B (23) equally stimulates binding of both eIF4A1 and eIF4A2 to poly $r(AG)_8$ (SEQ ID NO: 2)(FIG. 17D). Due to the high degree of shared amino acid identity between the two paralogs, their apparent similarity with respect to RNA binding activity and response to CR-1-31-B (23), and the fact that eIF4A1 is essential but eIF4A2 is not, eIF4A1 was used in the majority of our subsequent experiments. CR-1-31-B (23) preferentially stimulated binding of eIF4A1 to RNA harboring polypurine bases, but not to polypyrimidine RNA oligonucleotides (poly $r(C)_{16}$ (SEQ ID NO: 6) or poly $r(UC)_8$ (SEQ ID NO: 7) (FIG. 17E). A single r(AG) dinucleotide embedded within a polypyrimidine track was sufficient for CR-1-31-B (23) to stimulate eIF4A1-RNA binding, but the extent of binding increased with higher AG content (FIG. 17F). The location of an AG dinucleotide within a 16 nt RNA probe harboring otherwise poly r(U) sequences influenced stimulation of RNA binding, with the optimal preference being 7 nucleotides downstream from the RNA 5' end (FIG. 18B). Taken together, these results indicate that: (i) eIF4A1 and eIF4A2 show similar RNA sequence binding specificity and have a distinct preference for polypurines, (ii) the RNA binding activity of both eIF4A1 and eIF4A2 is similarly stimulated by CR-1-31-B (23), and (iii) stimulation of RNA binding by CR-1-31-B (23) to eIF4A1 scales with polypurine content.

Figure 19:
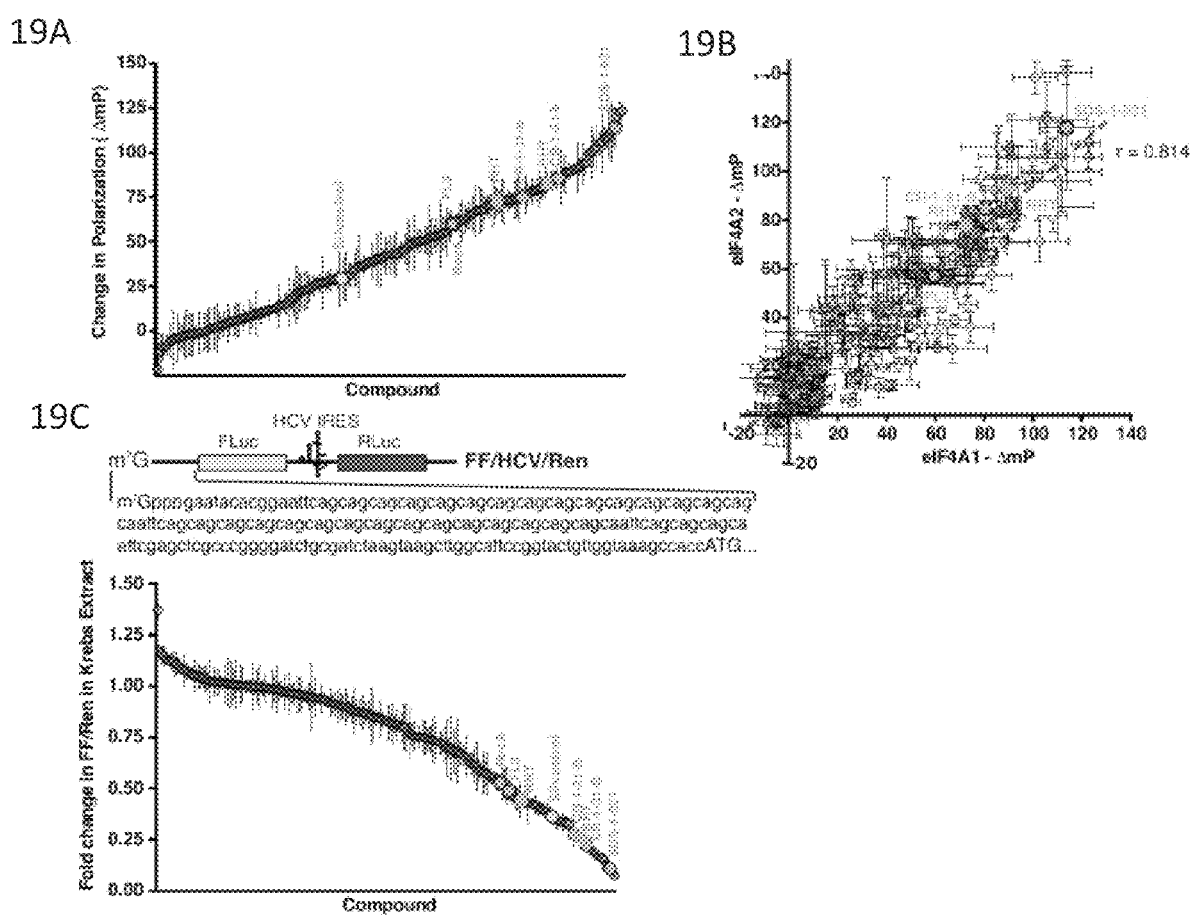
FIGS. 19A-19C shows rocaglate activity profiling.

In vitro assessment of rocaglate biological activity. The X-ray crystal structure of eIF4A1 complexed with RocA (2) and poly $r(AG)_5$ (SEQ ID NO: 8) RNA revealed that aryl rings A and B (FIG. 17A) stack with adjacent adenine and guanine bases, respectively. In addition, the $C_8$b-OH group hydrogen bonds to the N7 of the same guanine stacked to aryl ring B. We screened the BU-CM Dcollection of >200 rocaglates for compounds that could stimulate binding of eIF4A1 to RNA (FIGS. 19A-19C). No compound capable of enhancing binding of eIF4A1 to poly $r(UC)_7$ (SEQ ID NO: 7) was identified. However, a significant proportion of compounds stimulated binding of poly $r(AG)_8$ (SEQ ID NO: 2) RNA to eIF4A1 and eIF4A2. No rocaglate that significantly stimulated RNA binding to eIF4A1 over eIF4A2 or vice versa was identified (FIG. 19B), a finding that is not surprising since the two amino acids involved in rocaglate binding (F163 (F164 in eIF4A2) and Q195 (Q196 in eIF4A2)) are conserved between the two proteins.

The rocaglate collection was also tested in in vitro translation assays using cell-free extracts with a previously described bicistronic mRNA containing the HCV IRES, which is not dependent on eIF4A activity and served as an internal control (FIG. 19C). Among the commonly studied rocaglates, the ability of RocA (2), FL3, RHT (4), CR-1-31-B (23), and SDS-1-021 to inhibit cap-dependent translation correlated with their ability to stimulate eIF4A1-poly $r(AG)_8$ (SEQ ID NO: 2) binding, with SDS-1-021 being the most potent compound (FIG. 3). These experiments identified two novel rocaglates that exhibited comparable potency to SDS-1-021, the ADRs 9n (CMLD012072) and 9b (CMLD012073) (FIG. 20A).

Overall, the inhibitory activity of a rocaglate towards cap-dependent translation in vitro and its ability to induce RNA clamping correlated well ($r_p=-0.62$), but there were notable exceptions (FIG. 3). Silvestrol was a clear outlier, as it exhibits relatively weak activity in the FP assay but is able to potently inhibit cap-dependent translation (FIG. 3). Two synthetic silvestrol derivatives, WGD-57-591 and WGD-57-590, showed behavior similar to silvestrol (FIGS. 3 and 20B). Also noted are another group of compounds that were potent at inducing eIF4A1:RNA association, yet showed no or weak activity (0-25% inhibition) towards cap-dependent translation in vitro (FIGS. 3 and 20C). Among these were an aglaroxin C analogue (CMLD012077), a brominated rocaglamidoxime (CMLD011352), and two cis-diol-containing rocaglaols (CMLD011167 and CMLD011166) (FIG. 20C).

Figure 17:
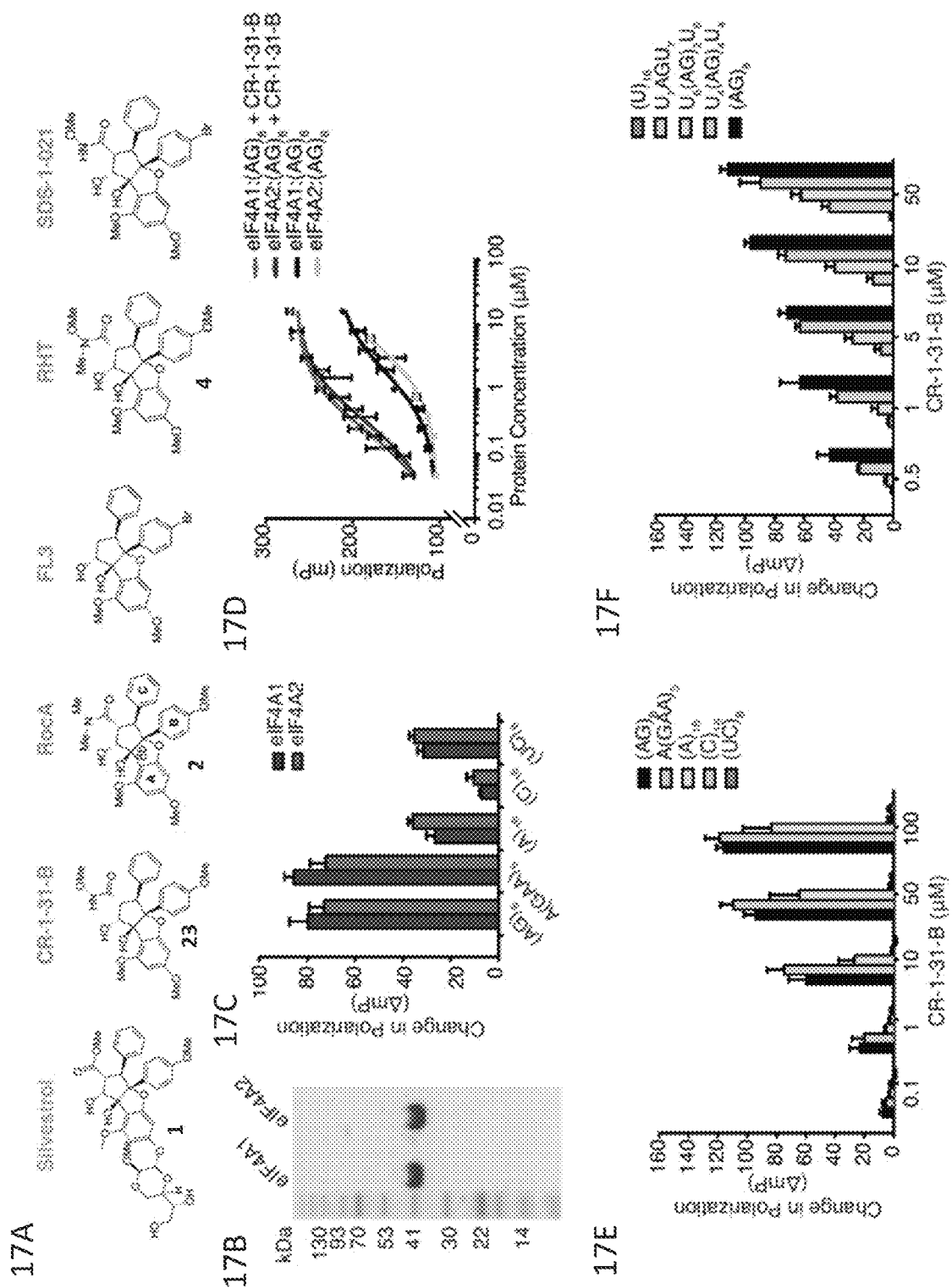
FIGS. 17A-17F shows assessment of eIF4A1 and eIF4A2 RNA binding specificity.

All of these identified compounds retained similar RNA sequence binding preference for eIF4A1 with a bias for polypurine-containing substrates over polypyrimidines (FIG. 17). In contrast, pateamine A, a structurally unrelated compound that also targets eIF4A potently induced binding to all RNA substrates tested RocA (2) showed activity similar to CR-1-31-B (23) in the FP assay (FIGS. 17A and 21) whereas both silvestrol 1 and WGD-57-591 were less potent across the concentrations tested. All eIF4A1:rocaglate:poly $r(AG)_{10}$ complexes dissociated significantly slower than eIF4A1:Poly $r(AG)_{10}$ complexes, as previously reported. Even in the presence of ATP, which stimulates release of eIF4A from RNA, the half-life of the complexes were much longer than the rates of translation initiation (median <1 min)

Rocaglates show differing mRNA targeting spectra in translation assays. The in vitro experiments described above investigating the rocaglate-mediated inhibition of cap-dependent translation were performed at a fixed rocaglate concentration (2 µM) using a generic bicistronic mRNA reporter in Krebs-2 cell-free translation extracts (FIG. 19C). To better assess the consequences of eIF4A:polypurine clamping on the initiation process, we designed a series of bicistronic reporters harboring cap-proximal polypurine tracks of varying lengths in their 5' leader region (FIG. 22A). We chose this location within the 5' leader region as it has previously been shown that cap-proximal steric barriers effectively inhibit translation initiation. We reasoned that these reporters would provide a sensitized readout for rocaglate-induce clamping of eIF4A at this location. Testing of mRNA reporters containing no AG dinucleotide, $(AG)_2$, $(AG)_5$ (SEQ ID NO: 8), or $(AG)_{16}$ (SEQ ID NO: 9) indicated that 5×(AG) was sufficient to elicit maximum inhibition of cap-dependent FF luciferase production by CR-1-31-B (23), while the HCV IRES remained recalcitrant to inhibition (FIG. 22B).

Figure 23:
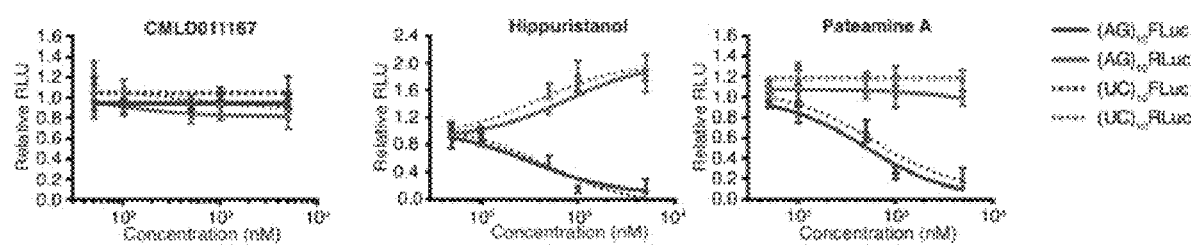
FIG. 23 shows plots of dose-response of $(AG)_{10}$- and $(UC)_{10}$-FF/HCV/Ren mRNAs to CMLD011167, hippuristanol and pateamine A in vitro. n=3±SEM.

We next tested the response of mRNA reporters containing cap-proximal $(AG)_{10}$ or $(UC)_{10}$ sequences (FIG. 22A). CR-1-31-B (23) and RocA (2) inhibited cap-dependent translation (FLuc) from only the $(AG)_{10}$-containing mRNA, while exerting little effect on translation from the $(UC)_{10}$ reporter (FIG. 22C). Unexpectedly, silvestrol equally inhibited both mRNA reporters (FIG. 22C), despite the fact that it does not stimulate binding of recombinant eIF4A1 to polypyrimidine RNA sequences. WGD-57-591 and CMLD012073 9b equally inhibited translation of both $(AG)_{10}$ and $(UC)_{10}$ reporters (FIG. 22C). CMLD011167 failed to inhibit either reporter at the concentrations tested (FIG. 23), consistent with its apparent lack of in vitro activity in the previous experiments. The structurally unrelated eIF4A inhibitors, hippuristanol and pateamine A, equally repressed cap-dependent translation from both $(AG)_{10}$ and $(UC)_{10}$ FF/HCV/Ren mRNAs, highlighting that purine selectivity in translation inhibition is not shared among all eIF4A-targeting molecules (FIG. 23). The difference in activity observed between CR-1-31-B (23) and silvestrol 1 was not restricted to cap-proximal polypurine tracks, but also observed with reporters where the polypurine/polypyrimidine tracks were situated 15 nt downstream from the cap (FIGS. 24A and 24B). Positioning a polypurine track within the 3' UTR did not sensitize translation of a test mRNA to CR-1-31-B (23) indicating that inhibition is 5' leader-dependent (FIG. 24C). These results revealed unexpected mRNA sequence targeting differences among members of the rocaglate family when assayed in vitro.

Figure 25:
FIG. 25A. shows RNA pulldowns (RPDs) performed with the indicated m$^7$GpppG- or ApppG-capped RNA species incubated in the presence of retic lysate and either vehicle or 500 nM rocaglate.
FIG. 25B shows RPDs performed with m$^7$GpppG-capped RNA species incubated in the presence of recombinant eIF4A (125 nM) eIF4F or Krebs-2 extracts and either vehicle or 500 nM of silvestrol.

To determine the ability of rocaglates to recruit eIF4A to RNA in translation extracts, RNA pulldowns (RPDs) using 30 nt polypurine—or polypyrimidine-biotinylated RNA baits were performed. RNA baits were added to in vitro translation extracts in the presence or absence of rocaglate followed by purification using immobilized streptavidin. RPDs performed in the presence of CR-1-31-B (23) or RocA (2) showed that eIF4A1 was recruited to the purine-rich mRNA template in a cap-independent manner (FIG. 25A). Contrary to the FP experiments, silvestrol induced eIF4A1 binding to both the polypurine and polypyrimidine baits and this was cap-independent (FIG. 25A, right panels). When the RPDs were performed using ApppG-capped RNA with purified eIF4A1 or eIF4F rather than translation extracts, an increase in eIF4A1:polypyrimidine RNA association with silvestrol was not observed (FIG. 25B). This suggests that a co-factor present in the translation lysate is required to stimulate eIF4A1 binding to pyrimidine sequences in the presence of silvestrol. Current efforts are aimed at identifying the nature of this activity and determine if this is related to the ability of silvestrol to equally inhibit the $(AG)_{10}$- and $(UC)_{10}$-FF/HCV/Ren mRNA reporters utilized herein.

Figure 4:
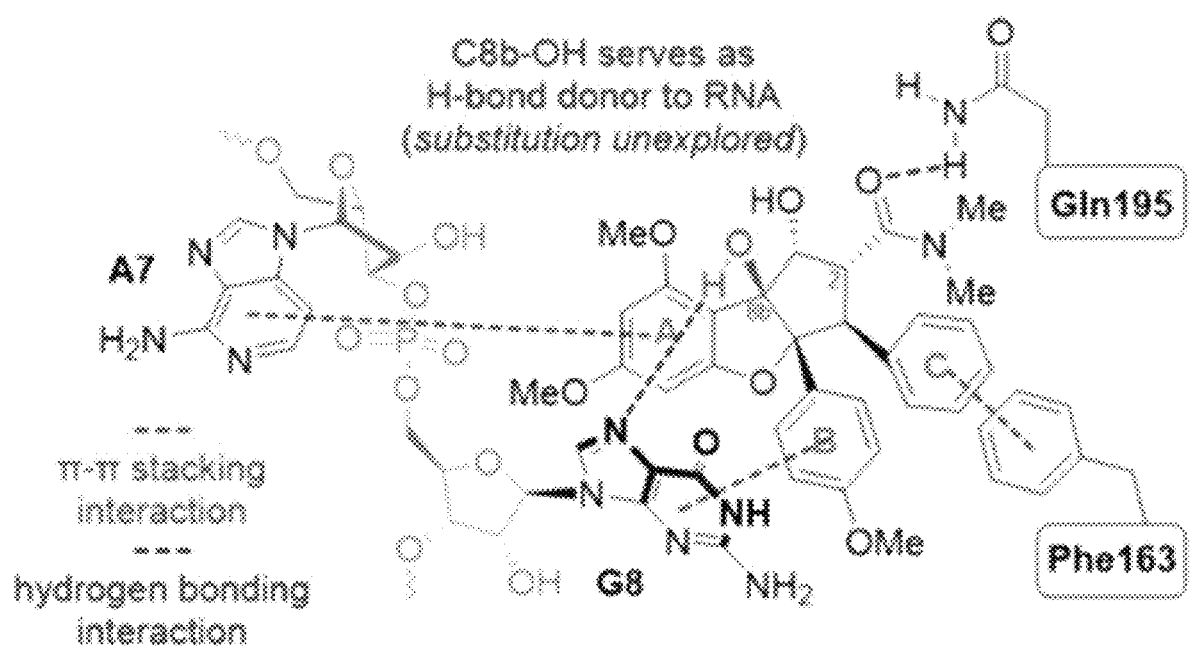
FIG. 4 shows the structural features of rocaglamide bound to eIF4A-polypurine RNA.

In cellula activity of rocaglates. All compounds in the rocaglate collection were assessed for cytotoxic activity towards NIH/3T3 cells as well as the rocaglate-resistant line, eIF4A$^{em1JP}$, which harbors an F163L mutation in eIF4A1. This mutation was originally identified following selection for RocA-resistant yeast mutants and F163 was subsequently shown to be critical for stacking with ring C of RocA (2) (FIG. 4). Although eIF4A2 is also a target of rocaglates, eIF4A1 F163L is sufficient to confer resistance to rocaglate-induced translation inhibition and cytotoxicity, likely due to eIF4A1 being the more abundant isoform in NIH/3T3 cells (250-fold higher). Fifteen compounds that induced >70% cell death relative to vehicle-treated cells when tested at 40 nM were identified (FIGS. 26A and 27. The rocaglate hydroxamates, SDS-1-021, CR-1-31-B (23), and RHT (4) were among these. Interestingly, CMLD011166 and CMLD011167, compounds which were inactive in vitro, were surprisingly cytotoxic towards NIH/3T3 cells. In contrast, compound CMLD011352 which showed robust activity in the FP assay was inactive in vitro (FIG. 20) and was also not cytotoxic towards NIH/3T3 cells. The two novel ADRs 9b and 9n (CMLD012073 and CMLD012072) which displayed potent activity in vitro were also among the top 15 cytotoxic rocaglates, ranking 10$^{th}$ and 15$^{th}$, respectively. Lastly, although effective at inhibiting cap-dependent translation in vitro, WGD-57-591 (no activity @ 40 nM) and WGD-57-590 (12% growth inhibition @ 40 nM) performed poorly in this assay. All cytotoxic rocaglates showed little or significantly diminished activity towards the rocaglate-resistant cell line eIF4A$^{em1JP}$, indicating that eIF4A1 on-target engagement is responsible for the observed phenotypic response (FIG. 26A).

Figure 28:
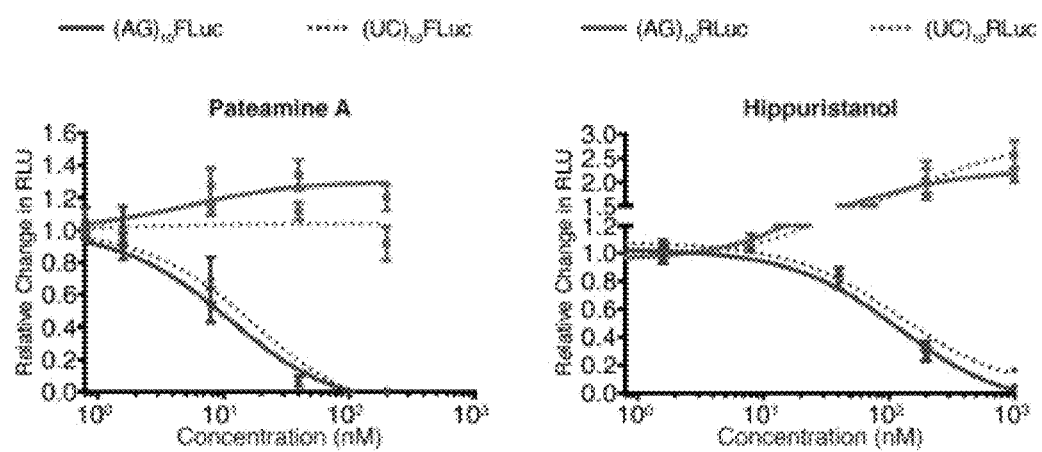
FIG. 28 shows in cellula dose-response of $(AG)_{10}$- and $(UC)_{10}$-FF/HCV/Ren mRNAs to hippuristanol and pateamine. n=3±SD FIG. 29 are bar plots showing that cap-independent clamping of eIF4A does not account for the full inhibitory effects of rocaglates.

We next asked if differences in behavior among rocaglates towards the (AG)$_{10}$- and (UC)$_{10}$-reporters observed in vitro also extended in cellula (FIG. 26B). This was important since in cells, mRNA transcripts need to compete for components of the translation initiation machinery from a complex cellular mRNA pool and this scenario is difficult to recapitulate in experiments using cell-free extracts. Following mRNA transfections, cells were exposed to compound and luciferase activity determined. CR-1-31-B (23) and silvestrol 1 showed distinct behaviors towards the (AG)$_{10}$ and (UC)$_{10}$ reporter mRNAs. CR-1-31-B (23) showed preference for inhibiting (AG)$_{10}$-FF/HCV/Ren over (UC)$_{10}$-FF/HCV/Ren mRNA (FIG. 26B), although the differences were not as pronounced as in vitro (FIG. 22C). Silvestrol 1 and a derivative, WGD-57-591, inhibited both reporters equally but WGD-57-591 was significantly less potent than silvestrol (FIG. 26B). CMLD011167, although inactive in vitro, showed a behavior that mirrored CR-1-31-B (23) with respect to a clear preference for inhibiting (AG)$_{10}$-FF/HCV/Ren mRNA. CMLD012073 showed a slight preference for inhibiting the (AG)$_{10}$-FF/HCV/Ren reporter mRNA (FIG. 4b).—The unrelated eIF4A inhibitors, pateamine A and hippuristanol, inhibited both reporters equally (FIG. 28).

Figure 29:
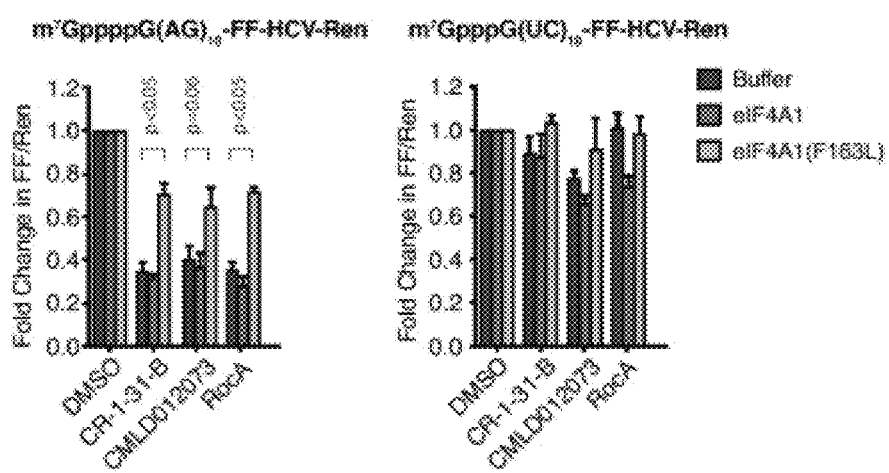

Rocaglates sequester eIF4F onto RNA. RocA (2) induced clamping of eIF4A to 5' leader regions have been proposed to inhibit translation by blocking scanning of 43S PICs. We therefore sought to test if this mechanism was sufficient to account for the translation inhibition observed with RocA, CR-1-31-B (23), and the newly identified ADRs. We supplemented translation extracts programmed with m$^7$G-(AG)$_{10}$-FF/HCV/Ren mRNA with wild-type (wt) or rocaglate-resistant eIF4A1(F163L) recombinant protein. The dissociation rates of eIF4A from (AG)$_{10}$ changes from t$_{1/2}$<2 min in the presence of vehicle to t$_{1/2}$=27 min the presence of RocA. Thus, if stabilization of endogenous eIF4A in translation extracts onto mRNA is sufficient to mediate translation inhibition, then the addition of recombinant eIF4A1$^{F163L}$ should not be able to rescue this inhibition. However, for all compounds tested, we observed rescue of rocaglate-induced translation inhibition of the polypurine-containing reporter by eIF4A1(F163L) (FIG. 29). These results suggest that rocaglate-induced clamping to polypurine tracts cannot be solely responsible for mediating full inhibition of the reporters under testing.

We previously found that crosslinking of eIF4A from the eIF4F complex to the cap is increased in the presence of rocaglates. To extend these results, RPDs with m$^7$G-capped RNA baits was performed to assess whether rocaglates could stimulate the binding and retention of eIF4F to mRNA. Here, was observed an increase in eIF4E, eIF4A, and eIF4G association with capped polypurine RNA in the presence of the tested rocaglates (FIG. 30A). These results indicate that in addition to inducing cap-independent RNA clamping, rocaglates can trap eIF4F at the cap structure of mRNAs containing cap-proximal polypurine sequences. To assess the stability of these complexes, we pre-formed eIF4F/Rocaglate/mRNA complexes and found that these repressed subsequent translations only when preformed on m$^7$G-(AG)$_{10}$-FF/HCV/Ren mRNA.

In addition to a primary effect on translation of the target mRNA to which eIF4F is clamped by the rocaglate, this retention is predicted to lead to a reduction in the limiting eIF4F pool available for ribosome recruitment and could exert a trans-inhibitory effect on mRNAs that are not directly-targeted by rocaglates (i.e., absence of polypurine regions in their 5' leader regions). To test this, we programmed in vitro translation reactions with (UC)$_{10}$-FF/HCV/Ren mRNA which we found to be unresponsive to CR-1-31-B (23) and RocA (2) (FIG. 22). These were then supplemented with a 25-fold molar excess m$^7$GpppG-(AG)$_{10}$ (SEQ ID NO: 10) or ApppG-(AG)$_{10}$ (SEQ ID NO: 11) competitor RNA (FIG. 30B). The addition of m$^7$GpppG-(AG)$_{10}$ (SEQ ID NO: 10) competitor sensitized (UC)$_{10}$-FF/HCV/Ren mRNA to inhibition by CR-1-31-B (23) and RocA (2) (FIG. 30C, solid blue lines). In contrast, addition of ApppG-(AG)$_{10}$ (SEQ ID NO: 11) and CR-1-31-B (23) or RocA (2) had little impact on translation of (UC)$_{10}$-FF/HCV/Ren mRNA, indicating this to be a cap-dependent phenomenon (FIG. 30C, blue dotted line). If rocaglates decrease the pool of active eIF4F complexes, we posit that the addition of eIF4F to translation extracts should rescue rocaglate-mediated inhibition. The addition of eIF4F was able to partially rescue the cap-dependent inhibition of the (UC)$_{10}$-FF/HCV/Ren mRNA induced by CR-1-31-B (23), silvestrol 1, or the ADR, (−)-9aa (CMLD012612) (FIG. 30D). Taken together, these results are consistent with the notion that cap-proximal polypurine sequences can sequester eIF4F at the cap, leading to inhibition of translation of target mRNAs and in trans inhibition of otherwise unresponsive mRNAs (see Discussion).

The mechanism of action of rocaglates suggest a gain-of-function activity imparted to eIF4A and eIF4F. To test this hypothesis in cells, it was reasoned that expression of wt eIF4A1 into eIF4A1$^{em1JP}$ cells should re-sensitize these to rocaglates since wt eIF4A1 could be able to clamp onto RNA, either as free eIF4A1 and/or as part of the eIF4F complex. NIH3T3 and eIF4A1$^{em1JP}$ cells were transduced with an empty MSCV cassette, MSCV/His6-eIF4A1, or MSCV/His$_6$-eIF4A1(F163L) (FIG. 31A). NIH/3T3 cells overexpressing wt eIF4A1 or eIF4A1(F163L) were similarly sensitive to rocaglates and there were little differences noted among them (FIG. 31B, compare grey and red to black lines, respectively). Introduction of eIF4A1(F163L) into eIF4A1$^{em1JP}$ cells also had little effect on rocaglate-responsiveness (FIG. 31B, compare light blue to dark blue lines). However, introduction of wt eIF4A1 into eIF4A1$^{em1JP}$ cells significantly sensitized these to all tested rocaglates (FIG. 31B, compare orange to dark blue lines), a result consistent with the notion that rocaglates exert their effects through imparting a gain-of-function activity to eIF4A1.

Figure 32:
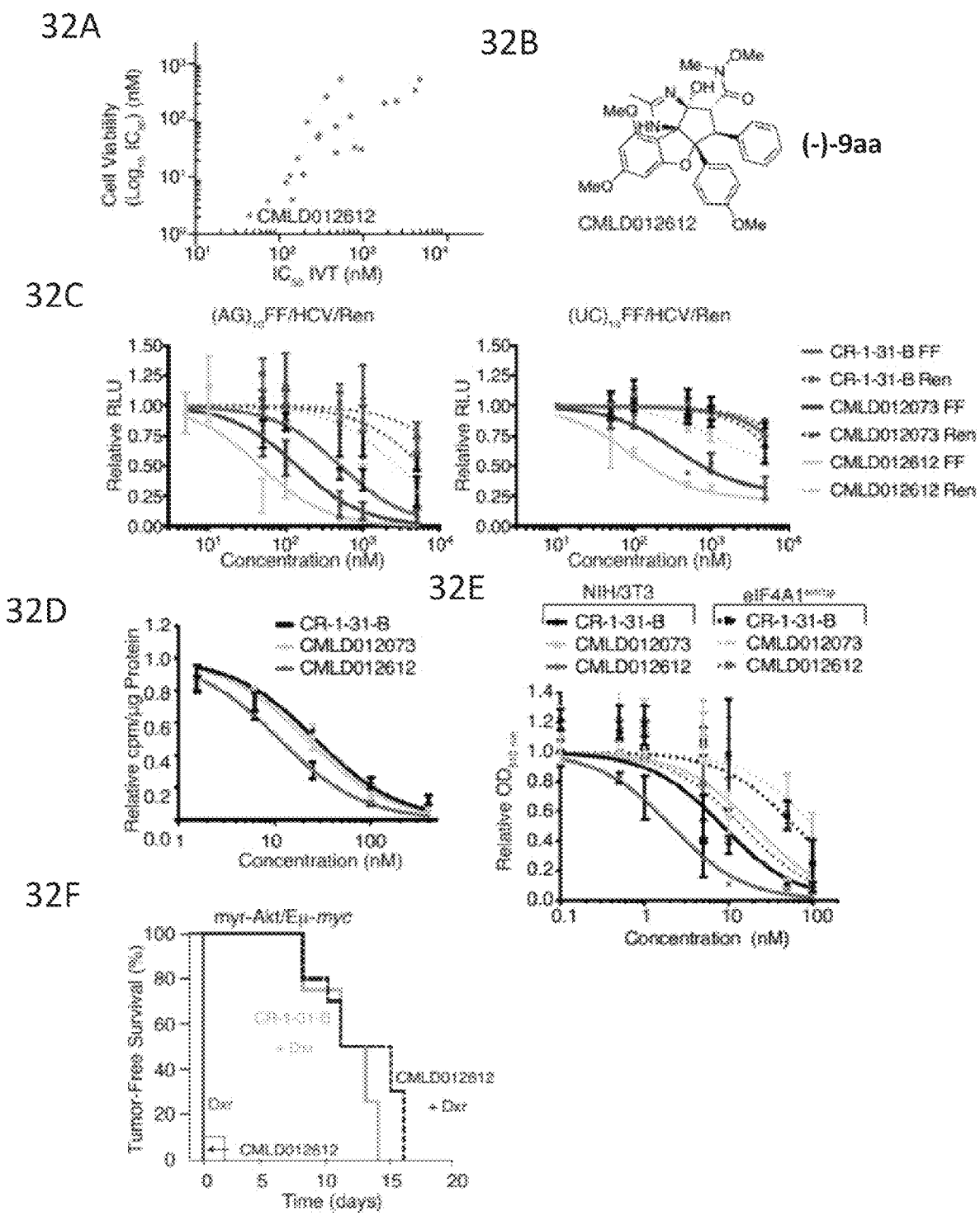
FIG. 32A is a plot of IC$_{50}$ for inhibiting NIH/3T3 cell survival versus blocking translation of FF/HCV/Ren in vitro by amidino-rocaglates (ADRs).
FIG. 32B shows the chemical structure of the amidino-rocaglate CMLD012612.
FIG. 32C demonstrates that CMLD012612 inhibits capped m$^7$GpppG-(AG)$_{10}$-FF/HCV/Ren and m$^7$GpppG-(UC)$_{10}$-FF/HCV/Ren mRNA in Krebs-2 extracts.
FIG. 32D is a plot showing inhibition of $^{35}$S-methioinine incorporation in HEK293 cells following a 1 h exposure to the indicated compound concentrations. n=3±SD.
FIG. 32E is a plot showing cytotoxicity of CMLD012612 towards NI/3T3 and eIF4A1$^{em1JP}$ cells following exposure to the indicated compound concentration. n=3±SD
FIG. 32F is a Kaplan-Meier plot showing tumor-free survival of mice bearing myr-Akt/Eµ-Myc tumors following treatment with doxorubicin (Dxr, red line; n=10), CMLD012612 (solid black line; n=10), CR-1-31-D+Dox (blue line; n=4), or CMLD012612+doxorubicin (dashed black line; n=10).

ADRs represent a novel class of potent rocaglates. Among the most potent inhibitors of translation uncovered by our screen (FIGS. 20A and 20B) were two novel amidino-rocaglates (ADR), which we sought to characterize more thoroughly. These arose as a consequence of a recently described intercepted retro-Nazarov reaction that could be harnessed to generate novel rocaglates. A series of were synthesized and their relative potency towards inhibiting translation in vitro and cellular cytotoxicity determined (FIG. 32A). These assays identified the amidino hydroxamate, (−)-9aa (CMLD012612), as the most potent ADR analogue (FIGS. 32A and 28B). (−)-9aa (CMLD012612), inhibited both (AG)$_{10}$- and (UC)$_{10}$-FF/HCV/Ren mRNA reporters in vitro (FIG. 32 C), potently inhibited cellular translation (FIG. 32D), and exhibited strong cytotoxicity towards NIH/3T3 cells (FIG. 32E; IC$_{50}$~2 nM). This cytotoxicity was significantly reduced in eIF4A1$^{em1JP}$ cells.

Figure 33:
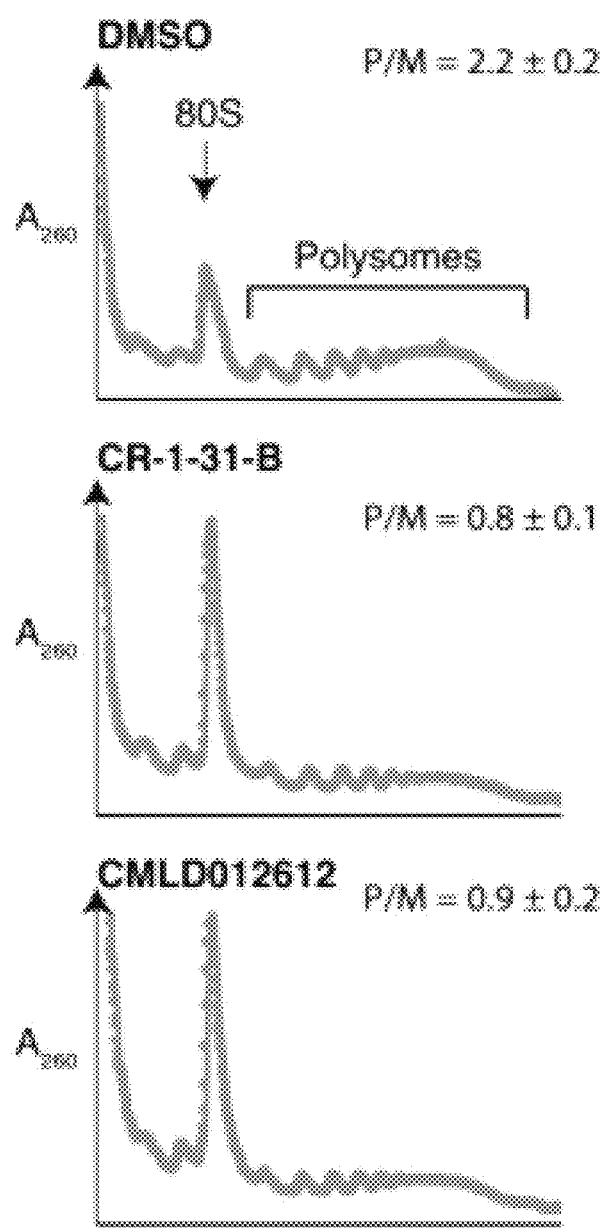
FIG. 33 are plots showing that CMLD012612 inhibits translation in vivo in mouse liver cells.

We next assessed the in vivo activity of CMLD012612. Liver polysomes from mice treated with (−)-9aa (CMLD012612), were effectively suppressed indicating in vivo inhibitory activity towards protein synthesis (FIG. 33). There have been several reports demonstrating that rocaglates are capable of chemo-sensitizing drug resistant tumor, as first shown in the Eμ-Myc model towards Pten$^{+/-}$ Eμ-myc and Eμ-myc/eIF4E tumors. (−)-9aa (CMLD012612), effectively sensitized myr-Akt/Eμ-Myc lymphomas in vivo to the effects of doxorubicin, with only mice that received both compounds showing tumor loss that extended to 15-16 days (FIG. 32F). Taken together, these results identify ADRs as commanding powerful translation inhibitory activity towards eIF4A-mediated initiation in vitro and in vivo.

A surprising revelation of this study is that structurally related rocaglates can exert different effects on gene expression. Overall, we observe a strong correlation between the degree of eIF4A1 stabilization onto RNA and extent of translation inhibition. However, we found a clear difference between rocaglates in their targeting preference for mRNA reporters containing a cap-proximal purine-versus pyrimidine-rich 5' leader region. For example, CR-1-31-B 23 preferentially inhibited purine-rich reporters in vitro and in cells compared to silvestrol, which equally inhibited both (FIGS. 22A-22C, and FIG. 26B). Although features such as cell permeability and intracellular stability come in play in dictating an in cellula response, the stimulation of eIF4A1: RNA association was generally a good predictor for compound cytotoxicity. Silvestrol, WGD-57-590 and WGD-57-591 are the only molecules within the collection containing a 1,4-dioxanyloxy moiety and that inhibit translation in vitro far more potently than what one might have predicted based solely on their relatively weak ability to stimulate eIF4A1: RNA association (FIG. 3). RNA pulldown assays in cell-free translation systems using poly r(UC)$_{10}$ (SEQ ID NO: 38) as bait reveal that silvestrol was able to stimulate eIF4A association to this RNA template (FIGS. 25A-25B). However, this effect was not recapitulated using recombinant eIF4A or purified eIF4F indicating that there is likely an additional co-factor required for mediating association of eIF4A1 with polypyrimidine RNA in the presence of silvestrol (FIG. 25B). We do not understand the molecular basis for the broader mRNA targeting range of silvestrol but suspect that the 1,4-dioxanyloxy moiety is responsible. Current efforts are aimed towards resolving this deficiency in our understanding. Our results caution against generalizations attributing specific mRNA responsive features to all biologically active rocaglates.

Figure 26:
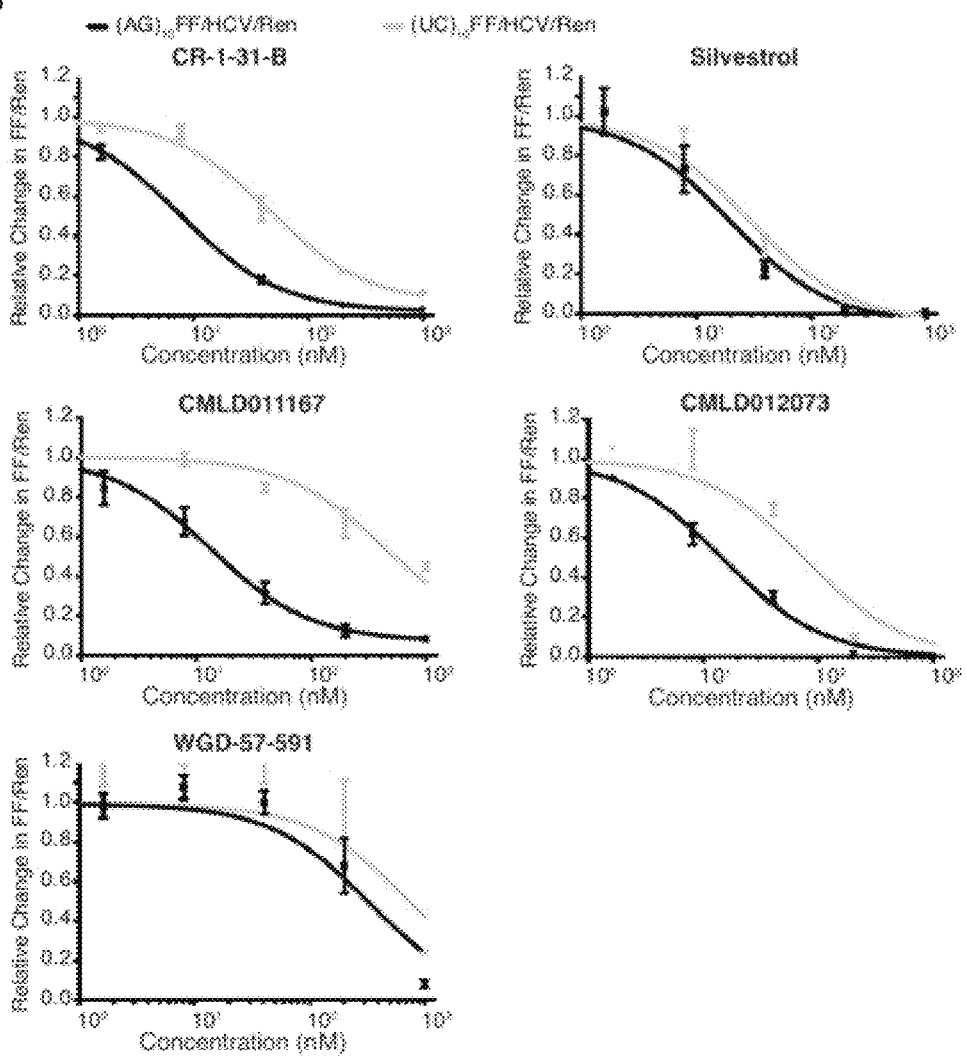
FIG. 26A Cytotoxicity of rocaglates towards NIH/3T3 (grey circle) and eIF4A1$^{em1JP}$ (red triangle) cells. Cells were exposed to 40 nM compound for 4 days and viability was measured using the SRB assay. n=3±SEM.
FIG. 26B is a plot demonstrating rocaglates showing different sequence preferences for inhibiting cap-dependent translation in cellula. HEK 293T cells were transfected with the indicated mRNA reporters, compounds added 1 h later, and luciferase activity. n=3±SD.

Another class of outlier rocaglates included the rocaglaols CMLD011166 and CMLD011167, the only compounds in our collection having a cis-1,2 cyclopentadiol moiety, rather than a trans-1,2 cyclopentadiol core. In spite of their potent ability to stimulate eIF4A1:RNA association, the cis-diol rocaglaols did not inhibit translation in in vitro cell-free translation systems. Nevertheless, these compounds are able to inhibit translation in cells and are highly cytotoxic (FIG. 26). The mechanism of action the cis-diol rocaglaols is dependent on their ability to target eIF4A1 since eIF4A1$^{em1JP}$ cells are resistant. Why these compounds are active in cells, but show no translation inhibitory activity in vitro currently remains unanswered.

In addition to demonstrating that active rocaglates may exert differing effects to the translatome, the observations made in this report address some of the discrepancies in the literature regarding rocaglate mechanism of action. It has been reported that RocA (2) does not inhibit translation but instead acts through inhibiting the MAPK signalling pathway. The absence of translation inhibition by RocA (2) in their study could be an attribute of the 5' leader regions of the luciferase mRNA under study. It was found that the luciferase reporter provided by commercial RRL systems (Promega) is recalcitrant to RocA (2) inhibition when tested in RRL (data not shown).

This large-scale screen identified a novel, potent class of rocaglates—the ADRs. Among newly synthesized analogues, an ADR (−)-9aa (CMLD012612) that is more potent relative to other rocaglates was identified. Whereas the IC$_{50}$ of CR-1-31-B (23) (in terms of cytotoxicity towards NIH3T3 cells) is ~8.5 nM, (−)-9aa (CMLD012612), displays an IC$_{50}$ of ~2 nM (FIG. 32E). The primary mechanism of action of (−)-9aa (CMLD012612), appears to be dependent on eIF4A1, since eIF4A$^{em1jp}$ are at least 10-fold more resistant than parental NIH/3T3 cells. The sensitivity of eIF4A$^{em1jp}$ cells to (−)-9aa (CMLD012612), observed at higher concentrations may be due to the presence of eIF4A2 or the ability of (−)-9aa (CMLD012612), to interact with other DEAD-box (SEQ ID NO: 1) helicase family members. Our results highlight the value of further exploring modification of the C$_8$b position for extending the potency of rocaglates.

The stabilization of eIF4A1 onto RNA is a critical aspect of rocaglate activity as introduction of wt eIF4A1 is able to resensitize the eIF4A1$^{em1JP}$ cell line to the cytotoxicity of these compounds. This likely explains why eIF4A1$^{em1JP}$ cells are not completely resistant to rocaglates at high concentrations (FIG. 26A), since eIF4A1$^{em1JP}$ cells also express wt eIF4A2 which could be recruited for clamping. Moreover, the addition of recombinant eIF4A1 F163L to cell-free translation extracts is able to partially alleviate the inhibition of protein synthesis by rocaglates. This rescue occurs in spite of the fact that rocaglates can still induce clamping of wt eIF4A present in lysates onto the 5' leader, suggesting that rocaglates impair eIF4F function in addition to inducing eIF4A1 clamping.

Figure 34:
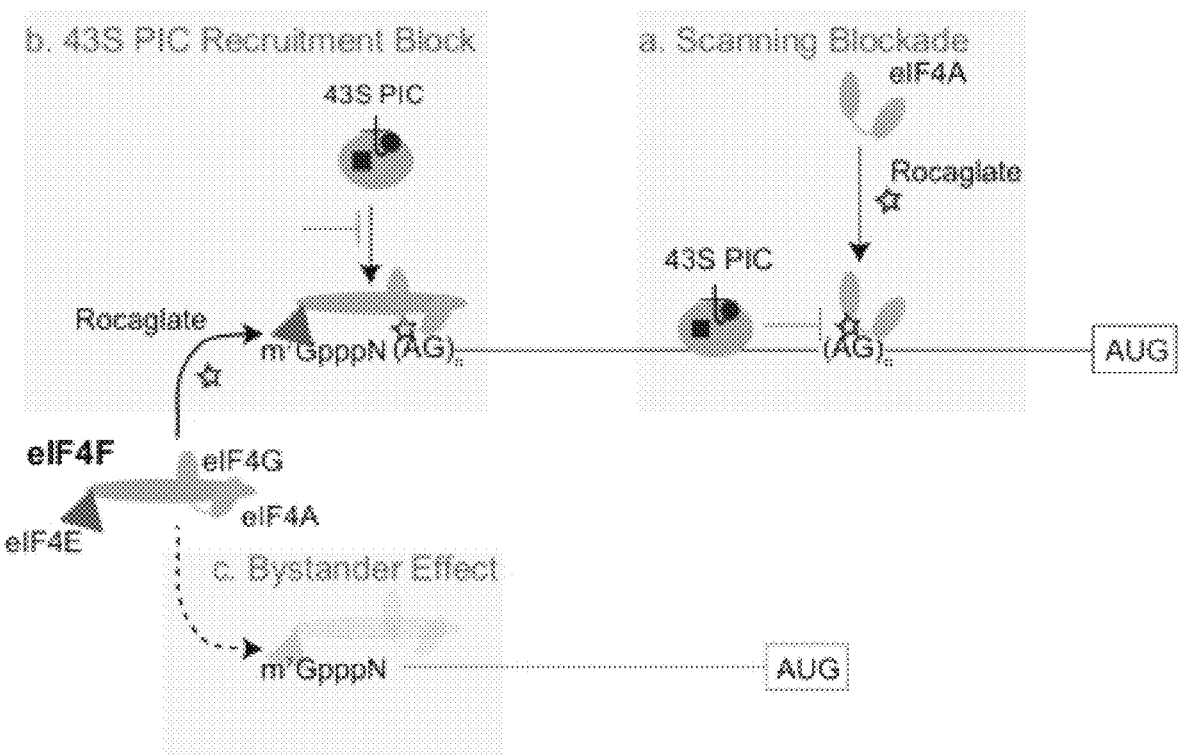
FIG. 34 is a schematic diagram highlighting different ways in which rocaglates inhibit translation initiation.

Overall, these results suggest that rocaglates can inhibit translation in several ways and that scanning inhibition is insufficient to explain the repression mediate by eIF4A: rocaglate:mRNA complexes. (FIG. 34). Firstly, and consistent with previously published data, there is cap-independent clamping of eIF4A1 to polypurine sequences that can redirect ribosomes to alternative upstream initiation codons. However, scanning inhibition per se is insufficient to explain the repression mediate by rocaglate:eIF4A complexes (FIG. 29). This work indicates that eIF4F complexes can be trapped at the cap when cap-proximal polypurine sequences are present (FIG. 30A). This is associated with reduced translation (FIG. 22A-22C and FIG. 26A-26B), presumably due to diminished 43S PIC recruitment to the targeted mRNA (FIG. 34, Mechanism b, 43S PIC Recruitment Block). This mechanism is different to the one reported for inhibition of translation by dominant-negative mutants of eIF4A, which when incorporated into the eIF4F complex prevent eIF4F from interacting with the cap. By extending the resident time of eIF4F at the cap, rocaglates exert a bystander effect leading to trans-inhibition of translation on otherwise normally unresponsive mRNAs (FIG. 34, Mechanism c, Bystander Effect). As this effect is partially rescued by addition of eIF4F we surmise it results from a decrease in levels of free eIF4F.

Material and Methods

Compounds. Rocaglate derivatives provided from the BU-CM Dcollection were synthesized using ESIPT photocycloaddition of 3-hydroxyflavones with cinnamates as previously published followed by further functionalization. Note that there are duplicate values for some compounds in this collection from different synthesis batches or containing two enantiomers (see Supp Table 1). Compounds were resuspended to 10 mM in neat DMSO and stored at −80° C.

Recombinant DNA Constructs. Plasmids expressing the $(AG)_{10}$- and $(UC)_{10}$-reporters were constructed through modification of pKS/FF/HCV/Ren vector[14]. To facilitate the replacement of 5' leader sequences, a MluI restriction site was introduced immediately upstream of T3 promoter and a NdeI restriction site was added immediately upstream of the AUG start codon of FF. These sites were added to Gblocks containing the described modifications and cloned into the pKS/FF/HCV/REN vector through the PciI and NarI restriction sites. Different 5' leader sequences were then introduced to the reporters by annealing two overlapping phosphorylated oligonucleotides with the desired sequences, and directional cloning into the vector using the MluI and NdeI restriction sites.

Cell Culture and Retroviral Transduction: All cell lines used in this study were maintained in DMEM supplemented with 10% FBS (Wisent), 100 U/ml penicillin/streptomycin, and 2 mM L-glutamine at 37° C. and 5% $CO_2$. For overexpression studies with eIF4A1 in NIH/3T3 or eIF4A1$^{em1jp}$ cells, ecotropic Phoenix cells were first transfected with retroviral vectors expressing codon optimized $His_6$-tagged (SEQ ID NO: 12) eIF4A1 (WT or F163L). Forty-eight hours post-transfection, the viral supernatant was harvested, filtered, and added to NIH/3T3 or eIF4A1$^{em1jp}$ cells in the presence of 4 µg/mL polybrene once every 12 h for a total of 4 infections. Two days after the final infection, cells were seeded for SRB assays (described above) and western blotting.

Purification of Recombinant Proteins. BL21 (DE3) *E. coli* cells were transformed with pET15b-$His_6$-eIF4A1 or pET15b-$His_6$-eIF4A2 plasmids. Single colonies were picked and grown in an overnight starter culture at 37° C. in LB media supplemented with 100 mg/L ampicillin. On the following day, the starter culture was used to inoculate at a 1:50 dilution, and the cultures continued growing at 37° C. When the $OD_{600}$ reached 0.6-0.8, 1 mM IPTG was added to induce protein production and the cultures were grown for an additional 3 h. Cells were pelleted, resuspended in a buffer containing 20 mM Tris (pH 7.5), 10% glycerol, 0.1 mM EDTA, 200 mM KCl, 0.1% Triton X-100, 3.4 mM β-mercaptoethanol, and sonicated. The lysates were cleared via centrifugation and supplemented with 20 mM imidazole prior to loading onto a Ni-NTA agarose column (Qiagen). The column was washed 3 times with 4 column volumes of wash buffer 1 (20 mM Tris (pH 7.5), 10% glycerol, 0.1 mM EDTA, 800 mM KCl, 20 mM imidazole), and then washed 3 more times with 4 column volumes of wash buffer 2 (Wash buffer 1 containing 300 mM KCl). Elution was achieved using Wash buffer 2 supplemented with 200 mM imidazole and dialyzed overnight in a buffer containing 20 mM Tris (pH 7.5), 10% glycerol, 0.1 mM EDTA, 100 mM KCl, and 2 mM DTT. The resulting samples were further purified using a Q-Sepharose Fast Flow (Amersham) column and eluted with a 100 mM-500 mM KCl gradient supplemented with 20 mM Tris (pH 7.5,) 10% glycrerol and 0.1 mM EDTA. Eluted fractions of high protein yield and purity (as assessed by Coomassie blue staining) were combined and dialyzed against 20 mM Tris (pH 7.5), 10% glycerol, 0.1 mM EDTA and 2 mM DTT.

In Vitro Translation Assays. In vitro translation assays performed in Krebs-2 cell extracts were supplemented with 5 mM $MgCl_2$, 30 mM Tris-HCl (pH 7.5), 1.5 mM ATP, 0.1 mM GTP, 0.6 mM CTP, 10 mM dipotassium creatine phosphate, 80 µg/mL creatine kinase, and 0.04 mM amino acids. The specified mRNA reporters were added to each reaction at a final concentration of 10 ng/µL. The translation reactions were incubated with or without compound for 60 minutes at 30° C. prior to the measurement of luciferase activities.

Fluorescence Polarization (FP) Assays. Unless otherwise specified, eIF4A (500 nM) was incubated with 10 nM FAM-labelled RNA for 30 min in FP buffer (14.4 mM HEPES-NaOH (pH 8), 108 mM NaCl, 1 mM $MgCl_2$, 14.4% glycerol, 0.1% DMSO, 2 mM DTT, 1 mM AMPPNP) at room temperature in black low volume 384 well plates (Corning 3820). FP readings were performed on a Pherastar FS microplate reader (BMG Labtech).

RNA Transfections. HEK 293 cells were transfected in a 24 well plate with 0.25 µg/well of in vitro synthesized capped $m^7GpppG(AG)_{10}$-FF/HCV/Ren or $m^7GpppG$ $(UC)_{10}FF/HCV/Ren$ mRNA and 1 h later were exposed to the indicated concentrations of compounds for an additional 6 h. Following this, extracts were prepared using passive lysis buffer (PLB, Promega) and luciferase activity measured on a Berthold Lumt LB 9507 luminometer.

Sulforhodamine B (SRB) assay. NIH/3T3 cells were seeded at a density of 1000 cells/well in a 96 well format and incubated in presence of each 40 nM compound. After 4 days of culture, cells were washed with PBS, fixed with 50% trichloroacetic (TCA) acid for 1 hour, and then stained with 0.5% sulforhodamine B in 1% acetic acid for 15 min. Plates were then washed 5 times with 1% acetic acid, dried, and the stained wells were resuspended with 10 mM Tris (pH 9) prior to measuring the absorbance at 510 nm using (Spectramax M5, Molecular Devices)

RNA Pull Down (RPD) Experiments. Rabbit reticulocyte lysates (Promega) were pre-incubated with 500 nM of the indicated compound for 15 minutes at 30° C. prior to the addition of m7GpppG- or ApppG-capped biotinylated RNAs (added to a final concentration of 1 µM biotinylated RNA bait). The reactions were incubated for an additional 15 minutes at 30° C. and then diluted 10× with ice cold wash buffer (0.5% v/v NP-40, 50 mM HEPES (pH 7.3), 150 mM KCl, 2 mM EDTA, 2 mM $MgC_2$,). Magnetic streptavidin beads (NEB) were used to capture the biotinylated RNA baits and the reactions were incubated end over end for 1 hour at 4° C. The beads were then washed three times with ice cold wash buffer (10 minutes per wash) and the RNA bound proteins were eluted by digesting with 50 U of RNaseI (Ambion, AM2294) for 15 minutes at 37° C. Eluted proteins were analyzed by Western blotting.

[$^{35}$S]-Methionine Labeling. 293T cells were seeded at a density of 40 000 cells per well in a 24 well plate and on the following day, incubated in the presence of the indicated concentration of compound in methionine/cysteine free media supplemented with 10% dialyzed FBS for 1 hour. De novo protein synthesis was monitored through the addition $S^{35}$methionine/cysteine labelling mix (1175 $C_1$/mmol) and incubating the cells for an additional 15 min. The labeling reaction was terminated by washing the cells twice with ice cold PBS and lysing with RIPA buffer. Half of the lysate was then spotted onto 3 MM Whatman paper that had been pre-blocked with amino acids and precipitated using 10% trichloroacetic acid (TCA) at 4° C. for 20 minutes. The spotted samples were boiled in 5% TCA for 15 minutes., washed twice with 5% TCA, followed by one wash with 75% EtOH, dried, and quantitated using scintillation counting. Protein concentration was determined with the DC Protein assay (BioRad) and used for normalization.

Western Blotting. Cells were pelleted, washed with PBS and lysed with NP40 lysis buffer (150 mM NaCl, 2 mM EDTA, 0.5% NP40, 20 mM Tris pH 7.3, supplemented with 1 mM PMSF, 4 µg/mL aprotinin, 2 µg/mL leupeptin, 2 µg/mL pepstatin). The cellular debris was pelleted by centrifugation at 16000×g for 5 minutes and the protein concentration of the lysates was quantitated using DC assay (BioRad) according to manufacturer's instructions. The prepared lysates were then resolved on a 10% NuPAGE gel. The antibodies used for protein expression analysis were directed against eIF4A1 (Abcam, ab31217), eIF4E (Cell Signaling, #9742), eIF4G (Cell Signaling, #2498), and eEF2 (Cell Signaling, #2332).

Liver polysomes. For polysome profiling analysis on liver extracts, female $C_{57}$/B16 mice were treated at a single dose of either vehicle (5.2% PEG400/5.2% Tween-80), 0.2 mg/kg CR-1-31-B or 0.5 mg/kg CMLD012612 and animals sacrificed 3 h after injection. Livers were excised, washed in cold PBS containing 100ug/mL cycloheximide and homogenized in 3 volumes of lysis buffer (40 mM HEPES [7.5], 100 mM KCl, 5 mM MgCl2, 100ug/mL cycloheximide) in a Eurostar Power-b homogenizer (IKA Liver Labortechnik, Staufen, Germany). After homogenization, samples were spun for 10 min at 1200×g and 4 degrees and supernatant transferred to a new tube.

Three hundred microliter of lysis buffer (0.5% Triton X-100 and 0.5% sodium deoxycholate) were added to 150ul of supernatant and the sample spun briefly (10,000×g for 10 min) before loading onto 10-50% sucrose gradients and centrifuged in an SW40 rotor at 35 000 rpm for 135 min. Gradients were analyzed by piercing the tube with a Brandel tube piercer passing 60% sucrose through the bottom of the tube. Recording of the data was performed using InstaCal Version 5.70 and TracerDaq Version 1.9.0.0 (Measurement Computing Corporation, Norton, Mass.).

Lymphoma Studies. A total of $2\times10^6$ Eµ-Myc/myr-Akt lymphoma cells were injected into the tail vein of 6-8 week-old female C57BL/6 mice. Upon development of well-palpable tumors (auxiliary and inguinal lymph nodes), mice were injected intraperitoneal (IP) with doxorubicin (once at 10 mg/kg) or (−)-9aa (CMLD012612), (0.2 mg/kg daily for 5 days). In combination studies, (−)-9aa (CMLD012612) was administered once daily for 5 consecutive days, while doxorubicin was administered on day 2. Tumor-free survival is defined as the time between disappearance and reappearance of a palpable lymphoma following treatment. All animal studies were approved by the McGill University Faculty of Medicine Animal Care Committee.

Statistics. All indicated replicates represent biological replicates. Statistical evaluation of tumor-free survival data was performed in the Kaplan-Meier format with the log rank test for statistical significance using SigmaStat software. The difference between ΔZ-scores for different treatments and genes containing either polypurine or polypyrimidine tracts was tested using Mann Whitney U-test.

Additional Details Regarding Figures

FIGS. 17A-17F. Assessment of eIF4A1 and eIF4A2 RNA binding specificity. 17A. Chemical structure of the most commonly used rocaglates in biological studies 17B. Coomassie blue staining of SDS-PAGE showing eIF4A1 and eIF4A2 preparations used herein. 17C. eIF4A1 and eIF4A2 have similar RNA binding specificities. eIF4A1 or eIF4A2 (500 nM) were incubated in the presence of FAM-labelled RNA (10 nM) having the indicated sequence composition for 30 mins, after which FP measurements were taken. The change in FP obtained relative to vehicle controls is presented. n=3±SD. 17D. Binding of eIF4A1 and eIF4A2 to RNA is equally responsive to CR-1-31-B (23). FAM labeled poly $r(AG)_8$ (SEQ ID NO: 2) (10 nM) was mixed with the indicated concentrations of eIF4A1 or eIF4A2 either in the presence of vehicle (DMSO) or 10 µM CR-1-31-B(23). Reactions were equilibrated at RT for 30 minutes prior to measuring light polarization. n=3±SD. 17E. Stimulation of eIF4A1-RNA binding by CR-1-31-B (23) shows preference for polypurine-enriched sequences. FAM-labelled RNA was incubated in the presence of 500 nM eIF4A1 and the indicated concentration of CR-1-31-B (23) for 30 min, after which time FP measurements were obtained. The change in FP relative to vehicle controls is presented. n=3±SD. 17F. The extent of eIF4A-RNA binding stimulated by CR-1-31-B 23 scales with polypurine content. FAM-labelled RNA was incubated with 500 nM eIF4A1 and the indicated concentration of CR-1-31-B (23) for 30 min, after which time FP measurements were obtained. The change in FP obtained relative to vehicle controls is presented. n=3±SD.

Figure 18A:
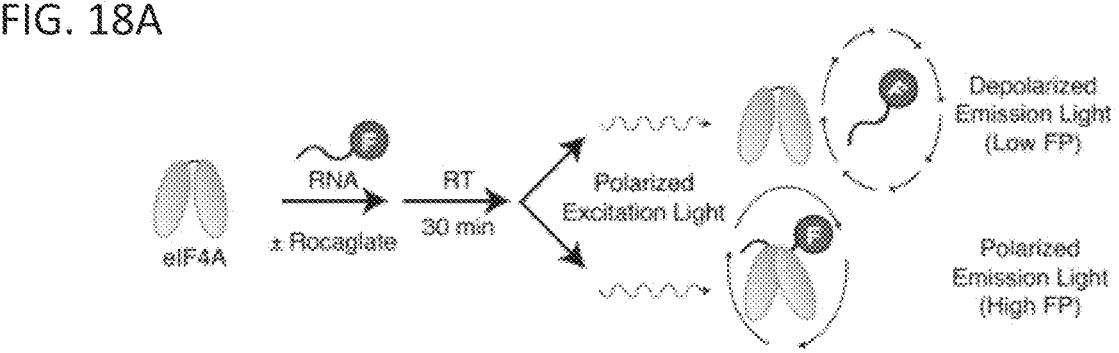
FIG. 18A shows schematic diagrams of FP assays used to measure eIF4A:RNA association.
Figure 18B:
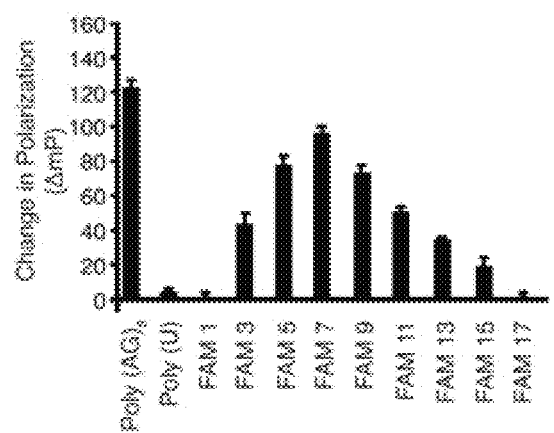
FIG. 18B shows RNA sequences used in this experiment indicated to the left and the FP results obtained with these are plotted to the right, and discloses SEQ ID NOS 2, 13, and 17-25, respectively, in order of appearance. The location of a single AG dinucleotide within a poly r(U) track promotes rocaglate-stimulated eIF4A1:RNA binding. The RNA sequences used in this experiment are indicated to the left and the FP results obtained with these are plotted to the right. eIF4A1:RNA binding assays were performed in the presence of vehicle or 50 μM CR-1-31-B. n=4±SD.

FIGS. 18A-18B. Fluorescence polarization assay reporting on eIF4A:RNA binding. 18A. Schematic diagram of FP assay used to measure eIF4A:RNA association. FAM-labeled RNA probes are excited by plane-polarized light in the presence of eIF4A rocaglate. In the absence of eIF4A binding, the RNA probe rapidly tumbles and the emitted light becomes depolarized. Binding of eIF4A to RNA hinders probe rotation and results in polarized light emission. 18B. The location of a single AG dinucleotide within a poly r(U) track enables rocaglate-stimulated eIF4A1:RNA binding. The RNA sequences used in this experiment are indicated to the left and the FP results obtained with these are plotted to the right. eIF4A1:RNA binding assays were performed in the presence of vehicle or 50 µM CR-1-31-B (23). n=4±SD.

FIGS. 19A-19C. Rocaglate activity profiling. 19A. Assessing eIF4A1:poly $r(AG)_8$ (SEQ ID NO: 2) RNA binding by FP in the presence of 10 µM rocaglate. Values are expressed relative to vehicle controls and data is rank ordered. n=3±SD. 19B. The change in polarization obtained with eIF4A1:poly $r(AG)_8$ (SEQ ID NO: 2) and eIF4A2:poly $r(AG)_8$ (SEQ ID NO: 2) RNA. Pearson r=0.814; p<0.0001. 19C. Inhibition of cap-dependent translation by rocaglates was measured using the indicated mRNA bicistronic reporter (4 ng/ul) in Krebs-2 extracts at a final compound concentration of 2 µM. n=3±SD.

As noted, FIG. 3, Shows (comparison of rocaglate biological activity). FIGS. 20A-2C show some of the structures. FIG. 20A shows the structures of the two most potent rocaglates that show activity towards stimulating eIF4A1:RNA binding and inhibiting cap-dependent translation. FIG. 20B shows structure of two rocaglates that potently inhibit cap-dependent translation, but modestly stimulate eIF4A1:RNA binding. FIG. 20C. shows structures of four rocaglates that potently stimulate eIF4A1:RNA binding, but are inactive or show weak activity as protein synthesis inhibitors in vitro.

Figure 21:
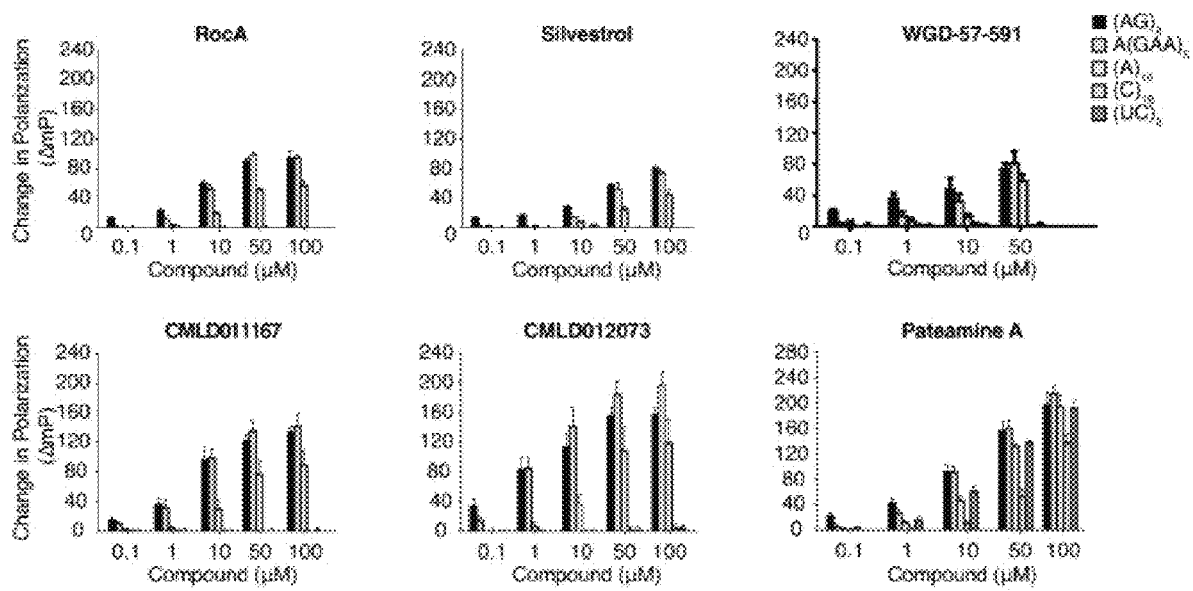
FIG. 21 shows plots of experiments assessing stimulation of eIF4A1:RNA binding by both rocaglates and pateamine. The figure also discloses SEQ ID NOS 2 and 4-7, respectively, in order of appearance.

FIG. 21. Assessing stimulation of eIF4A1:RNA binding by rocaglates and pateamine. FAM-labelled RNA was incubated in the presence of 500 nM eIF4A1 and the indicated concentrations of compound for 30 min, after which time FP measurements were taken. Limitations in WGD-57-591 availability prevented us from extending the titrations to 100 µM. The change in FP obtained relative to vehicle controls is presented. n=3±SD. FP results of competition assays in which preformed eIF4A1:rocaglate:FAM-poly $r(AG)_{10}$ complexes were incubated in the presence of poly $r(AG)_{10}$ (SEQ ID NO: 39) and dissociation measured as a function of time. n=3±SD.

FIGS. 23A-23C. The presence of polypurines bases in mRNA 5' leader regions are not universal predictors of rocaglate-responsiveness. FIG. 23A. Schematic diagram of FF/HCV/Ren mRNA reporters containing cap-proximal (AG) or (UC) dinucleotide repeats. 23B. Firefly and renilla luciferase activity in response to the indicated CR-1-31-B (23) concentrations (relative to DMSO controls) in Krebs-2 extracts programmed with 4 ng/uL of the indicated mRNAs. n=3±SD. 23C. Dose response of the indicated compounds in Krebs-2 extracts programmed with 4 ng/µL of the indicated mRNAs. n=3± SD.

FIG. 23. Dose-response of $(AG)_{10}$- and $(UC)_{10}$-FF/HCV/Ren mRNAs to CMLD011167, hippuristanol and pateamine A in vitro. Firefly and renilla luciferase activity in response to the indicated compound concentrations (relative to DMSO controls) in Krebs-2 extracts programmed with 4 ng/µL of the indicated mRNAs. n=3± SD.

FIGS. 24A-24B. Rocaglates show differing sequence preferences for inhibition of cap-dependent translation in vitro. 24A. Schematic diagram of FF/HCV/Ren mRNA reporters containing $(AG)_{10}$ or $(UC)_{10}$ tracks embedded within the 5' leader region. 24B. Firefly and renilla luciferase activity in response to the indicated compound concentrations (relative to DMSO controls) in Krebs-2 extracts programmed with 4 ng/µL of the indicated mRNAs. n=3±SD. 25C. Assessing CR-1-31-B (23) responsiveness on translation of a reporter mRNA harboring a polypurine track within the 3' untranslated region. n=3±SD.

FIGS. 25A-25B. Cap-independent clamping of eIF4A does not account for the full inhibitory effects of rocaglates. 25A. RPDs performed with the indicated $m^7GpppG$- or ApppG-capped RNA species incubated in the presence of retic lysate and either vehicle or 500 nM rocaglate. 25B. RPDs performed with $m^7GpppG$-capped RNA species incubated in the presence of recombinant eIF4A (125 nM) eIF4F or Krebs-2 extracts and either vehicle or 500 nM silvestrol.

FIGS. 26A-26B. In cellula activity of rocaglates. 26A. Cytotoxicity of rocaglates towards NIH/3T3 (grey circle) and the NIH/3T3 rocaglate-resistant line, eIF4A$^{em1JP}$(red-triangle). Cells were exposed to 40 nM compound for 4 days and viability was measured using the SRB assay. n=3±SD. 26B. Rocaglates show different sequence preferences for inhibiting cap-dependent translation in cellula. HEK 293 cells were transfected with 0.5 µg of in vitro synthesized capped $(AG)_{10}$-FF/HCV/Ren or $(UC)_{10}$-FF/HCV/Ren mRNA and 1h later exposed to the indicated concentrations of compounds for an additional 6 h, at which time extracts were prepared and luciferase activity measured. n=3 SD.

FIG. 27. Structures of the most potent cytotoxic rocaglates exhibiting activity towards NIH/3T3 cells.

FIG. 28. In cellula dose-response of $(AG)_{10}$- and $(UC)_{10}$-FF/HCV/Ren mRNAs to hippuristanol and pateamine. Firefly and renilla luciferase activity in response to the indicated compound concentrations (relative to DMSO controls) following mRNA transfections in 293 cells. n=3±SD.

FIG. 29. Cap-independent clamping of eIF4A does not account for the full inhibitory effects of rocaglates. Addition of recombinant eIF4A1(F163L), but not wt eIF4A, to rabbit reticulocyte lysates programmed with the indicated reporters partially rescues rocaglate-induced translation inhibition. Translation reactions contained 100 nM compound and recombinant wt eIF4A1 or eIF4A1(F163L) protein to a final concentration of 0.17 µg/µL (3.6 µM). Translation reactions were performed at 30° C. for 60 min, followed by assessment of FLuc and RLuc activity. n=3±SD.

FIGS. 30A-30B. Rocaglates exert effects on eIF4F activity. 30A. RPDs performed with $m^7GpppG$-capped RNA incubated in the presence of retic lysate and either vehicle or 500 nM rocaglate. 30B. Schematic diagram showing assay assessing trans-inhibition of rocaglates. 30C. The presence of $m^7GpppG$ capped, but not ApppG capped, purine-rich RNAs sensitizes the rocaglate-unresponsive $m^7GpppG$ $(UC)_{10}$-FF/HCV/Ren reporter to inhibition. Translation reactions were performed in Krebs-2 extracts with 10 nM of $m^7GpppG(UC)_{10}$-FF/HCV/Ren reporter and 250 nM of competitor RNA. Reactions were incubated at 30° C. for 60 min prior to luciferase measurement. n=3±SD. 30D. The addition of recombinant eIF4F rescues rocaglate mediated translation inhibition. The $m^7GpppG(AG)_{10}$-FF/HCV/Ren reporter was added to Krebs-2 translation extracts in the presence eIF4F and 100 nM of the indicated compound. Reactions were incubated at 30° C. for 60 min prior to luciferase measurement. n≥3, ±SEM FIGS. 31A-31B. Rocaglates function through a conditional gain-of-function mechanism. 31A. Western blot documenting endogenous and ectopic eIF4A1 levels. 31B. Ectopic expression of wt eIF4A1 in rocaglate-resistant cells sensitizes these to cell death. NIH/3T3 or eIF4A1$^{em1JP}$ cells were infected with an empty MSCV cassette or expressing either wt eIF4AI or the eIF4AI(F163L) rocaglate-resistant mutant. Viability was assessed following a 4 day exposure to 40 nM of the indicated compounds. n=3, SD.

FIGS. 32A-32F. Characterization of (−)-9aa (CMLD012612). 32A. The $IC_{50}$ for inhibiting NIH/3T3 cell survival versus blocking translation of FF/HCV/Ren in vitro is plotted for the most active ADRs. Translations were performed in RRL programmed with 4 ng/mL $m^7GpppG$- $(AG)_{10}$-FF/HCV/Ren mRNA. (−)-9aa (CMLD012612) is highlighted in red. Average of n=3. 28B. Chemical structure of (−)-9aa (CMLD012612). 32C. (−)-9aa (CMLD012612) inhibits capped $m^7GpppG$-$(AG)_{10}$-FF/HCV/Ren and $m^7GpppG$-$(UC)_{10}$-FF/HCV/Ren mRNA in Krebs-2 extracts. 32D. Inhibition of $^{35}S$-methioinine incorporation in HEK293 cells following a 1 h exposure to the indicated compound concentrations. n=3±SD. 32E. Cytotoxicity of (−)-9aa (CMLD012612), towards NIH/3T3 and eIF4A1$^{em1JP}$ cells following a 4 day exposure to the indicated compound concentration. n=3±SD. f. (−)-9aa (CMLD012612) sensitizes myr-Akt/Eµ-Myc tumors to the effects of doxorubicin in vivo. Kaplan-Meier plot showing tumor-free survival of mice bearing myr-Akt/Eµ-Myc tumors following treatment with doxorubicin (Dxr, red line; n=10), (−)-9aa (CMLD012612) (solid black line; n=10), CR-1-31-D+Dox (blue line; n=4), or (−)-9aa (CMLD012612)+doxorubicin (dashed black line; n=10). p<0003 for significance of CR-1-31-B+Dox versus Dxr alone and p<0.00001 for (−)-9aa (CMLD012612)+Dxr versus Dxr.

FIG. 33. (−)-9aa (CMLD012612) inhibits translation in vivo in the liver. Mice were injected with vehicle or (−)-9aa (CMLD012612) (0.5 mg/kg). Cytoplasmic extracts were prepared from livers 3 h later and resolved on 10%-50% sucrose gradients by centrifugation in an SW40 rotor at 150,000×g for 2 h. Fractions were collected and monitored using an ISCO UA-6 UV detector. Plotted are results of one representative experiment of two that showed similar results. The positions of 80S ribosomes and polysomes in the gradient are labeled, and the polysome/monosome (P/M) ratios indicated.

FIG. 34. Schematic diagram highlighting different ways by which rocaglates target translation initiation. Rocaglates can induce binding of eIF4A to polypurine-rich sequences present in mRNA 5' leader regions and may cause a scanning blockade (a). Messenger RNAs with cap-proximal polypurines can recruit eIF4F to the cap, an event that inhibits 43S PIC recruitment (b) and that leads to a by-stander effect by decreasing eIF4F pools (c).

FIG. 35A-35E are plots showing dose-response curve of FF-HCV-Ren mRNA translation in Krebs extracts with $IC_{50}$s shown for inhibition of cap-dependent protein synthesis. Values are plotted relative to DMSO controls. n=2 technical replicates performed in duplicate. FIG. 35A shows CMLD012612 having a $IC_{50}$~67 nM; FIG. 35B shows BUCMD00512 having a $IC_{50}$~18 nM; FIG. 35C shows CMLD013333 having a $IC_{50}$~41 nM; FIG. 35D shows BUCMD00513 having a $IC_{50}$~55 nM; FIG. 35E shows CMLD013334 having a $IC_{50}$~55 nM.

FIG. 36 is a bar plot showing titrations on HEK 293 cells for compounds according to some implementations of the disclosure. The ploted data is for inhibition of $^{35}$S-methioinine incorporation in HEK293 cells following 1 h compound exposure. Compounds were tested at the indicated concentrations and values are plotted relative to DMSO controls.

References

1 Sonenberg, N. & Hinnebusch, A. G. Regulation of translation initiation in eukaryotes: mechanisms and biological targets. Cell 136, 731-745, doi:S00928674(09)00090-7 [pii] 10.1016/j.cell.2009.01.042 (2009).
2 Bhat, M. et al. Targeting the translation machinery in cancer. Nat Rev Drug Discov 14, 261-278, doi:10.1038/nrd4505 (2015).
3 King, M. L. et al. X-Ray Crystal Structure of Rocaglamide, a Novel Antileukemic I H-Cyclopenta[b] benzofuran from *Aglaia elliptifolia*. J. Chem. Sco. Chem. Commun. 20, 1150-1151 (1982).
4 Bordeleau, M. E. et al. Therapeutic suppression of translation initiation modulates chemosensitivity in a mouse lymphoma model. J Clin Invest 118, 2651-2660, doi: 10.1172/JC134753 (2008).
5. Iwasaki, S., Floor, S. N. & Ingolia, N. T. Rocaglates convert DEAD-box protein eIF4A (SEQ ID NO: 1) into a sequence-selective translational repressor. Nature 534, 558-561, doi:10.1038/nature17978 (2016).
6 Chu, J. et al. CRISPR-Mediated Drug-Target Validation Reveals Selective Pharmacological Inhibition of the RNA Helicase, eIF4A. Cell Rep 15, 2340-2347, doi:10.1016/j.celrep.2016.05.005(2016).
7 Cencic, R. et al. Antitumor activity and mechanism of action of the cyclopenta[b]benzofuran, silvestrol. PLoS One 4, e5223, doi:10.1371/journal.pone.0005223(2009).
8 Rubio, C. A. et al. Transcriptome-wide characterization of the eIF4A signature highlights plasticity in translation regulation. Genome Biol 15, 476, doi:10.1186/s13059-014-0476-1 (2014).
9 Wolfe, A. L. et al. RNA G-quadruplexes cause eIF4A-dependent oncogene translation in cancer. Nature 513, 65-70, doi:10.1038/nature13485 (2014).
10 Iwasaki, S. et al. The Translation Inhibitor Rocaglamide Targets a Bimolecular Cavity between eIF4A and Polypurine RNA. Mol Cell 73, 738-748 e739, doi:10.1016/j.molcel.2018.11.026(2019).
11 Pommier, Y., Kiselev, E. & Marchand, C. Interfacial inhibitors. Bioorg Med Chem Lett 25, 3961-3965, doi: 10.1016/j.bmcl.2015.07.032 (2015).
12 Abramson, R. D. et al. The ATP-dependent interaction of eukaryotic initiation factors with mRNA. J Biol Chem 262, 3826-3832 (1987).
13 Galicia-Vazquez, G., Chu, J. & Pelletier, J. eIF4AII is dispensable for miRNA-mediated gene silencing. RNA 21, 1826-1833, doi:10.1261/rna.052225.115 (2015).
14 Novac, O., Guenier, A. S. & Pelletier, J. Inhibitors of protein synthesis identified by a high throughput multiplexed translation screen. Nucleic Acids Res 32, 902-915 (2004).
15 Lorsch, J. R. & Herschlag, D. The DEAD box protein eIF4A (SEQ ID NO: 1). 1. A minimal kinetic and thermodynamic framework reveals coupled binding of RNA and nucleotide. Biochemistry 37, 2180-2193 (1998).
16 Shah, P., Ding, Y., Niemczyk, M., Kudla, G. & Plotkin, J. B. Rate-limiting steps in yeast protein translation. Cell 153, 1589-1601, doi:10.1016/j.cell.2013.05.049 (2013).
17 Yan, X., Hoek, T. A., Vale, R. D. & Tanenbaum, M. E. Dynamics of Translation of Single mRNA Molecules In Vivo. Cell 165, 976-989, doi:10.1016/j.cell.2016.04.034 (2016).
18 Svitkin, Y. V. et al. The requirement for eukaryotic initiation factor 4A (eF4A) in translation is in direct proportion to the degree of mRNA 5' secondary structure. RNA 7, 382-394. (2001).
19 Pelletier, J. & Sonenberg, N. Photochemical cross-linking of cap binding proteins to eucaryotic mRNAs: effect of mRNA 5' secondary structure. Mol Cell Biol 5, 3222-3230 (1985).
20 Muckenthaler, M., Gray, N. K. & Hentze, M. W. IRP-1 binding to ferritin mRNA prevents the recruitment of the small ribosomal subunit by the cap-binding complex eIF4F. Mol Cell 2, 383-388. (1998).
21 Sadlish, H. et al. Evidence for a functionally relevant rocaglamide binding site on the eIF4A-RNA complex. ACS Chem Biol 8, 1519-1527, doi:10.1021/cb400158t (2013).
22 Schwanhausser, B. et al. Global quantification of mammalian gene expression control. Nature 473, 337-342, doi:10.1038/nature10098 (2011).
23 Bleumink, M. et al. Rocaglamide breaks $TR^AIL$ resistance in HTLV-1-associated adult T-cell leukemia/lymphoma by translational suppression of c-FLIP expression. Cell Death Differ 18, 362-370, doi:cdd201099 [pii] 10.1038/cdd.2010.99 (2011).
24 Stone, S. D., Lajkiewicz, N. J., Whitesell, L., Hilmy, A. & Porco, J. A., Jr. Biomimetic kinetic resolution: highly enantio- and diastereoselective transfer hydrogenation of aglain ketones to access flavagline natural products. J Am Chem Soc 137, 525-530, doi:10.1021/ja511728b (2015).
25 Rodrigo, C. M., Cencic, R., Roche, S. P., Pelletier, J. & Porco, J. A. Synthesis of rocaglamide hydroxamates and related compounds as eukaryotic translation inhibitors: synthetic and biological studies. J Med Chem 55, 558-562, doi:10.1021/jm201263k (2012).
26 Yueh, H., Gao, Q., Porco, J. A., Jr. & Beeler, A. B. A photochemical flow reactor for large scale syntheses of aglain and rocaglate natural product analogues. Bioorg Med Chem 25, 6197-6202, doi:10.1016/j.bmc.2017.06.010 (2017).
27 Clough, E. & Barrett, T. The Gene Expression Omnibus Database. Methods Mol Biol1418, 93-110, doi:10.1007/978-1-4939-3578-9_5 (2016).
28 Langmead, B., Trapnell, C., Pop, M. & Salzberg, S. L. Ultrafast and memory-efficient alignment of short DNA sequences to the human genome. Genome Biol 10, $R_{25}$, doi:10.1186/gb-2009-10-3-r25 (2009).
29 Andreev, D. E. et al. Oxygen and glucose deprivation induces widespread alterations in mRNA translation within 20 minutes. Genome Biol 16, 90, doi:10.1186/s13059-015-0651-z (2015).

As used herein the term "comprising" or "comprises" is used in reference to compositions, methods, and respective component(s) thereof, that are essential to the claimed invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the claimed invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A compound having the structure of Formula (A):

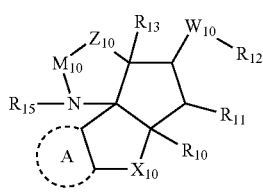

(A)

or stereoisomers, tautomers, or pharmaceutically acceptable salts thereof,
wherein:
$W_{10}$ is C(=O) and $R^{12}$ is H, $OR^A$ or $NR^AR^B$; or $W_{10}$ is $CH_2$ and $R_{12}$ is $NR^AR^B$;
$M_{10}$ is $C(R_{14}R_{17})$;
$R_{13}$ is H or OH; or $W_{10}$-$R_{12}$ and $R_{13}$ together with the carbon atoms they are attached to form a 3-8 membered cycloalkyl or heterocyclyl;
$X_{10}$ is O;
$Z_{10}$ is $NR_{15}'$;
Ring A is an optionally substituted phenyl, optionally substituted pyridinyl, optionally substituted thiazolyl or optionally substituted isothiazolyl;
$R_{10}$ is an optionally substituted phenyl;
$R_{11}$ is an optionally substituted phenyl, optionally substituted furanyl, $NO_2$, CN, or $SO_2R^A$;
$R_{12}$ is H, $(C_1-C_8)$alkyl, $OR^A$ or $NR^AR^B$; or $R_{12}$ and $R_{13}$ together with the carbon atoms they are attached to form a 3-8 membered cycloalkyl or heterocyclyl;
$R_{14}$ is H, $C_1-C_8$(alkyl), $(C_1-C_8)$haloalkyl, $(C_2-C_8)$alkenyl, $(C_2-C_8)$alkynyl, $NR^AR^B$, $[(C_1-C_8)$alkylene]$OR^A$, $[(C_1-C_8)$alkylene]$NHR^A$, $[(C_1-C_8)$alkylene]$NR^AR^B$, $CD_3$, aryl, heteroaryl, cycloalkyl or heterocyclyl;
$R_{15}$ and $R_{15}'$ independently are H; or $R_{14}$, and $R_{15}$ together with the carbon or nitrogen they are bound to form a 5-or 6- membered heterocyclyl or a 5-membered heteroaryl, or $R_{14}$, and $R_{15}'$ together with the carbon or nitrogen they are bound to form a 5-or 6- membered heterocyclyl or a 5-membered heteroaryl, or one of $R_{15}$ or $R_{15}'$ together with $R_{17}$ forms a second bond between the nitrogen and carbon atoms they are attached to;
$R^A$ is H or $(C_1-C_8)$alkyl; and
$R^B$ is and $R^C$ independently are H, OH, $(C_1-C_8)$alkyl or $(C_1-C_8)$alkoxy, and
provided that: (i) one of $R_{15}$ or $R_{15}'$ together with $R_{14}$ and together with the carbon or nitrogen they are bound to form a 5-or 6- membered heterocyclyl or a 5-membered heteroaryl; or (ii) one of $R_{15}$ or $R_{15}'$ together with $R_{17}$ forms a second bond between the nitrogen and carbon atoms they are attached to.

2. The compound of claim 1, wherein the compound is of Formula (A'):

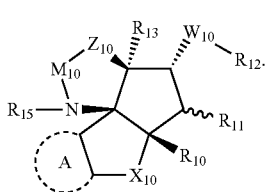

(A')

3. The compound of claim 1, wherein one of $R_{15}$ or $R_{15}'$ together with $R_{17}$ forms a second bond between the nitrogen and carbons atoms they are attached to.

4. The compound of claim 1, wherein $R_{14}$ is $C_1-C_8$(alkyl), $(C_1-C_8)$haloalkyl, $[(C_1-C_8)$alkylene]$OR^A$, $[(C_1-C_8)$alkylene]$NHR^A$, $[(C_1-C_8)$alkylene]$NR^AR^B$, $CD_3$, optionally substituted phenyl, optionally substituted thiazolyl, optionally substituted pyridinyl, optionally substituted morpholinyl, or optionally substituted piperdinyl.

5. The compound of claim 1, wherein:
$R_{11}$ is an optionally substituted phenyl.

6. The compound of claim 1, wherein:
$R_{13}$ is OH.

7. The compound of claim 1, wherein:
$R_{10}$ is an optionally substituted phenyl;
$Ru_{11}$ is an optionally substituted phenyl;
$W_{10}$ is C(=O);
$R_{12}$ is $OR^A$ or $NR^AR^B$;
$R_{13}$ is OH;
$R_{14}$ is $C_1-C_8$(alkyl), $(C_1-C_8)$haloalkyl, $[(C_1-C_8)$alkylene]$OR^A$, $[(C_1-C_8)$alkylene]$NHR^A$, $[(C_1-C_8)$alkylene]$NR^AR^B$, $CD_3$, optionally substituted phenyl, optionally substituted thiazolyl, optionally substituted pyridinyl, optionally substituted morpholinyl, or optionally substituted piperdinyl; and
$R_{15}$ and $R_{15}'$ independently are H, provide that one of $R_{15}$ or $R_{15}'$ together with $R_{17}$ forms a second bond between the nitrogen and carbon atoms they are attached to.

8. The compound of claim 1, wherein Ring A is an optionally substituted phenyl

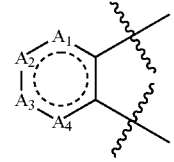

9. The compound of claim 1, wherein:
$R_{10}$ is an optionally substituted phenyl;
$R_{11}$ is an optionally substituted phenyl, nitro, cyano, or $SO_2R^A$;
$W_{10}$ is C(=O);
$R_{12}$ is $OR^A$ or $NR^AR^B$;
$R_{13}$ is OH, or $W_{10}$-$R_{12}$ and $R_{13}$ together with the carbon atoms they are attached to form a 3-8 membered cycloalkyl or heterocyclyl;
$R_{14}$ is $C_1-C_8$(alkyl), $(C_1-C_8)$haloalkyl, $[(C_1-C_8)$alkylene]$OR^A$, $[(C_1-C_8)$alkylene]$NHR^A$, $[(C_1-C_8)$alkylene]$NR^AR^B$, $CD_3$, optionally substituted phenyl, optionally substituted thiazolyl, optionally substituted pyridinyl, optionally substituted morpholinyl, or optionally substituted piperdinyl;
$R_{15}$ and $R_{15}'$ independently are H, provide that one of $R_{15}$ or $R_{15}'$ together with $R_{17}$ forms a second bond between the nitrogen and carbon atoms they are attached to

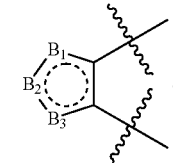

10. The compound of claim 1, wherein the compound is of Formula (I):

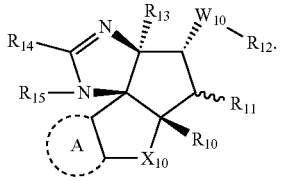
(I)

11. The compound of claim 1, wherein the compound is of Formula (II):

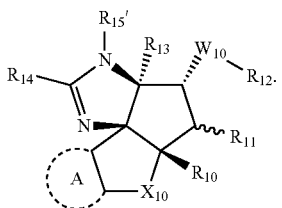
(II)

12. A method for preparing a compound having the Formula (A), the method comprising:

providing a solution of a compound having Formula (V), and reacting the compound (VI) or salts thereof, with a base to provide an intermediate in the solution, and reacting the intermediate with the compound having Formula (VI) or salts thereof;

wherein the structures of (V) and (VI) are:

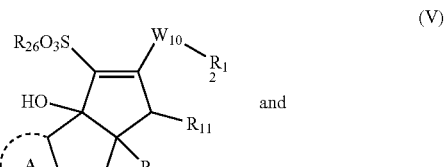
(V)

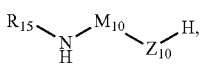
(VI)

wherein $R_{26}$ is a $(C_1-C_3)$alkyl, $CH_3$, aryl, $CF_3$, alkyl substituted aryl, or methyl aryl.

* * * * *

SEQUENCE LISTING

```
<160> NUMBER OF SEQ ID NOS: 39

<210> SEQ ID NO 1
<211> LENGTH: 4
<212> TYPE: PRT
<213> ORGANISM: Unknown
<220> FEATURE:
<223> OTHER INFORMATION: Description of Unknown:
      DEAD-box helicase sequence

<400> SEQUENCE: 1

Asp Glu Ala Asp
1

<210> SEQ ID NO 2
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agagagagag agagag                                                     16

<210> SEQ ID NO 3
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: This sequence may encompass 3-4 repeats of
      "cgg"

<400> SEQUENCE: 3
cggcggcggc gg                                                         12

<210> SEQ ID NO 4
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 4
agaagaagaa gaagaa                                                16

<210> SEQ ID NO 5
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaaaaaaaa aaaaaa                                                16

<210> SEQ ID NO 6
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cccccccccc cccccc                                                16

<210> SEQ ID NO 7
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ucucucucuc ucucuc                                                16

<210> SEQ ID NO 8
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
agagagagag                                                       10

<210> SEQ ID NO 9
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
agagagagag agagagagag agagagagag ag                              32

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 10
gagagagaga gagagagaga g                                              21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gagagagaga gagagagaga g                                              21

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 12

His His His His His His
1               5

<210> SEQ ID NO 13
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uuuuuuuuuu uuuuuu                                                    16

<210> SEQ ID NO 14
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uuuuuuuagu uuuuuu                                                    16

<210> SEQ ID NO 15
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uuuuuuagag uuuuuu                                                    16

<210> SEQ ID NO 16
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 16
uuuuagagag aguuuu                                                    16

<210> SEQ ID NO 17
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aguuuuuuuu uuuuuu                                                    16

<210> SEQ ID NO 18
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uuaguuuuuu uuuuuu                                                    16

<210> SEQ ID NO 19
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uuuuaguuuu uuuuuu                                                    16

<210> SEQ ID NO 20
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uuuuuuaguu uuuuuu                                                    16

<210> SEQ ID NO 21
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uuuuuuuagu uuuuuu                                                    16

<210> SEQ ID NO 22
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
```

<210> SEQ ID NO 22
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uuuuuuuuag uuuuuu                                                       16

<210> SEQ ID NO 23
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
uuuuuuuuuu aguuuu                                                       16

<210> SEQ ID NO 24
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uuuuuuuuuu uuaguu                                                       16

<210> SEQ ID NO 25
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uuuuuuuuuu uuuuag                                                       16

<210> SEQ ID NO 26
<211> LENGTH: 196
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gaatacacgg aattcagcag cagcagcagc agcagcagca gcagcagcag cagcagcagc       60
aattcagcag cagcagcagc agcagcagca gcagcagcag cagcagcagc aattcagcag      120
cagcaattcg agctcgcccg gggatctgcg atctaagtaa gcttggcatt ccggtactgt      180
tggtaaagcc accatg                                                      196

<210> SEQ ID NO 27
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gacauuugcu ucugacacaa cuguguucac uagcaaccuc auaug                       45

```
<210> SEQ ID NO 28
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gagaguugcu ucugacacaa cuguguucac uagcaaccuc auaug            45

<210> SEQ ID NO 29
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gagagagaga gcugacacaa cuguguucac uagcaaccuc auaug            45

<210> SEQ ID NO 30
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gagagagaga gagagagaga gagagagaga gagcaaccuc auaug            45

<210> SEQ ID NO 31
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gagagagaga gagagagaga guguguucac uagcaaccuc auaug            45

<210> SEQ ID NO 32
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gucucucucu cucucucucu cuguguucac uagcaaccuc auaug            45

<210> SEQ ID NO 33
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gacauuugcu ucugacagag agagagagag agagagccuc auaug            45
```

```
<210> SEQ ID NO 34
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gacauuugcu ucugacucuc ucucucucuc ucucucccuc auaug              45

<210> SEQ ID NO 35
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uagagagaga gagagagaga gagagagaga gagagagaga gaagcuucgg gugggga   57

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gucucucucu cucucucucu c                                          21

<210> SEQ ID NO 37
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
agagagagag agagagagag agagagagag agagagagag                      40

<210> SEQ ID NO 38
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ucucucucuc ucucucucuc                                            20

<210> SEQ ID NO 39
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
agagagagag agagagagag                                            20
```